United States Patent
Hattori et al.

(10) Patent No.: US 11,987,586 B1
(45) Date of Patent: May 21, 2024

(54) PYRROLO[1,2-C]IMIDAZOLE DERIVATIVES AS OREXIN TYPE 2 RECEPTOR AGONISTS

(71) Applicant: TAKEDA PHARMACEUTICAL COMPANY LIMITED, Osaka (JP)

(72) Inventors: Yasushi Hattori, Kanagawa (JP); Marilena Pira, Kanagawa (JP); Yoshiteru Ito, Kanagawa (JP); Kohei Takeuchi, Kanagawa (JP); Eiji Kimura, Kanagawa (JP); Norihito Tokunaga, Kanagawa (JP); Shuhei Ikeda, Kanagawa (JP); Martin Alexander Pawliczek, Kanagawa (JP); Noriyuki Tezuka, Kanagawa (JP); Yasutaka Hoashi, Kanagawa (JP); Yuhei Miyanohana, Kanagawa (JP); Yuichi Kajita, Kanagawa (JP); Tatsuki Koike, Kanagawa (JP)

(73) Assignee: Takeda Pharmaceutical Company Limited (JP)

( * ) Notice: Subject to any disclaimer, the term of this patent is extended or adjusted under 35 U.S.C. 154(b) by 0 days.

(21) Appl. No.: 18/497,602

(22) Filed: Oct. 30, 2023

Related U.S. Application Data

(60) Provisional application No. 63/381,736, filed on Oct. 31, 2022.

(51) Int. Cl.
| | |
|---|---|
| *C07D 487/04* | (2006.01) |
| *A61P 25/00* | (2006.01) |
| *C07D 413/04* | (2006.01) |
| *C07D 519/00* | (2006.01) |

(52) U.S. Cl.
CPC ............ *C07D 487/04* (2013.01); *A61P 25/00* (2018.01); *C07D 413/04* (2013.01); *C07D 519/00* (2013.01)

(58) Field of Classification Search
CPC .. C07D 487/04; C07D 413/04; C07D 519/00; A61P 25/00
See application file for complete search history.

(56) References Cited

U.S. PATENT DOCUMENTS

| | | |
|---|---|---|
| 9,527,807 B2 | 12/2016 | Fukumoto et al. |
| 10,287,305 B2 | 5/2019 | Fujimoto et al. |
| 10,428,023 B2 | 10/2019 | Kajita et al. |
| 10,508,083 B2 | 12/2019 | Fujimoto et al. |
| 10,584,097 B2 | 3/2020 | Kajita et al. |
| 10,898,737 B2 | 1/2021 | Fujimoto et al. |
| 11,028,048 B2 | 6/2021 | Hattori et al. |
| 11,034,700 B2 | 6/2021 | Mikami et al. |
| 11,059,780 B2 | 7/2021 | Daini et al. |
| 11,292,766 B2 | 4/2022 | Fujimoto et al. |
| 11,319,286 B2 | 5/2022 | Fujimoto et al. |
| 11,440,883 B2 | 9/2022 | Kajita et al. |
| 11,655,241 B2 | 5/2023 | Oda et al. |
| 2021/0269420 A1 | 9/2021 | Fujimoto et al. |
| 2022/0017514 A1 | 1/2022 | Kajita et al. |
| 2023/0037557 A1 | 2/2023 | Ito et al. |
| 2023/0042358 A1 | 2/2023 | Miyanohana et al. |
| 2023/0063805 A1 | 3/2023 | Kajita et al. |

FOREIGN PATENT DOCUMENTS

| | | | |
|---|---|---|---|
| WO | WO-2012152663 A1 | 11/2012 | |
| WO | WO-2012137982 A9 | 2/2013 | |
| WO | WO-2015048091 A1 | 4/2015 | |
| WO | WO-2015073707 A1 | 5/2015 | |
| WO | WO-2015147240 A1 | 10/2015 | |
| WO | WO-2017088759 A1 | 6/2017 | |
| WO | WO-2017135306 A1 | 8/2017 | |
| WO | WO-2018164191 A1 | 9/2018 | |
| WO | WO-2018164192 A1 | 9/2018 | |
| WO | WO-2019027003 A1 | 2/2019 | |
| WO | WO-2019027058 A1 | 2/2019 | |
| WO | WO-2020004536 A1 | 1/2020 | |
| WO | WO-2020004537 A1 | 1/2020 | |
| WO | WO-2020122092 A1 * | 6/2020 | ............. A61P 25/26 |
| WO | WO-2020122093 A1 | 6/2020 | |
| WO | WO-2020158958 A1 | 8/2020 | |

(Continued)

OTHER PUBLICATIONS

Busquets, X., et al., "Decreased plasma levels of orexin-A in sleep apnea," Respiration 71(6):575-579, Karger Publishers, Switzerland (Nov.-Dec. 2004).

Chemelli, R.M., et al., "Narcolepsy in orexin knockout mice: molecular genetics of sleep regulation," Cell 98(4):437-451, Elsevier, Netherlands (Aug. 1999).

Funato, H., et al., "Enhanced orexin receptor-2 signaling prevents diet-induced obesity and improves leptin sensitivity," Cell Metab 9(1):64-76, Elsevier, Netherlands (Jan. 2009).

Jaeger, L.B., et al., "Effects of orexin-A on memory processing," Peptides 23(9):1683-1688, Elsevier, Netherlands (Sep. 2002).

(Continued)

*Primary Examiner* — Sarah Pihonak
*Assistant Examiner* — Padmaja S Rao
(74) *Attorney, Agent, or Firm* — Sterne, Kessler, Goldstein & Fox, P.L.L.C.

(57) ABSTRACT

The present invention provides a heterocyclic compound having an orexin type 2 receptor agonist activity.
A compound represented by the formula (I):

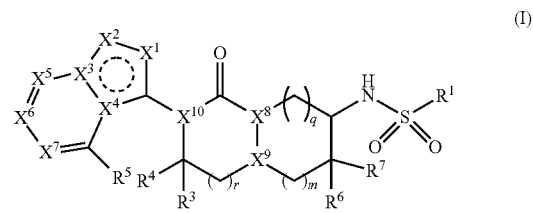

wherein each symbol is as described in the specification, or a salt thereof, is useful as an agent for the prophylaxis or treatment of narcolepsy.

16 Claims, No Drawings

(56) References Cited

FOREIGN PATENT DOCUMENTS

| WO | WO-2020167701 A1 | 8/2020 |
|---|---|---|
| WO | WO-2020167706 A1 | 8/2020 |
| WO | WO-2021106975 A1 | 6/2021 |

OTHER PUBLICATIONS

Kushikata, T., et al., "Orexinergic neurons and barbiturate anesthesia," Neuroscience 121(4):855-863, Elsevier, Netherlands (Nov. 2003).

Lin, L., et al., "The sleep disorder canine narcolepsy is caused by a mutation in the hypocretin (orexin) receptor 2 gene," Cell 98(3):365-376, Elsevier, Netherlands (Aug. 1999).

Mieda, M., et al., "Orexin peptides prevent cataplexy and improve wakefulness in an orexin neuron-ablated model of narcolepsy in mice," Proc Natl Acad Sci USA 101(13):4649-4654, National Academy of Sciences, United States (Mar. 2004).

Mieda, M., and Sakurai, T., "Orexin (hypocretin) receptor agonists and antagonists for treatment of sleep disorders. Rationale for development and current status," CNS Drugs 27(2):83-90, Springer Nature, Germany (Feb. 2013).

Perez, M.V., et al., "Systems Genomics Identifies a Key Role for Hypocretin/Orexin Receptor-2 in Human Heart Failure," J Am Coll Cardiol 66(22):2522-2533, Elsevier, Netherlands (Dec. 2015).

Sakurai, T., et al., "Orexins and orexin receptors: a family of hypothalamic neuropeptides and G protein-coupled receptors that regulate feeding behavior," Cell 92(4):573-585, Elsevier, Netherlands (Feb. 1998).

Thannickal, T.C., et al., "Hypocretin (orexin) cell loss in Parkinson's disease," Brain 130(6):1586-1595, Oxford University Press, United Kingdom (Jun. 2007).

Willie, J.T., et al., "Distinct narcolepsy syndromes in Orexin receptor-2 and Orexin null mice: molecular genetic dissection of Non-REM and REM sleep regulatory processes," Neuron 38(5):715-730, Elsevier, Netherlands (Jun. 2003).

International Search Report and Written Opinion for International Application No. PCT/IB2023/060928, European Patent Office, Rijswijk, The Netherlands, mailed on Feb. 9, 2024, 13 pages.

\* cited by examiner

PYRROLO[1,2-C]IMIDAZOLE DERIVATIVES AS OREXIN TYPE 2 RECEPTOR AGONISTS

TECHNICAL FIELD

The present invention relates to a heterocyclic compound, particularly, a heterocyclic compound having an orexin type 2 receptor agonist activity.

BACKGROUND OF THE INVENTION

Orexin is a neuropeptide specifically produced in particular neurons located sparsely in the lateral hypothalamus and its surrounding area, and consists of two subtypes, orexin A and orexin B. Both orexin A and orexin B are endogenous ligands of the orexin receptors, which are G protein-coupled receptors mainly present in the brain, and two types of subtypes, type 1 and type 2, are known for the orexin receptors (non-patent document 1).

Since orexin-producing neurons (orexin neurons) are localized in the vicinity of the feeding center, and intraventricular administration of orexin peptide results in an increase in food intake, orexin initially attracted attention as a neuropeptide having a feeding behavioral regulation. Thereafter, however, it was reported that the cause of dog narcolepsy is a genetic variation of orexin type 2 receptor (non-patent document 2), and the role of orexin in controlling sleep and wakefulness also has been studied.

From the studies using a transgenic mouse having denatured orexin neurons and a double transgenic mouse obtained by crossing this mouse with an orexin overexpressing transgenic mouse, it was observed that narcolepsy-like symptoms that appear by degeneration of orexin neurons disappear due to sustained expression of orexin. Similarly, when orexin peptide was intraventricularly administered to a transgenic mouse having denatured orexin neuron, improvement of narcolepsy-like symptoms was observed (non-patent document 3). Studies of orexin type 2 receptor knockout mice have suggested that orexin type 2 receptor is important for maintaining arousal (non-patent document 4, non-patent document 5). Such background suggests that orexin type 2 receptor agonists become therapeutic drugs for narcolepsy or therapeutic drugs for other sleep disorders exhibiting excessive sleepiness (non-patent document 6).

In addition, it is suggested that a peptidic agonist that selectively acts on the orexin type 2 receptor improves obesity due to high fat diet load in mice (non-patent document 7).

In addition, it is suggested that intraventricular administration of orexin peptide shortens the systemic anesthetic time of rats (non-patent document 8).

In addition, it is suggested that patients with sleep apnea syndrome show a low orexin A concentration levels in plasma (non-patent document 9).

In addition, it is suggested that intraventricular administration of orexin peptide improves memory retention of senescence-accelerated model mouse (SAMP8) with cognitive dysfunction (non-patent document 10).

In addition, it is suggested that an Orexin type 2 receptor agonist will be a therapeutic drug for cardiac failure (patent document 1, non-patent document 11). In addition, it is suggested that the daytime sleepiness of Parkinson's disease patients is caused by orexin nerve fallout (non-patent document 12).

In addition, it is suggested that orexin regulates bone formation and bone loss, and an orexin type 2 receptor agonist will be a therapeutic drug for diseases related to bone loss such as osteoporosis, rheumatoid arthritis, and the like (patent document 2).

In addition, it is suggested that an orexin receptor agonist is useful for the prophylaxis or treatment of sepsis, severe sepsis and septic shock, since the mortality was significantly improved by mere continuous administration of orexin from the periphery in septic shock model mouse (patent document 3).

Therefore, a compound having an orexin type 2 receptor agonist activity is expected to be useful as a therapeutic drug for the treatment of narcolepsy, idiopathic hypersomnia, hypersomnia, sleep apnea syndrome, disturbance of consciousness, such as coma and the like, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer, obesity, insulin resistance syndrome, cardiac failure, diseases related to bone loss, sepsis, and the like. Further, an orexin type 2 receptor agonist can be usedful as an anesthetic antagonist or as a prophylactic or therapeutic drug for side effects and complications due to anesthesia.

As sulfonamide derivatives, a compound represented by the formula

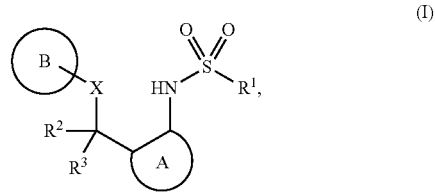

wherein each symbol is as described in the document (Patent Document 4) has been reported.

In addition, as compounds having an orexin type 2 receptor agonist activity, the following compounds have been reported.

A compound represented by the formula

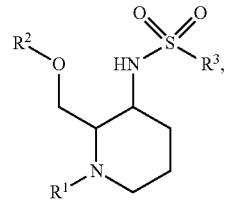

wherein each symbol is as described in the document (Patent Document 5).

A compound represented by the formula

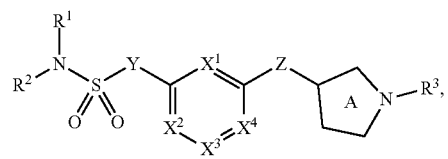

wherein each symbol is as described in the document (Patent Document 6).

A compound represented by the formula

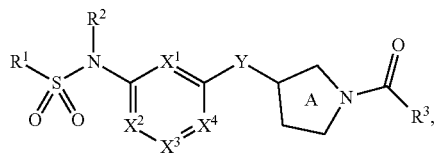

wherein each symbol is as described in the document (Patent Document 7).

A compound represented by the formula

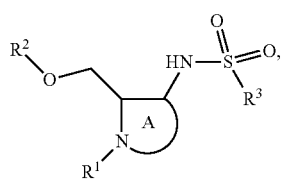

wherein each symbol is as described in the document (Patent Document 8).

A compound represented by the formula

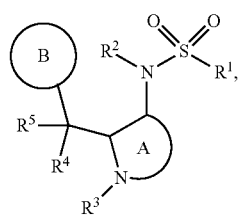

wherein each symbol is as described in the document (Patent Document 9).

A compound represented by the formula

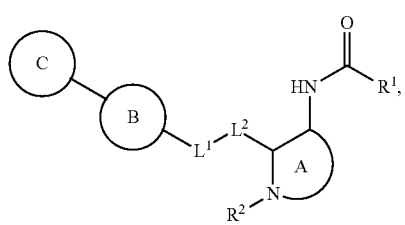
(I)

wherein each symbol is as described in the document (Patent Document 10).

A compound represented by the formula

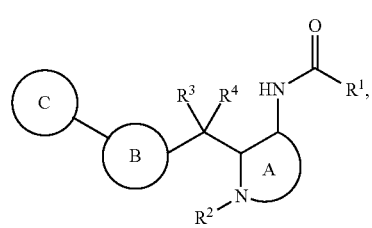
(I)

wherein each symbol is as described in the document (Patent Document 11).

A compound represented by the formula

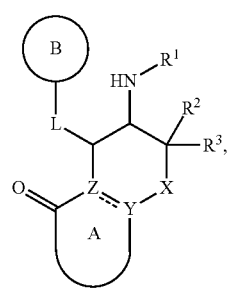
(I)

wherein each symbol is as described in the document (Patent Document 12).

A compound represented by the formula

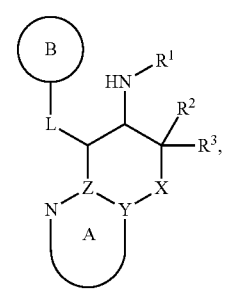
(I)

wherein each symbol is as described in the document (Patent Document 13).

A compound represented by the formula

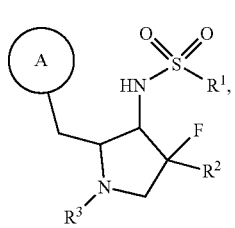
(I)

wherein each symbol is as described in the document (Patent Document 14).

A compound represented by the formula

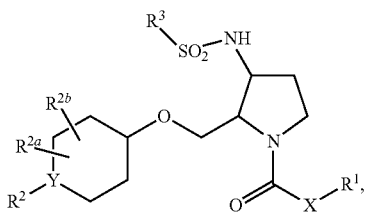

wherein each symbol is as described in the document (Patent Document 15).

A compound represented by the formula

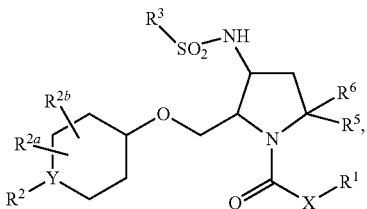

wherein each symbol is as described in the document (Patent Document 16).

A compound represented by the formula

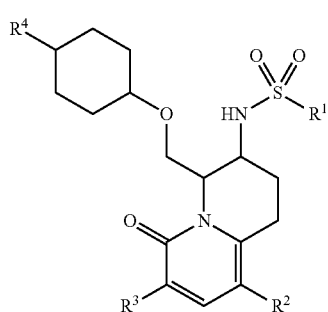

wherein each symbol is as described in the document (Patent Document 17).

However, these compounds are considered to be insufficient in terms of activity, pharmacokinetics or safety, and development of compounds compound having an orexin type 2 receptor agonist activity is still desired.

DOCUMENT LIST

Patent Document

[Patent Document 1] WO 2015/073707 A1
[Patent Document 2] WO 2015/048091 A1
[Patent Document 3] WO 2015/147240 A1
[Patent Document 4] WO 2012/137982 A9
[Patent Document 5] WO 2017/135306 A1
[Patent Document 6] WO 2018/164191 A1
[Patent Document 7] WO 2018/164192 A1
[Patent Document 8] WO 2019/027003 A1
[Patent Document 9] WO 2019/027058 A1
[Patent Document 10] WO 2020/004536 A1
[Patent Document 11] WO 2020/004537 A1
[Patent Document 12] WO 2020/122092 A1
[Patent Document 13] WO 2020/122093 A1
[Patent Document 14] WO 2020/158958 A1
[Patent Document 15] WO 2020/167701 A1
[Patent Document 16] WO 2020/167706 A1
[Patent Document 17] WO 2021/106975 A1

Non-Patent Document

[Non-Patent Document 1] Cell, Vol. 92, 573-585, 1998)
[Non-Patent Document 2] Cell, Vol. 98, 365-376, 1999)
[Non-Patent Document 3] Proc. Natl. Acad. Sci. USA, Vol. 101, 4649-4654, 2004)
[Non-Patent Document 4] Cell, Vol. 98, 437-451, 1999)
[Non-Patent Document 5] Neuron, Vol. 38, 715-730, 2003)
[Non-Patent Document 6] CNS Drugs, Vol. 27, 83-90, 2013)
[Non-Patent Document 7] Cell Metabolism, Vol. 9, 64-76, 2009)
[Non-Patent Document 8] Neuroscience, Vol. 121, 855-863, 2003)
[Non-Patent Document 9] Respiration, Vol. 71, 575-579, 2004)
[Non-Patent Document 10] Peptides, Vol. 23, 1683-1688, 2002)
[Non-Patent Document 11] Journal of the American College of Cardiology. Vol. 66, 2015, Pages 2522-2533)
[Non-Patent Document 12] Brain. Vol. 130, 2007, Pages 1586-1595)

SUMMARY OF THE INVENTION

Problems to be Solved by the Invention

The present invention aims to provide a heterocyclic compound having an orexin type 2 receptor agonist activity.

Means of Solving the Problems

The present inventors have found that a compound represented by the following formula (I) or a salt thereof (sometimes to be referred to as compound (I) in the present specification) has an orexin type 2 receptor agonist activity. As a result of further studies, they have completed the present invention.

Accordingly, the present invention provides the following.

[1] A compound represented by the formula (I):

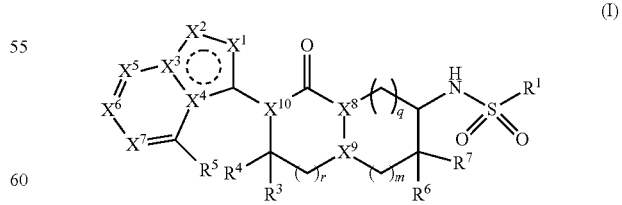

wherein
X$^1$ is NR$^8$, or CR$^9$;
X$^2$ is O, NR$^{10}$, or S;
X$^3$ and X$^4$ are both C, or one of X$^3$ and X$^4$ is N and the other is C;

$X^5$ is $CR^{11}$ or N;
$X^6$ is $CR^{12}$;
$X^7$ is $CR^{13}$ or N;
$X^8$ is $CR^{14}$ or N;
$X^9$ is $CR^2$ or N;
$X^{10}$ is $CR^{15}$ or N;
$R^1$ is an optionally substituted $C_{1-6}$ alkyl group, an optionally substituted $C_{3-10}$ cycloalkyl group, or an optionally substituted mono- or di-$C_{1-6}$ alkylamino group;
$R^2$ and $R^3$ are each independently a hydrogen atom, or an optionally substituted $C_{1-6}$ alkyl group, or
when r is 0, then $R^2$ and $R^3$ may be taken together each other to form a bond, or
when $X^{10}$ is $CR^{15}$, then $R^3$ may be taken together with $R^{15}$ to form a bond;
$R^4$ is a hydrogen atom, an optionally substituted $C_{1-6}$ alkyl group, an optionally substituted $C_{1-6}$ alkoxy group, or a hydroxy group;
$R^5$ is an optionally substituted 4-, 5-, or 6-membered monocyclic group;
$R_6$ and $R^7$ are each independently a hydrogen atom, a halogen atom, or an optionally substituted $C_{1-6}$ alkyl group;
m is 0 or 1;
q is 1 or 2;
r is 0 or 1;
$R^9$, $R^{11}$, $R^{12}$, and $R^{13}$ are each independently a hydrogen atom, an optionally substituted $C_{1-6}$ alkyl group, a halogen atom, an optionally substituted $C_{3-6}$ cycloalkyl group, an optionally substituted 3- to 7-membered nitrogen-containing heterocyclic group, an optionally substituted $C_{1-6}$ alkoxy group, or a hydroxy group;
$R^8$ and $R^{10}$ are each independently absent, or selected from a hydrogen atom and an optionally substituted $C_{1-6}$ alkyl group; and
$R^{14}$ is a hydrogen atom, a halogen atom, or an optionally substituted $C_{1-6}$ alkyl group;
$R^{15}$ is a hydrogen atom, a halogen atom, or an optionally substituted $C_{1-6}$ alkyl group, or
$R^{15}$ may be taken together with $R^3$ to form a bond;
or a salt thereof.

[2] The compound according to the above-mentioned [1], wherein m is 0; q is 1; and r is 0;
or a salt thereof.

[3] The compound according to the above-mentioned [1], wherein m is 1; q is 1; and r is 0;
or a salt thereof.

[4] The compound according to the above-mentioned [1], wherein m is 0; q is 1; and r is 1;
or a salt thereof.

[5] The compound according to the above-mentioned [1], wherein m is 0; q is 2; and r is 0;
or a salt thereof.

[6] The compound according to the above-mentioned [1], wherein
$X^1$ is $NR^8$ wherein $R^8$ is absent;
$X^2$ is O;
$X^3$ and $X^4$ are both C;
$X^5$ is $CR^{11}$ or N, wherein $R^{11}$ is a hydrogen atom;
$X^6$ is $CR^{12}$ wherein $R^{12}$ is a hydrogen atom, a $C_{1-6}$ alkyl group, or a halogen atom; and
$X^7$ is $CR^{13}$ wherein $R^{13}$ is a hydrogen atom, or a halogen atom;
or a salt thereof.

[7] The compound according to the above-mentioned [1], wherein
$X^8$ is N;
$X^9$ is $CR^2$ wherein $R^2$ is a hydrogen atom, or when r is 0, then $R^2$ may be taken together with $R^3$ to form a bond; and
$X^{10}$ is N;
or a salt thereof.

[8] The compound according to the above-mentioned [1], wherein $R^1$ is
(1) a $C_{1-6}$ alkyl group optionally substituted with 1 to 3 substituents independently selected from
 (i) a halogen atom,
 (ii) a $C_{1-6}$ alkoxy group, and
 (iii) a $C_{3-6}$ cycloalkyl group,
(2) a $C_{3-10}$ cycloalkyl group, or
(3) a mono- or di-$C_{1-6}$ alkylamino group;
$R^2$ and $R^3$ are each independently a hydrogen atom, or a $C_{1-6}$ alkyl group, or
when r is 0, then $R^2$ and $R^3$ may be taken together each other to form a bond, or
when $X^{10}$ is $CR^{15}$, then $R^3$ is taken together with $R^{15}$ to form a bond;
$R^4$ is a hydrogen atom, a $C_{1-6}$ alkyl group, a $C_{1-6}$ alkoxy group, or a hydroxy group;
$R^5$ is phenyl, pyrazolyl, furyl, thienyl, thiazolyl, pyridyl, piperidyl, or cyclobutyl, any of which is optionally substituted by one or more substituents independently selected from a $C_{1-6}$ alkyl group, a halogen atom, a halo ($C_{1-6}$) alkyl group, and a $C_{1-6}$ alkoxy group;
$R^6$ and $R^7$ are each independently a hydrogen atom, a halogen atom, or a $C_{1-6}$ alkyl group;
$X^1$, $X^2$, $X^3$, $X^4$, $X^5$, $X^6$, and $X^7$ are selected to form a ring system that is one of:
 (i) $X^1$ is $NR^8$ and $R^8$ is absent, $X^2$ is O; $X^3$ and $X^4$ are both C, $X^5$ is $CR^{11}$, $X^6$ is $CR^{12}$, and $X^7$ is $CR^{13}$;
 (ii) $X^1$ is $NR^8$ and $R^8$ is absent, $X^2$ is O, $X^3$ and $X^4$ are both C, $X^5$ is N, $X^6$ is $CR^{12}$, and $X^7$ is $CR^{13}$;
 (iii) $X^1$ is $NR^8$ and $R^8$ is absent, $X^2$ is O, $X^3$ and $X^4$ are both C, $X^5$ is $CR^{11}$, $X^6$ is $CR^{12}$, and $X^7$ is N;
 (iv) $X^1$ is $NR^8$ and $R^8$ is absent, $X^2$ is S, $X^3$ and $X^4$ are both C, $X^5$ is N, $X^6$ is $CR^{12}$, and $X^7$ is $CR^{13}$;
 (v) $X^1$ is $NR^8$ and $R^8$ is absent, $X^2$ is S; $X^3$ and $X^4$ are both C, $X^5$ is $CR^{11}$, $X^6$ is $CR^{12}$, and $X^7$ is $CR^{13}$;
 (vi) $X^1$ is $NR^8$ and $X^2$ is $NR^{10}$, and one of $R^8$ and $R^{10}$ is absent and the other of $R^8$ and $R^{10}$ is a $C_{1-6}$ alkyl group, $X^3$ and $X^4$ are both C, $X^5$ is $CR^{11}$, $X^6$ is $CR^{12}$, and $X^7$ is $CR^{13}$;
 (vii) $X^1$ is $CR^9$, $X^2$ is $NR^{10}$ and $R^{10}$ is absent, $X^3$ is N, $X^4$ is C, $X^5$ is $CR^{11}$, $X^6$ is $CR^{12}$, and $X^7$ is $CR^{13}$; and
 (viii) $X^1$ is $CR^9$, $X^2$ is $NR^{10}$ and $R^{10}$ is absent, $X^3$ is C, $X^4$ is N, $X^5$ is $CR^{11}$, $X^6$ is $CR^{12}$, and $X^7$ is $CR^{13}$;
$X^8$, $X^9$, $X^{10}$, m, q, and r are selected to form a ring system that is one of:
 (i) $X^8$ is N, $X^9$ is $CR^2$, $X^{10}$ is N, m is 0, q is 1, and r is 0;
 (ii) $X^8$ is N, $X^9$ is $CR^2$, $X^{10}$ is N, m is 1, q is 1, and r is 0;
 (iii) $X^8$ is N, $X^9$ is $CR^2$, $X^{10}$ is N, m is 0, q is 1, and r is 1;
 (iv) $X^8$ is N, $X^9$ is N, $X^{10}$ is $CR^{15}$, m is 0, q is 1, and r is 0;
 (v) $X^8$ is $CR^{14}$, $X^9$ is $CR^2$, $X^{10}$ is N, m is 0, q is 1, and r is 0; and
 (vi) $X^8$ is N, $X^9$ is $CR^2$, $X^{10}$ is N, m is 0, q is 2, and r is 0;

$R^9$, $R^{11}$, $R^{12}$, and $R^{13}$ are each independently selected from a hydrogen atom, a $C_{1-6}$ alkyl group, a halogen atom, a $C_{3-6}$ cycloalkyl group, a $C_{3-6}$ cycloalkyl ($C_{1-6}$) alkoxy group, a halo ($C_{1-6}$) alkyl group, a halo ($C_{1-6}$) alkoxy group, a $C_{1-6}$ alkoxy ($C_{1-6}$) alkyl group, an azetidinyl group, a $C_{1-6}$ alkoxy group, a hydroxy group, and a hydroxy ($C_{1-6}$) alkyl group; and $R^{14}$ is a hydrogen atom, a halogen atom, or a $C_{1-6}$ alkyl group; and $R^{15}$ is taken together with $R^3$ to form a bond;

or a salt thereof.

[9] The compound according to the above-mentioned [1], wherein the partial structure represented by the following formula:

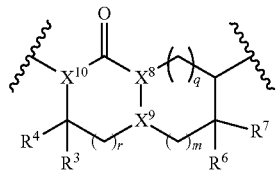

wherein each symbol is as defined in the above-mentioned [1], is one of partial structures represented by the following formulas:

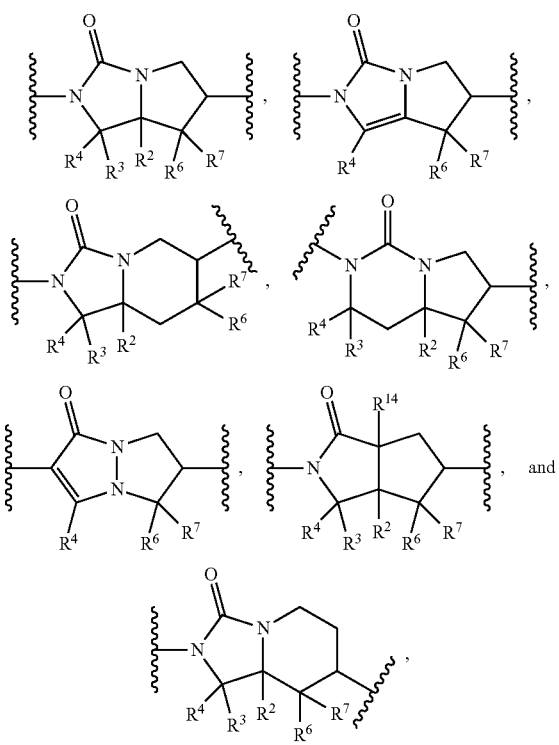

wherein each symbol is as defined in the above-mentioned [1].

[10] The compound according to the above-mentioned [1], wherein the compound is represented by the formula (Ia):

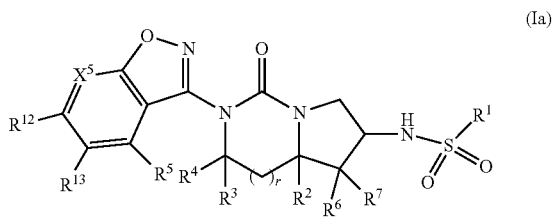

wherein $R^1$ is a $C_{1-6}$ alkyl group, a $C_{3-10}$ cycloalkyl group, or a mono-$C_{1-6}$ alkylamino group;

r is 0 or 1;

$R^2$ and $R^3$ are each independently a hydrogen atom, or when r is 0, then $R^2$ and $R^3$ may be taken together each other to form a bond;

$R^4$ is a hydrogen atom;

$R^5$ is a phenyl group optionally substituted by 1 to 3 halogen atoms;

$R^6$ and $R^7$ are each independently a hydrogen atom, or a halogen atom;

$X^5$ is CH or N; and $R^{12}$ and $R^{13}$ are each independently a hydrogen atom, a $C_{1-6}$ alkyl group, or a halogen atom;

or a salt thereof.

[11] The compound according to the above-mentioned [10], wherein $R^1$ is a $C_{1-6}$ alkyl group;

r is 0 or 1;

$R^2$ and $R^3$ are each a hydrogen atom, or when r is 0, then $R^2$ and $R^3$ may be taken together each other to form a bond;

$R^4$ is a hydrogen atom;

$R^5$ is a phenyl group substituted by 1 to 3 halogen atoms;

$R^6$ and $R^7$ are each a halogen atom;

$X^5$ is CH; and $R^{12}$ and $R^{13}$ are each independently a hydrogen atom, or a halogen atom;

or a salt thereof.

[12] The compound according to the above-mentioned [1], wherein the compound is represented by the formula (Ib):

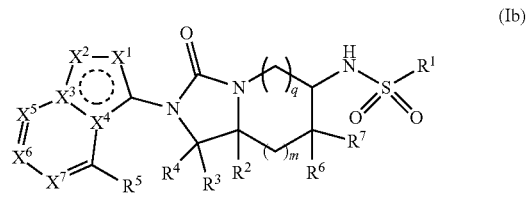

wherein $R^1$ is an optionally substituted $C_{1-6}$ alkyl group, an optionally substituted $C_{3-10}$ cycloalkyl group, or an optionally substituted mono- or di-$C_{1-6}$ alkylamino group;

$R^2$ and $R^3$ are each independently a hydrogen atom, or an optionally substituted $C_{1-6}$ alkyl group, or $R^2$ and $R^3$ are taken together each other to form a bond;

$R^4$ is a hydrogen atom, an optionally substituted $C_{1-6}$ alkyl group, an optionally substituted $C_{1-6}$ alkoxy group, or a hydroxy group;

$R^5$ is an optionally substituted 5- or 6-membered monocyclic group;

$R^6$ and $R^7$ are each independently a hydrogen atom, a halogen atom, or an optionally substituted $C_{1-6}$ alkyl group;

m is 0 or 1;

q is 1 or 2;

$X^1$ is $NR^8$, or $CR^9$;

$X^2$ is O, $NR^{10}$, or S;

$X^3$ and $X^4$ are both C, or one of $X^3$ and $X^4$ is N and the other is C;

$X^5$ is CR or N;

$X^6$ is $CR^{12}$;

$X^7$ is $CR^{13}$ or N;

$R^9$, $R^{11}$, $R^{12}$, and $R^{13}$ are each independently a hydrogen atom, an optionally substituted $C_{1-6}$ alkyl group, a halogen atom, an optionally substituted $C_{3-6}$ cycloalkyl group, an optionally substituted 3- to 7-membered nitrogen-containing heterocyclic group, an optionally substituted $C_{1-6}$ alkoxy group, or a hydroxy group; and $R^8$ and $R^{10}$ are each independently absent, or selected from a hydrogen atom and an optionally substituted $C_{1-6}$ alkyl group;

or a salt thereof.

[12a] The compound according to the above-mentioned [12], wherein $R^2$ and $R^3$ are each a hydrogen atom; or a salt thereof.

[12b] The compound according to the above-mentioned [12], wherein $R^2$ and $R^3$ are taken together each other to form a bond;

or a salt thereof.

[12c] The compound according to the above-mentioned [12], wherein m is 0; and q is 1; or a salt thereof.

[12d] The compound (I) according to the above-mentioned [12], wherein m is 1; and q is 1; or a salt thereof.

[12e] The compound according to the above-mentioned [12], wherein $R^1$ is a $C_{1-6}$ alkyl group; or a salt thereof.

[12f] The compound according to the above-mentioned [12], wherein $X^1$ is $NR^8$ and $R^8$ is absent;

$X^2$ is O;

$X^3$ and $X^4$ are both C;

$X^5$ is CH or N;

$X^6$ is $CR^{12}$, and $R^{12}$ is a hydrogen atom, a $C_{1-6}$ alkyl, or a halogen atom; and $X^7$ is $CR^{13}$, and $R^{13}$ is a hydrogen atom, or a halogen atom;

or a salt thereof.

[13] The compound according to the above-mentioned [12], wherein (1) a $C_{1-6}$ alkyl group optionally substituted with 1 to 3 substituents independently selected from
 (i) a halogen atom,
 (ii) a $C_{1-6}$ alkoxy group, and
 (iii) a $C_{3-6}$ cycloalkyl group,
(2) a $C_{3-10}$ cycloalkyl group, or
(3) a mono- or di-$C_{1-6}$ alkylamino group;

$R^2$ and $R^3$ are each independently a hydrogen atom, or a $C_{1-6}$ alkyl group, or $R^2$ and $R^3$ are taken together each other to form a bond;

$R^4$ is a hydrogen atom, a $C_{1-6}$ alkyl group, a $C_{1-6}$ alkoxy group, or a hydroxy group;

$R^5$ is phenyl, pyrazolyl, furyl, thienyl or thiazolyl, any of which is optionally substituted by one or more substituents independently selected from a $C_{1-6}$ alkyl group, a halogen atom, a halo ($C_{1-6}$) alkyl group, and a $C_{1-6}$ alkoxy group;

m is 0 or 1;

q is 1 or 2;

$R^6$ and $R^7$ are each independently a hydrogen atom, a halogen atom, or a $C_{1-6}$ alkyl group;

$X^1$, $X^2$, $X^3$, $X^4$, $X^5$, $X^6$, and $X^7$ are selected to form a ring system that is one of:
(i) $X^1$ is $NR^8$ and $R^8$ is absent, $X^2$ is O; $X^3$ and $X^4$ are both C, $X^5$ is $CR^{11}$, $X^6$ is $CR^{12}$, and $X^7$ is $CR^{13}$;
(ii) $X^1$ is $NR^8$ and $R^8$ is absent, $X^2$ is O, $X^3$ and $X^4$ are both C, $X^5$ is N, $X^6$ is $CR^{12}$, and $X^7$ is $CR^{13}$;
(iii) $X^1$ is $NR^8$ and $R^8$ is absent, $X^2$ is O, $X^3$ and $X^4$ are both C, $X^5$ is $CR^{11}$, $X^6$ is $CR^{12}$, and $X^7$ is N;
(iv) $X^1$ is $NR^8$ and $R^8$ is absent, $X^2$ is S, $X^3$ and $X^4$ are both C, $X^5$ is N, $X^6$ is $CR^{12}$, and $X^7$ is $CR^{13}$;
(v) $X^1$ is $NR^8$ and $R^8$ is absent, $X^2$ is S; $X^3$ and $X^4$ are both C, $X^5$ is $CR^{11}$, $X^6$ is $CR^{12}$, and $X^7$ is $CR^{13}$;
(vi) $X^1$ is $NR^8$ and $X^2$ is $NR^{10}$, and one of $R^8$ and $R^{10}$ is absent and the other of $R^8$ and $R^{10}$ is a $C_{1-6}$ alkyl group, $X^3$ and $X^4$ are both C, $X^5$ is $CR^{11}$, $X^6$ is $CR^{12}$, and $X^7$ is $CR^{13}$;
(vii) $X^1$ is $CR^9$, $X^2$ is $NR^{10}$ and $R^{10}$ is absent, $X^3$ is N, $X^4$ is C, $X^5$ is $CR^{11}$, $X^6$ is $CR^{12}$, and $X^7$ is $CR^{13}$; and
(viii) $X^1$ is $CR^9$, $X^2$ is $NR^{10}$ and $R^{10}$ is absent, $X^3$ is C, $X^4$ is N, $X^5$ is $CR^{11}$, $X^6$ is $CR^{12}$, and $X^7$ is $CR^{13}$; and $R^9$, $R^{11}$, $R^{12}$, and $R^{13}$ are each independently selected from a hydrogen atom, a $C_{1-6}$ alkyl group, a halogen atom, a $C_{3-6}$ cycloalkyl group, a $C_{3-6}$ cycloalkyl ($C_{1-6}$) alkoxy group, a halo ($C_{1-6}$) alkyl group, a halo ($C_{1-6}$) alkoxy group, a $C_{1-6}$ alkoxy ($C_{1-6}$) alkyl group, an azetidinyl group, a $C_{1-6}$alkoxy group, a hydroxy group, and a hydroxy ($C_{1-6}$) alkyl group;

or a salt thereof.

[14] The compound according to the above-mentioned [1], wherein the compound is represented by the formula (Ic):

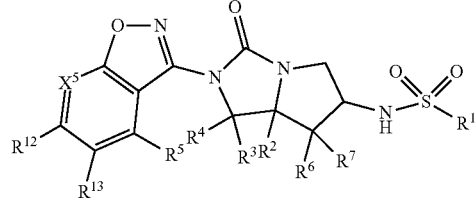

wherein $R^1$ is a $C_{1-6}$ alkyl group, or a mono-$C_{1-6}$ alkylamino group;

$R^2$ and $R^3$ are each a hydrogen atom, or $R^2$ and $R^3$ are taken together each other to form a bond;

$R^4$ is a hydrogen atom;

$R^5$ is a phenyl group optionally substituted by 1 to 3 halogen atoms;

$R^6$ and $R^7$ are each independently a hydrogen atom, or a halogen atom;

$X^5$ is CH or N; and $R^{12}$ and $R^{13}$ are each independently a hydrogen atom, a $C_{1-6}$ alkyl group, or a halogen atom;

or a salt thereof.

[15] The compound according to the above-mentioned [14], wherein $R^1$ is a $C_{1-6}$ alkyl group;

$R^2$ and $R^3$ are each a hydrogen atom, or $R^2$ and $R^3$ are taken together each other to form a bond;

$R^4$ is a hydrogen atom;

$R^5$ is a phenyl group substituted by 1 to 3 halogen atoms;

$R^6$ and $R^7$ are each a halogen atom;

X⁵ is CH; and
R¹² and R¹³ are each independently a hydrogen atom, or a halogen atom;
or a salt thereof.

[16] The compound according to the above-mentioned [1], wherein the compound is selected from the group consisting of:
N-{(6S,7aS)-2-[4-(2,6-difluorophenyl)-1,2-benzoxazol-3-yl]-3-oxohexahydro-1H-pyrrolo[1,2-c]imidazol-6-yl}ethanesulfonamide;
N-{(6R)-7,7-difluoro-3-oxo-2-[4-(2,4,6-trifluorophenyl)-1,2-benzoxazol-3-yl]-2,5,6,7-tetrahydro-3H-pyrrolo[1,2-c]imidazol-6-yl}methanesulfonamide;
N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}ethanesulfonamide;
N-{(6S,7aS)-2-[6-chloro-4-(2,6-difluorophenyl)-1,2-benzoxazol-3-yl]-3-oxohexahydro-1H-pyrrolo[1,2-c]imidazol-6-yl}ethanesulfonamide;
N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}methanesulfonamide;
N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide;
N-{(6R,7aR)-7,7-difluoro-2-[6-fluoro-4-(2,4,6-trifluorophenyl)-1,2-benzoxazol-3-yl]-3-oxohexahydro-1H-pyrrolo[1,2-c]imidazol-6-yl}methanesulfonamide;
N-{(4aR,6R)-5,5-difluoro-1-oxo-2-[4-(2,4,6-trifluorophenyl)-1,2-benzoxazol-3-yl]octahydropyrrolo[1,2-c]pyrimidin-6-yl}methanesulfonamide;
N-{(4aR,6R)-2-[5,6-difluoro-4-(2,4,6-trifluorophenyl)-1,2-benzoxazol-3-yl]-5,5-difluoro-1-oxooctahydropyrrolo[1,2-c]pyrimidin-6-yl}methanesulfonamide;
N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}methanesulfonamide; and
N-{(6R)-2-[4-(2,6-difluorophenyl)-6-fluoro-1,2-benzoxazol-3-yl]-7,7-difluoro-3-oxo-2,5,6,7-tetrahydro-3H-pyrrolo[1,2-c]imidazol-6-yl}ethanesulfonamide;
or a salt thereof.

[17] A medicament comprising the compound as defined in any one of the above-mentioned [1] to [16] or a salt thereof.

[18] The medicament according to the above-mentioned [17], which is an orexin type 2 receptor agonist.

[19] The medicament according to the above-mentioned [17], which is an agent for the prophylaxis or treatment of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, or side effects and complications due to anesthesia.

[20] The medicament according to the above-mentioned [17], which is an agent for the prophylaxis or treatment of narcolepsy, idiopathic hypersomnia, hypersomnia, or sleep apnea syndrome.

[21] The medicament according to the above-mentioned [17], which is an agent for the prophylaxis or treatment of narcolepsy.

[22] A method for the prophylaxis or treatment of a disease or disorder associated with an orexin type 2 receptor in a mammal in need thereof, comprising administering to the mammal a therapeutically effective amount of the compound as defined in any one of the above-mentioned [1] to [16] or a salt thereof.

[23] The method according to the above-mentioned [22], wherein the disease or disorder is selected from narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, and side effects and complications due to anesthesia.

[24] The method according to the above-mentioned [22], wherein the disease or disorder is selected from narcolepsy, idiopathic hypersomnia, hypersomnia, and sleep apnea syndrome.

[25] The method according to the above-mentioned [22], wherein the disease or disorder is narcolepsy.

[26] The compound as defined in any one of the above-mentioned [1] to [16] or a salt thereof, for use in therapy.

[27] The compound or salt according to the above-mentioned [26], wherein the therapy comprises treatment of a disease or disorder associated with an orexin type 2 receptor.

[28] The compound or salt according to the above-mentioned [27], wherein the disease or disorder is selected from the group consisting of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, and side effects and complications due to anesthesia.

[29] The compound or salt according to the above-mentioned [27], wherein the disease or disorder is selected from the group consisting of narcolepsy, idiopathic hypersomnia, hypersomnia, and sleep apnea syndrome.

[30] The compound or salt according to the above-mentioned [27], wherein the disease or disorder is narcolepsy.

[31] Use of the compound as defined in any one of the above-mentioned [1] to [16] or a salt thereof, in the manufacture of a medicament for the treatment of a disease or disorder associated with an orexin type 2 receptor.

[32] Use according to the above-mentioned [31], wherein the disease or disorder is selected from the group consisting of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, and side effects and complications due to anesthesia.

[33] Use according to the above-mentioned [31], wherein the disease or disorder is selected from the group consisting of narcolepsy, idiopathic hypersomnia, hypersomnia, and sleep apnea syndrome.

[34] Use according to the above-mentioned [31], wherein the disease or disorder is narcolepsy.

Effect of the Invention

The compound of the present invention has an orexin type 2 receptor agonist activity, and is useful as an agent for the prophylaxis or treatment of certain diseases, such as narcolepsy.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, more preferably 1 to 3, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "halo $C_{1-6}$ alkyl group" include "halogenated $C_{1-6}$alkyl group" among the above "optionally halogenated $C_{1-6}$alkyl group".

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 2-methyl-1-propenyl, 1-butynyl, 2-butynyl, 3-butynyl, 3-methyl-2-butenyl, 1-pentynyl, 2-pentynyl, 3-pentynyl, 4-pentynyl, 4-methyl-3-pentenyl, 1-hexynyl, 3-hexynyl, and 5-hexynyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, more preferably 1 to 3, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "halo $C_{1-6}$ alkoxy group" include "halogenated $C_{1-6}$ alkoxy group" among the above "optionally halogenated $C_{1-6}$ alkoxy group".

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "optionally substituted mono- or di-$C_{1-6}$ alkylamino group" include an amino group with one or two $C_{1-6}$ alkyl groups. The $C_{1-6}$ alkyl portion of the amino group can optionally have 1 or 2 substituents selected from a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A.

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A."

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, the "hydroxy group" refers to —OH. In the present specification, the "hydroxyl" and "hydroxy" are the same.

In the present specification, examples of the "4-, 5- or 6-membered monocyclic group" include a 4-, 5- or 6-membered monocyclic group, from among a $C_{3-10}$ cycloalkyl group, a $C_{3-10}$ cycloalkenyl group, a $C_{6-14}$ aryl group, and a heterocyclic group (e.g., an aromatic heterocyclic group or a non-aromatic heterocyclic group), as described herein.

In the present specification, examples of the "$C_{6-14}$ aryl group" include phenyl, 1-naphthyl, 2-naphthyl, 1-anthryl, 2-anthryl, and 9-anthryl.

In the present specification, examples of the "heterocycle" include an aromatic heterocycle and a non-aromatic heterocycle, each containing, as a ring-constituting atom besides carbon atom, 1 to 4 (e.g., 1, 2, 3, or 4) heteroatoms selected from a nitrogen atom, a sulfur atom, an oxygen atom, and combinations thereof.

In the present specification, examples of the "aromatic heterocycle" include a 5- to 14-membered (preferably 5- to 10-membered, more preferably 5- to 6-membered) aromatic heterocycle containing, as a ring-constituting atom besides carbon atom, 1 to 4 heteroatoms selected from a nitrogen atom, a sulfur atom, an oxygen atom, and combinations thereof. Examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi- or tri-cyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered, more preferably 5- to 6-membered) non-aromatic heterocycle containing, as a ring-constituting atom besides carbon atom, 1 to 4 heteroatoms selected from a nitrogen atom, a sulfur atom, an oxygen atom, and combinations thereof. Examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi- or tri-cyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "3- to 7-membered nitrogen-containing heterocyclic" include a 3- to 7-membered "heterocyclic group," as described herein, containing at least one (e.g., 1, 2, 3, etc.) nitrogen atom as a ring-constituting atom.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group."

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A."

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A."

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A."

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A."

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A."

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi- or tri-cyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi- or tri-cyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "nitrogen-containing heterocycle" include a heterocycle containing at least one nitrogen atom as a ring-constituting atom, from among the "heterocycle."

In the present specification, examples of the "4- to 6-membered heterocyclic group" include an aromatic or non-aromatic 4- to 6-membered heterocyclic group. Specific examples thereof include oxetanyl, furyl, pyrazolyl, pyridyl and pyrimidinyl.

In the present specification, examples of the "ring" include "hydrocarbon ring" and "heterocycle."

In the present specification, certain moieties can be "optionally substituted," which means that the group optionally has substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., tetrahydropyranyloxy, morpholinyloxy, piperidinyloxy),
(11) a $C_{1-6}$alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$alkoxy-carbonyloxy group (e.g., methoxycarbonyloxy, ethoxycarbonyloxy, propoxycarbonyloxy, butoxycarbonyloxy),
(14) a mono- or di-$C_{1-6}$alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,

(29) a $C_{1-6}$alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$alkylsulfonylamino group (e.g., methylsulfonylamino, ethylsulfonylamino),
(56) a $C_{6-14}$ arylsulfonylamino group optionally substituted by a $C_{1-6}$alkyl group (e.g., phenylsulfonylamino, toluenesulfonylamino),
(57) an optionally halogenated $C_{1-6}$alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

In some aspects, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

The number of the above-mentioned substituents is, for example, 1 to 5 (e.g., 1, 2, 3, 4, or 5), preferably 1 to 3 (e.g., 1, 2, or 3). When the number of the substituents is two or more, the respective substituents can be the same or different.

The definition of each symbol in compound (I) is explained in detail.

$R^1$ is an optionally substituted $C_{1-6}$alkyl group, an optionally substituted $C_{3-10}$ cycloalkyl group, or an optionally substituted mono- or di-$C_{1-6}$alkylamino group.

In some aspects, $R^1$ is
(1) a $C_{1-6}$alkyl group (e.g., methyl, ethyl) optionally substituted with 1 to 3 substituents independently selected from
  (i) a halogen atom (e.g., a fluorine atom),
  (ii) a $C_{1-6}$alkoxy group (e.g., methoxy), and
  (iii) a $C_{3-6}$ cycloalkyl group (e.g., cyclopropyl),
(2) a $C_{3-10}$ cycloalkyl group (e.g., cyclopropyl), or
(3) a mono- or di-$C_{1-6}$alkylamino group (e.g., methylamino, dimethylamino).

In some aspects, $R^1$ is a $C_{1-6}$alkyl group (e.g., methyl, ethyl), a $C_{3-10}$ cycloalkyl group (preferably a $C_{3-6}$ cycloalkyl group, e.g., cyclopropyl), or a mono-$C_{1-6}$ alkylamino group (e.g., methylamino).

In some aspects, $R_1$ is a $C_{1-6}$ alkyl group (e.g., methyl, ethyl), or a mono-$C_{1-6}$ alkylamino group (e.g., methylamino).

In some aspects, $R_1$ is a $C_{1-6}$ alkyl group (e.g., methyl, ethyl).

$R^2$ and $R^3$ are each independently a hydrogen atom, or an optionally substituted $C_{1-6}$ alkyl group. Alternatively, when r is 0, then $R^2$ and $R^3$ may be taken together each other to form a bond. Alternatively, when $X^{10}$ is $R^{15}$, then $R^3$ may be taken together with $R^{15}$ to form a bond.

In some aspects, $R^2$ and $R^3$ are each independently a hydrogen atom, or a $C_{1-6}$ alkyl group (e.g., methyl), or
  when r is 0, then $R^2$ and $R^3$ may be taken together each other to form a bond, or
  when $X^{10}$ is $R^{15}$, then $R^3$ is taken together with $R^{15}$ to form a bond.

In some aspects, $R^2$ and $R^3$ are each a hydrogen atom, or
  when r is 0, then $R^2$ and $R^3$ may be taken together each other to form a bond, or
  when $X^{10}$ is $R^{15}$, then $R^3$ is taken together with $R^{15}$ to form a bond.

In some aspects, in case that $X^{10}$ is N, $R^2$ and $R^3$ are each independently a hydrogen atom, or
  when r is 0, then $R^2$ and $R^3$ may be taken together each other to form a bond.

In some aspects, in case that $X^{10}$ is N, $R^2$ and $R^3$ are each a hydrogen atom, or
  when r is 0, then $R^2$ and $R^3$ may be taken together each other to form a bond.

In case that $R^2$ and $R^3$ are taken together each other to form a bond, the ring containing $X^8$, $X^9$ and $X^{10}$ includes a double bond between the carbons attached to $R^2$ and $R^3$.

$R^4$ is a hydrogen atom, an optionally substituted $C_{1-6}$ alkyl group, an optionally substituted $C_{1-6}$ alkoxy group, or a hydroxy group.

In some aspects, $R^4$ is a hydrogen atom, a $C_{1-6}$ alkyl group (e.g., methyl), a $C_{1-6}$ alkoxy group (e.g., ethoxy), or a hydroxy group.

In some aspects, $R^4$ is a hydrogen atom.

$R^5$ is an optionally substituted 4-, 5- or 6-membered monocyclic group.

In some aspects, $R^5$ is phenyl, pyrazolyl, furyl, thienyl, thiazolyl, pyridyl, piperidyl, or cyclobutyl, any of which is optionally substituted by one or more (e.g., 1, 2, 3, etc.) substituents independently selected from a $C_{1-6}$ alkyl group (e.g., methyl), a halogen atom (e.g., a fluorine atom, a chlorine atom), a halo ($C_{1-6}$) alkyl group (e.g., trifluoromethyl), and a $C_{1-6}$ alkoxy group (e.g., methoxy).

In some aspects, $R^5$ is a phenyl group optionally substituted by 1 to 3 (e.g., 1, 2, 3, etc.) halogen atoms (e.g., a fluorine atom).

In some aspects, $R^5$ is a phenyl group substituted by 1 to 3 (e.g., 1, 2, 3, etc.) halogen atoms (e.g., a fluorine atom).

In some aspects, $R^5$ is a phenyl group substituted by 2 or 3 fluorine atoms (e.g., 2,6-substituted or 2,4,6-substituted).

In some aspects, $R^5$ is a phenyl group substituted by 3 fluorine atoms (e.g., 2,4,6-substituted).

$R^6$ and $R^7$ are each independently a hydrogen atom, a halogen atom, or an optionally substituted $C_{1-6}$alkyl group.

In some aspects, $R^6$ and $R^7$ are each independently a hydrogen atom, a halogen atom (e.g., a fluorine atom), or a $C_{1-6}$ alkyl group (e.g., methyl).

In some aspects, $R^6$ and $R^7$ are each independently a hydrogen atom, or a halogen atom (e.g., a fluorine atom).

In some aspects, $R^6$ and $R^7$ are each a hydrogen atom, or each a halogen atom (e.g., a fluorine atom).

In some aspects, $R^6$ and $R^7$ are each a halogen atom (e.g., a fluorine atom).

The subscript "m" is either 0 (forming a 5- or 6-membered ring) or 1 (forming a 6- or 7-membered ring) with "q".

The subscript "q" is either 1 (forming a forming a 5- or 6-membered ring) or 2 (forming a 6- or 7-membered ring) with "m".

In some aspects, m is 0; and q is 1 to form a 5-membered ring.

In some aspects, m is 1; and q is 1 to form a 6-membered ring.

The subscript "r" is either 0 (forming a 5-membered ring) or 1 (forming a 6-membered ring).

In some aspects, the combination of m, q and r is m is 0; q is 1; and r is 0.

In some aspects, the combination of m, q and r is m is 1; q is 1; and r is 0.

In some aspects, the combination of m, q and r is m is 0; q is 1; and r is 1.

In some aspects, the combination of m, q and r is m is 0; q is 2; and r is 0.

$X^1$ is $NR^8$ or $CR^9$, wherein $R^8$ is absent (i.e., =N—), or selected from a hydrogen atom, and an optionally substituted $C_{1-6}$ alkyl group, and $R^9$ is a hydrogen atom, an optionally substituted $C_{1-6}$ alkyl group, a halogen atom, an optionally substituted $C_3$s cycloalkyl group, an optionally substituted 3- to 7-membered nitrogen-containing heterocyclic group, an optionally substituted $C_{1-6}$ alkoxy group, or a hydroxy group.

In some aspects, $X^1$ is $NR^8$ wherein $R^8$ is absent (i.e., =N—), or a $C_{1-6}$ alkyl group (e.g., methyl).

In some aspects, $X^1$ is $NR^8$ wherein $R^8$ is absent (i.e., =N—).

In some aspects, $X^1$ is $CR^9$ wherein $R^9$ is a hydrogen atom, or a $C_{1-6}$ alkyl group (e.g., methyl).

$X^2$ is O, $NR^{10}$, or S, wherein $R^{10}$ is absent (i.e., =N—), or selected from a hydrogen atom, and an optionally substituted $C_{1-6}$ alkyl group.

In some aspects, $X^2$ is O.

In some aspects, $X^2$ is $NR^{10}$ wherein $R^{10}$ is absent, or a $C_{1-6}$ alkyl group (e.g., methyl).

In some aspects, $X^2$ is S.

$X^3$ and $X^4$ are either (i) both C, or (ii) one of $X^3$ and $X^4$ is N and the other is C.

In some aspects, $X^3$ and $X^4$ are both C.

In some aspects, $X^3$ is N, and $X^4$ is C.

In some aspects, $X^3$ is C, and $X^4$ is N.

$X^5$ is $CR^{11}$ or N, wherein $R^{11}$ is a hydrogen atom, an optionally substituted $C_{1-6}$ alkyl group, a halogen atom, an optionally substituted $C_{3-6}$ cycloalkyl group, an optionally substituted 3- to 7-membered nitrogen-containing heterocyclic group, an optionally substituted $C_{1-6}$ alkoxy group, or a hydroxy group.

In some aspects, $X^5$ is N.

In some aspects, $X^5$ is $CR^{11}$ wherein $R^{11}$ is a hydrogen atom, a halogen atom (e.g., a fluorine atom), or a $C_{1-6}$ alkyl group (e.g., methyl).

In some aspects, $X^5$ is $CR^{11}$ or N, wherein $R^{11}$ is a hydrogen atom.

$X^6$ is $CR^{12}$, wherein $R^{12}$ is a hydrogen atom, an optionally substituted $C_{1-6}$ alkyl group, a halogen atom, an optionally substituted $C_{3-6}$ cycloalkyl group, an optionally substituted 3- to 7-membered nitrogen-containing heterocyclic group, an optionally substituted $C_{1-6}$ alkoxy group, or a hydroxy group.

In some aspects, $R^{12}$ is a hydrogen atom, a $C_{1-6}$ alkyl group (e.g., methyl, ethyl), a halogen atom (e.g., a fluorine atom, a chlorine atom, a bromine atom), a $C_{3-6}$ cycloalkyl group (e.g., cyclopropyl), a $C_{3-6}$ cycloalkyl ($C_{1-6}$) alkoxy group (e.g., cyclopropylmethoxy), a halo ($C_{1-6}$) alkyl group (e.g., difluoromethyl, trifluoromethyl), a halo ($C_{1-6}$) alkoxy group (e.g., difluoromethoxy, trifluoromethoxy), a $C_{1-6}$ alkoxy ($C_{1-6}$) alkyl group (e.g., methoxymethyl), an azetidinyl group, a $C_{1-6}$ alkoxy group (e.g., methoxy, ethoxy), a hydroxy group, or a hydroxy ($C_{1-6}$) alkyl group (e.g., hydroxymethyl, 2-hydroxyethyl);

In some aspects, $R^{12}$ is a hydrogen atom, a $C_{1-6}$ alkyl group (e.g., methyl), or a halogen atom (e.g., a chlorine atom or a fluorine atom).

In some aspects, $R^{12}$ is a hydrogen atom, or a halogen atom (e.g., a fluorine atom).

$X^7$ is $CR^{13}$ or N, wherein $R^{13}$ is a hydrogen atom, an optionally substituted $C_{1-6}$ alkyl group, a halogen atom, an optionally substituted $C_{3-6}$ cycloalkyl group, an optionally substituted 3- to 7-membered nitrogen-containing heterocyclic group, an optionally substituted $C_{1-6}$ alkoxy group, or a hydroxy group.

In some aspects, $X^7$ is N.

In some aspects, $X^7$ is $CR^{13}$ wherein $R^{13}$ is a hydrogen atom, or a halogen atom (e.g., a fluorine atom, a chlorine atom).

In some aspects, $X^1$, $X^2$, $X^3$, $X^4$, $X^5$, $X^6$, and $X^7$ are selected so as to form a ring system that is pyrazolopyridine, 1,2-benzoxazole, indazole, imidazolopyridine, 1,2-benzothiazole, [1,2]oxazolo[4,5-c]pyridine, isooxazolo[5,4-b]pyridine, or isothiazolo[5,4-b]pyridine.

In these aspects, $R^9$, $R^{11}$, $R^{12}$, and $R^{13}$ are each independently selected from a hydrogen atom, a $C_{1-6}$ alkyl group (e.g., methyl, ethyl), a halogen atom (e.g., a fluorine atom, a chlorine atom, a bromine atom), a $C_{3-6}$ cycloalkyl group (e.g., cyclopropyl), a $C_{3-6}$ cycloalkyl ($C_{1-6}$) alkoxy group (e.g., cyclopropylmethoxy), a halo ($C_{1-6}$) alkyl group (e.g., difluoromethyl, trifluoromethyl), a halo ($C_{1-6}$) alkoxy group (e.g., difluoromethoxy, trifluoromethoxy), a $C_{1-6}$ alkoxy ($C_{1-6}$) alkyl group (e.g., methoxymethyl), an azetidinyl group, a $C_{1-6}$ alkoxy group (e.g., methoxy, ethoxy), a hydroxy group, and a hydroxy ($C_{1-6}$) alkyl group (e.g., hydroxymethyl, 2-hydroxyethyl); and $R^8$ and $R^{10}$ are each independently absent (i.e., =N—), or selected from a hydrogen atom and a $C_{1-6}$ alkyl group (e.g., methyl).

In some aspects,
$X^1$ is $NR^8$ wherein $R^8$ is absent (i.e., =N—);
$X^2$ is O;
$X^3$ and $X^4$ are both C;
$X^5$ is $CR^{11}$ or N, wherein $R^{11}$ is a hydrogen atom;
$X^6$ is $CR^{12}$ wherein $R^{12}$ is a hydrogen atom, a $C_{1-6}$ alkyl group (e.g., methyl), or a halogen atom (e.g., a chlorine atom or a fluorine atom); and
$X^7$ is $CR^{13}$ wherein $R^{13}$ is a hydrogen atom, or a halogen atom (e.g., a fluorine atom).

In some aspects, $X^1$, $X^2$, $X^3$, $X^4$, $X^5$, $X^6$, and $X^7$ are selected to form a ring system that is one of:
(i) $X^1$ is $NR^8$ and $R^8$ is absent, $X^2$ is O; $X^3$ and $X^4$ are both C, $X^5$ is $CR^{11}$, $X^6$ is $CR^{12}$, and $X^7$ is $CR^{13}$;
(ii) $X^1$ is $NR^8$ and $R^8$ is absent, $X^2$ is O, $X^3$ and $X^4$ are both C, $X^5$ is N, $X^6$ is $CR^{12}$, and $X^7$ is $CR^{13}$;
(iii) $X^1$ is $NR^8$ and $R^8$ is absent, $X^2$ is O, $X^3$ and $X^4$ are both C, $X^5$ is $CR^{11}$, $X^6$ is $CR^{12}$, and $X^7$ is N;
(iv) $X^1$ is $NR^8$ and $R^8$ is absent, $X^2$ is S, $X^3$ and $X^4$ are both C, $X^5$ is N, $X^6$ is $CR^{12}$, and $X^7$ is $CR^{13}$;
(v) $X^1$ is $NR^8$ and $R^8$ is absent, $X^2$ is S; $X^3$ and $X^4$ are both C, $X^5$ is $CR^{11}$, $X^6$ is $CR^{12}$, and $X^7$ is $CR^{13}$;
(vi) $X^1$ is $NR^8$ and $X^2$ is $NR^{10}$, and one of $R^8$ and $R^{10}$ is absent and the other of $R^8$ and $R^{10}$ is a $C_{1-6}$ alkyl group (e.g., methyl), $X^3$ and $X^4$ are both C, $X^5$ is $CR^{11}$, $X^6$ is $CR^{12}$, and $X^7$ is $CR^{13}$;
(vii) $X^1$ is $CR^9$, $X^2$ is $NR^{10}$ and $R^{10}$ is absent, $X^3$ is N, $X^4$ is C, $X^5$ is $CR^{11}$, $X^6$ is $CR^{12}$, and $X^7$ is $CR^{13}$; and
(viii) $X^1$ is $CR^9$, $X^2$ is $NR^{10}$ and $R^{10}$ is absent, $X^3$ is C, $X^4$ is N, $X^5$ is $CR^{11}$, $X^6$ is $CR^{12}$, and $X^7$ is $CR^{13}$.

In some aspects, $X^1$, $X^2$, $X^3$, $X^4$, $X^5$, $X^6$, and $X^7$ are selected to form a ring system that is one of:
(i) $X^1$ is $NR^8$ and $R^8$ is absent, $X^2$ is O; $X^3$ and $X^4$ are both C, $X^5$ is $CR^{11}$, $X^6$ is $CR^{12}$, and $X^7$ is $CR^{13}$; and
(ii) $X^1$ is $NR^8$ and $R^8$ is absent, $X^2$ is O, $X^3$ and $X^4$ are both C, $X^5$ is N, $X^6$ is $CR^{12}$, and $X^7$ is $CR^{13}$.

In some aspects, $X^1$, $X^2$, $X^3$, $X^4$, $X^5$, $X^6$, and $X^7$ are selected to form a ring system that (i) $X^1$ is $NR^8$ and $R^8$ is absent, $X^2$ is O; $X^3$ and $X^4$ are both C, $X^5$ is $CR^{11}$, $X^6$ is $CR^{12}$, and $X^7$ is $CR^{13}$.

In some aspects, $X^1$, $X^2$, $X^3$, $X^4$, $X^5$, $X^6$, and $X^7$ are selected to form a ring system that (i) $X^1$ is $NR^8$ and $R^8$ is absent, $X^2$ is O; $X^3$ and $X^4$ are both C, $X^5$ is CH, $X^6$ is $CR^{12}$, and $X^7$ is $CR^{13}$.

In these aspects, $R^9$, $R^{11}$, $R^{12}$, and $R^{13}$ are each independently selected from a hydrogen atom, a $C_{1-6}$ alkyl group (e.g., methyl, ethyl), a halogen atom (e.g., a fluorine atom, a chlorine atom, a bromine atom), a $C_{3-6}$ cycloalkyl group (e.g., cyclopropyl), a $C_{3-6}$ cycloalkyl ($C_{1-6}$) alkoxy group (e.g., cyclopropylmethoxy), a halo ($C_{1-6}$) alkyl group (e.g., difluoromethyl, trifluoromethyl), a halo ($C_{1-6}$) alkoxy group (e.g., difluoromethoxy, trifluoromethoxy), a $C_{1-6}$ alkoxy ($C_{1-6}$) alkyl group (e.g., methoxymethyl), an azetidinyl group, a $C_{1-6}$ alkoxy group (e.g., methoxy, ethoxy), a hydroxy group, and a hydroxy ($C_{1-6}$) alkyl group (e.g., hydroxymethyl, 2-hydroxyethyl)

$X^8$ is $CR^{14}$ or N, wherein $R^{14}$ is a hydrogen atom, a halogen atom, or an optionally substituted $C_{1-6}$ alkyl group.

In some aspects, $X^8$ is N.

In some aspects, $X^8$ is $CR^{14}$ wherein $R^{14}$ is a hydrogen atom.

$X^9$ is $CR^2$ or N, wherein $R^2$ is a hydrogen atom, or an optionally substituted $C_{1-6}$ alkyl group, or when r is 0, then $R^2$ may be taken together with $R^3$ to form a bond.

In some aspects, $X^9$ is $CR^2$ wherein $R^2$ is a hydrogen atom, or a $C_{1-6}$ alkyl group (e.g., methyl), or when r is 0, then $R^2$ may be taken together with $R^3$ to form a bond.

In some aspects, $X^9$ is $CR^2$ wherein $R^2$ is a hydrogen atom, or when r is 0, then $R^2$ may be taken together with $R^3$ to form a bond.

In some aspects, $X^9$ is $CR^2$ wherein $R^2$ is a hydrogen atom.

In some aspects, $X^9$ is $CR^2$, r is 0, and $R^2$ is taken together with $R^3$ to form a bond.

In some aspects, $X^9$ is N.

$X^{10}$ is $CR^{15}$ or N, wherein $R^{15}$ is a hydrogen atom, a halogen atom, or an optionally substituted $C_{1-6}$ alkyl group, or $R^{15}$ may be taken together with $R^3$ to form a bond.

In some aspects, $X^{10}$ is N.

In some aspects, $X^{10}$ is $CR^{15}$ wherein $R^{15}$ is taken together with $R^3$ to form a bond.

In some aspects,
$X^8$ is N;
$X^9$ is $CR^2$ wherein $R^2$ is a hydrogen atom, or when r is 0, then $R^2$ may be taken together with $R^3$ to form a bond; and
$X^{10}$ is N.

In some aspects,
$X^8$ is N;
$X^9$ is $CR^2$ wherein $R^2$ is a hydrogen atom; and
$X^{10}$ is N.

In some aspects,
$X^8$ is N;
$X^9$ is $CR^2$ wherein r is 0 and $R^2$ is taken together with $R^3$ to form a bond; and
$X^{10}$ is N.

In some aspects, $X^8$, $X^9$, $X^{10}$, m, q, and r are selected to form a ring system that is one of:
(i) $X^8$ is N, $X^9$ is $CR^2$, $X^{10}$ is N, m is 0, q is 1, and r is 0;
(ii) $X^8$ is N, $X^9$ is $CR^2$, $X^{10}$ is N, m is 1, q is 1, and r is 0;
(iii) $X^8$ is N, $X^9$ is $CR^2$, $X^{10}$ is N, m is 0, q is 1, and r is 1;
(iv) $X^8$ is N, $X^9$ is N, $X^{10}$ is $CR^{15}$, m is 0, q is 1, and r is 0;
(v) $X^8$ is $CR^{14}$, $X^9$ is $CR^2$, $X^{10}$ is N, m is 0, q is 1, and r is 0; and
(vi) $X^8$ is N, $X^9$ is $CR^2$, $X^{10}$ is N, m is 0, q is 2, and r is 0.

In some aspects, $X^8$, $X^9$, $X^{10}$, m, q, and r are selected to form a ring system that is one of:
(i) $X^8$ is N, $X^9$ is $CR^2$, $X^{10}$ is N, m is 0, q is 1, and r is 0; and
(iii) $X^8$ is N, $X^9$ is $CR^2$, $X^{10}$ is N, m is 0, q is 1, and r is 1.

In these aspects,
$R^2$ is a hydrogen atom, or a $C_{1-6}$ alkyl group (e.g., methyl), or when r is 0, then $R^2$ may be taken together with $R^3$ to form a bond;
$R^{14}$ is a hydrogen atom, a halogen atom, or a $C_{1-6}$ alkyl group; and
$R^{15}$ is taken together with $R^3$ to form a bond;

In some aspects, the partial structure represented by the following formula:

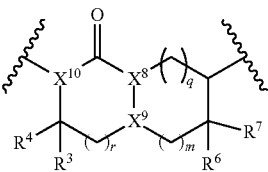

wherein each symbol is as defined above, is one of partial structures represented by the following formulas:

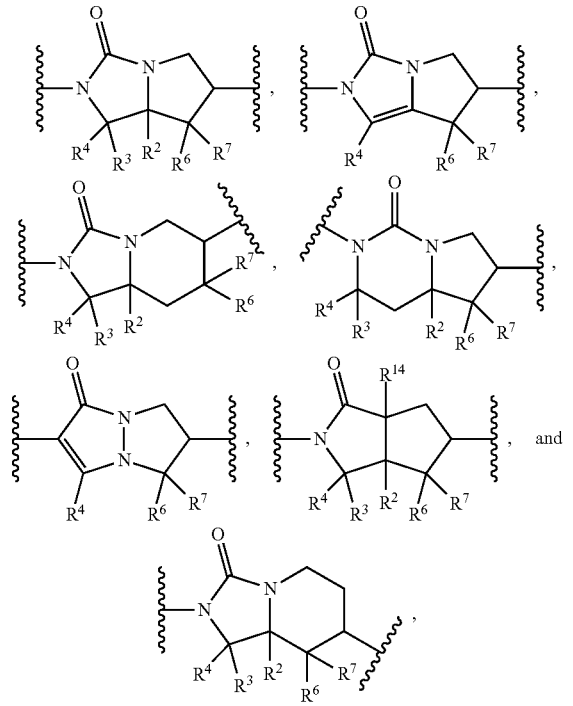

wherein each symbol is as defined above.

In some aspects of compound (I), $R^1$ is
(1) a $C_{1-6}$ alkyl group (e.g., methyl, ethyl) optionally substituted with 1 to 3 substituents independently selected from
  (i) a halogen atom (e.g., a fluorine atom),
  (ii) a $C_{1-6}$ alkoxy group (e.g., methoxy), and
  (iii) a $C_{3-6}$ cycloalkyl group (e.g., cyclopropyl),
(2) a $C_{3-10}$ cycloalkyl group (e.g., cyclopropyl), or
(3) a mono- or di-$C_{1-6}$ alkylamino group (e.g., methylamino, dimethylamino);

$R^2$ and $R^3$ are each independently a hydrogen atom, or a $C_{1-6}$ alkyl group (e.g., methyl), or
when r is 0, then $R^2$ and $R^3$ may be taken together each other to form a bond, or
when $X^{10}$ is $CR^{15}$, then $R^3$ is taken together with $R^{15}$ to form a bond;

$R^4$ is a hydrogen atom, a $C_{1-6}$ alkyl group (e.g., methyl), a $C_{1-6}$ alkoxy group (e.g., ethoxy), or a hydroxy group;

$R^5$ is phenyl, pyrazolyl, furyl, thienyl, thiazolyl, pyridyl, piperidyl, or cyclobutyl, any of which is optionally substituted by one or more (e.g., 1, 2, 3, etc.) substituents independently selected from a $C_{1-6}$ alkyl group (e.g., methyl), a halogen atom (e.g., a fluorine atom, a chlorine atom), a halo ($C_{1-6}$) alkyl group (e.g., trifluoromethyl), and a $C_{1-6}$ alkoxy group (e.g., methoxy);

$R^6$ and $R^7$ are each independently a hydrogen atom, a halogen atom (e.g., a fluorine atom), or a $C_{1-6}$ alkyl group (e.g., methyl);

$X^1, X^2, X^3, X^4, X^5, X^6$, and $X^7$ are selected to form a ring system that is one of:
(i) $X^1$ is $NR^8$ and $R^8$ is absent, $X^2$ is O; $X^3$ and $X^4$ are both C, $X^5$ is $CR^{11}$, $X^6$ is $CR^{12}$, and $X^7$ is $CR^{13}$;
(ii) $X^1$ is $NR^8$ and $R^8$ is absent, $X^2$ is O, $X^3$ and $X^4$ are both C, $X^5$ is N, $X^6$ is $CR^{12}$, and $X^7$ is $CR^{13}$;
(iii) $X^1$ is $NR^8$ and $R^8$ is absent, $X^2$ is O, $X^3$ and $X^4$ are both C, $X^5$ is $CR^{11}$, $X^6$ is $CR^{12}$, and $X^7$ is N;
(iv) $X^1$ is $NR^8$ and $R^8$ is absent, $X^2$ is S, $X^3$ and $X^4$ are both C, $X^5$ is N, $X^6$ is $CR^{12}$, and $X^7$ is $CR^{13}$;
(v) $X^1$ is $NR^8$ and $R^8$ is absent, $X^2$ is S; $X^3$ and $X^4$ are both C, $X^5$ is $CR^{11}$, $X^6$ is $CR^{12}$, and $X^7$ is $CR^{13}$;
(vi) $X^1$ is $NR^8$ and $X^2$ is $NR^{10}$, and one of $R^8$ and $R^{10}$ is absent and the other of $R^8$ and $R^{10}$ is a $C_{1-6}$ alkyl group (e.g., methyl), $X^3$ and $X^4$ are both C, $X^5$ is $CR^{11}$, $X^6$ is $CR^{12}$, and $X^7$ is $CR^{13}$;
(vii) $X^1$ is $CR^9$, $X^2$ is $NR^{10}$ and $R^{10}$ is absent, $X^3$ is N, $X^4$ is C, $X^5$ is $CR^{11}$, $X^6$ is $CR^{12}$, and $X^7$ is $CR^{13}$; and
(viii) $X^1$ is $CR^9$, $X^2$ is $NR^{10}$ and $R^{10}$ is absent, $X^3$ is C, $X^4$ is N, $X^5$ is $CR^{11}$, $X^6$ is $CR^{12}$, and $X^7$ is $CR^{13}$;

$X^8, X^9, X^{10}$, m, q, and r are selected to form a ring system that is one of:
(i) $X^8$ is N, $X^9$ is $CR^2$, $X^{10}$ is N, m is 0, q is 1, and r is 0;
(ii) $X^8$ is N, $X^9$ is $CR^2$, $X^{10}$ is N, m is 1, q is 1, and r is 0;
(iii) $X^8$ is N, $X^9$ is $CR^2$, $X^{10}$ is N, m is 0, q is 1, and r is 1;
(iv) $X^8$ is N, $X^9$ is N, $X^{10}$ is $CR^{15}$, m is 0, q is 1, and r is 0;
(v) $X^8$ is $CR^{14}$, $X^9$ is $CR^2$, $X^{10}$ is N, m is 0, q is 1, and r is 0; and
(vi) $X^8$ is N, $X^9$ is $CR^2$, $X^{10}$ is N, m is 0, q is 2, and r is 0;

$R^9, R^{11}, R^{12}$, and $R^{13}$ are each independently selected from a hydrogen atom, a $C_{1-6}$ alkyl group (e.g., methyl, ethyl), a halogen atom (e.g., a fluorine atom, a chlorine atom, a bromine atom), a $C_{3-6}$ cycloalkyl group (e.g., cyclopropyl), a $C_{3-6}$ cycloalkyl ($C_{1-6}$) alkoxy group (e.g., cyclopropylmethoxy), a halo ($C_{1-6}$) alkyl group (e.g., difluoromethyl, trifluoromethyl), a halo ($C_{1-6}$) alkoxy group (e.g., difluoromethoxy, trifluoromethoxy), a $C_{1-6}$ alkoxy ($C_{1-6}$) alkyl group (e.g., methoxymethyl), an azetidinyl group, a $C_{1-6}$ alkoxy group (e.g., methoxy, ethoxy), a hydroxy group, and a hydroxy ($C_{1-6}$) alkyl group (e.g., hydroxymethyl, 2-hydroxyethyl); and $R^{14}$ is a hydrogen atom; and
$R^{15}$ is taken together with $R^3$ to form a bond.

In some aspects, compound (I) is represented by the formula (I a):

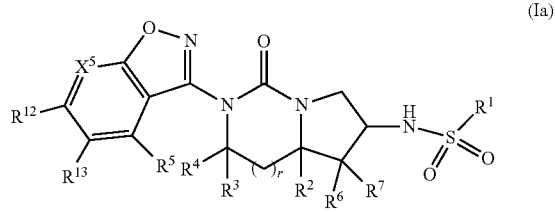

wherein
- $R^1$ is a $C_{1-6}$ alkyl group (e.g., methyl, ethyl), a $C_{3-10}$ cycloalkyl group (preferably a $C_{3-6}$ cycloalkyl group, e.g., cyclopropyl), or a mono-$C_{1-6}$alkylamino group (e.g., methylamino);
- r is 0 or 1;
- $R^2$ and $R^3$ are each independently a hydrogen atom, or when r is 0, then $R^2$ and $R^3$ may be taken together each other to form a bond;
- $R^4$ is a hydrogen atom;
- $R^5$ is a phenyl group optionally substituted by 1 to 3 (e.g., 1, 2, 3, etc.) halogen atoms (e.g., a fluorine atom);
- $R^6$ and $R^7$ are each independently a hydrogen atom, or a halogen atom (e.g., a fluorine atom);
- $X^5$ is CH or N; and
- $R^{12}$ and $R^{13}$ are each independently a hydrogen atom, a $C_{1-6}$alkyl group (e.g., methyl), or a halogen atom (e.g., a fluorine atom, a chlorine atom);

or a salt thereof (sometimes to be referred to as compound (Ia)).

In some aspects of compound (Ia),
- $R^1$ is a $C_{1-6}$ alkyl group (e.g., methyl, ethyl);
- r is 0 or 1;
- $R^2$ and $R^3$ are each a hydrogen atom, or when r is 0, then $R^2$ and $R^3$ may be taken together each other to form a bond;
- $R^4$ is a hydrogen atom;
- $R^5$ is a phenyl group substituted by 1 to 3 (e.g., 1, 2, 3, etc.) halogen atoms (e.g., a fluorine atom);
- $R^6$ and $R^7$ are each a halogen atom (e.g., a fluorine atom);
- $X^5$ is CH; and
- $R^{12}$ and $R^{13}$ are each independently a hydrogen atom, or a halogen atom (e.g., a fluorine atom).

In some aspects, compound (I) is represented by the formula (Ib):

(Ib)

wherein
- $R^1$ is an optionally substituted $C_{1-6}$alkyl group, an optionally substituted $C_{3-10}$ cycloalkyl group, or an optionally substituted mono- or di-$C_{1-6}$alkylamino group;
- $R^2$ and $R^3$ are each independently a hydrogen atom, or an optionally substituted $C_{1-6}$alkyl group, or $R^2$ and $R^3$ are taken together each other to form a bond;
- $R^4$ is a hydrogen atom, an optionally substituted $C_{1-6}$alkyl group, an optionally substituted $C_{1-6}$alkoxy group, or a hydroxy group;
- $R^5$ is an optionally substituted 5- or 6-membered monocyclic group;
- $R^6$ and $R^7$ are each independently a hydrogen atom, a halogen atom, or an optionally substituted $C_{1-6}$ alkyl group;
- m is 0 or 1;
- q is 1 or 2;
- $X^1$ is $NR^8$, or $CR^9$;
- $X^2$ is O, $NR^{10}$, or S;
- $X^3$ and $X^4$ are both C, or one of $X^3$ and $X^4$ is N and the other is C;
- $X^5$ is $CR^{11}$ or N;
- $X^6$ is $CR^{12}$;
- $X^7$ is $CR^{13}$ or N;
- $R^9$, $R^{11}$, $R^{12}$, and $R^{13}$ are each independently a hydrogen atom, an optionally substituted $C_{1-6}$ alkyl group, a halogen atom, an optionally substituted $C_{3-6}$ cycloalkyl group, an optionally substituted 3- to 7-membered nitrogen-containing heterocyclic group, an optionally substituted $C_{1-6}$ alkoxy group, or a hydroxy group; and
- $R^8$ and $R^{10}$ are each independently absent, or selected from a hydrogen atom and an optionally substituted $C_{1-6}$ alkyl group;

or a salt thereof (sometimes to be referred to as compound (Ib)).

In some aspects of compound (Ib),
- $R^1$ is
  - (1) a $C_{1-6}$ alkyl group (e.g., methyl, ethyl) optionally substituted with 1 to 3 substituents independently selected from
    - (i) a halogen atom (e.g., a fluorine atom),
    - (ii) a $C_{1-6}$ alkoxy group (e.g., methoxy), and
    - (iii) a $C_{3-6}$ cycloalkyl group (e.g., cyclopropyl),
  - (2) a $C_{3-10}$ cycloalkyl group (e.g., cyclopropyl), or
  - (3) a mono- or di-$C_{1-6}$ alkylamino group (e.g., methylamino, dimethylamino);
- $R^2$ and $R^3$ are each independently a hydrogen atom, or a $C_{1-6}$ alkyl group (e.g., methyl), or $R^2$ and $R^3$ are taken together each other to form a bond;
- $R^4$ is a hydrogen atom, a $C_{1-6}$ alkyl group (e.g., methyl), a $C_{1-6}$ alkoxy group (e.g., ethoxy), or a hydroxy group;
- $R^5$ is phenyl, pyrazolyl, furyl, thienyl or thiazolyl, any of which is optionally substituted by one or more substituents independently selected from a $C_{1-6}$ alkyl group (e.g., methyl), a halogen atom (e.g., a fluorine atom, a chlorine atom), a halo ($C_{1-6}$) alkyl group (e.g., trifluoromethyl), and a $C_{1-6}$ alkoxy group (e.g., methoxy);
- m is 0 or 1;
- q is 1 or 2;
- $R^6$ and $R^7$ are each independently a hydrogen atom, a halogen atom (e.g., a fluorine atom), or a $C_{1-6}$ alkyl group (e.g., methyl);
- $X^1$, $X^2$, $X^3$, $X^4$, $X^5$, $X^6$, and $X^7$ are selected to form a ring system that is one of:
  - (i) $X^1$ is $NR^8$ and $R^8$ is absent, $X^2$ is O; $X^3$ and $X^4$ are both C, $X^5$ is $CR^{11}$, $X^6$ is $CR^{12}$, and $X^7$ is $CR^{13}$;
  - (ii) $X^1$ is $NR^8$ and $R^8$ is absent, $X^2$ is O, $X^3$ and $X^4$ are both C, $X^5$ is N, $X^6$ is $CR^{12}$, and $X^7$ is $CR^{13}$;
  - (iii) $X^1$ is $NR^8$ and $R^8$ is absent, $X^2$ is O, $X^3$ and $X^4$ are both C, $X^5$ is $CR^{11}$, $X^6$ is $CR^{12}$, and $X^7$ is N;
  - (iv) $X^1$ is $NR^8$ and $R^8$ is absent, $X^2$ is S, $X^3$ and $X^4$ are both C, $X^5$ is N, $X^6$ is $CR^{12}$, and $X^7$ is $CR^{13}$;
  - (v) $X^1$ is $NR^8$ and $R^8$ is absent, $X^2$ is S; $X^3$ and $X^4$ are both C, $X^5$ is $CR^{11}$, $X^6$ is $CR^{12}$, and $X^7$ is $CR^{13}$;
  - (vi) $X^1$ is $NR^8$ and $X^2$ is $NR^{10}$, and one of $R^8$ and $R^{10}$ is absent and the other of $R^8$ and $R^{10}$ is a $C_{1-6}$ alkyl group (e.g., methyl), $X^3$ and $X^4$ are both C, $X^5$ is $CR^{11}$, $X^6$ is $CR^{12}$, and $X^7$ is $CR^{13}$;
  - (vii) $X^1$ is $CR^9$, $X^2$ is $NR^{10}$ and $R^{10}$ is absent, $X^3$ is N, $X^4$ is C, $X^5$ is $CR^{11}$, $X^6$ is $CR^{12}$, and $X^7$ is $CR^{13}$; and
  - (viii) $X^1$ is $CR^9$, $X^2$ is $NR^{10}$ and $R^{10}$ is absent, $X^3$ is C, $X^4$ is N, $X^5$ is $CR^{11}$, $X^6$ is $CR^{12}$, and $X^7$ is $CR^{13}$; and
- $R^9$, $R^{11}$, $R^{12}$, and $R^{13}$ are each independently selected from a hydrogen atom, a $C_{1-6}$ alkyl group (e.g., methyl, ethyl), a halogen atom (e.g., a fluorine atom, a chlorine atom, a bromine atom), a $C_{3-6}$ cycloalkyl group (e.g., cyclopropyl), a $C_{3-6}$ cycloalkyl ($C_{1-6}$) alkoxy group (e.g., cyclopropylmethoxy), a halo ($C_{1-6}$) alkyl group (e.g., difluoromethyl, trifluoromethyl), a halo (C$_{1-6}$) alkoxy group (e.g., difluoromethoxy, trifluoromethoxy), a C$_{1-6}$ alkoxy (C$_{1-6}$) alkyl group (e.g., methoxymethyl), an azetidinyl group, a C$_{1-6}$ alkoxy group (e.g., methoxy, ethoxy), a hydroxy group, and a hydroxy (C$_{1-6}$) alkyl group (e.g., hydroxymethyl, 2-hydroxyethyl).

In some aspects, compound (I) is represented by the formula (Ic)

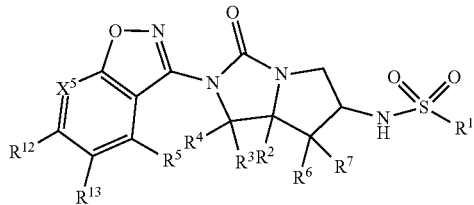

(Ic)

wherein
R$^1$ is a C$_{1-6}$ alkyl group (e.g., methyl, ethyl), or a mono-C$_{1-6}$ alkylamino group (e.g., methylamino);
R$^2$ and R$^3$ are each a hydrogen atom, or R$^2$ and R$^3$ are taken together each other to form a bond;
R$^4$ is a hydrogen atom;
R$^5$ is a phenyl group optionally substituted by 1 to 3 (e.g., 1, 2, 3, etc.) halogen atoms (e.g., a fluorine atom);
R$^6$ and R$^7$ are each independently a hydrogen atom, or a halogen atom (e.g., a fluorine atom);
X$^5$ is CH or N; and
R$^{12}$ and R$^{13}$ are each independently a hydrogen atom, a C$_{1-6}$ alkyl group (e.g., methyl), or a halogen atom (e.g., a fluorine atom, a chlorine atom);
or a salt thereof (sometimes to be referred to as compound (Ic).

In some aspects of compound (Ic),
R$^1$ is a C$_{1-6}$ alkyl group (e.g., methyl, ethyl);
R$^2$ and R$^3$ are each a hydrogen atom, or R$^2$ and R$^3$ are taken together each other to form a bond;
R$^4$ is a hydrogen atom;
R$^5$ is a phenyl group substituted by 1 to 3 (e.g., 1, 2, 3, etc.) halogen atoms (e.g., a fluorine atom);
R$^6$ and R$^7$ are each a halogen atom (e.g., a fluorine atom);
X$^5$ is CH; and
R$^{12}$ and R$^{13}$ are each independently a hydrogen atom, or a halogen atom (e.g., a fluorine atom).

Exemplary examples of compound (I), including compounds (Ia), (Ib) and (Ic), include the compounds set forth in the Examples and Table 1.

In some aspects, the disclosure provides a compound selected from the group consisting of:
N-{(6S,7aS)-2-[4-(2,6-difluorophenyl)-1,2-benzoxazol-3-yl]-3-oxohexahydro-1H-pyrrolo[1,2-c]imidazol-6-yl}ethanesulfonamide;
N-{(6R)-7,7-difluoro-3-oxo-2-[4-(2,4,6-trifluorophenyl)-1,2-benzoxazol-3-yl]-2,5,6,7-tetrahydro-3H-pyrrolo[1,2-c]imidazol-6-yl}methanesulfonamide;
N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}methanesulfonamide;
N-{(6S,7aS)-2-[6-chloro-4-(2,6-difluorophenyl)-1,2-benzoxazol-3-yl]-3-oxohexahydro-1H-pyrrolo[1,2-c]imidazol-6-yl}ethanesulfonamide;
N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}methanesulfonamide;
N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide;
N-{(6R,7aR)-7,7-difluoro-2-[6-fluoro-4-(2,4,6-trifluorophenyl)-1,2-benzoxazol-3-yl]-3-oxohexahydro-1H-pyrrolo[1,2-c]imidazol-6-yl}methanesulfonamide;
N-{(4aR,6R)-5,5-difluoro-1-oxo-2-[4-(2,4,6-trifluorophenyl)-1,2-benzoxazol-3-yl]octahydropyrrolo[1,2-c]pyrimidin-6-yl}methanesulfonamide;
N-{(4aR,6R)-2-[5,6-difluoro-4-(2,4,6-trifluorophenyl)-1,2-benzoxazol-3-yl]-5,5-difluoro-1-oxooctahydropyrrolo[1,2-c]pyrimidin-6-yl}methanesulfonamide;
N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}methanesulfonamide; and
N-{(6R)-2-[4-(2,6-difluorophenyl)-6-fluoro-1,2-benzoxazol-3-yl]-7,7-difluoro-3-oxo-2,5,6,7-tetrahydro-3H-pyrrolo[1,2-c]imidazol-6-yl}ethanesulfonamide;
or a salt thereof.

In some aspects, the disclosure provides a compound that is N-{(6S,7aS)-2-[4-(2,6-difluorophenyl)-1,2-benzoxazol-3-yl]-3-oxohexahydro-1H-pyrrolo[1,2-c]imidazol-6-yl}ethanesulfonamide or a salt thereof.

In some aspects, the disclosure provides a compound that is N-{(6R)-7,7-difluoro-3-oxo-2-[4-(2,4,6-trifluorophenyl)-1,2-benzoxazol-3-yl]-2,5,6,7-tetrahydro-3H-pyrrolo[1,2-c]imidazol-6-yl}methanesulfonamide or a salt thereof.

In some aspects, the disclosure provides a compound that is N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}ethanesulfonamide or a salt thereof.

In some aspects, the disclosure provides a compound that is N-{(6S,7aS)-2-[6-chloro-4-(2,6-difluorophenyl)-1,2-benzoxazol-3-yl]-3-oxohexahydro-1H-pyrrolo[1,2-c]imidazol-6-yl}ethanesulfonamide or a salt thereof.

In some aspects, the disclosure provides a compound that is N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}methanesulfonamide or a salt thereof.

In some aspects, the disclosure provides a compound that is N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide or a salt thereof.

In some aspects, the disclosure provides a compound that is N-{(6R,7aR)-7,7-difluoro-2-[6-fluoro-4-(2,4,6-trifluorophenyl)-1,2-benzoxazol-3-yl]-3-oxohexahydro-1H-pyrrolo[1,2-c]imidazol-6-yl}methanesulfonamide or a salt thereof.

In some aspects, the disclosure provides a compound that is N-{(4aR,6R)-5,5-difluoro-1-oxo-2-[4-(2,4,6-trifluorophenyl)-1,2-benzoxazol-3-yl]octahydropyrrolo[1,2-c]pyrimidin-6-yl}methanesulfonamide or a salt thereof.

In some aspects, the disclosure provides a compound that is N-{(4aR,6R)-2-[5,6-difluoro-4-(2,4,6-trifluorophenyl)-1,2-benzoxazol-3-yl]-5,5-difluoro-1-oxooctahydropyrrolo[1,2-c]pyrimidin-6-yl}methanesulfonamide or a salt thereof.

In some aspects, the disclosure provides a compound that is N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}methanesulfonamide or a salt thereof.

In some aspects, the disclosure provides a compound that is N-{(6R)-2-[4-(2,6-difluorophenyl)-6-fluoro-1,2-benzoxazol-3-yl]-7,7-difluoro-3-oxo-2,5,6,7-tetrahydro-3H-pyrrolo[1,2-c]imidazol-6-yl}ethanesulfonamide or a salt thereof.

As a salt of a compound represented by the formula (I), a pharmacologically acceptable salt is preferable, and examples of such salt include a salt with inorganic base, a salt with organic base, a salt with inorganic acid, a salt with organic acid, a salt with basic or acidic amino acid and the like.

Examples of the salt with inorganic base include alkali metal salts such as sodium salt, potassium salt and the like, alkaline earth metal salts such as calcium salt, magnesium salt and the like, aluminum salt, ammonium salt and the like.

Examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N-dibenzylethylenediamine and the like.

Examples of the salt with inorganic acid include salts with hydrochloric acid, hydrobromic acid, nitric acid, sulfuric acid, phosphoric acid and the like.

Examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Examples of the salt with basic amino acid include salts with arginine, lysine, ornithine and the like. Examples of the salt with acidic amino acid include salts with aspartic acid, glutamic acid and the like.

The production method of the compound of the present invention is explained below.

The raw material compound and reagent used and the compound obtained in each step in the following production method can be each in a form of a salt, and examples of such salt include those similar to the salts of the compound represented by the formula (I), and the like.

When the compound obtained in each step is a free form, it can be converted to the objective salt according to a known method. When the compound obtained in each step is a salt, it can be converted to the objective free form or the other salt according to a known method.

The compound obtained in each step can be used directly as the reaction mixture or as a crude product for the next reaction. Alternatively, the compound obtained in each step can be isolated and purified from a reaction mixture according to a known method, for example, a separation means such as concentration, crystallization, recrystallization, distillation, solvent extraction, fractional distillation, column chromatography and the like.

When the raw material compound and/or reagent used in each step is commercially available, the commercially available product can also be used directly.

In the reaction in each step, the reaction time varies depending on the kind of the reagent and solvent to be used. Generally, the reaction time is 1 min-48 hr, preferably 10 min-8 hr, unless otherwise specified.

In the reaction in each step, the reaction temperature varies depending on the kind of the reagent and solvent to be used. Generally, the reaction temperature is −78° C.-300° C., preferably −78° C.-150° C., unless otherwise specified.

In the reaction in each step, the pressure varies depending on the kind of the reagent and solvent to be used. Generally, the pressure is 1 atm-20 atm, preferably 1 atm-3 atm, unless otherwise specified.

A microwave synthesizer, such as Initiator+ manufactured by Biotage and the like, can be used for the reaction in each step. While the reaction temperature varies depending on the kind of the reagent and solvent to be used, it is generally room temperature–300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in the Examples and the following solvents:

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like; amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and water.

The above-mentioned solvents can be used singly or in a mixture of two or more kinds thereof in an appropriate ratio.

When a base is used for the reaction in each step, examples thereof include those described in Examples and the following bases:

inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like; and organic lithiums: n-butyllithium and the like.

When an acid or an acid catalyst is used for the reaction in each step, examples thereof include those described in Examples and the following acids and acid catalysts:

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a known method, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or a method described in the Examples.

In each step, the protection or deprotection reaction of a functional group is carried out according to a known method, for example, a method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or a method described in the Examples.

Examples of the protecting group for a hydroxy group of an alcohol and the like and a phenolic hydroxy group include, e.g., ether-type protecting groups such as methoxymethyl ether, benzyl ether, tert-butyldimethylsilyl ether, tetrahydropyranyl ether and the like; carboxylate ester-type protecting groups, such as acetate ester and the like; sulfonate ester-type protecting groups, such as methanesulfonate ester and the like; and carbonate ester-type protecting groups, such as tert-butylcarbonate and the like.

Examples of the protecting group for a carbonyl group of an aldehyde include, e.g., acetal-type protecting groups, such as dimethylacetal and the like; and cyclic acetal-type protecting groups, such as 1,3-dioxane and the like.

Examples of the protecting group for a carbonyl group of a ketone include, e.g., ketal-type protecting groups, such as dimethylketal and the like; cyclic ketal-type protecting groups, such as 1,3-dioxane and the like; oxime-type protecting groups, such as O-methyloxime and the like; and hydrazone-type protecting groups, such as N,N-dimethylhydrazone and the like.

Examples of the protecting group for a carboxyl group include, e.g., ester-type protecting groups, such as methyl ester and the like; and amide-type protecting groups, such as N,N-dimethylamide and the like.

Examples of the protecting group for a thiol include, e.g., ether-type protecting groups, such as benzyl thioether and the like; and ester-type protecting groups, such as thioacetate ester, thiocarbonate, thiocarbamate and the like.

Examples of the protecting group for an amino group and an aromatic heterocycle, such as imidazole, pyrrole, indole and the like, include, e.g., carbamate-type protecting groups, such as benzyl carbamate and the like; amide-type protecting groups, such as acetamide and the like; alkyl amine-type protecting groups, such as N-triphenylmethylamine and the like; and sulfonamide-type protecting groups, such as methanesulfonamide and the like.

The protecting groups can be removed according to a known method, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When a reduction reaction is carried out in each step, examples of the reducing agent to be used include metal hydrides, such as lithium aluminum hydride, sodium triacetoxyborohydride, sodium cyanoborohydride, diisobutylaluminum hydride (DIBAL-H), sodium borohydride, tetramethylammonium triacetoxyborohydride, and the like; boranes, such as borane tetrahydrofuran complex and the like; Raney nickel; Raney cobalt; hydrogen; formic acid; triethylsilane, and the like. When a carbon-carbon double bond or triple bond is reduced, a method using a catalyst, such as palladium-carbon, Lindlar's catalyst, and the like can be employed.

When an oxidation reaction is carried out in each step, examples of the oxidizing agent to be used include, e.g., peroxides, such as m-chloroperbenzoic acid (mCPBA), hydrogen peroxide, tert-butylhydroperoxide, and the like; perchlorates, such as tetrabutylammonium perchlorate and the like; chlorates, such as sodium chlorate and the like; chlorites, such as sodium chlorite and the like; periodates, such as sodium periodate and the like; hypervalent iodine reagents, such as iodosylbenzene and the like; reagents containing manganese, such as manganese dioxide, potassium permanganate and the like; leads, such as lead tetraacetate and the like; reagents containing chromium, such as pyridinium chlorochromate (PCC), pyridinium dichromate (PDC), Jones reagent, and the like; halogen compounds, such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ), and the like.

When a radical cyclization reaction is carried out in each step, examples of the radical initiator to be used include an azo compound, such as azobisisobutyronitrile (AIBN) and the like; a water-soluble radical initiator, such as 4-4'-azobis-4-cyanopentanoic acid (ACPA) and the like; triethylboron in the presence of air or oxygen; benzoyl peroxide, and the like. Examples of the radical reagent to be used include tributylstannane, tristrimethylsilylsilane, 1,1,2,2-tetraphenyldisilane, diphenylsilane, samarium iodide, and the like.

When a Wittig reaction is carried out in each step, examples of the Wittig reagent to be used include alkylidene phosphoranes and the like. The alkylidene phosphoranes can be prepared according to a known method, for example, by reacting a phosphonium salt with a strong base.

When a Horner-Emmons reaction is carried out in each step, examples of the reagent to be used include phosphonoacetates, such as methyl dimethylphosphonoacetate, ethyl diethylphosphonoacetate, and the like; and bases, such as alkali metal hydrides, organic lithiums, and the like.

When a Friedel-Crafts reaction is carried out in each step, a combination of a Lewis acid and an acid chloride or a combination of a Lewis acid and an alkylating agent (e.g., an alkyl halide, an alcohol, an olefin, etc.) is used as a reagent. Alternatively, an organic acid or an inorganic acid, as described herein, can also be used instead of a Lewis acid, and an anhydride, such as acetic anhydride and the like can also be used instead of an acid chloride.

When an aromatic nucleophilic substitution reaction is carried out in each step, a nucleophile (e.g., an amine, imidazole etc.) and a base (e.g., an organic base etc.) are used as a reagent.

When a nucleophilic addition reaction by a carbo anion, nucleophilic 1,4-addition reaction (Michael addition reaction) by a carbo anion or nucleophilic substitution reaction by a carbo anion is carried out in each step, examples of the base to be used for generation of the carbo anion include organic lithiums, metal alkoxides, inorganic bases, organic bases, and the like.

When a Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When a Knoevenagel condensation reaction is carried out in each step, a compound having an activated methylene group with two electron withdrawing groups (e.g., malonic acid, diethyl malonate, malononitrile, etc.) and a base (e.g., an organic base, a metal alkoxide, an inorganic base, each as described herein) are used as a reagent.

When a Vilsmeier-Haack reaction is carried out in each step, phosphoryl chloride and an amide derivative (e.g., N,N-dimethylformamide, etc.) are used as a reagent.

When an azidation reaction of an alcohol, an alkyl halide or a sulfonate is carried out in each step, examples of the azidating agent to be used include diphenylphosphorylazide (DPPA), trimethylsilylazide, sodium azide, and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When a reductive amination reaction is carried out in each step, examples of the reducing agent to be used include sodium triacetoxyborohydride, sodium cyanoborohydride, hydrogen, formic acid, and the like. When the substrate is an amine compound, examples of the carbonyl compound to be used include paraformaldehyde, aldehydes, such as acetaldehyde and the like, and ketones, such as cyclohexanone and the like. When the substrate is a carbonyl compound, examples of the amine to be used include ammonia, primary amines, such as methylamine and the like; secondary amines such, as dimethylamine and the like, and the like.

When a Mitsunobu reaction is carried out in each step, an azodicarboxylate (e.g., diethyl azodicarboxylate (DEAD), diisopropyl azodicarboxylate (DIAD), etc.) and triphenylphosphine are used as a reagent.

When an esterification reaction, amidation reaction, or urea formation reaction is carried out in each step, examples of the reagent to be used include acyl halides, such as acid chlorides, acid bromides and the like; activated carboxylic acids such as acid anhydrides, activated esters, sulfates and the like. Examples of the activating agent of the carboxylic acid include carbodiimide condensing agents, such as 1-ethyl-3-(3-dimethylaminopropyl)carbodiimide hydrochloride (WSCD) and the like; triazine condensing agents, such as 4-(4,6-dimethoxy-1,3,5-triazin-2-yl)-4-methylmorpholinium chloride n-hydrate (DMT-MM) and the like; carbonate condensing agents, such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; 0-(7-azabenzotriazol-1-yl)-N,N,N',N'-tetramethyluronium hexafluorophosphorate (HATU); sulfuric acid; combinations thereof and the like. When a carbodiimide condensing agent is used, an additive such as 1-hydroxybenzotriazole (HOBt),  N-hydroxysuccinimide (HOSu), dimethylaminopyridine (DMAP) and the like can be added to the reaction system.

When a coupling reaction is carried out in each step, examples of the metal catalyst to be used include, palladium compounds, such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis (diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds, such as copper oxide, copper(I) iodide and the like; and platinum compounds and the like. In addition, a base can be added to the reaction system, and examples thereof include inorganic bases, as described herein, and the like.

When a thiocarbonylation reaction is carried out in each step, phosphorus pentasulfide typically is used as the thiocarbonylating agent. Alternatively, a reagent having a 1,3,2,4-dithiadiphosphetane-2,4-disulfide structure (e.g., 2,4-bis (4-methoxyphenyl)-1,3,2,4-dithiadiphosphetane-2,4-disulfide (Lawesson reagent) etc.) can also be used instead of phosphorus pentasulfide.

When a Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride, and the like. In addition, the reaction can be accelerated by subjecting a radical initiator, such as heat, light, benzoyl peroxide, azobisisobutyronitrile, and the like, to the reaction system reaction.

When a halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid, and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride, or sodium iodide also can be employed.

When an Arbuzov reaction is carried out in each step, examples of the reagent to be used include alkyl halides, such as ethyl bromoacetate and the like; and phosphites, such as triethyl phosphite, tri(isopropyl) phosphite, and the like.

When a sulfonate esterification reaction is carried out in each step, examples of the sulfonating agent to be used include methanesulfonyl chloride, p-toluenesulfonyl chloride, methanesulfonic anhydride, p-toluenesulfonic anhydride, and the like.

When a hydrolysis reaction is carried out in each step, an acid or a base is used as a reagent. For acid hydrolysis reaction of tert-butyl ester, formic acid, triethylsilane, and the like can be added to reductively-trap the tert-butyl cation which is by-produced.

When a dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid, and the like.

Compound (7) used in the below-mentioned Scheme 2 can be produced from compound (1) according to the method shown in the following Scheme 1. In the formulas, P¹ and P² are each a protecting group or a hydrogen atom, LG¹ is a leaving group, $R^{16}$ is an optionally substituted $C_{1-6}$alkyl group or an optionally substituted $C_{6-14}$ aryl group, and the other symbols are as defined above.

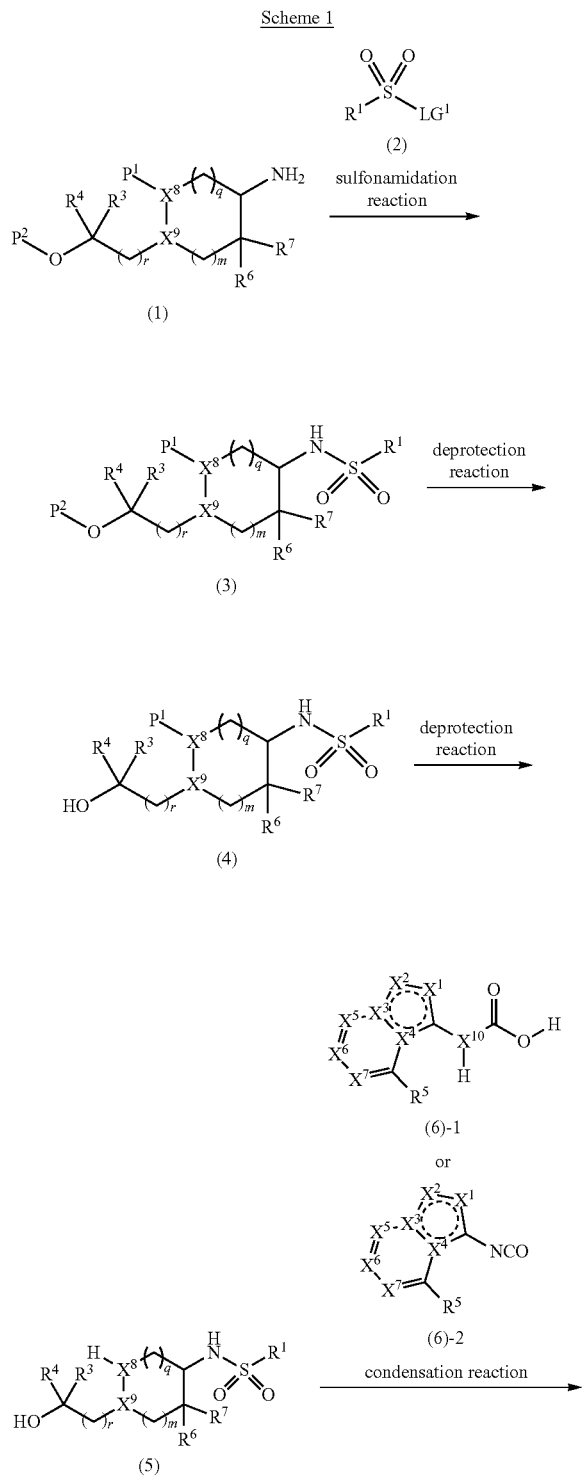

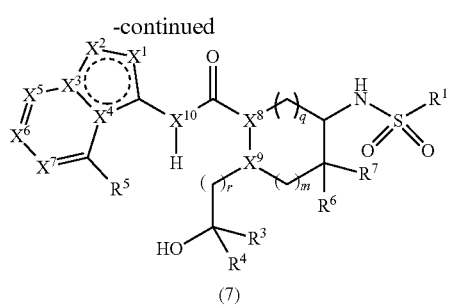

Examples of the "protecting group" for P¹ include those exemplified as the above-mentioned "protecting group for an amino group and an aromatic heterocycle such as imidazole, pyrrole, indole and the like".

Examples of the "protecting group" for P² include those exemplified as the above-mentioned "protecting group for a hydroxy group of an alcohol and the like".

Examples of the "leaving group" for LG¹ include halogen atoms, optionally halogenated $C_{1-6}$alkylsulfonyloxy (e.g., methanesulfonyloxy, ethanesulfonyloxy, trifluoromethanesulfonyloxy), $C_{6-14}$ arylsulfonyloxy optionally substituted by $C_{1-6}$alkyl (e.g., benzenesulfonyloxy, toluenesulfonyloxy) and the like.

Compound (1) may be commercially easily available or can be produced according to a method known per se.

Compound (3) can be produced by subjecting compound (1) to a sulfonamidation reaction with compound (2). Examples of compound (2) to be used include sulfonyl chloride, sulfamoyl chloride and the like. Compound (2) may be commercially easily available or can be produced according to a method known per se.

Compound (7) can be produced, for example, by subjecting compound (5) wherein $X^8$ is a nitrogen atom to a condensation reaction with compound (6)-1 or compound (6)-2. Compound (6)-1 and compound (6)-2 may be commercially easily available or can be produced according to a method known per se.

Compound (I) can be produced from compound (7) according to the method shown in the following Scheme 2. In the formulas, $R^{17}$ is an optionally substituted $C_{1-6}$alkyl group or an optionally substituted $C_{6-14}$ aryl group, and the other symbols are as defined above.

Scheme 2

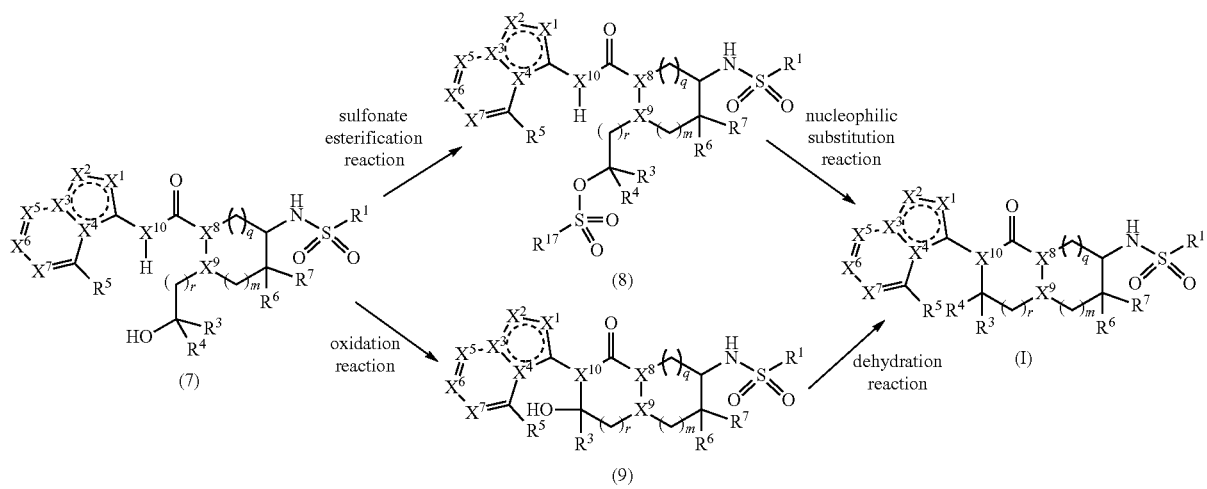

Compound (8) can be produced by subjecting compound (7) to a sulfonate esterification reaction. Examples of the sulfonating agent to be used include methanesulfonyl chloride, p-toluenesulfonyl chloride, methanesulfonic anhydride, p-toluenesulfonic anhydride, trifluoromethanesulfonic anhydride and the like.

Compound (9) can be produced, for example, by subjecting compound (7) wherein $R^4$ is a hydrogen atom to an oxidation reaction.

Compound (I) can be produced, for example, by subjecting compound (8) to a nucleophilic substitution reaction in the presence of a base. Examples of the base to be used include inorganic bases, organic bases, alkali metal hydrides and the like.

Compound (I) wherein $X^9$ is $CR^2$, r is 0, and $R^2$ and $R^3$ is taken together to form a bond can be produced, for example, by subjecting compound (9) to a dehydration reaction.

Compound (I) wherein $X^{10}$ is $CR^{15}$ and $R^3$ and $R^{15}$ is taken together to form a bond can be produced, for example, by subjecting compound (9) to a dehydration reaction.

In compound (I), an intramolecular functional group can also be converted to an object functional group by a combination of known chemical reactions. Examples of the chemical reaction include an oxidation reaction, reduction reaction, alkylation reaction, acylation reaction, ureation reaction, hydrolysis reaction, amination reaction, esterification reaction, aryl coupling reaction, deprotection reaction, and the like.

In the production method, when a starting compound has an amino group, a carboxyl group, a hydroxy group, a carbonyl group, or a mercapto group as a substituent, a protecting group generally used in the peptide chemistry can be introduced into these groups, and the object compound can be obtained by removing the protecting group as necessary after the reaction.

Compound (I) can be isolated and purified by a known method, such as solvent extraction, liquid conversion, phase transfer, crystallization, recrystallization, chromatography, and the like.

When compound (I) contains an optical isomer, stereoisomer, regio isomer, or rotamer, these compounds are also included in compound (I), and each can be obtained as a single product by a synthesis method or a separation method.

For example, when an optical isomer exists in compound (I), an optical isomer resolved from the compound also is encompassed in compound (I).

An optical isomer can be produced by a known method.

Compound (I) can be a crystal.

A crystal of compound (I) (hereinafter sometimes to be abbreviated as the crystal of the present invention) can be produced by crystallizing compound (I), by applying a crystallization known method.

In the present specification, the melting point means a melting point measured, for example, by a micro melting point apparatus (Yanako, MP-500D or Buchi, B-545), DSC (differential scanning calorimetry analysis) apparatus (METTLER TOLEDO, DSC1), and the like.

Generally, the melting point can vary depending on the measurement device, measurement conditions, and the like. The crystal in the present specification can be a crystal with a melting point different from the values described in the present specification as long as the difference is within a general error range.

The crystal of the present invention is superior in the physicochemical properties (e.g., melting point, solubility, stability) and biological properties (e.g., pharmacokinetics (absorbability, distribution, metabolism, excretion), efficacy expression), and can be extremely useful as a medicament.

Compound (I) can be used as a prodrug. A prodrug of the compound (I) means a compound that is converted to the compound (I) of the present invention with a reaction due to an enzyme, an gastric acid, etc. under the physiological condition in the living body. For example, a prodrug of compound (I) can be a compound that is converted to the compound (I) of the present invention by oxidation, reduction, hydrolysis, etc. in the presence of an enzyme or a compound which is converted to the compound (I) of the present invention by hydrolysis etc. due to gastric acid, etc.

A prodrug of compound (I) can be:
a compound obtained by subjecting an amino group in compound (I) to an acylation, alkylation, or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.);

a compound obtained by subjecting a hydroxy group in compound (I) to an acylation, alkylation, phosphorylation, or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); or a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.).

Any of these compounds can be produced from compound (I) by a known method.

A prodrug for compound (I) can also be one which is converted into compound (I) under a physiological condition, such as those described in *IYAKUHIN no KAIHATSU* (Development of Pharmaceuticals), Vol. 7, Design of Molecules, p. 163-198, Published by HIROKAWA SHOTEN (1990).

In the present specification, a prodrug can form a salt, and as such salt, those exemplified as a salt of the compound represented by the above-mentioned formula (I) can be mentioned.

Compound (I) can be labeled with an isotope (e.g., $^3$H, $^{13}$C, $^{14}$C, $^{18}$F, $^{35}$S, $^{125}$I) and the like.

Compound (I) labeled with or substituted by an isotope can be used, for example, as a tracer used for Positron Emission Tomography (PET) (PET tracer), and is useful in the field of medical diagnosis and the like.

Furthermore, compound (I) can be a hydrate or a non-hydrate, or a non-solvate (e.g., anhydride), or a solvate (e.g., hydrate).

Compound (I) also encompasses a deuterium conversion form wherein 1H is converted to $^2$H(D).

Furthermore, compound (I) can be a pharmaceutically acceptable cocrystal or cocrystal salt. The cocrystal or cocrystal salt means a crystalline substance constituted with two or more special solids at room temperature, each having different physical properties (e.g., structure, melting point, melting heat, hygroscopicity, solubility and stability). The cocrystal or cocrystal salt can be produced by a cocrystallization known method.

Compound (I) or a prodrug thereof (hereinafter sometimes to be simply abbreviated as the compound of the present invention) can be used as it is or in the form of a pharmaceutical composition (also referred to as a medicament) by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations; or solvent, solubilizing agent, suspending agent, isotonicity agent, buffer and soothing agent for liquid preparations; and the like; and preparation additives such as preservative, antioxidant, colorant, sweetening agent and the like can be added as necessary.

Examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate, and magnesium alumino metasilicate.

Examples of the lubricant include magnesium stearate, calcium stearate, talc, and colloidal silica.

Examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, and polyvinylpyrrolidone.

Examples of the disintegrant include lactose, sucrose, starch, carboxymethylcellulose, calcium carboxymethylcellulose, croscarmellose sodium, sodium carboxymethyl starch, light anhydrous silicic acid, and low-substituted hydroxypropylcellulose.

Examples of the solvent include water for injection, physiological brine, Ringer's solution, alcohol, propylene glycol, polyethylene glycol, sesame oil, corn oil, olive oil, and cottonseed oil.

Examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Examples of the isotonicity agent include sodium chloride, glycerol, D-mannitol, D-sorbitol and glucose.

Examples of the buffer include buffers of phosphate, acetate, carbonate, citrate etc.

Examples of the soothing agent include benzyl alcohol.

Examples of the preservative include p-oxybenzoate esters, chlorobutanol, benzyl alcohol, phenethyl alcohol, dehydroacetic acid and sorbic acid.

Examples of the antioxidant include sulfite salts and ascorbate salts.

Examples of the colorant include aqueous food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the above-mentioned aqueous food tar color), natural dyes (e.g., β-carotene, chlorophyll, red iron oxide) and the like.

Examples of the sweetening agent include saccharin sodium, dipotassium glycyrrhizinate, aspartame, and *stevia*.

Examples of the dosage form of the above-mentioned pharmaceutical composition include oral preparations such as tablet (including sugar-coated tablet, film-coated tablet, sublingual tablet, orally disintegrating tablet, buccal tablet), capsule (including soft capsule, microcapsule), pill, granule, powder, troche, syrup, liquid, emulsion, suspension, aerosol, films (e.g., orally disintegrable films, oral mucosa-adhesive film), and the like; and parenteral agents such as injection (e.g., subcutaneous injection, intravenous injection, intramuscular injection, intraperitoneal injection, drip infusion), external preparation (e.g., transdermal absorption type preparation, ointment, lotion, adhesive preparation), suppository (e.g., rectal suppository, vaginal suppository), pellet, nasal preparation, pulmonary preparation (inhalant), eye drop and the like. The compound and medicament of the present invention can be respectively safely administered orally or parenterally (e.g., intrarectal, intravenous, intraarterial, intramuscular, subcutaneous, intraorgan, intranasal, intradermal, instillation, intracerebral, intravaginal, intraperitoneal, intratumoral, proximal tumor administrations, and administration to the lesion).

These preparations can be a release control preparation (e.g., sustained-release microcapsule), such as an immediate-release preparation, a sustained-release preparation, and the like.

The pharmaceutical composition can be produced according to a method conventionally used in the field of pharmaceutical formulation, for example, a method described in the Japanese Pharmacopoeia, and the like.

While the content of the compound of the present invention in the pharmaceutical composition of the present invention varies depending on the dosage form, dose of the compound of the present invention and the like, it is, for example, about 0.1 to 100 wt %.

When an oral preparation is produced, a coating can be applied where necessary for the purpose of taste masking, enteric solubility, and/or sustainability.

Examples of a coating base used for the coating include a sugar coating base, water-soluble film coating base, enteric film coating base, and sustained-release film coating base.

As the sugar coating base, sucrose can be used, and one or more kinds selected from talc, and the precipitated calcium carbonate, gelatin, gum arabic, pullulan, carnauba wax, and the like can be further used in combination.

Examples of the water-soluble film coating base include cellulose polymers, such as hydroxypropylcellulose, hydroxypropylmethylcellulose, hydroxyethylcellulose, methylhydroxyethylcellulose and the like; synthetic polymers, such as polyvinyl acetal diethylaminoacetate, aminoalkylmethacrylate copolymer E [Eudragit E (trade name)], polyvinylpyrrolidone and the like; and polysaccharides, such as pullulan and the like.

Examples of the enteric film coating base include cellulose polymers, such as hydroxypropylmethylcellulose phthalate, hydroxypropylmethylcellulose acetate succinate, carboxymethylethylcellulose, cellulose acetate phthalate and the like; acrylic acid polymers, such as methacrylic acid copolymer L [Eudragit L (trade name)], methacrylic acid copolymer LD [Eudragit L-30D-55 (trade name)], methacrylic acid copolymer S [Eudragit S (trade name)] and the like; and naturally-occurring substances, such as shellac and the like.

Examples of the sustained-release film coating base include cellulose polymers, such as ethylcellulose and the like; and acrylic acid polymers, such as aminoalkylmethacrylate copolymer RS [Eudragit RS (trade name)], ethyl acrylate-methyl methacrylate copolymer suspension [Eudragit NE (trade name)], and the like.

Two or more kinds of the above-mentioned coating bases can be used in a mixture at an appropriate ratio. In addition, for example, light shielding agents such as titanium oxide, red ferric oxide and the like may also be used during coating.

Since the compound of the present invention shows low toxicity (e.g., acute toxicity, chronic toxicity, genetic toxicity, reproductive toxicity, cardiotoxicity, carcinogenicity) and less side effects, it can be used as a prophylactic or therapeutic agent, or diagnostic agent for various diseases in mammals (e.g., human, bovine, horse, dog, cat, monkey, mouse, rat).

The compound of the present invention has an excellent orexin type 2 receptor agonist activity, and can treat, prevent or ameliorate the risk of various neurological and psychiatric diseases associated with an orexin type 2 receptor. The compound of the present invention is useful as an agent for the prophylaxis or treatment of various diseases, such as narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Kleine Levin syndrome, major depression with hypersomnia, Lewy body dementia, Parkinson's disease, progressive supranuclear paralysis, Prader-Willi syndrome, Moebius syndrome, hypoventilation syndrome, Niemann-Pick disease type C, brain contusion, cerebral infarction, brain tumor, muscular dystrophy, multiple sclerosis, acute disseminated encephalomyelitis, Guillain-Barre syndrome, Rasmussen's encephalitis, Wernicke's encephalitis, limbic encephalitis, Hashimoto's encephalopathy), coma, loss of consciousness, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), insulin resistance syndrome, Alzheimer's disease, disturbance of consciousness such as coma and the like, side effects and complications due to anesthesia, sleep disturbance, sleep problem, insomnia, Intermittent sleep, nocturnal myoclonus, REM sleep interruption, jet lag, jet lag syndrome, sleep disorder of alternating worker, sleep disorder, night terror, depression, major depression, sleepwalking disease, enuresis, sleep disorder, Alzheimer's dusk, diseases associated with circadian rhythm, fibromyalgia, condition arising from decline in the quality of sleep, overeating, obsessive compulsive eating disorder, obesity-related disease, hypertension, diabetes, elevated plasma insulin concentration and insulin resistance, hyperlipidemia, hyperlipemia, endometrial cancer, breast cancer, prostate cancer, colorectal cancer, cancer, osteoarthritis, obstructive sleep apnea, cholelithiasis, gallstones, cardiac disease, abnormal heartbeat, arrhythmia, myocardial infarction, congestive cardiac failure, cardiac failure, coronary heart disease, cardiovascular disorder, sudden death, polycysticovarian disease, craniopharingioma, Froelich's syndrome, growth hormone deficient, normal mutant short stature, Turner's syndrome, children suffering from acute lymphoblastic leukemia, syndrome X, reproductive hormone abnormality, declining fertility, infertility, male gonadal function decline, sexual and reproductive dysfunction such as female male hirsutism, fetal defects associated with pregnant women obesity, gastrointestinal motility disorders such as obesity-related gastroesophageal reflux, obesity hypoventilation syndrome (Pickwick syndrome), respiratory diseases such as dyspnea, inflammation such as systemic inflammation of the vascular system, arteriosclerosis, hypercholesterolemia, hyperuricemia, lower back pain, gall bladder disease, gout, kidney cancer, risk of secondary outcomes of obesity such as lowering the risk of left ventricular hypertrophy, migraine pain, headache, neuropathic pain, Parkinson's disease, psychosis, schizophrenia, facial flushing, night sweats, diseases of the genital/urinary system, diseases related to sexual function or fertility, dysthymic disorder, bipolar disorder, bipolar I disorder, bipolar II disorder, cyclothymic disorder, acute stress disorder, agoraphobia, generalized anxiety disorder, obsessive disorder, panic attack, panic disorder, posttraumatic stress disorder, separation anxiety disorder, social phobia, anxiety disorder, acute neurological and psychiatric disorders such as cardiac bypass surgery and post-transplant cerebral deficit, stroke, ischemic stroke, cerebral ischemia, spinal cord trauma, head trauma, perinatal hypoxia, cardiac arrest, hypoglycemic nerve injury, Huntington's disease, amyotrophic lateral sclerosis, multiple sclerosis, eye damage, retinopathy, cognitive impairment, muscle spasm, tremor, epilepsy, disorders associated with muscle spasticity, delirium, amnestic disorder, age-related cognitive decline, schizoaffective disorder, delusional disorder, drug addiction, dyskinesia, chronic fatigue syndrome, fatigue, medication-induced Parkinsonism syndrome, Jill-do La Tourette's syndrome, chorea, myoclonus, tic, restless legs syndrome, dystonia, dyskinesia, attention deficit hyperactivity disorder (ADHD), behavior disorder, urinary incontinence, withdrawal symptoms, trigeminal neuralgia, hearing loss, tinnitus, nerve damage, retinopathy, macular degeneration, vomiting, cerebral edema, pain, bone pain, arthralgia, toothache, cataplexy, and traumatic brain injury.

Particularly, the compound of the present invention is useful as an agent for the prophylaxis or treatment of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer's disease, obesity, insulin resistance syndrome, cardiac failure, diseases related to bone loss, sepsis, disturbance of consciousness, such as coma and the like, side effects and complications due to anesthesia, and the like, or as an anesthetic antagonist.

In some aspects, the compound of the present invention is useful as an agent for the prophylaxis or treatment of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, side effects and complications due to anesthesia.

In some aspects, the compound of the present invention is useful as an agent for the prophylaxis or treatment of narcolepsy, idiopathic hypersomnia, hypersomnia, or sleep apnea syndrome.

In some aspects, the compound of the present invention is useful as an agent for the prophylaxis or treatment of narcolepsy.

Central disorders of hypersomnolence (CDH) are characterized by excessive daytime sleepiness in the absence of other sleep disorders but with the setting of adequate and regular sleep habits. Central disorders of hypersomnolence (CDH) include narcolepsy type 1, narcolepsy type 2 and idiopathic hypersomnia. Kleine-Levin syndrome as well as insufficient sleep syndrome and hypersomnia caused by a medical condition, medication or substance, or psychiatric condition are also considered central orders of hypersomnolence. Evaluation of central disorders of hypersomnolence (CDH) includes sleep testing in the sleep lab (polysomnography, PSG) followed by a multiple sleep latency test (MSLT).

Symptoms that are associated with narcolepsy involve abnormal intrusions of REM sleep features into wake: for example, sleep-related hallucinations, sleep paralysis, or vivid dreams and dream-reality confusion. These symptoms can also occur in people without a sleep disorder.

Some patients with narcolepsy also experience cataplexy (narcolepsy, type 1) which is loss of muscle tone triggered by emotion, typically laughter or anticipation. Cataplexy can be generalized or partial and isn't associated with any loss of consciousness. This muscle weakness typically improves within seconds to minutes.

Patients with idiopathic hypersomnia (IDH) often describe excessive daytime sleepiness, prolonged sleep duration (more than 10-11 hours of sleep nightly), and severe difficulty waking up in the morning (sleep inertia). In contrast to narcolepsy, patients with IDH often describe long, unrefreshing daytime naps. Another common symptom of IDH is "brain fog," a feeling of cognitive clouding during the day. Klein-Levin syndrome is a rare disorder of cyclic hypersomnia.

An aspect of the disclosure is a method for treating a subject having one or more central disorders of hypersomnolence (CDH), the method comprising administering to the subject a compound of the present invention.

Another aspect of the disclosure is the use of a compound of the present invention for the manufacture of an agent for treating one or more central disorders of hypersomnolence (CDH) in a subject.

Another aspect of the disclosure is a compound of the present invention for use in treating one or more central disorders of hypersomnolence (CDH) in a subject. Another aspect is a method or use of the previous aspects, wherein the subject is narcoleptic. In one aspect, the subject has been diagnosed with narcolepsy type 1. In another aspect, the subject has been diagnosed with narcolepsy type 2. In still another aspect, the subject has been diagnosed with idiopathic hypersomnia.

Another aspect is a method or use of the previous aspects, wherein administering the compound of the invention reduces daytime sleepiness, reduces instances of loss of muscle control, and/or reduces instances of interrupted sleep in the subject. Another aspect is a method or use wherein a compound of the present invention is administered in an amount effective to reduce excessive daytime sleepiness in adults with narcolepsy. Another aspect is a method or use wherein a compound of the present invention is administered in an amount effective to increase in mean sleep latency.

Another aspect is a method or use wherein a compound of the present invention is administered in an amount effective to reduce cataplexy events.

Another aspect is a method or use wherein a compound of the present invention is administered in an amount effective to decrease disrupted nocturnal sleep in the subject.

While the dose of the compound of the present invention varies depending on the subject of administration, administration route, target disease, symptom, and the like, for example, when the compound of the present invention is administered orally or parenterally to an adult patient, its dose is for example, about 0.01 to 100 mg/kg body weight per dose, preferably 0.1 to 50 mg/kg body weight per dose and more preferably 0.5 to 20 mg/kg body weight per dose. This amount is desirably administered in one to 3 portions daily.

The compound of the present invention can be used in combination with other drugs (hereinafter to be abbreviated as a concomitant drug).

By combining the compound of the present invention and a concomitant drug, a superior effect can be achieved, for example, (1) the dose can be reduced as compared to single administration of the compound of the present invention or a concomitant drug,
(2) the drug to be combined with the compound of the present invention can be selected according to the condition of patients (mild case, severe case, and the like),
(3) the period of treatment can be set longer by selecting a concomitant drug having a different action and mechanism from the compound of the present invention,
(4) a sustained treatment effect can be designed by selecting a concomitant drug having a different action and mechanism from the compound of the present invention,
(5) a synergistic effect can be afforded by a combined use of the compound of the present invention and a concomitant drug, and the like.

In the present specification, the compound of the present invention and a concomitant drug used in combination are referred to as the "combination agent of the present invention."

When using the combination agent of the present invention, the administration time of the compound of the present invention and the concomitant drug is not restricted, and the compound of the present invention or a pharmaceutical composition thereof, or the concomitant drug or a pharmaceutical composition thereof can be administered to an administration subject simultaneously, or can be administered at different times. The dosage of the concomitant drug can be determined according to the dose clinically used, and can be appropriately selected depending on an administration subject, administration route, disease, combination and the like.

The administration mode of the combination agent of the present invention and the concomitant drug is not particularly limited, and the compound of the present invention and the concomitant drug only need to be combined on administration. Examples of such administration mode include the following:
(1) administration of a single preparation obtained by simultaneously processing the compound of the present invention and the concomitant drug,
(2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner,
(4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and typically is from about 0.01 to about 100 wt %, preferably from about 0.1 to about 50 wt %, further preferably from about 0.5 to about 20 wt %, based on the whole preparation.

The content of the concomitant drug in the combination agent of the present invention differs depending on the form of a preparation, and typically is from about 0.01 to about 100 wt %, preferably from about 0.1 to about 50 wt %, further preferably from about 0.5 to about 20 wt %, based on the whole preparation.

The content of additives, such as a carrier and the like, in the combination agent of the present invention differs depending on the form of a preparation, and typically is from about 1 to about 99.99 wt %, preferably from about 10 to about 90 wt %, based on the preparation.

Similar contents can be used even when the compound of the present invention and a concomitant drug are separately formulated into preparations.

Examples of the concomitant drug include the following: a therapeutic drug for narcolepsy (e.g., methylphenidate, amphetamine, pemoline, phenelzine, protriptyline, sodium oxybate, modafinil, caffeine), antiobesity drug (amphetamine, benzfetamine, bromocriptine, bupropion, diethylpropion, exenatide, fenfluramine, liothyronine, liraglutide, mazindol, methamphetamine, octreotide, octreotide, orlistat, phendimetrazine, phendimetrazine, phenmetrazine, phentermine, Qnexa (registered trade mark), phenylpropanolamine, pramlintide, propylhexedrine, recombinant leptin, sibutramine, topiramate, zimelidine, zonisamide, Lorcaserin, metformin), acetylcholine esterase inhibitor (e.g., donepezil, rivastigmine, galanthamine, zanapezil, idebenone, tacrine), antidementia agent (e.g., memantine), inhibitor of β amyloid protein production, secretion, accumulation, aggregation and/or deposition, β secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl) methoxytetralin, 6-(4-biphenylyl)methoxy-2-[2-(N,N-diethylamino)ethyl]tetralin, 2-[2-(N,N-dimethylamino) ethyl]-6-(4'-methylbiphenyl-4-yl)methoxytetralin, 2-[2-(N, N-dimethylamino)ethyl]-6-(4'-methoxybiphenyl-4-yl) methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitor, β amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior accompanying progress of dementia, wandering and the like (e.g., sedative, anti-anxiety drug), apoptosis inhibitor (e.g., CPI-1189, IDN-6556, CEP-1347), neuronal differentiation-regenerate promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin etc.), steroid drug (dexamethasone, hexestrol, cortisone acetate etc.), disease-modifying anti-rheumatic drug (DMARDs), anti-cytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil (citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-HT$_{1A}$ agonist, (buspirone hydrochloride, tandospirone citrate, osemozotan hydrochloride etc.), 5-HT$_{2A}$ antagonist, 5-HT$_{2A}$ inverse agonist, 5-HT$_3$ antagonist (cyamemazine etc.), heart non-selective β inhibitor (propranolol hydrochloride, oxprenolol hydrochloride etc.), histamine H$_1$ antagonist (hydroxyzine hydrochloride etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent and the like.

Two or more kinds of the above-mentioned concomitant drug can be used in a mixture at an appropriate ratio.

When the compound of the present invention is used for treatment of the above-mentioned diseases, it can also be used in combination with biologics (e.g., antibody drug, nucleic acid or nucleic acid derivative, aptamer drug, vaccine preparation), or can be used in combination with a gene therapy method and the like, or can also be used in combination with a treatment in psychiatric field without using drugs.

Examples of the antibody drug and vaccine preparation include vaccine preparation against angiotensin II, vaccine preparation against CETP, CETP antibody, antibody against TNFα antibody and other cytokines, amyloid β vaccine preparation, vaccine for type 1 diabetes (e.g., DIAPEP-277 of Peptor), anti-HIV antibody and HIV vaccine preparation, as well as antibodies or vaccine preparations against cytokines, renin-angiotensin type enzymes and products thereof, antibodies or vaccine preparations against enzymes or proteins involved in blood lipid metabolism, antibodies or vaccines relating to enzymes and proteins involved in blood coagulation or fibrinolysis system, antibodies or vaccine preparations against proteins involved in sugar metabolism and insulin resistance, and the like. In addition, it can be used in combination with biologics relating to growth factors such as GH, IGF and the like.

Examples of the gene therapy method include a treatment method using gene relating to cytokine, renin-angiotensin type enzyme and product thereof, G protein, G protein conjugated receptor and phosphorylating enzyme thereof, a treatment method using a DNA decoy such as NFκB decoy and the like, a treatment method using antisense, a treatment method using a gene relating to an enzyme or protein involved in blood lipid metabolism (e.g., a gene relating to metabolism, excretion and absorption of cholesterol or triglyceride or HDL-cholesterol or blood phospholipid), a treatment method using a gene relating to an enzyme or protein involved in angiogenesis therapy for peripheral vascular obstruction and the like (e.g., growth factors such as HGF, VEGF etc.), a treatment method using a gene relating to a protein involved in glucose metabolism and insulin resistance, antisense against cytokines such as TNF etc., and the like.

Examples of the treatment method in the psychiatric field without using drug include modified electroconvulsive therapy, deep brain stimulation therapy, repetitive transcranial magnetic stimulation therapy, psychotherapy including cognitive behavioral therapy, and the like.

The compound of the present invention can also be used in combination with various organ regeneration methods, such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

EXAMPLES

The present invention is explained in detail in the following by referring to Examples, Experimental Examples and Formulation Examples. However, the examples do not limit the present invention and the examples can be modified within the scope of the present invention.

The "room temperature" in the following Examples is generally about 10 C to about 35 C. The ratio for mixed solvent is, unless otherwise specified, a volume mixing ratio and % means wt % unless otherwise specified.

The elution by column chromatography in the Examples was performed under observation by TLC (Thin Layer Chromatography) unless otherwise specified. In the observation by TLC, 60 $F_{254}$ manufactured by Merck was used a saturated LC plate, the solvent used as an elution solvent in column chromatography was used as an eluent, and UV detector was used for the detection. In silica gel column chromatography, the indication of NH means use of aminopropylsilane-bonded silica gel and the indication of DIOL means use of 3-(2,3-dihydroxypropoxy)propylsilane-bonded silica gel. Preparative HPLC (high performance liquid chromatography) was performed under the following conditions; column: Boston Prime C18 (150 mm×30 mm, 5 μm), Xtimate C18 (100 mm×30 mm, 3 μm), Gemini NX C18 (150 mm×30 mm, 5 μm), YMC Triart C18 (250 mm×50 mm, 7 μm), Exsil plus C18 (150 mm×50 mm, 5 μm), or Water Xbridge C18 (150 mm×30 mm, 5 μm), mobile phase: aqueous ammonia/MeCN, water/MeCN (both containing 0.1% TFA), water containing ammonia hydroxide/MeCN. The indication of C18 means use of octadecyl-bonded silica gel. The ratio for elution solvent is, unless otherwise specified, a volume mixing ratio.

For the analysis of $^1$H NMR, ACD/SpecManager (trade name) software and the like were used. Peaks of a hydroxy group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

In the following Examples, the following abbreviations are used.
MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
Boc: tert-butoxycarbonyl
CPME: cyclopentyl methyl ether
DBU: 1,8-diazabicyclo[5.4.0]undec-7-ene
Dess Martin periodinane: 3-oxo-115-benzo[d] [1,2]iodaoxole-1,1,1(3H)-triyl triacetate
DMA: N,N-dimethylacetamide
DME: 1,2-dimethoxyethane
DMF: N,N-dimethylformamide
EtOAc: ethyl acetate
EtOH: ethanol
IPE: diisopropyl ether
MeCN: acetonitrile
MeOH: methanol
TEA: triethylamine
TFA: trifluoroacetic acid
THF: tetrahydrofuran
$Pd_2(dba)_3$: Tris(dibenzylideneacetone)dipalladium(0)

Example 1

N-{(6S,7aS)-2-[4-(2,6-Difluorophenyl)-1,2-benzoxazol-3-yl]-3-oxohexahydro-1H-pyrrolo[1,2-c]imidazol-6-yl}ethanesulfonamide A) 4-(2,6-Difluorophenyl)-1,2-benzoxazol-3-amine To a mixture of 4-Bromo-1,2-benzoxazol-3-amine (7.20 g), (2,6-difluorophenyl)boronic acid pinacol ester (24.3 g) and potassium fluoride (5.94 g) in DMA (60 mL) and water (15 mL) were added tri-tert-butylphosphonium tetrafluoroborate (0.986 g) and $Pd_2(dba)_3$ (1.55 g). The mixture was stirred at 120° C. for 3 h under argon atmosphere. After cooling, the mixture was diluted with water and extracted with THF/EtOAc. The extract was washed with water and brine and concentrated under reduced pressure. The residue was purified by silica gel column chromatography (EtOAc/hexane) to give the crude product. The crude was triturated with cold IPE, and the precipitate was collected by filtration to give the title compound (5.01 g).
MS: [M+H]$^+$ 247.0.

B) 2,2,2-Trichloroethyl [4-(2,6-difluorophenyl)-1,2-benzoxazol-3-yl]carbamate

To a mixture of 4-(2,6-difluorophenyl)-1,2-benzoxazol-3-amine (6.92 g) in THF (130 mL) was added 1 M Lithium bis(trimethylsilyl)amide THF solution (60 mL) at 0° C. The mixture was stirred at 0° C. for 30 min. To the mixture was added 2,2,2-trichloroethoxycarbonyl chloride (6.60 g) at 0° C. The mixture was stirred at 0° C. for 30 min. To the mixture were added ammonium chloride aqueous solution and EtOAc. The aqueous layer was separated and extracted with EtOAc. The organic layers were combined, washed with water and brine, dried over anhydrous sodium sulfate, and concentrated under reduced pressure. The residue was purified by silica gel column chromatography (EtOAc/hexane) to give the title compound (8.34 g).
MS: [M+H]+ 420.9.

C) 1-tert-Butyl 2-methyl (2S,4S)-4-[(ethanesulfonyl)amino]pyrrolidine-1,2-dicarboxylate Ethanesulfonyl chloride (7.54 mL) was added dropwise to a mixture of 1-(tert-butyl) 2-methyl (2S,4S)-4-aminopyrrolidine-1,2-dicarboxylate hydrochloride (15.9 g) and TEA (39.6 mL) in DME (189 mL) at 0° C. The mixture was stirred at room temperature overnight, then filtered to remove the insoluble material. The filtrate was diluted with EtOAc, washed with 1 M hydrogen chloride aqueous solution and brine, dried over anhydrous sodium sulfate, filtered, and concentrated under reduced pressure. The residue was purified by silica gel column chromatography (EtOAc/hexane) to give the title compound (18.4 g).
MS: [M+H-Boc]+ 237.1.

D) tert-Butyl (2S,4S)-4-[(ethanesulfonyl)amino]-2-(hydroxymethyl)pyrrolidine-1-carboxylate To a suspension of lithium aluminum hydride (0.36 g) in THF (30 mL) was added dropwise a solution of 1-tert-butyl 2-methyl (2S,4S)-4-[(ethanesulfonyl)amino]pyrrolidine-1,2-dicarboxylate (2.65 g) in THF (30.0 mL) at 0° C. under argon atmosphere. The mixture was stirred at 0° C. under argon atmosphere for 2 h. Saturated potassium sodium tartrate aqueous solution was added to the mixture at 0° C. The mixture was diluted with EtOAc and the organic layer was separated, washed with brine, dried over anhydrous sodium sulfate and concentrated under reduced pressure. The residue was purified by silica gel column chromatography (EtOAc/hexane) to give the title compound (2.18 g).
MS: [M+H-Boc]+ 209.1.

E) N-[(3S,5S)-5-(Hydroxymethyl)pyrrolidin-3-yl]ethanesulfonamide hydrochloride

A 4 M hydrogen chloride EtOAc solution (5 mL) was added to a solution of tert-butyl (2S,4S)-4-[(ethanesulfonyl)amino]-2-(hydroxymethyl)pyrrolidine-1-carboxylate (2.18 g) in EtOAc (5 mL) at room temperature. The mixture was stirred at room temperature overnight. A white solid formed and was collected by filtration to give the title compound (1.40 g).
1H NMR (300 MHz, DMSO-d6) δ 1.20 (3H, t, J=7.3 Hz), 1.58-1.71 (1H, m), 2.23-2.36 (1H, m), 2.88-3.17 (3H, m), 3.29-3.45 (1H, m), 3.51-3.71 (3H, m), 3.91-4.06 (1H, m), 5.39 (1H, br s), 7.56 (1H, d, J=7.5 Hz), 8.98 (1H, br s), 9.51 (1H, br S)

F) (2S,4S)—N-[4-(2,6-Difluorophenyl)-1,2-benzoxazol-3-yl]-4-[(ethanesulfonyl)amino]-2-(hydroxymethyl)pyrrolidine-1-carboxamide A mixture of 2,2,2-trichloroethyl [4-(2,6-difluorophenyl)-1,2-benzoxazol-3-yl]carbamate (0.7 g), N-[(3S,5S)-5-(hydroxymethyl)pyrrolidin-3-yl]ethanesulfonamide hydrochloride (0.406 g) and N,N-diisopropylethylamine (0.568 mL) in THF (8.30 mL) was stirred at 70° C. for 44 h. After cooling, the mixture was purified by silica gel column chromatography (MeOH/EtOAc) to give the title compound (0.39 g).
MS: [M+H]+ 481.1.

G) N-{(6S,7aS)-2-[4-(2,6-Difluorophenyl)-1,2-benzoxazol-3-yl]-3-oxohexahydro-1H-pyrrolo[1,2-c]imidazol-6-yl}ethanesulfonamide To a mixture of (2S,4S)—N-[4-(2,6-difluorophenyl)-1,2-benzoxazol-3-yl]-4-[(ethanesulfonyl)amino]-2-(hydroxymethyl)pyrrolidine-1-carboxamide (260 mg), TEA (0.302 mL) and THF (2.0 mL) was added methanesulfonyl chloride (0.084 mL) at 0° C. The mixture was stirred at room temperature for 30 min. The mixture was quenched with saturated ammonium chloride aqueous solution and extracted with EtOAc. The organic layer was separated, dried over anhydrous sodium sulfate, and concentrated under reduced pressure. The residue was dissolved in THF (2.0 mL). To the mixture was added 60% sodium hydride (23.8 mg) at 0° C. The mixture was stirred at 0° C. for 30 min. The mixture was quenched with saturated ammonium chloride aqueous solution at 0° C. and extracted with EtOAc. The organic layer was separated, washed with brine, dried over anhydrous magnesium sulfate, and concentrated under reduced pressure. The residue was purified by silica gel column chromatography (EtOAc/hexane). The solid was crystallized from EtOAc-heptane to give the title compound (82 mg).
1H NMR (300 MHz, CDCl3) δ 1.34 (3H, t, J=7.4 Hz), 1.45-1.53 (1H, m), 2.37-2.52 (1H, m), 2.95-3.13 (3H, m), 3.18-3.28 (1H, m), 3.77-3.94 (2H, m), 4.04-4.23 (3H, m), 6.95-7.08 (2H, m), 7.30-7.44 (2H, m), 7.58-7.70 (2H, m).

Example 16

N-{(6R)-7,7-Difluoro-3-oxo-2-[4-(2,4,6-trifluorophenyl)-1,2-benzoxazol-3-yl]-2,5,6,7-tetrahydro-3H-pyrrolo[1,2-c]imidazol-6-yl}methanesulfonamide A)
4-(2,4,6-Trifluorophenyl)-1,2-benzoxazol-3-amine A mixture of 4-bromo-1,2-benzoxazol-3-amine (10.0 g), (2,4,6-trifluorophenyl)boronic acid (33.0 g), Pd2(dba)3 (2.15 g), tri-tert-butylphosphonium tetrafluoroborate (1.36 g) and potassium fluoride (8.18 g) in DME (150 mL) and water (30.0 mL) was heated under argon atmosphere at 80° C. for 16 h. The solid was removed by filtration, and the filtrate was concentrated under reduced pressure to the half of the original volume. Water was added to the mixture. The mixture was extracted with EtOAc. The organic layer was separated, washed with brine, dried over anhydrous sodium sulfate, and concentrated under reduced pressure. The residue was purified by preparative HPLC (YMC-Actus Triant C18, mobile phase: water (containing 10 mM ammonium bicarbonate)/MeCN) to give the title compound (3.23 g).
MS: [M+H]+ 265.0.

B) 2,2,2-Trichloroethyl [4-(2,4,6-trifluorophenyl)-1,2-benzoxazol-3-yl]carbamate To a mixture of 4-(2,4,6-trifluorophenyl)-1,2-benzoxazol-3-amine (5.0 g) in THF (95 mL) was added 1 M lithium bis(trimethylsilyl)amide THF solution (47.3 mL) at 0° C. The mixture was stirred for 30 min. To the mixture was added 2,2,2-trichloroethoxycarbonyl chloride (2.79 mL). The mixture was stirred for 1 h. The mixture was quenched with saturated ammonium chloride aqueous solution and extracted with EtOAc. The organic layer was separated, washed with brine, dried over anhydrous sodium sulfate, and concentrated under reduced pressure. The residue was purified by silica gel column chromatography (EtOAc/hexane). The residue was recrystallized from IPE-hexane to give the title compound (5.72 g).

MS: [M+H]$^+$ 438.9.

C) 1-(Benzyloxy)-3,3-difluoropent-4-en-2-ol

To a solution of ((2,2-diethoxyethoxy)methyl)benzene (31.4 g) in THF (240 mL) and water (120 mL) was added 1 M hydrogen chloride aqueous solution (120 mL) at room temperature. The mixture was stirred at 70° C. for 2 h. To the mixture were added EtOAc and water at room temperature. The aqueous layer was separated and extracted with EtOAc. The combined organic layers were washed with brine, dried over anhydrous sodium sulfate and concentrated under reduced pressure to give a residue. To a mixture of the residue, 3-bromo-3,3-difluoroprop-1-ene (20.0 g) and DMF (240 mL) was added indium powder (16.1 g) at room temperature. The mixture was stirred at room temperature under argon atmosphere overnight. To the mixture were added EtOAc and water at 0° C. The aqueous layer was separated and extracted with EtOAc. The combined organic layers were washed with water and brine, dried over anhydrous sodium sulfate, and concentrated under reduced pressure. The residue was purified by silica gel column chromatography (EtOAc/hexane) to give the title compound (27.2 g).

$^1$H NMR (300 MHz, CDCl$_3$) δ 2.62 (1H, d, J=4.9 Hz), 3.56-3.75 (2H, m), 3.96-4.10 (1H, m), 4.58 (2H, s), 5.50-5.57 (1H, m), 5.68-5.77 (1H, m), 5.91-6.09 (1H, m), 7.28-7.40 (5H, m).

D) tert-Butyl [1-(benzyloxy)-3,3-difluoropent-4-en-2-yl]carbamate

To a mixture of 1-(benzyloxy)-3,3-difluoropent-4-en-2-ol (27.1 g) and pyridine (77 mL) in MeCN (400 mL) was added trifluoromethanesulfonic anhydride (28 mL) at 0° C. The mixture was stirred under argon atmosphere at 0° C. for 30 min. To the mixture were added EtOAc and water at 0° C. The aqueous layer was separated and extracted with EtOAc. The combined organic layers were washed with water and brine, dried over anhydrous sodium sulfate and concentrated under reduced pressure. The residue was diluted with MeCN (400 mL). To the mixture was added tetra-n-butylammonium azide (66.9 g) at 0° C. The mixture was stirred under argon atmosphere at room temperature overnight. To the mixture were added EtOAc-toluene and water. The aqueous layer was separated, and the organic phase was washed with water and 1 M hydrogen chloride aqueous solution, filtered through a silica gel pad and concentrated under reduced pressure. To this residue was added water (40 mL) at room temperature. To the mixture was slowly added a mixture of triphenylphosphine (34.3 g) and toluene (40 mL). The mixture was stirred at 70° C. for 5 h. After cooling, to the mixture were added di-tert-butyl dicarbonate (41.0 mL) and sodium hydrogen carbonate (11.0 g) at room temperature. The mixture was stirred at room temperature overnight. To the mixture was added water at room temperature. The organic layer was separated, washed with water and brine, dried over anhydrous sodium sulfate and concentrated under reduced pressure. The residue was purified by silica gel column chromatography (EtOAc/hexane) to give the title compound (37.3 g).

MS: [M+1-Boc]$^+$ 228.1

E) 1-O-Benzyl-2-[(tert-butoxycarbonyl)amino]-2,3-dideoxy-3,3-difluoropentitol To a mixture of tert-butyl [1-(benzyloxy)-3,3-difluoropent-4-en-2-yl]carbamate (37.3 g) and 4-methylmorpholine 4-oxide (26.7 g), acetone (360 mL) and water (36 mL) was added 4% osmium (VIII) oxide in water (40 g) at room temperature. The mixture was stirred under argon atmosphere overnight. To the mixture were added EtOAc and 10% sodium thiosulfate aqueous solution at 0° C. The aqueous layer was separated and extracted with EtOAc. The combined organic layers were washed with 0.1 M hydrogen chloride aqueous solution and brine, dried over anhydrous sodium sulfate, then filtered through a silica gel pad, and concentrated under reduced pressure to give the title compound (42.1 g).

MS: [M+1-Boc]$^+$ 262.1

F) rac-tert-Butyl (2R,4S)-2-[(benzyloxy)methyl]-3,3-difluoro-4-hydroxypyrrolidine-1-carboxylate To a mixture of 1-O-benzyl-2-[(tert-butoxycarbonyl)amino]-2,3-dideoxy-3,3-difluoropentitol (42.0 g), 2,8-dimethyl-10H-dibenzo[b,e][1,4]oxaborinin-10-ol (1.30 g) and N,N-diisopropylethylamine (30 mL) in MeCN (300 mL) was added a solution of toluenesulfonyl chloride (24.4 g) in MeCN (100 mL) at room temperature. The mixture was stirred at room temperature under argon atmosphere for 1 h. To the mixture were added EtOAc, toluene and water at 0° C. The organic layer was separated, washed with 10% citric acid aqueous solution and brine, and concentrated under reduced pressure. To this residue was added toluene (300 mL) and TFA (300 mL) at 0° C. The mixture was stirred at room temperature for 30 min. The mixture was concentrated under reduced pressure. The residue was diluted with MeOH (400 mL). To the mixture was added sodium carbonate (49.3 g) at 0° C. The mixture was stirred at room temperature overnight. To the mixture was added 10% acetic acid aqueous solution (300 mL) at 0° C. The mixture was concentrated under reduced pressure, then was diluted with toluene and EtOAc. The organic layer was separated and extracted with 20% acetic acid aqueous solution. The combined aqueous layers were quenched with potassium carbonate at 0° C. adjusting to pH 10. The aqueous layer was extracted with THF-EtOAc. The combined organic layers were dried over anhydrous sodium sulfate and concentrated under reduced pressure. To the residue were added toluene (300 mL), water (300 mL), sodium carbonate (24.6 g) and di-tert-butyl dicarbonate (32.0 mL) at room temperature. The mixture was stirred at room temperature for 1 h. The aqueous layer was separated and extracted with toluene. The combined organic layers were washed with brine and concentrated under reduced pressure. The residue was purified by silica gel column chromatography (EtOAc/hexane) to give the title compound (11.9 g).

MS: [M+1-Boc]$^+$ 244.0

G) rac-tert-Butyl (2R,4R)-4-azido-2-[(benzyloxy)methyl]-3,3-difluoropyrrolidine-1-carboxylate To a mixture of rac-tert-butyl (2R,4S)-2-[(benzyloxy)methyl]-3,3-difluoro-4-hydroxypyrrolidine-1-carboxylate (11.9 g) and pyridine (22.3 mL) in MeCN (120 mL) was added trifluoromethanesulfonic anhydride (11.7 mL) at 0° C. The mixture was stirred at 0° C. under nitrogen atmosphere for 30 min. To the mixture were added EtOAc and water at 0° C. The organic layer was separated, washed with 10% citric acid aqueous solution, water, and brine, dried over anhydrous sodium sulfate, and concentrated under reduced pressure. The residue was diluted with DMF (120 mL). To the mixture was added tetra-n-butylammonium azide (21.6 g) at 0° C. The mixture was stirred at 0° C. under nitrogen atmosphere for 30 min, then at room temperature overnight. To the mixture were added EtOAc and water at 0° C. The combined organic layers were washed with water and brine, dried over anhydrous sodium sulfate and concentrated under reduced pressure. The residue was purified by silica gel column chromatography (EtOAc/hexane) to give the title compound (5.65 g).

MS: [M+1-Boc]$^+$ 269.1

H) rac-tert-Butyl (2R,4R)-4-amino-2-[(benzyloxy)methyl]-3,3-difluoropyrrolidine-1-carboxylate To a mixture of rac-tert-butyl (2R,4R)-4-azido-2-[(benzyloxy)methyl]-3,3-difluoropyrrolidine-1-carboxylate (5.65 g) and THF (50 mL) was slowly added a solution of triphenylphosphine (4.83 g) in THF (10 mL) at room temperature. The mixture was stirred at room temperature for 1 h. To the mixture was added water (30 mL), then the mixture was heated to 50° C. The mixture was stirred at 50° C. overnight. To the mixture were added EtOAc and brine at room temperature. The aqueous layer was separated and extracted with EtOAc. The organic layers were combined, washed with brine, dried over anhydrous sodium sulfate, and concentrated under reduced pressure. The residue was purified by silica gel column chromatography (EtOAc/hexane) to give the title compound (4.98 g).

MS: [M+1-Boc]$^+$ 243.1

I) tert-Butyl (2R,4R)-4-amino-2-[(benzyloxy)methyl]-3,3-difluoropyrrolidine-1-carboxylate rac-tert-Butyl (2R,4R)-4-amino-2-[(benzyloxy)methyl]-3,3-difluoropyrrolidine-1-carboxylate (16.0 g) was resolved by SFC (column: DAICEL CHIRALPAK AY, 250 mm×50 mm, 10 μm, mobile phase: CO$_2$/0.1% ammonium hydroxide containing EtOH=75/25 v/v) to give the title compound (7.12 g) having a longer retention time.

MS: [M+1]$^+$ 343.2

J) tert-Butyl (2R,4R)-2-[(benzyloxy)methyl]-3,3-difluoro-4-[(methanesulfonyl)amino]pyrrolidine-1-carboxylate To a solution of tert-butyl (2R,4R)-4-amino-2-[(benzyloxy)methyl]-3,3-difluoropyrrolidine-1-carboxylate (5.37 g) and TEA (10.9 mL) in DME (52.3 mL) was added methanesulfonyl chloride (1.86 mL) dropwise at 0° C. The mixture was stirred at 0° C. for 15 min, then at room temperature overnight. To the mixture were added EtOAc and water at room temperature. The aqueous layer was separated and extracted with EtOAc. The organic layers were combined, washed with water and brine, dried over anhydrous sodium sulfate and concentrated under reduced pressure. The residue was purified by silica gel column chromatography (EtOAc/hexane) to give the title compound (5.84 g).

MS: [M−H]$^+$ 419.0.

K) tert-Butyl (2R,4R)-3,3-difluoro-2-(hydroxymethyl)-4-[(methanesulfonyl)amino]pyrrolidine-1-carboxylate A mixture of tert-butyl (2R,4R)-2-[(benzyloxy)methyl]-3,3-difluoro-4-[(methanesulfonyl)amino]pyrrolidine-1-carboxylate (5.84 g) and 20% palladium hydroxide on carbon (1.18 g) in MeOH (120 mL) was hydrogenated under balloon pressure at 20° C. for 15 h. The catalyst was removed by filtration and the solution was concentrated under reduced pressure to give the title compound (4.45 g).

MS: [M−H]$^+$ 329.0.

L) N-[(3R,5R)-4,4-Difluoro-5-(hydroxymethyl)pyrrolidin-3-yl]methanesulfonamide hydrochloride To a mixture of tert-butyl (2R,4R)-3,3-difluoro-2-(hydroxymethyl)-4-[(methanesulfonyl)amino]pyrrolidine-1-carboxylate (4.45 g) and EtOAc (16 mL) was added 4 M hydrogen chloride CPME solution (56 mL) at 0° C. The mixture was stirred at room temperature under nitrogen atmosphere for 2 h. The volatiles were removed under reduced pressure to give the title compound (3.40 g).

$^1$H NMR (400 MHz, DMSO-d$_6$) δ 3.01 (3H, s), 3.04-3.13 (1H, m), 3.68-3.88 (3H, m), 3.96-4.12 (1H, m), 4.49-4.64 (1H, m), 5.44-5.62 (1H, m), 8.07 (1H, d, J=8.9 Hz), 9.50-10.23 (2H, m).

M) (2R,4R)-3,3-Difluoro-2-(hydroxymethyl)-4-[(methanesulfonyl) amino]-N-[4-(2,4,6-trifluorophenyl)-1,2-benzoxazol-3-yl]pyrrolidine-1-carboxamide A mixture of N-[(3R,5R)-4,4-difluoro-5-(hydroxymethyl) pyrrolidin-3-yl]methanesulfonamide hydrochloride (2.50 g), 2,2,2-trichloroethyl [4-(2,4,6-trifluorophenyl)-1,2-benzoxazol-3-yl]carbamate (5.60 g), TEA (3.93 mL) and THF (75 mL) was stirred at room temperature for 2 h, then heated at 60° C. under argon atmosphere overnight. The mixture was filtered and washed with EtOAc. The filtrate was concentrated under reduced pressure. The residue was purified by silica gel column chromatography (EtOAc/hexane) to give the title compound (3.47 g).

MS: [M+H]$^+$ 521.1.

N) N-{(6R,7aR)-7,7-Difluoro-1-hydroxy-3-oxo-2-[4-(2,4,6-trifluorophenyl)-1,2-benzoxazol-3-yl]hexahydro-1H-pyrrolo[1,2-c]imidazol-6-yl}methanesulfonamide A mixture of (2R,4R)-3,3-difluoro-2-(hydroxymethyl)-4-[(methanesulfonyl)amino]-N-[4-(2,4,6-trifluorophenyl)-1,2-benzoxazol-3-yl]pyrrolidine-1-carboxamide (387 mg), sodium hydrogen carbonate (312 mg) in MeCN (7.5 mL) and water (7.50 mL) was stirred at 0° C. for 5 min. To the mixture were added tetra-n-butylammonium bromide (47.9 mg), 2,2,6,6-tetramethylpiperidine 1-oxyl (23.2 mg) and iodosobenzene I,I-diacetate (263 mg) at 0° C. The mixture was vigorously stirred at 0° C. for 5 min, then at room temperature for 15 min. To the mixture were added EtOAc and water at 0° C. The aqueous layer was separated and extracted with EtOAc. The organic layers were combined, washed with water and brine, dried over anhydrous sodium sulfate, and concentrated under reduced pressure. The residue was purified by silica gel column chromatography (EtOAc/hexane) to give the title compound (279 mg).

MS: [M+H]$^+$ 519.1.

O) N-{(6R)-7,7-Difluoro-3-oxo-2-[4-(2,4,6-trifluorophenyl)-1,2-benzoxazol-3-yl]-2,5,6,7-tetrahydro-3H-pyrrolo[1,2-c]imidazol-6-yl}methanesulfonamide Trifluoroacetic anhydride (0.152 mL) was added to a solution of N-{(6R,7aR)-7,7-difluoro-1-hydroxy-3-oxo-2-[4-(2,4,6-trifluorophenyl)-1,2-benzoxazol-3-yl]hexahydro-1H-pyrrolo[1,2-c]imidazol-6-yl}methanesulfonamide (279 mg) in TFA (7.5 mL) at room temperature. The mixture was stirred at 40° C. for 16 h and then at room temperature over the weekend. The mixture was concentrated under reduced pressure, then the residue was diluted with EtOAc. To the mixture was added saturated sodium hydrogen carbonate aqueous solution. The solution was extracted with EtOAc/THF. The combined organic layer was dried over anhydrous sodium sulfate, filtered, and concentrated under reduced pressure. The residue was crystallized from EtOAc and two pure crops of the precipitate were recovered. The residue oil was purified by silica gel column chromatography (EtOAc/hexane). The pure fractions were combined with the precipitate already obtained. The material was recrystallized from EtOH/heptane to give the title compound (165 mg).

$^1$H NMR (400 MHz, CDCl$_3$) δ 3.15 (3H, s), 3.22 (1H, dd, J=11.1, 8.6 Hz), 4.13 (1H, dd, J=11.0, 8.7 Hz), 4.63-4.76 (1H, m), 4.95-5.02 (1H, m), 6.64-6.84 (3H, m), 7.37-7.43 (1H, m), 7.71-7.80 (2H, m).

Example 24

N-{(6R,7aR)-7,7-Difluoro-3-oxo-2-[4-(2,4,6-trifluorophenyl)-1,2-benzoxazol-3-yl]hexahydro-1H-pyrrolo[1,2-c]imidazol-6-yl}ethanesulfonamide A) tert-Butyl (2R,4R)-2-[(benzyloxy)methyl]-4-[(ethanesulfonyl)amino]-3,3-difluoropyrrolidine-1-carboxylate To a mixture of tert-butyl (2R,4R)-4-amino-2-[(benzyloxy)methyl]-3,3-difluoropyrrolidine-1-carboxylate (2.00 g) and TEA (4.05 mL) in DME (19.5 mL) was added ethanesulfonyl chloride (0.773 mL) at 0° C. The mixture was stirred at 0° C. for 15 min, then stirred at room temperature overnight. To the mixture were added EtOAc and water at room temperature. The aqueous layer was separated and extracted with EtOAc. The organic layers were combined, washed with water and brine, dried over anhydrous sodium sulfate and concentrated under reduced pressure. The residue was purified by silica gel column chromatography (EtOAc/hexane) to give the title compound (2.56 g).

MS: [M+H-Boc]$^+$ 335.1.

B) N-[(3R,5R)-4,4-Difluoro-5-(hydroxymethyl)pyrrolidin-3-yl]ethanesulfonamide hydrochloride A mixture of tert-butyl (2R,4R)-2-[(benzyloxy)methyl]-4-[(ethanesulfonyl)amino]-3,3-difluoropyrrolidine-1-carboxylate (2.56 g) and 20% palladium hydroxide on carbon (663 mg) in MeOH (29.5 mL) was hydrogenated under balloon pressure at room temperature overnight. The catalyst was removed by filtration and the filtrate was concentrated under reduced pressure to give a residue. To a mixture of the residue and EtOAc (4 mL) was added 4 M hydrogen chloride EtOAc solution (20 mL) at 0° C. The mixture was stirred at room temperature for 5 h. The mixture was concentrated under reduced pressure. The residue was triturated with EtOAc and the white solid was collected by filtration and washed with EtOAc to give the title compound (1.50 g).

MS: [M+H]$^+$ 245.1.

C) (2R,4R)-4-[(Ethanesulfonyl)amino]-3,3-difluoro-2-(hydroxymethyl)-N-[4-(2,4,6-trifluorophenyl)-1,2-benzoxazol-3-yl]pyrrolidine-1-carboxamide To a mixture of N-[(3R,5R)-4,4-difluoro-5-(hydroxymethyl)pyrrolidin-3-yl]ethanesulfonamide hydrochloride (1.78 g) and TEA (1.93 g) in THF (50 mL) was added 2,2,2-trichloroethyl [4-(2,4,6-trifluorophenyl)-1,2-benzoxazol-3-yl]carbamate (3.34 g) at 0° C. The mixture was stirred at 60° C. for 15 h. The mixture was concentrated under reduced pressure. The residue was diluted with EtOAc and filtered. The filtrate was concentrated under reduced pressure. The residue was purified by silica gel column chromatography (EtOAc/hexane) to give the title compound (3.14 g).

MS: [M+H]$^+$ 535.1.

D) N-{(6R,7aR)-7,7-Difluoro-3-oxo-2-[4-(2,4,6-trifluorophenyl)-1,2-benzoxazol-3-yl]hexahydro-1H-pyrrolo[1,2-c]imidazol-6-yl}ethanesulfonamide To a mixture of (2R,4R)-4-[(ethanesulfonyl)amino]-3,3-difluoro-2-(hydroxymethyl)-N-[4-(2,4,6-trifluorophenyl)-1,2-benzoxazol-3-yl]pyrrolidine-1-carboxamide (3.14 g) and methanesulfonyl chloride (1.35 g) in dichloromethane (30 mL) was added DBU (2.68 g) at 0° C. The mixture was stirred at room temperature for 1 h. To the mixture was added DBU (1.34 g) at room temperature. The mixture was stirred at room temperature for 1 h. The mixture was concentrated under reduced pressure. To the mixture was added saturated ammonium chloride aqueous solution at room temperature. The mixture was extracted with EtOAc. The organic layer was separated, washed with water and brine, dried over anhydrous magnesium sulfate and concentrated under reduced pressure. The residue was purified by silica gel column chromatography (EtOAc/hexane), followed by NH-silica gel column chromatography (EtOAc/hexane). The residue was recrystallized from EtOAc-heptane to give the title compound (1.58 g).

$^1$H NMR (300 MHz, DMSO-d$_6$) δ 1.20 (3H, t, J=7.3 Hz), 2.96-3.14 (3H, m), 3.40-3.53 (1H, m), 3.97-4.10 (1H, m), 4.15-4.26 (1H, m), 4.37-4.71 (2H, m), 7.18-7.28 (1H, m), 7.29-7.38 (1H, m), 7.40-7.48 (1H, m), 7.78-7.86 (1H, m), 7.88-7.94 (1H, m), 7.99 (1H, br s).

Example 33

N-{(6R,7aR)-2-[4-(2,6-Difluorophenyl)-1,2-benzoxazol-3-yl]-7,7-difluoro-3-oxohexahydro-1H-pyrrolo[1,2-c]imidazol-6-yl}ethanesulfonamide A) (2R,4R)—N-[4-(2,6-Difluorophenyl)-1,2-benzoxazol-3-yl]-4-[(ethanesulfonyl)amino]-3,3-difluoro-2-(hydroxymethyl)pyrrolidine-1-carboxamide To a mixture of 4-(2,6-difluorophenyl)-1,2-benzoxazol-3-amine (200 mg) in THF (4 mL) were added 1 M lithium bis(trimethylsilyl)amide toluene solution (1.63 mL) and 2,2,2-trichloroethoxycarbonyl chloride (0.120 mL) at 0° C. After being stirred for 1 h, the mixture was quenched with saturated ammonium chloride aqueous solution and extracted with EtOAc. The organic layer was separated, dried over anhydrous sodium sulfate and concentrated under reduced pressure. The residue was dissolved in THF (4 mL). To the mixture were added N-[(3R,5R)-4,4-difluoro-5-(hydroxymethyl)pyrrolidin-3-yl]ethanesulfonamide hydrochloride (228 mg) and DBU (371 mg) at 60° C. After being stirred for 16 h, the mixture was concentrated under reduced pressure. The residue was purified by preparative HPLC (YMC-Actus Triant C18, mobile phase: water (containing 10 mM ammonium bicarbonate)/MeCN) to give the title compound (252 mg).
MS: [M+H]$^+$ 517.1.

B) N-{(6R,7aR)-2-[4-(2,6-Difluorophenyl)-1,2-benzoxazol-3-yl]-7,7-difluoro-3-oxohexahydro-1H-pyrrolo[1,2-c]imidazol-6-yl}ethanesulfonamide To a mixture of (2R,4R)—N-[4-(2,6-difluorophenyl)-1,2-benzoxazol-3-yl]-4-[(ethanesulfonyl)amino]-3,3-difluoro-2-(hydroxymethyl)pyrrolidine-1-carboxamide (252 mg) in dichloromethane (2.0 mL) were added DBU (0.22 mL) and methanesulfonyl chloride (0.057 mL) at room temperature. The mixture was stirred for 30 min. To the reaction mixture was added DBU (0.22 mL). The mixture was quenched with saturated ammonium chloride aqueous solution and extracted with EtOAc. The organic layer was separated, dried over anhydrous sodium sulfate, and concentrated under reduced pressure. The residue was purified by silica gel column chromatography (EtOAc/hexane). The residue was crystallized from EtOH/hexane to give the title compound (72.2 mg).
$^1$H NMR (400 MHz, CDCl$_3$) δ 1.41 (3H, t, J=7.3 Hz), 3.02-3.15 (3H, m), 3.66-3.79 (1H, m), 4.04-4.21 (2H, m), 4.30-4.42 (2H, m), 4.50 (1H, br d, J=9.3 Hz), 6.95-7.05 (2H, m), 7.30-7.41 (2H, m), 7.61-7.70 (2H, m).

Example 34

N-{(6R,7aR)-2-[4-(2,6-Difluorophenyl)-1,2-benzoxazol-3-yl]-7,7-difluoro-3-oxohexahydro-1H-pyrrolo[1,2-c]imidazol-6-yl}methanesulfonamide A) (2R,4R)—N-[4-(2,6-Difluorophenyl)-1,2-benzoxazol-3-yl]-3,3-difluoro-2-(hydroxymethyl)-4-[(methanesulfonyl)amino]pyrrolidine-1-carboxamide A mixture of N-[(3R,5R)-4,4-difluoro-5-(hydroxymethyl)pyrrolidin-3-yl]methanesulfonamide hydrochloride (300 mg), 2,2,2-trichloroethyl [4-(2,6-difluorophenyl)-1,2-benzoxazol-3-yl]carbamate (484 mg), DBU (0.504 mL) and THF (10 mL) was heated at 70° C. for 2 h under microwave irradiation. To the mixture were added EtOAc and water. The aqueous layer was separated and extracted with EtOAc. The organic layers were combined, washed with brine, dried over anhydrous sodium sulfate, and concentrated under reduced pressure. The residue was purified by silica gel column chromatography (EtOAc/hexane) to give the title compound (408 mg).
MS: [M+H]$^+$ 503.1.

B) N-{(6R,7aR)-2-[4-(2,6-Difluorophenyl)-1,2-benzoxazol-3-yl]-7,7-difluoro-3-oxohexahydro-1H-pyrrolo[1,2-c]imidazol-6-yl}methanesulfonamide To a mixture of (2R,4R)—N-[4-(2,6-difluorophenyl)-1,2-benzoxazol-3-yl]-3,3-difluoro-2-(hydroxymethyl)-4-[(methanesulfonyl)amino]pyrrolidine-1-carboxamide (122 mg) and methanesulfonyl chloride (0.038 mL) in dichloromethane (1.0 mL) was added DBU (0.109 mL) at room temperature. The mixture was stirred at room temperature for 30 min. To the mixture was added DBU (54 μL) at room temperature. The mixture was stirred at room temperature for 30 min. The residue was purified by silica gel column chromatography (EtOAc/hexane). The residue was crystallized from EtOAc-hexane to give the title compound (43.6 mg).
$^1$H NMR (400 MHz, CDCl$_3$) δ 3.04-3.11 (4H, m), 3.58 (1H, dd, J=12.2, 8.9 Hz), 4.06-4.24 (2H, m), 4.30-4.48 (2H, m), 4.51-4.60 (1H, m), 6.99 (2H, br d, J=4.4 Hz), 7.32-7.36 (2H, m), 7.61-7.71 (2H, m)

Example 47

N-{(6R,7aR)-7,7-Difluoro-2-[5-fluoro-4-(2,4,6-trifluorophenyl)-1,2-benzoxazol-3-yl]-3-oxohexahydro-1H-pyrrolo[1,2-c]imidazol-6-yl}methanesulfonamide A) 2-Bromo-3,6-difluorobenzaldehyde To a mixture of 1-bromo-2,5-difluorobenzene (50.0 g) and THF (250 mL) was dropwise added 2 M lithium diisopropylamide THF solution (155 mL) at −70° C. After the reaction mixture was stirred at the same temperature for 45 min, DMF (38.4 g) was added. The reaction solution was stirred at the same temperature for 2 h. Saturated ammonium chloride aqueous solution was added to the reaction mixture at 0° C. The mixture was diluted with water and extracted with EtOAc. The organic layer was washed with brine, dried over anhydrous sodium sulfate, filtered, and concentrated under reduced pressure. The residue was purified by silica gel column chromatography (EtOAc/petroleum ether) to give the title compound (46.0 g).
$^1$H NMR (400 MHz, CDCl$_3$) δ 7.16-7.20 (1H, m), 7.24-7.40 (1H, m), 10.33 (1H, s).

B) 2-Bromo-3,6-difluorobenzonitrile

A mixture of 2-bromo-3,6-difluorobenzaldehyde (46.0 g), iodobenzene diacetate (100 g), ammonium acetate (80.2 g) and sodium dodecyl sulfate (12.0 g) in water (200 mL) was stirred at 70° C. for 0.5 h. Sodium thiosulfate aqueous solution was added to the reaction mixture, and the mixture was stirred at 25° C. for 15 min. The mixture was diluted with water and extracted with dichloromethane. The combined organic layer was washed with brine, dried over anhydrous sodium sulfate, and concentrated under reduced pressure. The residue was purified by silica gel column chromatography (EtOAc/petroleum ether) to give the title compound (36.6 g).
$^1$H NMR (400 MHz, CDCl$_3$) δ 7.12-7.26 (1H, m), 7.26-7.45 (1H, m).

C) 4-Bromo-5-fluorobenzo[d]isoxazol-3-amine

To a solution of acetohydroxamic acid (18.6 g) in DMF (300 mL) and water (60 mL) was added potassium carbonate (34.2 g). After the mixture was stirred at 25° C. for 2 h, a solution of 2-bromo-3,6-difluorobenzonitrile (18.0 g) in DMF (60 mL) was added and the resulting mixture was stirred at 60° C. for 18 h. The reaction mixture was quenched by water at 0° C., then the precipitate was collected to give the title compound (14.1 g).

¹H NMR (400 MHz, DMSO-d₆) δ 6.12 (2H, s), 7.45-7.62 (2H, m).

D) 5-Fluoro-4-(2,4,6-trifluorophenyl)-1,2-benzoxazol-3-amine

To a solution of 4-bromo-5-fluorobenzo[d]isoxazol-3-amine (12.5 g) in DME (200 mL) and water (20 mL) were added 2,4,6-trifluorophenylboronic acid (47.6 g), potassium fluoride (9.43 g), tri-tert-butylphosphonium tetrafluoroborate (3.14 g) and Pd₂(dba)₃ (4.95 g). The mixture was stirred at 110° C. under nitrogen atmosphere for 16 h. The mixture was diluted with water and extracted with EtOAc. The organic layers were washed with brine, dried over sodium sulfate, filtered, and concentrated under reduced pressure. The residue was purified by silica gel column chromatography (EtOAc/petroleum ether) to give the title compound (9.1 g).
MS: [M+H]⁺ 283.0.

E) 2,2,2-Trichloroethyl [5-fluoro-4-(2,4,6-trifluorophenyl)-1,2-benzoxazol-3-yl]carbamate To a solution of 5-fluoro-4-(2,4,6-trifluorophenyl)-1,2-benzoxazol-3-amine (2.85 g) in THF (33.7 mL) was added dropwise 1 M lithium bis(trimethylsilyl)amide THF solution (22.2 mL) at 0° C. The mixture was stirred at the same temperature for 10 min. To the mixture was added dropwise 2,2,2-trichloroethoxycarbonyl chloride (1.53 mL) keeping the temperature below 5° C. The mixture was stirred at 0° C. for 30 min. The mixture was quenched with saturated ammonium chloride solution at 0° C. and extracted with EtOAc. The organic layer was separated, washed with brine, dried over anhydrous magnesium sulfate, and concentrated under reduced pressure. The resulting solid was triturated with 10% EtOAc in hexane. The solid was removed by filtration and the filtrate was purified by silica gel column chromatography (EtOAc/hexane) to give the title compound (3.64 g).
MS: [M+H]⁺ 456.9.

F) (2R,4R)-3,3-Difluoro-N-[5-fluoro-4-(2,4,6-trifluorophenyl)-1,2-benzoxazol-3-yl]-2-(hydroxymethyl)-4-[(methanesulfonyl)amino]pyrrolidine-1-carboxamide To a mixture of 2,2,2-trichloroethyl [5-fluoro-4-(2,4,6-trifluorophenyl)-1,2-benzoxazol-3-yl]carbamate (6.50 g), N-[(3R,5R)-4,4-difluoro-5-(hydroxymethyl)pyrrolidin-3-yl]methanesulfonamide hydrochloride (3.79 g) in THF (142 mL) was added TEA (5.91 mL) at room temperature. The mixture was stirred at 60° C. overnight under nitrogen atmosphere. The mixture was diluted with EtOAc, the insoluble material was removed by filtration, and the filtrate was concentrated under reduced pressure. The residue was purified by silica gel column chromatography (EtOAc/hexane) to give the title compound (6.78 g).
MS: [M+H]⁺ 539.1.

G) N-{(6R,7aR)-7,7-Difluoro-2-[5-fluoro-4-(2,4,6-trifluorophenyl)-1,2-benzoxazol-3-yl]-3-oxohexahydro-1H-pyrrolo[1,2-c]imidazol-6-yl}methanesulfonamide To a solution of (2R,4R)-3,3-difluoro-N-[5-fluoro-4-(2,4,6-trifluorophenyl)-1,2-benzoxazol-3-yl]-2-(hydroxymethyl)-4-[(methanesulfonyl)amino]pyrrolidine-1-carboxamide (60 mg) in dichloromethane (1.0 mL) were added DBU (0.05 mL) and methanesulfonyl chloride (0.013 mL) at room temperature and the mixture was stirred for 30 min. The mixture was concentrated under reduced pressure. The residue was purified by silica gel column chromatography (EtOAc/hexane). The residue was purified by preparative HPLC (YMC-Actus Triant C18, mobile phase: water/MeCN (both containing 0.1% TFA)) to give the title compound (27.2 mg).
¹H NMR (400 MHz, CDCl₃) δ 3.07 (3H, s), 3.09-3.14 (1H, m), 3.64 (1H, dd, J=12.2, 9.0 Hz), 4.10-4.22 (2H, m), 4.34-4.54 (2H, m), 4.61 (1H, br d, J=9.4 Hz), 6.71-6.84 (2H, m), 7.38-7.49 (1H, m), 7.63 (1H, dd, J=9.2, 3.7 Hz).

Example 50

N-{(6S,7aS)-2-[6-Chloro-4-(2,6-difluorophenyl)-1,2-benzoxazol-3-yl]-3-oxohexahydro-1H-pyrrolo[1,2-c]imidazol-6-yl}ethanesulfonamide

A) 4-Chloro-2-fluoro-6-iodobenzonitrile

A mixture of 4-chloro-2-fluorobenzonitrile (10 g), N-iodosuccinimide (15.9 g), 4-methylbenzenesulfonic acid monohydrate (6.11 g) and palladium(II) acetate (1.44 g) in DMF (150 mL) was stirred at 70° C. for 6 h. After cooling to room temperature, the mixture was poured into water and extracted with EtOAc. The combined organic layers were washed with sodium thiosulfate aqueous solution and brine, dried over anhydrous sodium sulfate, filtered, and concentrated under reduced pressure. The residue was purified by silica gel column chromatography (EtOAc/hexane) to give the title compound (7.78 g).
¹H NMR (400 MHz, DMSO-d₆) δ 7.82-7.88 (1H, m), 8.08 (1H, s).

B) 6-Chloro-4-iodo-1,2-benzoxazol-3-amine

To a mixture of 2-propanone oxime (1.94 g) and DMF (58.5 mL) was added potassium tert-butoxide (2.98 g) at room temperature. The mixture was stirred at room temperature under nitrogen atmosphere for 20 min. The mixture was added to a mixture of 4-chloro-2-fluoro-6-iodobenzonitrile (7.13 g) and DMF (19.5 mL) at 0° C. The mixture was stirred at 0° C. under nitrogen atmosphere for 5 min. The mixture was quenched with saturated ammonium chloride aqueous solution at 0° C. and extracted with EtOAc. The organic layer was separated, washed with brine, dried over anhydrous magnesium sulfate and concentrated under reduced pressure. The residue was diluted with EtOH (175 mL) and 6 M hydrogen chloride aqueous solution (60.8 mL). The mixture was stirred at 80° C. under nitrogen atmosphere overnight. The mixture was concentrated under reduced pressure. To the residue were added 8 M sodium hydroxide aqueous solution and saturated sodium hydrogen carbonate aqueous solution at 0° C. The precipitate was collected by filtration, and the solid was washed with water and IPE to give the title compound (4.70 g).
MS: [M+H]⁺ 294.9.

C) 6-Chloro-4-(2,6-difluorophenyl)-1,2-benzoxazol-3-amine

To a mixture of 6-chloro-4-iodo-1,2-benzoxazol-3-amine (5.0 g), (2,6-difluorophenyl)boronic acid, pinacol ester (12.2 g) and potassium carbonate (2.96 g) in DMA (34.0 mL) and water (8.50 mL) were added tri-tert-butylphosphonium tetrafluoroborate (0.493 g) and Pd$_2$(dba)$_3$ (0.777 g). The mixture was stirred at 90° C. under argon atmosphere for 30 min. After cooling, the mixture was diluted with water and extracted with EtOAc. The organic layer was separated, washed with water and brine, dried over anhydrous magnesium sulfate and concentrated under reduced pressure. The residue was triturated with IPE and the solid was recovered by filtration to give the tile compound (1.70 g).

MS: [M+H]$^+$ 281.0.

D) 2,2,2-Trichloroethyl [6-chloro-4-(2,6-difluorophenyl)-1,2-benzoxazol-3-yl]carbamate 1 M Lithium bis(trimethylsilyl)amide THF solution (36.2 mL) was added to a solution of 6-chloro-4-(2,6-difluorophenyl)-1,2-benzoxazol-3-amine (3.91 g) in THF (69.7 mL) at 0° C. The mixture was stirred at 0° C. under argon atmosphere for 30 min. 2,2,2-Trichloroethoxycarbonyl chloride (3.16 mL) was added to the mixture at 0° C. The mixture was stirred at 0° C. under argon atmosphere for 1 h. The mixture was quenched with saturated ammonium chloride aqueous solution at 0° C. and extracted with EtOAc. The organic layer was separated, washed with brine, dried over anhydrous sodium sulfate and concentrated under reduced pressure. The residue was purified by silica gel column chromatography (EtOAc/hexane) to give the title compound (3.80 g).

MS: [M+H]$^+$ 454.9.

E) (2S,4S)—N-[6-Chloro-4-(2,6-difluorophenyl)-1,2-benzoxazol-3-yl]-4-[(ethanesulfonyl) amino]-2-(hydroxymethyl)pyrrolidine-1-carboxamide A mixture of 2,2,2-trichloroethyl [6-chloro-4-(2,6-difluorophenyl)-1,2-benzoxazol-3-yl]carbamate (2.66 g), N-[(3S,5S)-5-(hydroxymethyl)pyrrolidin-3-yl]ethanesulfonamide hydrochloride (1.43 g), diisopropylethylamine (2.14 mL) and THF (34.3 mL) was stirred at 70° C. overnight. The mixture was concentrated under reduced pressure. The residue was purified by silica gel column chromatography (EtOAc/hexane) to give the title compound (2.73 g).

MS: [M+H]$^+$ 515.0.

F) N-{(6S,7aS)-2-[6-Chloro-4-(2,6-difluorophenyl)-1,2-benzoxazol-3-yl]-3-oxohexahydro-1H-pyrrolo[1,2-c]imidazol-6-yl}ethanesulfonamide A mixture of (2S,4S)—N-[6-chloro-4-(2,6-difluorophenyl)-1,2-benzoxazol-3-yl]-4-[(ethanesulfonyl)amino]-2-(hydroxymethyl)pyrrolidine-1-carboxamide (2.73 g), TEA (2.96 mL), and methanesulfonyl chloride (0.821 mL) in THF (64 mL) was stirred at room temperature for 30 min. The mixture was quenched with saturated ammonium chloride aqueous solution and extracted with EtOAc. The organic layer was separated, dried over anhydrous sodium sulfate and concentrated under reduced pressure. The residue was dissolved in THF (64 mL). To the mixture was added 60% sodium hydride (0.254 g) at 0° C. The mixture was allowed to warm to room temperature and stirred for 1 h, then it was quenched with saturated ammonium chloride aqueous solution and extracted with EtOAc. The organic layer was separated, dried over anhydrous sodium sulfate and concentrated under reduced pressure. The residue was purified by silica gel column chromatography (EtOAc/hexane). The residue was crystallized from EtOH/heptane to give the title compound (0.968 g).

$^1$H NMR (400 MHz, CDCl$_3$) δ 1.33 (3H, t, J=7.4 Hz), 1.46-1.57 (1H, m), 2.40-2.50 (1H, m), 2.95-3.11 (3H, m), 3.18-3.26 (1H, m), 3.81-3.94 (2H, m), 4.04-4.20 (3H, m), 7.02 (2H, q, J=9.1 Hz), 7.33 (1H, s), 7.35-7.43 (1H, m), 7.64 (1H, d, J=1.6 Hz).

Example 71

N-{(6R,7aR)-7,7-Difluoro-3-oxo-2-[4-(2,4,6-trifluorophenyl)-1,2-benzoxazol-3-yl]hexahydro-1H-pyrrolo[1,2-c]imidazol-6-yl}methanesulfonamide To a mixture of (2R,4R)-3,3-difluoro-2-(hydroxymethyl)-4-[(methanesulfonyl)amino]-N-[4-(2,4,6-trifluorophenyl)-1,2-benzoxazol-3-yl]pyrrolidine-1-carboxamide (2.71 g), methanesulfonyl chloride (0.806 mL) in dichloromethane (30 mL) was added DBU (2.33 mL) at 0° C. The mixture was stirred at room temperature for 30 min. To the mixture was added DBU (1.18 mL) at room temperature. The mixture was stirred at room temperature for 1 h. The mixture was concentrated under reduced pressure. The residue was diluted with EtOAc, and quenched with saturated ammonium chloride aqueous solution at 0° C. and extracted with EtOAc. The organic layer was separated, washed with water and brine, dried over anhydrous sodium sulfate and concentrated under reduced pressure. The residue was purified by silica gel column chromatography (EtOAc/hexane) followed by NH silica gel column chromatography (EtOAc/hexane). The residue was crystallized from EtOH-heptane to give the title compound (1.21 g).

$^1$H NMR (400 MHz, CDCl$_3$) δ ppm 3.07 (3H, s), 3.13 (1H, dd, J=12.0, 8.3 Hz), 3.64 (1H, dd, J=11.9, 9.0 Hz), 4.11-4.22 (2H, m), 4.36-4.53 (2H, m), 4.69 (1H, br d, J=8.9 Hz), 6.72-6.82 (2H, m), 7.31 (1H, d, J=6.2 Hz), 7.58-7.71 (2H, m).

Example 72

N-{(6R,7aR)-2-[4-(2,6-Difluorophenyl)-6-fluoro-1,2-benzoxazol-3-yl]-7,7-difluoro-3-oxohexahydro-1H-pyrrolo[1,2-c]imidazol-6-yl}methanesulfonamide

A) 2,4-Difluoro-6-iodobenzonitrile

A mixture of 2,4-difluorobenzonitrile (3 g), N-iodosuccinimide (5.34 g), 4-methylbenzenesulfonic acid hydrate (2.05 g) and palladium(II) acetate (0.242 g) in DMF (45 mL) was heated to 70° C. for 6 h. After cooling to room temperature, the mixture was poured into water and extracted with EtOAc. The combined organic layer was washed with brine, dried over anhydrous sodium sulfate and concentrated under reduced pressure. The residue was purified by silica gel column chromatography (EtOAc/hexane) to give the title compound (1.62 g).

$^1$H NMR (400 MHz, DMSO-d$_6$) δ 7.63-7.80 (1H, m), 7.91-7.98 (1H, m).

B) 6-Fluoro-4-iodo-1,2-benzoxazol-3-amine

1 M Potassium tert-butoxide THF solution (2.66 mL) was added to 2-propanone oxime (195 mg) in DMF (26 mL) at room temperature. The mixture was stirred at room temperature under nitrogen atmosphere for 30 min. Then this mixture was added dropwise to a solution of 2,4-difluoro-6-iodobenzonitrile (706 mg) in DMF (8.67 mL) at 0° C. The mixture was stirred at 0° C. under nitrogen for 5 min. The mixture was quenched with saturated ammonium chloride aqueous solution at 0° C. and extracted with EtOAc. The organic layer was separated, washed with brine, dried over anhydrous magnesium sulfate and concentrated under reduced pressure. The residue was diluted with EtOH (28.9 mL), and 6 M hydrogen chloride aqueous solution (14.4 mL) and the mixture was stirred at 80° C. under nitrogen atmosphere for 8 h. The mixture was concentrated under reduced pressure and then was neutralized with saturated sodium hydrogen carbonate aqueous solution at 0° C. and extracted with EtOAc. The organic layer was separated, washed with brine, dried over anhydrous magnesium sulfate and concentrated under reduced pressure. The residue was purified by NH silica gel column chromatography (EtOAc/hexane) to give the title compound (286 mg).

MS: [M+H]$^+$ 278.9.

C) 4-(2,6-Difluorophenyl)-6-fluoro-1,2-benzoxazol-3-amine

To a mixture of 6-fluoro-4-iodo-1,2-benzoxazol-3-amine (286 mg), 2-(2,6-difluorophenyl)-4,4,5,5-tetramethyl-1,3,2-dioxaborolane (741 mg), potassium fluoride (179 mg), tri-tert-butylphosphonium tetrafluoroborate (29.8 mg) in water (0.560 mL) and DME (2.8 mL) was added Pd$_2$(dba)$_3$ (47.1 mg) at room temperature. The mixture was stirred at 120° C. for 1 h under microwave irradiation. The water phase was removed, and the organic phase was concentrated under reduced pressure. Then the mixture was filtered through a NH silica gel pad eluting with EtOAc. After being concentrated under reduced pressure, the residue was purified by silica gel column chromatography (EtOAc/hexane) to give the title compound (240 mg).

MS: [M+H]$^+$ 265.0.

D) 2,2,2-Trichloroethyl [4-(2,6-difluorophenyl)-6-fluoro-1,2-benzoxazol-3-yl]carbamate 1 M Lithium bis(trimethylsilyl)amide THF solution (3.47 mL) was added to a solution of 4-(2,6-difluorophenyl)-6-fluoro-1,2-benzoxazol-3-amine (417 mg) in THF (7.89 mL) at 0° C. The mixture was stirred at 0° C. under argon atmosphere for 30 min. To the mixture was added 2,2,2-trichloroethoxycarbonyl chloride (282 µl) at 0° C. The mixture was stirred under argon atmosphere for 1 h. The mixture was quenched with saturated ammonium chloride aqueous solution at 0° C. and extracted with EtOAc. The organic layer was separated, washed with brine, dried over anhydrous sodium sulfate and concentrated under reduced pressure. The residue was purified by silica gel column chromatography (EtOAc/hexane) to give the title compound (460 mg).

MS: [M+H]$^+$ 438.9.

E) (2R,4R)—N-[4-(2,6-Difluorophenyl)-6-fluoro-1,2-benzoxazol-3-yl]-3,3-difluoro-2-(hydroxymethyl)-4-[(methanesulfonyl)amino]pyrrolidine-1-carboxamide To a solution of N-[(3R,5R)-4,4-difluoro-5-(hydroxymethyl)pyrrolidin-3-yl]methanesulfonamide hydrochloride (50.0 mg) and 2,2,2-trichloroethyl [4-(2,6-difluorophenyl)-6-fluoro-1,2-benzoxazol-3-yl]carbamate (82.0 mg) in THF (1.25 mL) was added DBU (0.084 mL). The mixture was stirred at 70° C. for 1.5 h under microwave irradiation. The reaction mixture was quenched with water, and then it was extracted with EtOAc. The combined organic layer was washed with brine, dried over anhydrous sodium sulfate and then concentrated under reduced pressure. The residue was purified by silica gel column chromatography (EtOAc/hexane) to give the title compound (73.6 mg).

MS: [M+H]$^+$ 521.1.

F) N-{(6R,7aR)-2-[4-(2,6-Difluorophenyl)-6-fluoro-1,2-benzoxazol-3-yl]-7,7-difluoro-3-oxohexahydro-1H-pyrrolo[1,2-c]imidazol-6-yl}methanesulfonamide To a solution of (2R,4R)—N-[4-(2,6-difluorophenyl)-6-fluoro-1,2-benzoxazol-3-yl]-3,3-difluoro-2-(hydroxymethyl)-4-[(methanesulfonyl)amino]pyrrolidine-1-carboxamide (73 mg) in dichloromethane (1.3 mL) were added DBU (0.126 mL) and methanesulfonyl chloride (0.022 mL). The mixture was stirred at 25° C. for 1 h. The reaction mixture was quenched with water, and then extracted with dichloromethane. The combined organic layers were washed with brine, dried over anhydrous sodium sulfate and then concentrated under reduced pressure. The residue was purified by silica gel column chromatography (EtOAc/hexane) followed by NH silica gel column chromatography (EtOAc/hexane) to give the title compound (18.7 mg).

$^1$H NMR (400 MHz, CDCl$_3$) δ 2.98-3.14 (4H, m), 3.58 (1H, dd, J=12.2, 9.0 Hz), 4.08-4.49 (4H, m), 4.61 (1H, br d, J=9.2 Hz), 7.01 (2H, q, J=8.2 Hz), 7.14 (1H, dd, J=9.4, 1.5 Hz), 7.31-7.44 (2H, m).

Example 75

N-{(6R)-2-[4-(2,6-Difluorophenyl)-5-fluoro-1,2-benzoxazol-3-yl]-7,7-difluoro-3-oxo-2,5,6,7-tetrahydro-3H-pyrrolo[1,2-c]imidazol-6-yl}methanesulfonamide A) 3,6-Difluoro-2-iodobenzamide A mixture of 2,5-difluorobenzonitrile (20 g), N-iodosuccinimide (35.6 g), palladium(II) acetate (1.61 g), and p-toluenesulfonic acid monohydrate (13.7 g) in DMF (500 mL) was stirred at 80° C. for 16 h. The mixture was quenched with water and extracted with IPE. The organic layer was separated, dried over anhydrous sodium sulfate and concentrated under reduced pressure. The residue was purified by preparative HPLC (YMC-Actus Triant C18, mobile phase: water (containing 10 mM ammonium bicarbonate)/MeCN) to give the title compound (8.76 g).

MS: [M+H]$^+$ 283.9.

B) 3,6-Difluoro-2-iodobenzonitrile

A mixture of 3,6-difluoro-2-iodobenzamide (8.9 g) and trifluoroacetic anhydride (13.3 mL) in pyridine (100 mL) was stirred at 80° C. for 16 h. The mixture was quenched with 1 M hydrogen chloride aqueous solution at 0° C. and extracted with EtOAc. The organic layer was separated, washed with water, dried over anhydrous sodium sulfate and concentrated under reduced pressure. The residue was purified by silica gel column chromatography (EtOAc/hexane) to give the title compound (7.83 g).

$^1$H NMR (300 MHz, CDCl$_3$) δ 7.17-7.34 (2H, m)

C) 2',3,6,6'-Tetrafluoro[1,1'-biphenyl]-2-carbonitrile

A mixture of 3,6-difluoro-2-iodobenzonitrile (500 mg), 2-(2,6-difluorophenyl)-4,4,5,5-tetramethyl-1,3,2-dioxaborolane (4.53 g), potassium fluoride (329 mg), tri-tert-butylphosphonium tetrafluoroborate (54.7 mg), Pd$_2$(dba)$_3$ (86 mg) and DME (0.5 mL) was stirred at 120° C. for 1 h under argon atmosphere in a microwave reactor. The same reaction was repeated a further 4 times, yielding five batches of crude material which were subsequently combined. The mixture was quenched with water and extracted with EtOAc. The organic layer was separated, dried over anhydrous sodium sulfate and concentrated under reduced pressure. The residue was purified by silica gel column chromatography (EtOAc/hexane). The residue was washed with hexane to give the title compound (1.98 g).

$^1$H NMR (300 MHz, CDCl$_3$) δ 7.04-7.16 (2H, m), 7.27-7.35 (1H, m), 7.40-7.56 (2H, m).

D) 4-(2,6-Difluorophenyl)-5-fluoro-1,2-benzoxazol-3-amine

A mixture of 2',3,6,6'-tetrafluoro[1,1'-biphenyl]-2-carbonitrile (1.98 g), 2-propanone oxime (1.73 g), and potassium 2-methylpropan-2-olate (1.77 g) in DMF (20 mL) was stirred at room temperature for 1.5 h. The mixture was quenched with saturated ammonium chloride aqueous solution and extracted with EtOAc. The organic layer was separated, dried over anhydrous sodium sulfate and concentrated under reduced pressure. A mixture of this crude product and 6 M hydrogen chloride aqueous solution (2 mL) in EtOH (20 mL) was stirred at 80° C. for 16 h. The mixture was concentrated under reduced pressure and the residue was purified by silica gel column chromatography (EtOAc/hexane) to give the title compound (1.56 g).

MS: [M+H]$^+$ 265.0.

E) (2R,4R)—N-[4-(2,6-Difluorophenyl)-5-fluoro-1,2-benzoxazol-3-yl]-3,3-difluoro-2-(hydroxymethyl)-4-[(methanesulfonyl)amino]pyrrolidine-1-carboxamide To a mixture of 4-(2,6-difluorophenyl)-5-fluoro-1,2-benzoxazol-3-amine (300 mg) in THF (2 mL) were added 1 M lithium bis(trimethylsilyl)amide THF solution (2.27 mL) and 2,2,2-trichloroethoxycarbonyl chloride (0.167 mL) at 0° C. The mixture was stirred for 1 h. The mixture was quenched with saturated ammonium chloride aqueous solution and extracted with EtOAc. The organic layer was separated, dried over anhydrous sodium sulfate and concentrated under reduced pressure to give a residue (500 mg). A mixture of the residue (250 mg), N-[(3R,5R)-4,4-difluoro-5-(hydroxymethyl)pyrrolidin-3-yl]methanesulfonamide hydrochloride (151 mg) and DBU (0.257 mL) in THF (2 mL) was stirred at 60° C. for 16 h. The mixture was concentrated under reduced pressure and the residue was purified by preparative HPLC (YMC-Actus Triant C18, mobile phase: water/MeCN (both containing 0.1% TFA)) to give the title compound (160 mg).

MS: [M+H]$^+$ 521.1.

F) N-{(6R)-2-[4-(2,6-Difluorophenyl)-5-fluoro-1,2-benzoxazol-3-yl]-7,7-difluoro-3-oxo-2,5,6,7-tetrahydro-3H-pyrrolo[1,2-c]imidazol-6-yl}methanesulfonamide A mixture of (2R,4R)—N-[4-(2,6-difluorophenyl)-5-fluoro-1,2-benzoxazol-3-yl]-3,3-difluoro-2-(hydroxymethyl)-4-[(methanesulfonyl)amino]pyrrolidine-1-carboxamide (50 mg), sodium hydrogen carbonate (40.4 mg), and Dess-Martin periodinane (48.9 mg) in MeCN (1.0 mL) was stirred at room temperature for 1 h. The mixture was quenched with saturate sodium hydrogen carbonate aqueous solution and extracted with EtOAc. The organic layer was separated, dried over anhydrous sodium sulfate and concentrated under reduced pressure. A mixture of the obtained residue, TFA (0.5 mL), and trifluoroacetic anhydride (0.5 mL) was stirred at room temperature for 16 h. The mixture was concentrated under reduced pressure and the residue was purified by preparative HPLC (YMC-Actus Triant C18, mobile phase: water/MeCN (both containing 0.1% TFA)) to give the title compound (12.9 mg).

$^1$H NMR (400 MHz, CDCl$_3$) δ 3.13-3.19 (4H, m), 3.97 (1H, dd, J=11.3, 8.4 Hz), 4.52-4.68 (1H, m), 4.95-5.05 (1H, m), 6.78 (1H, dd, J=4.8, 1.8 Hz), 6.95 (2H, tt, J=8.5, 1.2 Hz), 7.37-7.46 (1H, m), 7.50-7.55 (1H, m), 7.71 (1H, dd, J=9.2, 3.5 Hz).

Example 77

N-{(6R)-7,7-Difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide A) N-{(6R)-7,7-Difluoro-2-[5-fluoro-4-(2,4,6-trifluorophenyl)-1,2-benzoxazol-3-yl]-1-hydroxy-3-oxohexahydro-1H-pyrrolo[1,2-c]imidazol-6-yl}methanesulfonamide Tetra-n-butylammonium bromide (0.812 g), iodosobenzene I,I-diacetate (4.46 g) and 2,2,6,6-tetramethylpiperidine 1-oxyl (0.394 g) were added to a mixture of (2R,4R)-3,3-difluoro-N-[5-fluoro-4-(2,4,6-trifluorophenyl)-1,2-benzoxazol-3-yl]-2-(hydroxymethyl)-4-[(methanesulfonyl)amino]pyrrolidine-1-carboxamide (6.78 g) and sodium hydrogen carbonate (5.29 g) in MeCN (63 mL) and water (63 mL) at 0° C. The mixture was stirred at 0° C. for 30 min. To the mixture were added EtOAc and water at 0° C. The aqueous layer was separated and extracted with EtOAc. The organic layers were washed with water and brine, dried over anhydrous sodium sulfate and concentrated under reduced pressure. The residue was purified by silica gel column chromatography (EtOAc/hexane) to give the title compound (6.10 g).

MS: [M+Na]$^+$ 559.1.

B) N-{(6R)-7,7-Difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide Trifluoroacetic anhydride (3.21 mL) was added to a solution of N-(6R)-7,7-difluoro-2-[5-fluoro-4-(2,4,6-trifluorophenyl)-1,2-benzoxazol-3-yl]-1-hydroxy-3-oxohexahydro-1H-pyrrolo[1,2-c]imidazol-6-yl}methanesulfonamide (6.10 g) in TFA (0.876 mL) at room temperature. The reaction mixture was stirred at 40° C. overnight. The mixture was concentrated under reduced pressure. The residue was dissolved in EtOAc, neutralized with saturated sodium hydrogen carbonate aqueous solution and extracted with EtOAc. The organic layer was separated, washed with brine, dried over anhydrous sodium sulfate and concentrated under reduced pressure. The residue was purified by silica gel column chromatography (EtOAc/hexane). The residue was crystallized from EtOAc-heptane to give the title compound (3.36 g).

¹H NMR (300 MHz, DMSO-d₆) δ 3.04 (3H, s), 3.22-3.29 (1H, m), 4.08-4.19 (1H, m), 4.62-4.84 (1H, m), 7.18-7.38 (2H, m), 7.41-7.46 (1H, m), 7.91 (1H, t, J=9.6 Hz), 8.13-8.20 (1H, m), 8.36 (1H, d, J=9.4 Hz).

Example 92

N-{(6R)-7,7-Difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}ethanesulfonamide A) (2R,4R)-4-[(Ethanesulfonyl) amino]-3,3-difluoro-N-[5-fluoro-4-(2,4,6-trifluorophenyl)-1,2-benzoxazol-3-yl]-2-(hydroxymethyl)pyrrolidine-1-carboxamide To a mixture of 2,2,2-trichloroethyl [5-fluoro-4-(2,4,6-trifluorophenyl)-1,2-benzoxazol-3-yl]carbamate (196 mg) in THF (2 mL) were added DBU (0.194 mL) and N-[(3R, 5R)-4,4-difluoro-5-(hydroxymethyl)pyrrolidin-3-yl]ethanesulfonamide hydrochloride (121 mg) at room temperature. The mixture was heated at 60° C. for 16 h. The mixture was concentrated under reduced pressure. The residue was purified by preparative HPLC (YMC-Actus Triant C18, mobile phase: water/MeCN (both containing 0.1% TFA)) to give the title compound (111 mg).
MS: [M+H]⁺ 553.1.

B) N-{(6R)-7,7-Difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}ethanesulfonamide A mixture of (2R,4R)-4-[(ethanesulfonyl)amino]-3,3-difluoro-N-[5-fluoro-4-(2,4,6-trifluorophenyl)-1,2-benzoxazol-3-yl]-2-(hydroxymethyl)pyrrolidine-1-carboxamide (55.2 mg), Dess Martin periodinane (50.9 mg), and TFA (0.5 mL) in MeCN (1.0 mL) was stirred at 0° C. for 1 h. The mixture was quenched with saturated sodium hydrogen carbonate aqueous solution and extracted with ethyl acetate. The organic layer was separated, dried over anhydrous sodium sulfate and concentrated under reduced pressure. A mixture of this crude product, TFA (0.5 mL) and trifluoroacetic anhydride (0.5 mL) was stirred at room temperature for 16 h. The mixture was concentrated under reduced pressure and the residue was purified by preparative HPLC (YMC-Actus Triant C18, mobile phase: water/MeCN (both containing 0.1% TFA)) to give the title compound (20.9 mg).
¹H NMR (400 MHz, CDCl3) δ 1.46 (3H, t, J=7.4 Hz), 3.15-3.27 (3H, m), 4.11 (1H, dd, J=11.1, 8.3 Hz), 4.54-4.71 (1H, m), 4.91 (1H, br d, J=10.0 Hz), 6.62-6.92 (3H, m), 7.53 (1H, t, J=9.1 Hz), 7.72 (1H, dd, J=9.2, 3.4 Hz).

Example 102

N-{(6R)-2-[4-(2,6-Difluorophenyl)-1,2-benzoxazol-3-yl]-7,7-difluoro-3-oxo-2,5,6,7-tetrahydro-3H-pyrrolo[1,2-c]imidazol-6-yl}methanesulfonamide To a mixture of (2R,4R)—N-[4-(2,6-difluorophenyl)-1,2-benzoxazol-3-yl]-3,3-difluoro-2-(hydroxymethyl)-4-[(methanesulfonyl)amino]pyrrolidine-1-carboxamide (278 mg), sodium hydrogen carbonate (232 mg) in MeCN (3 mL) was added Dess-Martin periodinane (305 mg) at room temperature. The mixture was stirred for 2 h. To the mixture were added EtOAc and water at room temperature. The aqueous layer was separated and extracted with EtOAc. The organic layers were combined, washed with water and brine, dried over anhydrous sodium sulfate and concentrated under reduced pressure. The residue was purified by silica gel column chromatography (EtOAc/hexane). To the residue were added dichloromethane (4 mL) and trifluoroacetic anhydride (2 mL) at room temperature. The mixture was stirred at room temperature overnight. To the mixture were added EtOAc and saturated sodium hydrogen carbonate aqueous solution at 0° C. The aqueous layer was separated and extracted with EtOAc. The organic layers were combined, washed with water and brine, dried over anhydrous sodium sulfate and concentrated under reduced pressure. The residue was purified by silica gel column chromatography (EtOAc/hexane) to give the title compound (77 mg).
¹H NMR (400 MHz, CDCl₃) δ 3.13 (3H, s), 3.17 (1H, dd, J=11.2, 8.6 Hz), 3.97 (1H, dd, J=11.2, 8.4 Hz), 4.55-4.67 (1H, m), 5.07-5.15 (1H, m), 6.76-6.80 (1H, m), 6.89-6.96 (2H, m), 7.32-7.43 (2H, m), 7.68-7.82 (2H, m).

Example 124

N-{(6R,7aR)-7,7-Difluoro-2-[6-fluoro-4-(2,4,6-trifluorophenyl)-1,2-benzoxazol-3-yl]-3-oxohexahydro-1H-pyrrolo[1,2-c]imidazol-6-yl}ethanesulfonamide A) 6-Fluoro-4-(2,4,6-trifluorophenyl)-1,2-benzoxazol-3-amine A mixture of 6-fluoro-4-iodo-1,2-benzoxazol-3-amine (620 mg), (2,4,6-trifluorophenyl)boronic acid (1.57 g), Pd₂(dba)₃ (102 mg), tri-tert-butylphosphonium tetrafluoroborate (64.7 mg), potassium fluoride (389 mg) in DME (4 mL) and water (0.800 mL) was heated at 120° C. for 1 h under argon atmosphere in a microwave reactor.
The crude mixture was purified by preparative HPLC (YMC-Actus Triant C18, mobile phase: water (containing 10 mM ammonium bicarbonate)/MeCN) to give the title compound (511 mg).
MS: [M+H]⁺ 283.0.

B) (2R,4R)-4-[(Ethanesulfonyl) amino]-3,3-difluoro-N-[6-fluoro-4-(2,4,6-trifluorophenyl)-1,2-benzoxazol-3-yl]-2-(hydroxymethyl)pyrrolidine-1-carboxamide To a mixture of 6-fluoro-4-(2,4,6-trifluorophenyl)-1,2-benzoxazol-3-amine (100 mg) in THF (2 mL) was added 1 M lithium bis(trimethylsilyl)amide toluene solution (0.886 mL) at 0° C. The mixture was stirred for 30 min. To the mixture was added 2,2,2-trichloroethoxycarbonyl chloride (0.052 mL). The mixture was stirred for 1 h. The mixture was quenched with saturated ammonium chloride solution and extracted with EtOAc. The organic layer was separated, dried over anhydrous sodium sulfate and concentrated under reduced pressure. A mixture of this crude product, N-[(3R, 5R)-4,4-difluoro-5-(hydroxymethyl)pyrrolidin-3-yl]ethanesulfonamide hydrochloride (99 mg), and DBU (162 mg) in THF (2 mL) was stirred at 60° C. for 16 h. The mixture was concentrated under reduced pressure. The residue was purified by preparative HPLC (YMC-Actus Triant C18, mobile phase: water (containing 10 mM ammonium bicarbonate)/MeCN) to give the title compound (85.1 mg).
MS: [M+H]⁺ 553.1.

C) N-{(6R,7aR)-7,7-Difluoro-2-[6-fluoro-4-(2,4,6-trifluorophenyl)-1,2-benzoxazol-3-yl]-3-oxohexahydro-1H-pyrrolo[1,2-c]imidazol-6-yl}ethanesulfonamide To a mixture of (2R,4R)-4-[(ethanesulfonyl)amino]-3,3-difluoro-N-[6-fluoro-4-(2,4,6-trifluorophenyl)-1,2-benzoxazol-3-yl]-2-(hydroxymethyl)pyrrolidine-1-carboxamide (60 mg) in dichloromethane (2.0 mL) were added DBU (0.049 mL) and methanesulfonyl chloride (0.013 mL) at room temperature. The mixture was stirred for 15 min. To the mixture was added DBU (0.049 mL). The mixture was stirred for 30 min and concentrated under reduced pressure. The residue was purified by silica gel column chromatography (EtOAc/hexane) to give the title compound (16.5 mg).
$^1$H NMR (400 MHz, CDCl$_3$) δ 1.40 (3H, t, J=7.5 Hz), 2.99-3.22 (3H, m), 3.57-3.78 (2H, m), 4.15-4.19 (1H, m), 4.35-4.53 (3H, m), 6.71-6.85 (2H, m), 7.11 (1H, d, J=9.0 Hz), 7.33 (1H, d, J=7.8 Hz).

Example 126

N-{(6R,7aR)-2-[4-(2,6-Difluorophenyl)-6-methyl-1,2-benzoxazol-3-yl]-7,7-difluoro-3-oxohexahydro-1H-pyrrolo[1,2-c]imidazol-6-yl}methanesulfonamide A) 4-Bromo-6-methyl-1,2-benzoxazol-3-amine To a solution of ethanehydroxamic acid (5.26 g) in DMF (60 mL) was added potassium tert-butoxide (7.86 g). The mixture was stirred at 20° C. for 30 min. To the mixture was added a solution of 2-bromo-6-fluoro-4-methylbenzonitrile (5.00 g) in DMF (20 mL). The reaction mixture was stirred at 20° C. for 14 h. The reaction mixture was diluted with water and extracted with EtOAc. The organic layer was washed with brine, dried over anhydrous sodium sulfate and concentrated under reduced pressure. The residue was purified by silica gel column chromatography (EtOAc/petroleum ether) to give the title compound (4.08 g).
MS: [M+H]$^+$ 227.1.

B) 4-(2,6-Difluorophenyl)-6-methyl-1,2-benzoxazol-3-amine

A mixture of 4-bromo-6-methyl-1,2-benzoxazol-3-amine (770 mg), 2-(2,6-difluorophenyl)-4,4,5,5-tetramethyl-1,3,2-dioxaborolane (1.63 g), Pd$_2$(dba)$_3$ (310 mg), tri-tert-butylphosphonium tetrafluoroborate (197 mg) and potassium fluoride (591 mg) in DME (9 mL) and water (3 mL) was heated at 120° C. for 1 h under microwave irradiation. The reaction mixture was quenched with water and extracted with EtOAc. The combined organic layer was washed with brine, dried over anhydrous sodium sulfate and concentrated under reduced pressure. The residue was purified by silica gel column chromatography (EtOAc/petroleum ether) to give the title compound (567 mg).
MS: [M+H]$^+$ 261.0.

C) 2,2,2-Trichloroethyl [4-(2,6-difluorophenyl)-6-methyl-1,2-benzoxazol-3-yl]carbamate 1 M Lithium bis(trimethylsilyl)amide THF solution (12.8 mL) was added to a solution of 4-(2,6-difluorophenyl)-6-methyl-1,2-benzoxazol-3-amine (1.67 g) in THF (39 mL) at 0° C. The mixture was stirred at 0° C. for 10 min. 2,2,2-Trichloroethoxycarbonyl chloride (0.972 mL) was added to the mixture. The mixture was stirred at 0° C. for 30 min. The mixture was quenched with saturated ammonium chloride aqueous solution at 0° C. and extracted with EtOAc. The organic layer was separated and washed with brine. The solvent was removed under reduced pressure and the residue was purified by silica gel column chromatography (EtOAc/hexane) to give the title compound (1.86 g).
MS: [M+H]$^+$ 434.9.

D) (2R,4R)—N-[4-(2,6-Difluorophenyl)-6-methyl-1,2-benzoxazol-3-yl]-3,3-difluoro-2-(hydroxymethyl)-4-[(methanesulfonyl)amino]pyrrolidine-1-carboxamide To a mixture of N-[(3R,5R)-4,4-difluoro-5-(hydroxymethyl)pyrrolidin-3-yl]methanesulfonamide hydrochloride (0.162 mL) in THF (2.0 mL) was added 2,2,2-trichloroethyl [4-(2,6-difluorophenyl)-6-methyl-1,2-benzoxazol-3-yl]carbamate (187 mg) at 0° C. The mixture was stirred at 60° C. for 15 h then it was filtered and concentrated under reduced pressure. The residue was purified by silica gel column chromatography (EtOAc/hexane) to give the title compound (190 mg).
MS: [M+H]$^+$ 517.1

E) N-{(6R,7aR)-2-[4-(2,6-Difluorophenyl)-6-methyl-1,2-benzoxazol-3-yl]-7,7-difluoro-3-oxohexahydro-1H-pyrrolo[1,2-c]imidazol-6-yl}methanesulfonamide To a mixture of (2R,4R)—N-[4-(2,6-difluorophenyl)-6-methyl-1,2-benzoxazol-3-yl]-3,3-difluoro-2-(hydroxymethyl)-4-[(methanesulfonyl)amino]pyrrolidine-1-carboxamide (95 mg) in THF (1.84 mL) and 1 M sodium hydroxide aqueous solution (0.920 mL) was added 4-methylbenzenesulfonyl chloride (71.9 mg) at −3° C. The mixture was stirred for 1 h at −5° C. The mixture was diluted with EtOAc and washed with brine. The separated aqueous layer was extracted with EtOAc and the combined organic layer was dried over anhydrous sodium sulfate. The solvent was removed under reduced pressure and the residue was purified by silica gel column chromatography (EtOAc/hexane) to give the title compound (45.0 mg).
$^1$H NMR (300 MHz, CDCl$_3$) δ 2.55 (3H, s), 3.01-3.12 (4H, m), 3.51-3.63 (1H, m), 4.02-4.22 (2H, m), 4.24-4.50 (2H, m), 4.54-4.65 (1H, m), 6.92-7.03 (2H m), 7.14-7.18 (1H, m), 7.29-7.40 (1H, m), 7.41-7.44 (1H, m).

Example 144

N-{(6R,7aR)-7,7-Difluoro-2-[6-fluoro-4-(2,4,6-trifluorophenyl)-1,2-benzoxazol-3-yl]-3-oxohexahydro-1H-pyrrolo[1,2-c]imidazol-6-yl}-N'-methylsulfuric diamide A) tert-Butyl (2R,4R)-2-[(benzyloxy)methyl]-3,3-difluoro-4-[(methylsulfamoyl)amino]pyrrolidine-1-carboxylate To a mixture of tert-butyl (2R,4R)-4-amino-2-[(benzyloxy)methyl]-3,3-difluoropyrrolidine-1-carboxylate (210 mg), TEA (0.255 mL), 4-dimethylaminopyridine (13.1 mg) and THF (2 mL) was added a solution of methylsulfamoyl chloride (130 mg) in THF (1 mL) at 0° C. The mixture was stirred at room temperature under argon atmosphere overnight. The mixture was directly purified by silica gel column chromatography (EtOAc/hexane) to give the title compound (168 mg).

MS: [M+H-Boc]⁺ 336.1.

B) 2,2,2-Trichloroethyl [6-fluoro-4-(2,4,6-trifluorophenyl)-1,2-benzoxazol-3-yl]carbamate To a mixture of 6-fluoro-4-(2,4,6-trifluorophenyl)-1,2-benzoxazol-3-amine (8.18 g) in THF (120 ml) was added 1 M lithium bis(trimethylsilyl)amide THF solution (66.7 ml) at −22° C. After being stirred at −22° C. for 10 min, to the mixture was added a mixture of 2,2,2-trichloroethoxycarbonyl chloride (7.37 g) and THF (5.0 ml) at the same temperature. The mixture was stirred under argon atmosphere at −22° C. for 15 min. To the mixture were added ammonium chloride aqueous solution and EtOAc at 0° C. The aqueous layer was separated and extracted with ethyl acetate. The organic layers were combined, washed with water and brine, dried over anhydrous sodium sulfate and concentrated under reduced pressure. The residue was purified by silica gel column chromatography (EtOAc/hexane) to give the title compound (7.03 g).

MS: [M+H]⁺ 456.9.

C) (2R,4R)-3,3-Difluoro-N-[6-fluoro-4-(2,4,6-trifluorophenyl)-1,2-benzoxazol-3-yl]-2-(hydroxymethyl)-4-[(methylsulfamoyl)amino]pyrrolidine-1-carboxamide A mixture of tert-butyl (2R,4R)-2-[(benzyloxy)methyl]-3,3-difluoro-4-[(methylsulfamoyl) amino]pyrrolidine-1-carboxylate (168 mg) and 20% palladium hydroxide on carbon (27.2 mg) in MeOH (5 mL) was hydrogenated under balloon pressure at room temperature for 2 h. The mixture was diluted with EtOAc, and the catalyst was removed by filtration. The filtrate was concentrated under reduced pressure. To the residue was added EtOAc (5 mL) and 4 M hydrogen chloride CPME solution (3.0 mL) at room temperature. The mixture was stirred at room temperature under nitrogen atmosphere for 3 h. The mixture was concentrated under reduced pressure. To the residue were added THF (3 mL), TEA (0.160 mL), and 2,2,2-trichloroethyl [6-fluoro-4-(2,4,6-trifluorophenyl)-1,2-benzoxazol-3-yl]carbamate (177 mg) at room temperature. The mixture was stirred at 60° C. under argon atmosphere overnight. The mixture was diluted with EtOAc, and concentrated under reduced pressure. The residue was purified by silica gel column chromatography (EtOAc/hexane) to give the title compound (178 mg).

MS: [M+H]⁺ 554.1.

D) N-{(6R,7aR)-7,7-Difluoro-2-[6-fluoro-4-(2,4,6-trifluorophenyl)-1,2-benzoxazol-3-yl]-3-oxohexahydro-1H-pyrrolo[1,2-c]imidazol-6-yl}-N'-methylsulfuric diamide To a mixture of (2R,4R)-3,3-difluoro-N-[6-fluoro-4-(2,4,6-trifluorophenyl)-1,2-benzoxazol-3-yl]-2-(hydroxymethyl)-4-[(methylsulfamoyl)amino]pyrrolidine-1-carboxamide (80.4 mg), 1 M sodium hydroxide aqueous solution (0.800 mL) and THF (1.6 mL) was added 4-methylbenzenesulfonyl chloride (56.8 mg) at −20° C. The mixture was stirred at the same temperature for 2 h. To the mixture were added EtOAc and saturated sodium hydrogen carbonate aqueous solution at room temperature. The aqueous layer was separated and extracted with EtOAc. The organic layers were combined, washed with water and brine, dried over anhydrous sodium sulfate and concentrated under reduced pressure. The residue was purified by silica gel column chromatography (EtOAc/hexane) then NH silica gel column chromatography (EtOAc/hexane) to give the title compound (28.5 mg).

¹H NMR (300 MHz, CDCl₃) δ 2.72 (3H, d, J=5.3 Hz), 3.17 (1H, dd, J=12.0, 8.0 Hz), 3.62 (1H, dd, J=12.1, 8.7 Hz), 4.07-4.44 (5H, m), 4.65 (1H, br d, J=8.0 Hz), 6.69-6.86 (2H, m), 7.11 (1H, dd, J=9.3, 1.4 Hz), 7.33 (1H, dd, J=7.9, 2.1 Hz).

Example 149

N-{(6R,7aR)-7,7-Difluoro-2-[6-fluoro-4-(2,4,6-trifluorophenyl)-1,2-benzoxazol-3-yl]-3-oxohexahydro-1H-pyrrolo[1,2-c]imidazol-6-yl}methanesulfonamide

A) (2R,4R)-3,3-Difluoro-N-[6-fluoro-4-(2,4,6-trifluorophenyl)-1,2-benzoxazol-3-yl]-2-(hydroxymethyl)-4-[(methanesulfonyl)amino]pyrrolidine-1-carboxamide To a mixture of N-[(3R,5R)-4,4-difluoro-5-(hydroxymethyl)pyrrolidin-3-yl]methanesulfonamide hydrochloride (4.20 g), 2,2,2-trichloroethyl [6-fluoro-4-(2,4,6-trifluorophenyl)-1,2-benzoxazol-3-yl]carbamate (7.03 g) and THF (70 mL) was added TEA (7.0 mL) at room temperature. The mixture was stirred at 60° C. under nitrogen atmosphere overnight. The mixture was diluted with EtOAc, then was concentrated under reduced pressure. The residue was purified by silica gel column chromatography (EtOAc/hexane) to give the title compound (7.82 g).

MS: [M+H]⁺ 539.1.

B) N-{(6R,7aR)-7,7-Difluoro-2-[6-fluoro-4-(2,4,6-trifluorophenyl)-1,2-benzoxazol-3-yl]-3-oxohexahydro-1H-pyrrolo[1,2-c]imidazol-6-yl}methanesulfonamide To a mixture of (2R,4R)-3,3-difluoro-N-[6-fluoro-4-(2,4,6-trifluorophenyl)-1,2-benzoxazol-3-yl]-2-(hydroxymethyl)-4-[(methanesulfonyl)amino]pyrrolidine-1-carboxamide (7.82 g), 1 M sodium hydroxide aqueous solution (70 mL) and THF (140 mL) was added 4-methylbenzenesulfonyl chloride (5.76 g) at room temperature. The mixture was stirred at room temperature for 30 min. To the mixture were added water and EtOAc at room temperature. The aqueous layer was separated and extracted with EtOAc. The organic layers were combined, washed with water and brine, dried over anhydrous sodium sulfate and concentrated under reduced pressure. The residue was purified by silica gel column chromatography (EtOAc/hexane), followed by NH-silica gel column chromatography (EtOAc/hexane).

The residue was recrystallized (EtOAc/heptane) to give the title compound (4.37 g).

¹H NMR (300 MHz, DMSO-d₆) δ 2.97 (3H, s), 2.99-3.09 (1H, m), 3.51 (1H, t, J=10.2 Hz), 3.99-4.10 (1H, m), 4.19 (1H, dd, J=10.2, 4.1 Hz), 4.37-4.75 (2H, m), 7.20-7.41 (2H, m), 7.44-7.53 (1H, m), 7.88-8.00 (2H, m).

Example 171

N-{(6R,7aR)-2-[5,6-Difluoro-4-(2,4,6-trifluorophenyl)-1,2-benzoxazol-3-yl]-7,7-difluoro-3-oxohexahydro-1H-pyrrolo[1,2-c]imidazol-6-yl}methanesulfonamide

A) 2-Bromo-3,4,6-trifluorobenzaldehyde

A mixture of 2,4,5-trifluorobenzaldehyde (25.0 g), N-bromosuccinimide (33.4 g), palladium(II) acetate (3.51 g), and 4-amino-3-chlorobenzotrifluoride (4.41 mL) in trifluorotoluene (650 mL) and TFA (130 mL) was stirred at 60° C. for 16 h. The same reaction was conducted twice, yielding two batches of crude material which were subsequently combined. The mixture was quenched with 1 M sodium hydroxide aqueous solution at 0° C. and extracted with IPE-hexane. The organic layer was separated, washed with water, dried over anhydrous sodium sulfate and concentrated under reduced pressure. The residue was purified by silica gel column chromatography (EtOAc/hexane) to give the title compound (32.5 g).

$^1$H NMR (400 MHz, CDCl$_3$) δ 7.08 (1H, td, J=9.7, 6.0 Hz), 10.27 (1H, s).

B) N-[(E)-(2-Bromo-3,4,6-trifluorophenyl)methylidene]hydroxyamine

A mixture of 2-bromo-3,4,6-trifluorobenzaldehyde (32.5 g), and 50% hydroxyamine aqueous solution (18.0 g) in EtOH (600 mL) was stirred at 80° C. for 2 h. The mixture was concentrated under reduced pressure. To the resulting solid was added hexane and the mixture was stirred for 30 min. The solid was collected by filtration to give the title compound (28.8 g).

MS: [M+H]$^+$ 253.9.

C) 2-Bromo-3,4,6-trifluoro-N'-hydroxybenzene-1-carboximidamide

To a mixture of N-[(E)-(2-bromo-3,4,6-trifluorophenyl)methylidene]hydroxyamine (26.8 g) in DMF (400 mL) was added N-chlorosuccinimide (15.5 g) at 0° C. The mixture was heated to 60° C. and stirred for 1 h. The mixture was cooled to 0° C. The mixture was stirred for 15 min. To the mixture was added 27% ammonia aqueous solution (1.78 g). The mixture was quenched with water and extracted with EtOAc. The organic layer was separated, dried over anhydrous sodium sulfate and concentrated under reduced pressure. The residue was purified by silica gel column chromatography (EtOAc/hexane) to give the title compound (15.9 g).

MS: [M+H]$^+$ 268.9.

D) 4-Bromo-5,6-difluoro-1,2-benzoxazol-3-amine

A mixture of 2-bromo-3,4,6-trifluoro-N'-hydroxybenzene-1-carboximidamide (560 mg) and cesium carbonate (678 mg) in 1-methyl-2-pyrrolidone (10 mL) was heated at 150° C. for 15 min under argon atmosphere in a microwave reactor. This process was repeated a further two times, yielding three batches of crude material which were subsequently combined. The residue was purified by silica gel column chromatography (EtOAc/hexane) to give the title compound (571 mg).

MS: [M+H]$^+$ 248.9.

E) 5,6-Difluoro-4-(2,4,6-trifluorophenyl)-1,2-benzoxazol-3-amine

A mixture of 4-bromo-5,6-difluoro-1,2-benzoxazol-3-amine (500 mg), (2,4,6-trifluorophenyl)boronic acid (3.53 g), potassium fluoride (350 mg), tri-tert-butylphosphonium tetrafluoroborate (117 mg) and Pd$_2$(dba)$_3$ (184 mg) in DME (10 mL) and water (1.00 mL) was heated to 100° C. under argon atmosphere. The mixture was stirred for 2 h at 100° C. To the reaction mixture were added (2,4,6-trifluorophenyl) boronic acid (1.77 g), potassium fluoride (350 mg), tri-tert-butylphosphonium tetrafluoroborate (117 mg) and Pd$_2$(dba)$_3$ (184 mg). The mixture was stirred for 16 h at 100° C. The mixture was quenched with water and extracted with EtOAc. The organic layer was separated, dried over anhydrous sodium sulfate and concentrated under reduced pressure. The residue was purified by silica gel column chromatography (EtOAc/hexane) to give the title compound (379 mg).

MS: [M+H]$^+$ 301.0.

F) 2,2,2-Trichloroethyl [5,6-difluoro-4-(2,4,6-trifluorophenyl)-1,2-benzoxazol-3-yl]carbamate To a mixture of 5,6-difluoro-4-(2,4,6-trifluorophenyl)-1,2-benzoxazol-3-amine (379 mg) in THF (5 mL) was added 1 M lithium bis(trimethylsilyl)amide THF solution (2.78 mL) at 0° C. The mixture was stirred for 30 min at 0° C. To the reaction mixture was added 2,2,2-trichloroethoxycarbonyl chloride (0.191 mL). The mixture was stirred for 1 h. The mixture was quenched with saturated ammonium chloride aqueous solution and extracted with EtOAc. The organic layer was separated, dried over anhydrous sodium sulfate and concentrated under reduced pressure. The residue was purified by silica gel column chromatography (EtOAc/hexane) to give the title compound (378 mg).

MS: [M+H]$^+$ 474.9.

G) (2R,4R)—N-[5,6-Difluoro-4-(2,4,6-trifluorophenyl)-1,2-benzoxazol-3-yl]-3,3-difluoro-2-(hydroxymethyl)-4-[(methanesulfonyl)amino]pyrrolidine-1-carboxamide A mixture of 2,2,2-trichloroethyl [5,6-difluoro-4-(2,4,6-trifluorophenyl)-1,2-benzoxazol-3-yl]carbamate (185 mg), TEA (0.163 mL), and N-[(3R,5R)-4,4-difluoro-5-(hydroxymethyl)pyrrolidin-3-yl]methanesulfonamide hydrochloride (104 mg) in THF (3 mL) was stirred at 60° C. for 16 h. The mixture was concentrated under reduced pressure and the residue was purified by silica gel column chromatography (EtOAc/hexane) to give the title compound (186 mg).

MS: [M+H]$^+$ 557.0.

H) N-{(6R,7aR)-2-[5,6-Difluoro-4-(2,4,6-trifluorophenyl)-1,2-benzoxazol-3-yl]-7,7-difluoro-3-oxohexahydro-1H-pyrrolo[1,2-c]imidazol-6-yl}methanesulfonamide To a mixture of (2R,4R)—N-[5,6-difluoro-4-(2,4,6-trifluorophenyl)-1,2-benzoxazol-3-yl]-3,3-difluoro-2-(hydroxymethyl)-4-[(methanesulfonyl) amino]pyrrolidine-1-carboxamide (85.0 mg) and 4-methylbenzenesulfonyl chloride (58.2 mg) in THF (1 mL) was added 1 M sodium hydroxide aqueous solution (0.764 mL) at 0° C. The mixture was stirred for 2 h. The mixture was quenched with saturated sodium hydrogen carbonate aqueous solution and extracted with EtOAc. The organic layer was separated, dried over anhydrous sodium sulfate and concentrated under reduced pressure. The residue was purified by silica gel column chromatography (EtOAc/hexane) then crystallized from EtOAc-hexane to give the title compound (25.9 mg).

$^1$H NMR (300 MHz, CDCl$_3$) δ 3.07 (3H, s), 3.08-3.14 (1H, m), 3.64 (1H, dd, J=12.0, 8.7 Hz), 4.11-4.24 (2H, m), 4.34-4.55 (2H, m), 4.59-4.80 (1H, m), 6.80 (2H, d, J=8.3 Hz), 7.49 (1H, dd, J=8.5, 5.8 Hz).

Example 174

N-{(6R)-7,7-Difluoro-2-[6-methyl-4-(2,4,6-trifluorophenyl) [1,2]oxazolo [5,4-b]pyridin-3-yl]-3-oxo-2,5,6,7-tetrahydro-3H-pyrrolo[1,2-c]imidazol-6-yl}methanesulfonamide A) 2-Hydroxy-6-methyl-4-(2,4,6-trifluorophenyl) pyridine-3-carbonitrile A solution of 2,4,6-trifluorobenzaldehyde (20.0 g), ethyl 2-cyanoacetate (14.1 g), acetone (9.18 mL) and ammonium acetate (125 g) in n-butanol (400 mL) was stirred at 130° C. for 3 h. The reaction mixture was concentrated under reduced pressure to give a residue. The residue was purified by silica gel column chromatography (EtOAc/petroleum ether) to give the title compound (11.1 g).
MS: [M+H]+ 265.1.

B) 2-Chloro-6-methyl-4-(2,4,6-trifluorophenyl)pyridine-3-carbonitrile

A mixture of 2-hydroxy-6-methyl-4-(2,4,6-trifluorophenyl)pyridine-3-carbonitrile (11.1 g) in phosphoryl chloride (60 mL) was stirred at 110° C. for 14 h. The reaction mixture was cooled to room temperature, then it was added to water dropwise while stirring and then it was extracted with EtOAc. The combined organic layer was washed with brine, dried over anhydrous sodium sulfate and concentrated under reduced pressure to give a residue. The residue was purified by silica gel column chromatography (EtOAc/petroleum ether) to give the title compound (3.85 g).
MS: [M+H]+ 283.1.

C) 6-Methyl-4-(2,4,6-trifluorophenyl) [1,2]oxazolo [5,4-b]pyridin-3-amine

To a solution of 2-propanone oxime (597 mg) in THF (20 mL) was added potassium tert-butoxide (785 mg) at 25° C. The mixture was stirred at 25° C. for 1 h. 2-Chloro-6-methyl-4-(2,4,6-trifluorophenyl)pyridine-3-carbonitrile (2.10 g) in THF (10 mL) was added to the mixture at 0° C. The reaction mixture was stirred at 25° C. for 14 h. To the mixture was added water and then it was extracted with EtOAc. The organic layer was separated, washed with water, and concentrated under reduced pressure. The residue was diluted with EtOH (20 mL) and 6 M hydrogen chloride aqueous solution (10 mL). The mixture was stirred at 70° C. for 3 h under nitrogen atmosphere. The mixture was diluted with water and extracted with EtOAc. The combined organic layer was washed with brine, dried over anhydrous sodium sulfate and concentrated under reduced pressure to give a residue. The residue was purified by silica gel column chromatography (EtOAc/petroleum ether) to give the title compound (1.20 g).
MS: [M+H]+ 280.1.

D) 2,2,2-Trichloroethyl [6-methyl-4-(2,4,6-trifluorophenyl) [1,2]oxazolo [5,4-b]pyridin-3-yl]carbamate To a solution of 6-methyl-4-(2,4,6-trifluorophenyl) [1,2]oxazolo[5,4-b]pyridin-3-amine (1.28 g) in THF (20 mL) was added 1 M lithium bis(trimethylsilyl)amide THF solution (10.1 mL) at 0° C. and the reaction mixture was stirred at 0° C. for 0.5 h under nitrogen atmosphere. 2,2,2-Trichloroethoxycarbonyl chloride (1.46 g) was added to the reaction mixture. The mixture was stirred at 0° C. for 1 h under nitrogen atmosphere. The mixture was quenched with saturated ammonium chloride aqueous solution at 0° C. and then it was extracted with EtOAc. The combined organic layer was washed with brine, dried over anhydrous sodium sulfate and then concentrated under reduced pressure to give a residue. The residue was purified by silica gel column chromatography (EtOAc/petroleum ether) to give the title compound (1.10 g).
MS: [M+H]+ 454.0.

E) (2R,4R)-3,3-Difluoro-2-(hydroxymethyl)-4-[(methanesulfonyl)amino]-N-[6-methyl-4-(2,4,6-trifluorophenyl) [1,2]oxazolo[5,4-b]pyridin-3-yl] pyrrolidine-1-carboxamide To a solution of N-[(3R,5R)-4,4-difluoro-5-(hydroxymethyl)pyrrolidin-3-yl]methanesulfonamide hydrochloride (440 mg) and N,N-diisopropylethylamine (569 mg) in THF (10 mL) was added 2,2,2-trichloroethyl [6-methyl-4-(2,4,6-trifluorophenyl) [1,2]oxazolo [5,4-b]pyridin-3-yl]carbamate (500 mg) and the reaction mixture was stirred at 60° C. for 3 h under nitrogen atmosphere. The reaction mixture was quenched with water, and then it was extracted with EtOAc. The combined organic layer was washed with brine, dried over anhydrous sodium sulfate and concentrated under reduced pressure to give a residue. The residue was purified by silica gel column chromatography (EtOAc/petroleum ether) to give the title compound (310 mg).
MS: [M+H]+ 536.1.

F) N-{(6R)-7,7-Difluoro-1-hydroxy-2-[6-methyl-4-(2,4,6-trifluorophenyl) [1,2]oxazolo [5,4-b]pyridin-3-yl]-3-oxohexahydro-1H-pyrrolo[1,2-c]imidazol-6-yl}methanesulfonamide To a solution of (2R,4R)-3,3-difluoro-2-(hydroxymethyl)-4-[(methanesulfonyl)amino]-N-[6-methyl-4-(2,4,6-trifluorophenyl) [1,2]oxazolo[5,4-b]pyridin-3-yl]pyrrolidine-1-carboxamide (310 mg) in MeCN (5 mL) and water (5 mL) were added iodosobenzene diacetate (224 mg), tetrabutylammonium bromide (47 mg), 2,2,6,6-tetramethylpiperidine 1-oxyl (23 mg) and sodium hydrogen carbonate (268 mg). The mixture was stirred at 0° C. for 0.5 h. The reaction mixture was quenched with water and extracted with EtOAc. The combined organic layer was washed with brine, dried over anhydrous sodium sulfate and concentrated under reduced pressure to give a residue. The residue was purified by silica gel column chromatography (EtOAc/petroleum ether) to give the title compound (191 mg).
MS: [M+H]+ 534.1.

G) N-{(6R)-7,7-Difluoro-2-[6-methyl-4-(2,4,6-trifluorophenyl) [1,2]oxazolo [5,4-b]pyridin-3-yl]-3-oxo-2,5,6,7-tetrahydro-3H-pyrrolo[1,2-c]imidazol-6-yl}methanesulfonamide To a solution of N-{(6R)-7,7-difluoro-1-hydroxy-2-[6-methyl-4-(2,4,6-trifluorophenyl) [1,2]oxazolo[5,4-b]pyridin-3-yl]-3-oxohexahydro-1H-pyrrolo[1,2-c]imidazol-6-yl}methanesulfonamide (190 mg) in THF (6 mL) was added methyl N-(triethylammoniumsulfonyl)carbamate (594 mg), and then the mixture was stirred at 50° C. for 1 h. The mixture was quenched with water and extracted with EtOAc. The combined organic layers were washed with brine, dried over anhydrous sodium sulfate and concentrated under reduced pressure. The residue was purified by preparative HPLC (column: Boston Prime C18, mobile phase: water containing ammonia hydroxide/MeCN) to give the title compound (78.5 mg).

$^1$H NMR (400 MHz, CDCl$_3$) δ 2.80 (3H, s), 3.12 (3H, s), 3.21-3.31 (1H, m), 4.04-4.14 (1H, m), 4.61-4.78 (1H, m), 5.46 (1H, d, J=9.6 Hz), 6.67-6.82 (2H, m), 6.84-6.91 (1H, m), 7.29 (1H, s).

Example 213

N-{(4aR,6R)-5,5-Difluoro-1-oxo-2-[4-(2,4,6-trifluorophenyl)-1,2-benzoxazol-3-yl]octahydropyrrolo[1,2-c]pyrimidin-6-yl}methanesulfonamide A) tert-Butyl (2R,4R)-3,3-difluoro-2-(hydroxymethyl)-4-{(methanesulfonyl) [(4-methoxyphenyl)methyl]amino}pyrrolidine-1-carboxylate To a mixture of tert-butyl (2R,4R)-3,3-difluoro-2-(hydroxymethyl)-4-[(methanesulfonyl)amino]pyrrolidine-1-carboxylate (5.00 g), 1-(chloromethyl)-4-methoxybenzene (5.13 mL), and DMF (101 mL) was added potassium carbonate (10.5 g) at room temperature. The mixture was stirred at 60° C. under argon atmosphere overnight. To the mixture were added EtOAc and water at 0° C. The aqueous layer was separated and extracted with EtOAc. The organic layers were combined, washed with water and brine, dried over anhydrous sodium sulfate and concentrated under reduced pressure. The residue was purified by silica gel column chromatography (EtOAc/hexane) to give the title compound (3.85 g).

MS: [M+H-Boc]$^+$ 351.1.

B) tert-Butyl (2R,4R)-3,3-difluoro-4-{(methanesulfonyl) [(4-methoxyphenyl)methyl]amino}-2-{[(methanesulfonyl)oxy]methyl}pyrrolidine-1-carboxylate To a mixture of tert-butyl (2R,4R)-3,3-difluoro-2-(hydroxymethyl)-4-{(methanesulfonyl) [(4-methoxyphenyl)methyl]amino}pyrrolidine-1-carboxylate (2.77 g), N,N-diisopropyletylamine (2.15 mL), and MeCN (12 mL) was added methanesulfonic anhydride (1.61 g) at 0° C. and the mixture was stirred at 0° C. for 0.5 h. The mixture was diluted with EtOAc and water while stirring. The organic layer was washed with brine, dried over anhydrous sodium sulfate, filtered through a NH silica gel pad eluting with EtOAc and concentrated under reduced pressure to give the tile compound (3.11 g).

MS: [M+Na]$^+$ 551.2.

C) tert-Butyl (2R,4R)-2-(cyanomethyl)-3,3-difluoro-4-{(methanesulfonyl) [(4-methoxyphenyl)methyl]amino}pyrrolidine-1-carboxylate A mixture of tert-butyl (2R,4R)-3,3-difluoro-4-{(methanesulfonyl) [(4-methoxyphenyl)methyl]amino}-2-{[(methanesulfonyl)oxy]methyl}pyrrolidine-1-carboxylate (2.94 g), sodium cyanate (1.78 g), and dimethylsulfoxyde (36 mL) was stirred at 45-50° C. for 4.5 h. The mixture was diluted with EtOAc and ammonium chloride aqueous solution while stirring at 0° C. The organic layer was separated, washed with brine, dried over anhydrous sodium sulfate, filtered through a silica gel pad, and concentrated under reduced pressure. The residue was purified by silica gel column chromatography (EtOAc/hexane) to give the title compound (1.91 g).

MS: [M+Na]$^+$ 482.2.

D) Methyl [(2R,4R)-3,3-difluoro-4-{(methanesulfonyl) [(4-methoxyphenyl)methyl]amino}pyrrolidin-2-yl]acetate hydrochloride To a mixture of tert-butyl (2R,4R)-2-(cyanomethyl)-3,3-difluoro-4-{(methanesulfonyl) [(4-methoxyphenyl)methyl]amino}pyrrolidine-1-carboxylate (1.99 g), and MeOH (60 mL) was added trimethylsilyl chloride (16.6 mL) at room temperature and the mixture was refluxed for 2.5 h.

After addition of trimethylsilyl chloride (8.30 mL), the mixture was refluxed for 1.5 h. After further addition of trimethylsilyl chloride (5.54 mL), the mixture was refluxed for 1 h. The mixture was cooled to 0° C. and a white suspension formed. IPE (60 mL) was added and the mixture was stirred at 0° C. for 10 min. The precipitates were collected, washed with IPE, and dried under reduced pressure to give the title compound (1.75 g).

MS: [M+H]$^+$ 393.1.

E) tert-Butyl (2R,4R)-3,3-difluoro-4-{(methanesulfonyl) [(4-methoxyphenyl)methyl]amino}-2-(2-methoxy-2-oxoethyl)pyrrolidine-1-carboxylate To a cooled mixture of methyl [(2R,4R)-3,3-difluoro-4-{(methanesulfonyl) [(4-methoxyphenyl)methyl]amino}pyrrolidin-2-yl]acetate hydrochloride (1.64 g), sodium hydrogen carbonate (0.964 g), THF (30 mL), and water (10 mL) was added di-tert-butyl dicarbonate (1.15 mL) at 0° C. and the mixture was stirred at room temperature overnight. To the mixture were added EtOAc and water while stirring. The organic layers were washed with brine, dried over anhydrous sodium sulfate, filtered through a silica gel pad, and concentrated under reduced pressure. The residue was purified by silica gel column chromatography (EtOAc/hexane) to give the title compound (1.75 g).

MS: [M+Na]$^+$ 512.2.

F) tert-Butyl (2R,4R)-3,3-difluoro-4-[(methanesulfonyl)amino]-2-(2-methoxy-2-oxoethyl)pyrrolidine-1-carboxylate To a cooled mixture of tert-butyl (2R,4R)-3,3-difluoro-4-{(methanesulfonyl) [(4-methoxyphenyl)methyl]amino}-2-(2-methoxy-2-oxoethyl)pyrrolidine-1-carboxylate (1.71 g), MeCN (36 mL), and pH 6.8 phosphate buffer (24 mL) was added Cerium(IV) diammonium nitrate (6.28 g) and the mixture was stirred at 0° C. for 10 min and then at room temperature for 0.5 h. The mixture was diluted with EtOAc and 10% sodium thiosulfate aqueous solution was added at 0° C. until the yellow color of the reaction disappeared and saturated sodium hydrogen carbonate aqueous solution was added for neutralization while stirring. The organic layer was washed with brine, dried over anhydrous sodium sulfate, filtered through a NH silica gel pad and concentrated under reduced pressure. The residue was purified by silica gel column chromatography (EtOAc/hexane) to give the title compound (1.20 g).

$^1$H NMR (300 MHz, CDCl$_3$) δ 1.46 (9H, s), 2.76-3.02 (2H, m), 3.06 (3H, s), 3.15-3.32 (1H, m), 3.72 (3H, s), 4.02-4.56 (3H, m), 5.23 (1H, br d, J=9.6 Hz).

G) tert-Butyl (2R,4R)-3,3-difluoro-2-(2-hydroxyethyl)-4-[(methanesulfonyl)amino]pyrrolidine-1-carboxylate To a mixture of tert-butyl (2R,4R)-3,3-difluoro-4-[(methanesulfonyl)amino]-2-(2-methoxy-2-oxoethyl)pyrrolidine- 1-carboxylate (1.16 g) and THF (20 mL) was added 4 M lithium borohydride THF solution (3.89 mL) at room temperature and the mixture was stirred at 45-50° C. for 4.5 h. After that, the mixture was stirred at room temperature for 16 h. The reaction was diluted with EtOAc and ammonium chloride aqueous solution while stirring at 0° C. for 20 min and then stirred at room temperature for 20 min. The organic layer was separated, washed with water and brine, dried over anhydrous sodium sulfate, filtered through a silica gel pad, and concentrated under reduced pressure. The residue was purified by silica gel column chromatography (EtOAc/hexane) to give the title compound (0.966 g).

$^1$H NMR (300 MHz, CDCl$_3$) δ 1.48 (9H, s), 1.65-1.85 (1H, m), 1.94-2.13 (1H, m), 3.02-3.21 (4H, m), 3.36-3.87 (3H, m), 4.08-4.46 (3H, m), 4.91-5.24 (1H, m).

H) N-[(3R,5R)-4,4-Difluoro-5-(2-hydroxyethyl) pyrrolidin-3-yl]methanesulfonamide hydrochloride A mixture of tert-butyl (2R,4R)-3,3-difluoro-2-(2-hydroxyethyl)-4-[(methanesulfonyl)amino]pyrrolidine-1-carboxylate (32.7 mg) and 2 M hydrogen chloride solution in MeOH (2 mL) was refluxed for 0.5 h. After cooling to 0° C., IPE was added dropwise and the mixture was stirred at 0° C. for 0.5 h. After concentration under reduced pressure, the residue was triturated with EtOAc/heptane to form a white solid, which was collected, washed with EtOAc, and dried under reduced pressure at 50° C. to give the title compound (23.6 mg).

$^1$H NMR (300 MHz, DMSO-d$_6$) δ 1.85-1.96 (2H, m), 2.99-3.13 (4H, m), 3.51-3.64 (2H, m), 3.68-3.84 (1H, m), 3.99-4.24 (1H, m), 4.52-4.76 (1H, m), 4.83-5.10 (1H, m), 8.12 (1H, d, J=9.1 Hz), 9.73 (2H, br s).

I) (2R,4R)-3,3-Difluoro-2-(2-hydroxyethyl)-4-[(methanesulfonyl)amino]-N-[4-(2,4,6-trifluorophenyl)-1,2-benzoxazol-3-yl]pyrrolidine-1-carboxamide To a mixture of N-[(3R,5R)-4,4-difluoro-5-(2-hydroxyethyl)pyrrolidin-3-yl]methanesulfonamide hydrochloride (170 mg), 2,2,2-trichloroethyl [4-(2,4,6-trifluorophenyl)-1,2-benzoxazol-3-yl]carbamate (280 mg) and THF (3.0 mL) was added TEA (0.252 mL) at room temperature. The mixture was stirred at 60° C. under nitrogen atmosphere overnight. The mixture was diluted with EtOAc, and concentrated under reduced pressure. The residue was purified by silica gel column chromatography (EtOAc/hexane) to give the title compound (318 mg).

MS: [M+H]$^+$ 535.2.

J) N-{(4aR,6R)-5,5-Difluoro-1-oxo-2-[4-(2,4,6-trifluorophenyl)-1,2-benzoxazol-3-yl]octahydropyrrolo[1,2-c]pyrimidin-6-yl}methanesulfonamide To a mixture of (2R,4R)-3,3-difluoro-2-(2-hydroxyethyl)-4-[(methanesulfonyl)amino]-N-[4-(2,4,6-trifluorophenyl)-1,2-benzoxazol-3-yl]pyrrolidine-1-carboxamide (318 mg), triethylamine (0.412 mL), and MeCN (3.0 mL) was added methanesulfonic anhydride (187 mg) at room temperature. The mixture was stirred at room temperature under nitrogen atmosphere for 10 min, then the mixture was diluted with EtOAc, and concentrated under reduced pressure. The residue was purified by silica gel column chromatography (EtOAc/hexane). The solid was crystallized from EtOAc-heptane to give the title compound (198 mg).

$^1$H NMR (400 MHz, CDCl$_3$) δ 1.92-2.14 (1H, m), 2.15-2.30 (1H, m), 2.54-2.79 (1H, m), 3.10 (3H, s), 3.35-4.15 (4H, m), 4.17-4.45 (1H, m), 4.56-4.83 (1H, m), 6.60-6.88 (2H, m), 7.27-7.31 (1H, m), 7.60-7.68 (2H, m).

Example 242

N-{(4aR,6R)-5,5-Difluoro-1-oxo-2-[4-(2,4,6-trifluorophenyl)-1,2-benzoxazol-3-yl]octahydropyrrolo[1,2-c]pyrimidin-6-yl}cyclopropanesulfonamide A) tert-Butyl (2R,4R)-4-amino-3,3-difluoro-2-(hydroxymethyl)pyrrolidine-1-carboxylate A mixture of tert-butyl (2R,4R)-4-amino-2-[(benzyloxy)methyl]-3,3-difluoropyrrolidine-1-carboxylate (10.2 g) and 10% palladium hydroxyde on carbon (500 mg) in EtOH (200 mL) was hydrogenated under balloon pressure at room temperature for 16 h. The catalyst was removed by filtration and the filtrate was concentrated under reduced pressure to give the title compound (7.49 g).

MS: [M+H-Boc]$^+$ 153.1.

B) tert-Butyl (2R,4R)-4-amino-2-({[tert-butyl(dimethyl)silyl]oxy}methyl)-3,3-difluoropyrrolidine-1-carboxylate A mixture of tert-butyl (2R,4R)-4-amino-3,3-difluoro-2-(hydroxymethyl)pyrrolidine-1-carboxylate (7.52 g), 1H-imidazole (6.08 g), and tert-butyldimethylsilyl chloride (4.94 g) in DMF (50 mL) was stirred at room temperature for 40 min under argon atmosphere. The mixture was quenched with saturated ammonium chloride aqueous solution and extracted with EtOAc. The organic layer was separated, dried over anhydrous sodium sulfate and concentrated under reduced pressure. The crude product was purified by silica gel column chromatography (EtOAc/hexane) to give the title compound (11.4 g).

MS: [M+H-Boc]$^+$ 267.2.

C) tert-Butyl (2R,4R)-2-({[tert-butyl(dimethyl)silyl]oxy}methyl)-4-[(cyclopropanesulfonyl)amino]-3,3-difluoropyrrolidine-1-carboxylate To a solution of tert-butyl (2R,4R)-4-amino-2-({[tert-butyl(dimethyl)silyl]oxy}methyl)-3,3-difluoropyrrolidine-1-carboxylate (4.10 g) and TEA (9.34 mL) in anhydrous THF (50 mL) were added cyclopropanesulfonyl chloride (7.86 g) and 4-dimethylaminopyridine (1.37 g) at 20° C. and the mixture was stirred at 70° C. for 14 h under nitrogen atmosphere. The mixture was quenched with water and it was extracted with EtOAc. The combined organic layer was separated, washed with water and brine, dried over anhydrous sodium sulfate and concentrated under reduced pressure. The residue was purified by silica gel column chromatography (EtOAc/petroleum ether) to give the title compound (4.15 g).

$^1$H NMR (400 MHz, CDCl$_3$) δ 0.09-0.20 (6H, m), 0.92 (9H, s), 0.95-1.21 (4H, m), 1.47 (9H, s), 2.35-2.48 (1H, m), 3.36-3.54 (1H, m), 3.77-4.05 (3H, m), 4.09-4.27 (2H, m), 6.31-6.70 (1H, m).

D) tert-Butyl (2R,4R)-2-({[tert-butyl (dimethyl) silyl]oxy}methyl)-4-{(cyclopropanesulfonyl) [(4-methoxyphenyl)methyl]amino}-3,3-difluoropyrrolidine-1-carboxylate To a solution of tert-butyl (2R,4R)-2-({[tert-butyl (dimethyl) silyl]oxy}methyl)-4-[(cyclopropanesulfonyl)amino]-

3,3-difluoropyrrolidine-1-carboxylate (4.15 g) and 4-methoxybenzyl chloride (3.45 g) in anhydrous DMF (60 mL) was added potassium carbonate (6.09 g) at 20° C. and the mixture was stirred at 60° C. for 7 h under nitrogen atmosphere. The mixture was quenched with water and it was extracted with EtOAc. The combined organic layer was separated, washed with water and brine, dried over anhydrous sodium sulfate and concentrated under reduced pressure. The residue was purified by silica gel column chromatography (EtOAc/petroleum ether) to give the title compound (4.80 g).

MS: [M+H-Boc]$^+$ 491.2.

E) tert-Butyl (2R,4R)-4-{(cyclopropanesulfonyl) [(4-methoxyphenyl)methyl]amino}-3,3-difluoro-2-(hydroxymethyl)pyrrolidine-1-carboxylate To a solution of tert-butyl (2R,4R)-2-({[tert-butyl(dimethyl)silyl]oxy}methyl)-4-{(cyclopropanesulfonyl) [(4-methoxyphenyl)methyl]amino}-3,3-difluoropyrrolidine-1-carboxylate (4.80 g) in anhydrous THF (50 mL) was added 1 M tetrabutylammonium fluoride THF solution (12.2 mL) at 20° C. and the mixture was stirred at 20° C. for 1 h under nitrogen atmosphere. The mixture was quenched with water and it was extracted with EtOAc. The combined organic layer was separated, washed with water and brine, dried over anhydrous sodium sulfate and concentrated under reduced pressure to give the title compound (4.10 g).

MS: [M+Na]$^+$ 499.3.

F) tert-Butyl (2R,4R)-4-{(cyclopropanesulfonyl) [(4-methoxyphenyl)methyl]amino}-3,3-difluoro-2-{[(methanesulfonyl)oxy]methyl}pyrrolidine-1-carboxylate To a mixture of tert-butyl (2R,4R)-4-{(cyclopropanesulfonyl) [(4-methoxyphenyl)methyl]amino}-3,3-difluoro-2-(hydroxymethyl)pyrrolidine-1-carboxylate (4.10 g) and TEA (4.52 mL) in dichloromethane (40 mL) was added methanesulfonic anhydride (2.83 g) at 20° C. and the mixture was stirred at 20° C. for 0.5 h. The mixture was diluted with EtOAc and water while stirring. The organic layer was separated, washed with brine, dried over anhydrous sodium sulfate, and concentrated under reduced pressure. The residue was purified by silica gel column chromatography (EtOAc/petroleum ether) to give the title compound (4.18 g).

MS: [M+Na]$^+$ 577.1.

G) tert-Butyl (2R,4R)-2-(cyanomethyl)-4-{(cyclopropanesulfonyl) [(4-methoxyphenyl)methyl]amino}-3,3-difluoropyrrolidine-1-carboxylate To a mixture of tert-butyl (2R,4R)-4-{(cyclopropanesulfonyl) [(4-methoxyphenyl)methyl]amino}-3,3-difluoro-2-{[(methanesulfonyl)oxy]methyl}pyrrolidine-1-carboxylate (4.18 g) and dimethylsufoxyde (50 mL) was added sodium cyanide (1.58 g) and the mixture was stirred at 50° C. for 4 h under nitrogen atmosphere. The mixture was diluted with EtOAc and water while stirring. The organic layer was separated, washed with brine, dried over anhydrous sodium sulfate, and concentrated under reduced pressure. The residue was purified by silica gel column chromatography (EtOAc/petroleum ether) to give the title compound (2.75 g).

MS: [M+H-Boc]$^+$ 386.2.

H) Methyl [(2R,4R)-4-{(cyclopropanesulfonyl) [(4-methoxyphenyl)methyl]amino}-3,3-difluoropyrrolidin-2-yl]acetate hydrochloride To a mixture of tert-butyl (2R,4R)-2-(cyanomethyl)-4-{(cyclopropanesulfonyl) [(4-methoxyphenyl)methyl]amino}-3,3-difluoropyrrolidine-1-carboxylate (2.75 g) and MeOH (40 mL) was added trimethylsilyl chloride (9.23 g) at 25° C. and the mixture was stirred at 65° C. for 14 h under nitrogen atmosphere. Trimethylsilyl chloride (4.62 g) was added and the mixture was stirred at 65° C. for 1 h under nitrogen atmosphere. Trimethylsilyl chloride (4.62 g) was added and the mixture was stirred at 65° C. for 1 h under nitrogen atmosphere. The mixture was concentrated under reduced pressure to give the title compound (2.70 g).

MS: [M+H]$^+$ 419.0.

I) tert-Butyl (2R,4R)-4-{(cyclopropanesulfonyl) [(4-methoxyphenyl)methyl]amino}-3,3-difluoro-2-(2-methoxy-2-oxoethyl)pyrrolidine-1-carboxylate To a mixture of methyl [(2R,4R)-4-{(cyclopropanesulfonyl) [(4-methoxyphenyl)methyl]amino}-3,3-difluoropyrrolidin-2-yl]acetate hydrochloride (2.70 g), THF (30 mL) and water (15 mL) were added di-tert-butyl dicarbonate (2.47 g) and sodium hydrogen carbonate (2.38 g) at 25° C. and the mixture was stirred at 25° C. for 1 h under nitrogen atmosphere. The mixture was diluted with water and extracted with EtOAc. The combined organic layer was washed with brine, dried over anhydrous sodium sulfate, and concentrated under reduced pressure. The residue was purified by silica gel column chromatography (EtOAc/petroleum ether) to give the title compound (2.65 g).

MS: [M+Na]$^+$ 541.1.

J) tert-Butyl (2R,4R)-4-[(cyclopropanesulfonyl)amino]-3,3-difluoro-2-(2-methoxy-2-oxoethyl)pyrrolidine-1-carboxylate To a mixture of tert-butyl (2R,4R)-4-{(cyclopropanesulfonyl) [(4-methoxyphenyl)methyl]amino}-3,3-difluoro-2-(2-methoxy-2-oxoethyl)pyrrolidine-1-carboxylate (2.65 g), MeCN (50 mL) and pH 6.8 phosphate buffer (30 mL) was added Cerium(IV) diammonium nitrate (8.40 g) at 0° C. and the mixture was stirred at 20° C. for 2 h under nitrogen atmosphere. The mixture was diluted with EtOAc and 10% sodium thiosulfate aqueous solution was added until the yellow color of the reaction disappeared and saturated sodium hydrogen carbonate aqueous solution was added for neutralization while stirring. The mixture was filtered and the filtrate was extracted with EtOAc. The combined organic layer was washed with brine, dried over anhydrous sodium sulfate and concentrated under reduced pressure. The residue was purified by silica gel column chromatography (EtOAc/petroleum ether) to give the title compound (1.75 g).

MS: [M+H-Boc]$^+$ 298.9.

K) tert-Butyl (2R,4R)-4-[(cyclopropanesulfonyl)amino]-3,3-difluoro-2-(2-hydroxyethyl)pyrrolidine-1-carboxylate To a mixture of tert-butyl (2R,4R)-4-[(cyclopropanesulfonyl)amino]-3,3-difluoro-2-(2-methoxy-2-oxoethyl)pyrrolidine-1-carboxylate (1.75 g) and THF (20 mL) was added dropwise 2 M lithium borohydride THF solution (13.2 mL) at 20° C. The mixture was stirred at 60° C. for 2 h. The mixture was quenched slowly with saturated ammonium chloride aqueous solution and extracted with EtOAc. The combined organic layer was separated, washed with brine, dried over anhydrous sodium sulfate, and concentrated under reduced pressure to give the title compound (1.60 g).

MS: [M+H-Boc]$^+$ 270.9.

L) N-[(3R,5R)-4,4-Difluoro-5-(2-hydroxyethyl)pyrrolidin-3-yl]cyclopropanesulfonamide hydrochloride A solution of tert-butyl (2R,4R)-4-[(cyclopropanesulfonyl)amino]-3,3-difluoro-2-(2-hydroxyethyl)pyrrolidine-1-carboxylate (1.60 g) in 4 M hydrogen chloride EtOAc solution (25 mL) was stirred at 20° C. for 1 h. The mixture was filtered and the filtered cake was dried under reduced pressure to give the title compound (1.15 g).

$^1$H NMR (400 MHz, DMSO-d$_6$) δ 0.89-1.06 (4H, m), 1.83-2.22 (2H, m), 2.53-2.65 (1H, m), 3.09-3.23 (1H, m), 3.50-3.73 (3H, m), 4.06-4.20 (1H, m), 4.50-4.70 (1H, m), 8.08-8.20 (1H, m), 10.28 (2H, m).

M) (2R,4R)-4-[(Cyclopropanesulfonyl)amino]-3,3-difluoro-2-(2-hydroxyethyl)-N-[4-(2,4,6-trifluorophenyl)-1,2-benzoxazol-3-yl]pyrrolidine-1-carboxamide To a mixture of N-[(3R,5R)-4,4-difluoro-5-(2-hydroxyethyl)pyrrolidin-3-yl]cyclopropanesulfonamide hydrochloride (50.0 mg) and TEA (91.0 μL) in THF (4 mL) was added 2,2,2-trichloroethyl [4-(2,4,6-trifluorophenyl)-1,2-benzoxazol-3-yl]carbamate (107 mg) at 0° C. The mixture was stirred at 60° C. for 14 h under nitrogen atmosphere. The reaction mixture was poured into water and it was extracted with EtOAc. The combined organic layer was washed with brine, dried over anhydrous sodium sulfate and concentrated under reduced pressure. The residue was purified by preparative TLC (silica gel, EtOAc/petroleum ether) to give the title compound (45 mg).

MS: [M+H]$^+$ 561.0.

N) N-{(4aR,6R)-5,5-Difluoro-1-oxo-2-[4-(2,4,6-trifluorophenyl)-1,2-benzoxazol-3-yl]octahydropyrrolo[1,2-c]pyrimidin-6-yl}cyclopropanesulfonamide To a mixture of (2R,4R)-4-[(cyclopropanesulfonyl)amino]-3,3-difluoro-2-(2-hydroxyethyl)-N-[4-(2,4,6-trifluorophenyl)-1,2-benzoxazol-3-yl]pyrrolidine-1-carboxamide (45.0 mg) and MeCN (2 mL) were added TEA (65.0 mg) and methanesulfonic anhydride (42.0 mg) at 0° C. The mixture was stirred at 25° C. for 10 h. The reaction mixture was poured into water and it was extracted with EtOAc. The combined organic layer was washed with brine, dried over anhydrous sodium sulfate and concentrated under reduced pressure. The residue was purified by preparative HPLC (column: Boston Prime C18, mobile phase: water containing ammonia hydroxide/MeCN) followed by lyophilization to give the title compound (7.2 mg).

$^1$H NMR (400 MHz, CDCl$_3$) δ 1.02-1.13 (2H, m), 1.14-1.32 (2H, m), 1.97-2.29 (2H, m), 2.46-2.57 (1H, m), 2.58-2.80 (1H, m), 3.40-4.42 (5H, m), 4.46-4.64 (1H, m), 6.61-6.92 (2H, m), 7.27-7.31 (1H, m, overlapped with CDCl3's signal), 7.60-7.67 (2H, m).

Example 243

N-{(4aR,6R)-2-[5,6-Difluoro-4-(2,4,6-trifluorophenyl)-1,2-benzoxazol-3-yl]-5,5-difluoro-1-oxooctahydropyrrolo[1,2-c]pyrimidin-6-yl}methanesulfonamide A) (2R,4R)—N-[5,6-Difluoro-4-(2,4,6-trifluorophenyl)-1,2-benzoxazol-3-yl]-3,3-difluoro-2-(2-hydroxyethyl)-4-[(methanesulfonyl)amino]pyrrolidine-1-carboxamide To a mixture of N-[(3R,5R)-4,4-difluoro-5-(2-hydroxyethyl)pyrrolidin-3-yl]methanesulfonamide hydrochloride (39.5 mg), 2,2,2-trichloroethyl [5,6-difluoro-4-(2,4,6-trifluorophenyl)-1,2-benzoxazol-3-yl]carbamate (67.0 mg) and THF (1.0 mL) was added TEA (0.059 mL) at room temperature. The mixture was stirred at 60° C. under nitrogen overnight. The mixture was diluted with EtOAc, and concentrated under reduced pressure. The residue was purified by silica gel column chromatography (EtOAc/hexane) to give the title compound (66 mg).

MS: [M+H]$^+$ 571.2.

B) N-{(4aR,6R)-2-[5,6-Difluoro-4-(2,4,6-trifluorophenyl)-1,2-benzoxazol-3-yl]-5,5-difluoro-1-oxooctahydropyrrolo[1,2-c]pyrimidin-6-yl}methanesulfonamide To a mixture of (2R,4R)—N-[5,6-difluoro-4-(2,4,6-trifluorophenyl)-1,2-benzoxazol-3-yl]-3,3-difluoro-2-(2-hydroxyethyl)-4-[(methanesulfonyl)amino]pyrrolidine-1-carboxamide (66.0 mg), TEA (0.080 mL), and MeCN (1.0 mL) was added methanesulfonic anhydride (36.3 mg) at room temperature. The mixture was stirred at room temperature under nitrogen for 10 min, then the mixture was diluted with EtOAc and concentrated under reduced pressure. The residue was purified by silica gel column chromatography (EtOAc/hexane). The solid was crystallized from EtOAc-heptane to give the title compound (53.0 mg).

$^1$H NMR (400 MHz, CDCl$_3$) δ 1.92-2.10 (1H, m), 2.16-2.28 (1H, m), 2.49-2.81 (1H, m), 3.10 (3H, s), 3.18-4.18 (4H, m), 4.22-4.43 (1H, m), 4.50-4.67 (1H, m), 6.66-6.93 (2H, m), 7.43-7.55 (1H, m).

Example 260

N-{(4aR,6R)-5,5-Difluoro-1-oxo-2-[4-(2,4,6-trifluorophenyl)-1,2-benzoxazol-3-yl]octahydropyrrolo[1,2-c]pyrimidin-6-yl}ethanesulfonamide A) tert-Butyl (2R,4R)-2-({[tert-butyl(dimethyl)silyl]oxy}methyl)-4-[(ethanesulfonyl)amino]-3,3-difluoropyrrolidine-1-carboxylate To a solution of tert-butyl (2R,4R)-4-amino-2-({[tert-butyl(dimethyl)silyl]oxy}methyl)-3,3-difluoropyrrolidine-1-carboxylate (8.90 g) and TEA (7.37 g) in dichloromethane (100 mL) was added ethanesulfonyl chloride (4.68 g) at 0° C. and the reaction mixture was stirred at 20° C. for 1 h. The mixture was diluted with water and it was extracted with dichloromethane. The combined organic layer was washed with brine, dried over anhydrous sodium sulfate and concentrated under reduced pressure. The residue was purified by silica gel column chromatography (EtOAc/petroleum ether) to give the title compound (10.7 g).

¹H NMR (400 MHz, CDCl₃) δ 0.08-0.21 (6H, m), 0.90-0.96 (9H, m), 1.37 (3H, t, J=7.6 Hz), 1.47 (9H, s), 2.92-3.16 (2H, m), 3.36-3.55 (1H, m), 3.74-4.12 (4H, m), 4.14-4.30 (1H, m), 6.30-6.69 (1H, m).

B) tert-Butyl (2R,4R)-2-({[tert-butyl (dimethyl)silyl]oxy}methyl)-4-{(ethanesulfonyl) [(4-methoxyphenyl)methyl]amino}-3,3-difluoropyrrolidine-1-carboxylate To a mixture of tert-butyl (2R,4R)-2-({[tert-butyl(dimethyl)silyl]oxy}methyl)-4-[(ethanesulfonyl)amino]-3,3-difluoropyrrolidine-1-carboxylate (10.7 g) and 1-(chloromethyl)-4-methoxybenzene (9.11 g) in DMF (150 mL) was added potassium carbonate (16.1 g). The mixture was stirred at 60° C. for 7 h. The reaction mixture was quenched with water at 0° C., and then it was extracted with EtOAc. The combined organic layer was concentrated under reduced pressure. The residue was purified by silica gel column chromatography (EtOAc/petroleum ether) to give the title compound (10.8 g).

¹H NMR (400 MHz, CDCl₃) δ 0.01-0.07 (6H, m), 0.87 (9H, s), 1.36 (3H, t, J=7.2 Hz), 1.43 (9H, s), 2.82-3.37 (3H, m), 3.74-4.03 (7H, m), 4.38-4.87 (3H, m), 6.79-6.91 (2H, m), 7.22-7.26 (2H, m).

C) tert-Butyl (2R,4R)-4-{(ethanesulfonyl) [(4-methoxyphenyl)methyl]amino}-3,3-difluoro-2-(hydroxymethyl)pyrrolidine-1-carboxylate To a solution of tert-butyl (2R,4R)-2-({[tert-butyl (dimethyl) silyl]oxy}methyl)-4-{(ethanesulfonyl) [(4-methoxyphenyl)methyl]amino}-3,3-difluoropyrrolidine-1-carboxylate (10.8 g) in THF (200 mL) was added 1 M tetrabutylammonium fluoride THF solution (28.0 mL) at 20° C. and the mixture was stirred at 20° C. for 16 h under nitrogen atmosphere. The mixture was quenched with water and it was extracted with EtOAc. The combined organic layer was separated, washed with water and brine, dried over anhydrous sodium sulfate and concentrated under reduced pressure. The residue was purified by silica gel column chromatography (EtOAc/petroleum ether) to give the title compound (8.05 g).

¹H NMR (400 MHz, CDCl₃) δ 1.33 (3H, t, J=7.2 Hz), 1.43 (9H, s), 2.75-3.08 (2H, m), 3.22-3.41 (1H, m), 3.60-3.74 (1H, m), 3.76-3.85 (4H, m), 3.94-4.08 (2H, m), 4.34-4.54 (2H, m), 4.60-4.77 (2H, m), 6.84-6.92 (2H, m), 7.27-7.36 (2H, m).

D) tert-Butyl (2R,4R)-4-{(ethanesulfonyl) [(4-methoxyphenyl)methyl]amino}-3,3-difluoro-2-{[(methanesulfonyl)oxy]methyl}pyrrolidine-1-carboxylate To a mixture of tert-butyl (2R,4R)-4-{(ethanesulfonyl) [(4-methoxyphenyl)methyl]amino}-3,3-difluoro-2-(hydroxymethyl)pyrrolidine-1-carboxylate (400 mg) and TEA (349 mg) in dichloromethane (10 mL) was added methanesulfonic anhydride (300 mg) at 25° C. and the mixture was stirred at 25° C. for 1 h. The mixture was diluted with EtOAc and water while stirring. The organic layer was separated, washed with brine, dried over anhydrous sodium sulfate, and concentrated under reduced pressure to give the title compound (480 mg).

MS: [M+Na]⁺ 565.2.

E) tert-Butyl (2R,4R)-2-(cyanomethyl)-4-{(ethanesulfonyl) [(4-methoxyphenyl)methyl]amino}-3,3-difluoropyrrolidine-1-carboxylate To a mixture of tert-butyl (2R,4R)-4-{(ethanesulfonyl) [(4-methoxyphenyl)methyl]amino}-3,3-difluoro-2-{[(methanesulfonyl)oxy]methyl}pyrrolidine-1-carboxylate (8.42 g) and dimethylsulfoxide (120 mL) was added sodium cyanide (3.19 g) and the mixture was stirred at 50° C. for 2 h under nitrogen atmosphere. The mixture was diluted with EtOAc and water while stirring. The organic layer was separated, washed with brine, dried over anhydrous sodium sulfate, and concentrated under reduced pressure. The residue was purified by silica gel column chromatography (EtOAc/petroleum ether) to give the title compound (5.18 g).

MS: [M+Na]⁺ 496.2.

F) Methyl [(2R,4R)-4-{(ethanesulfonyl) [(4-methoxyphenyl)methyl]amino}-3,3-difluoropyrrolidin-2-yl]acetate hydrochloride To a mixture of tert-butyl (2R,4R)-2-(cyanomethyl)-4-{ (ethanesulfonyl) [(4-methoxyphenyl)methyl]amino}-3,3-difluoropyrrolidine-1-carboxylate (5.18 g) and MeOH (100 mL) was added trimethylsilyl chloride (17.8 g) at 25° C. and the mixture was stirred at 65° C. for 14 h under nitrogen atmosphere. The mixture was concentrated under reduced pressure to give the title compound (4.84 g).

MS: [M+H]⁺ 407.1.

G) tert-Butyl (2R,4R)-4-{(ethanesulfonyl) [(4-methoxyphenyl)methyl]amino}-3,3-difluoro-2-(2-methoxy-2-oxoethyl)pyrrolidine-1-carboxylate To a mixture of methyl [(2R,4R)-4-{(ethanesulfonyl) [(4-methoxyphenyl)methyl]amino}-3,3-difluoropyrrolidin-2-yl]acetate hydrochloride (4.84 g), THF (80 mL) and water (40 mL) were added di-tert-butyl dicarbonate (4.77 g) and sodium hydrogen carbonate (4.59 g) at 20° C. and the mixture was stirred at 20° C. for 1 h under nitrogen atmosphere. The mixture was diluted with water and extracted with EtOAc. The combined organic layer was washed with brine, dried over anhydrous sodium sulfate, and concentrated under reduced pressure. The residue was purified by silica gel column chromatography (EtOAc/petroleum ether) to give the title compound (4.53 g).

¹H NMR (400 MHz, CDCl₃) δ 1.35 (3H, t, J=7.2 Hz), 1.41 (9H, s), 2.63-3.10 (4H, m), 3.12-3.43 (1H, m), 3.67-3.84 (7H, m), 4.34-4.52 (2H, m), 4.60-4.83 (2H, m), 6.87 (2H, d, J=8.4 Hz), 7.26-7.37 (2H, m).

H) tert-Butyl (2R,4R)-4-[(ethanesulfonyl)amino]-3,3-difluoro-2-(2-methoxy-2-oxoethyl)pyrrolidine-1-carboxylate To a mixture of tert-butyl (2R,4R)-4-{(ethanesulfonyl) [(4-methoxyphenyl)methyl]amino}-3,3-difluoro-2-(2-methoxy-2-oxoethyl)pyrrolidine-1-carboxylate (180 mg), MeCN (8 mL) and pH 6.8 phosphate buffer (4 mL) was added Cerium(IV) diammonium nitrate (545 mg) at 0° C. and the mixture was stirred at 25° C. for 1 h under nitrogen atmosphere. Cerium(IV) diammonium nitrate (545 mg) was added and the mixture was stirred at 25° C. for 1 h. The mixture was diluted with EtOAc and 10% sodium thiosulfate aqueous solution was added until the yellow color of the reaction disappeared and saturated sodium hydrogen carbonate aqueous solution was added for neutralization while stirring. The organic layer was washed with brine, dried over anhydrous sodium sulfate and concentrated under reduced pressure. The residue was purified by silica gel column chromatography (EtOAc/petroleum ether) to give the title compound (110 mg).

MS: [M+H-Boc]$^+$ 286.9.

I) tert-Butyl (2R,4R)-4-[(ethanesulfonyl)amino]-3,3-difluoro-2-(2-hydroxyethyl)pyrrolidine-1-carboxylate To a mixture of tert-butyl (2R,4R)-4-[(ethanesulfonyl)amino]-3,3-difluoro-2-(2-methoxy-2-oxoethyl)pyrrolidine-1-carboxylate (162 mg) and THF (5 mL) was added dropwise 4 M lithium borohydride THF solution (0.53 mL) at 25° C. The mixture was stirred at 60° C. for 2 h. The mixture was quenched with saturated ammonium chloride aqueous solution and it was extracted with EtOAc. The combined organic layer was separated, washed with brine, dried over anhydrous sodium sulfate, and concentrated under reduced pressure to give the title compound (146 mg).

MS: [M+H-Boc]$^+$ 258.9.

J) N-[(3R,5R)-4,4-Difluoro-5-(2-hydroxyethyl)pyrrolidin-3-yl]ethanesulfonamide hydrochloride To a mixture of tert-butyl (2R,4R)-4-[(ethanesulfonyl)amino]-3,3-difluoro-2-(2-hydroxyethyl)pyrrolidine-1-carboxylate (146 mg) and EtOAc (2 mL) was added 4 M hydrogen chloride dioxane solution (2 mL) at 25° C. The mixture was stirred at 25° C. for 2 h. The mixture was concentrated under reduced pressure and co-evaporated with EtOAc to give the title compound (120 mg).

$^1$H NMR (400 MHz, DMSO-d$_6$) δ 1.22 (3H, t, J=7.2 Hz), 1.84-1.97 (2H, m), 2.99-3.17 (3H, m), 3.51-3.58 (2H, m, overlapped with dioxane's signal), 3.63-3.77 (1H, m), 4.06-4.16 (1H, m), 4.49-4.69 (1H, m), 6.53 (1H, brs), 8.15 (1H, d, J=8.8 Hz), 10.11 (2H, brs).

K) (2R,4R)-4-[(Ethanesulfonyl)amino]-3,3-difluoro-2-(2-hydroxyethyl)-N-[4-(2,4,6-trifluorophenyl)-1,2-benzoxazol-3-yl]pyrrolidine-1-carboxamide To a mixture of N-[(3R,5R)-4,4-difluoro-5-(2-hydroxyethyl)pyrrolidin-3-yl]ethanesulfonamide hydrochloride (20 mg) and TEA (28 mg) in THF (2 mL) was added 2,2,2-trichloroethyl [4-(2,4,6-trifluorophenyl)-1,2-benzoxazol-3-yl]carbamate (45 mg) at 0° C. The mixture was stirred at 60° C. for 14 h under nitrogen atmosphere. The reaction mixture was poured into water and it was extracted with EtOAc. The combined organic layer was washed with brine, dried over anhydrous sodium sulfate and concentrated under reduced pressure. The residue was purified by silica gel column chromatography (EtOAc/petroleum ether) to give the title compound (22 mg).

MS: [M+H]$^+$ 549.1.

L) N-{(4aR,6R)-5,5-Difluoro-1-oxo-2-[4-(2,4,6-trifluorophenyl)-1,2-benzoxazol-3-yl]octahydropyrrolo[1,2-c]pyrimidin-6-yl}ethanesulfonamide To a mixture of (2R,4R)-4-[(ethanesulfonyl)amino]-3,3-difluoro-2-(2-hydroxyethyl)-N-[4-(2,4,6-trifluorophenyl)-1,2-benzoxazol-3-yl]pyrrolidine-1-carboxamide (22 mg) and MeCN (2 mL) were added TEA (16 mg) and methanesulfonic anhydride (21 mg) at 0° C. The mixture was stirred for 14 h at 25° C. The reaction mixture was poured into water and it was extracted with EtOAc. The combined organic layer was washed with brine, dried over anhydrous sodium sulfate and concentrated under reduced pressure. The residue was purified by preparative HPLC (column: Boston Prime C18, mobile phase: water containing ammonia hydroxide/MeCN) followed by lyophilization to give the title compound (6.2 mg).

$^1$H NMR (400 MHz, CDCl$_3$) δ 1.45 (3H, t, J=7.2 Hz), 1.99-2.30 (2H, m), 2.47-2.90 (1H, m), 3.17 (2H, q, J=7.6 Hz), 3.38-4.45 (5H, m), 4.48-4.84 (1H, m), 6.60-6.97 (2H, m), 7.27-7.36 (1H, m), 7.61-7.70 (2H, m).

Example 265

N-{(4aR,6R)-5,5-Difluoro-1-oxo-2-[4-(2,4,6-trifluorophenyl)-1,2-benzoxazol-3-yl]octahydropyrrolo[1,2-c]pyrimidin-6-yl}ethanesulfonamide

A) 2,2,2-Trichloroethyl [4-(2,6-difluorophenyl)-5-fluoro-1,2-benzoxazol-3-yl]carbamate 1 M Lithium bis(trimethylsilyl)amide hexane solution (37.9 mL) was added dropwise to a solution of 4-(2,6-Difluorophenyl)-5-fluoro-1,2-benzoxazol-3-amine (4.00 g) in THF (40 mL) at 0° C. The mixture was stirred at 0° C. under nitrogen atmosphere for 0.5 h. 2,2,2-Trichloroethoxycarbonyl chloride (4.81 g) was added. The mixture was stirred at 0° C. under nitrogen atmosphere for 1 h. The mixture was diluted with water and extracted with EtOAc. The combined organic layer was dried over anhydrous sodium sulfate and concentrated under reduced pressure. The residue was purified by silica gel column chromatography (EtOAc/petroleum ether) to give the title compound (4.5 g).

$^1$H NMR (400 MHz, CDCl$_3$) δ 4.40-4.57 (2H, m), 6.85 (1H, brs), 7.04-7.12 (2H, m), 7.42-7.53 (2H, m), 7.61-7.68 (1H, m).

B) (2R,4R)—N-[4-(2,6-Difluorophenyl)-5-fluoro-1,2-benzoxazol-3-yl]-3,3-difluoro-2-(2-hydroxyethyl)-4-[(methanesulfonyl)amino]pyrrolidine-1-carboxamide To a solution of 2,2,2-trichloroethyl [4-(2,6-difluorophenyl)-5-fluoro-1,2-benzoxazol-3-yl]carbamate (500 mg) and N-[(3R,5R)-4,4-Difluoro-5-(hydroxymethyl)pyrrolidin-3-yl]ethanesulfonamide hydrochloride (335 mg) in THF (8 mL) was added TEA (288 mg), then the mixture was stirred at 60° C. for 14 h under nitrogen atmosphere. The reaction mixture was diluted with water and extracted with EtOAc. The combined organic layer was washed with brine, dried over anhydrous sodium sulfate and concentrated under reduced pressure. The residue was purified by silica gel column chromatography (EtOAc/petroleum ether) to give the title compound (551 mg).

MS: [M+H]$^+$ 534.9.

C) N-{(4aR,6R)-5,5-Difluoro-1-oxo-2-[4-(2,4,6-trifluorophenyl)-1,2-benzoxazol-3-yl]octahydropyrrolo[1,2-c]pyrimidin-6-yl}ethanesulfonamide To a mixture of (2R,4R)—N-[4-(2,6-difluorophenyl)-5-fluoro-1,2-benzoxazol-3-yl]-3,3-difluoro-2-(2-hydroxyethyl)-4-[(methanesulfonyl)amino]pyrrolidine-1-carboxamide (80 mg) and MeCN (3 mL) were added TEA (121 mg) and methylsulfonyl methanesulfonate (71 mg) at 0° C. The mixture was stirred at 28° C. for 2 h. The reaction mixture was poured into water and it was extracted with EtOAc. The combined organic layer was washed with brine, dried over anhydrous sodium sulfate and concentrated under reduced pressure. The residue was purified by preparative HPLC (column: Boston Prime C18, mobile phase: water containing ammonia hydroxide/MeCN) followed by lyophilization to give the title compound (48 mg).
le;3q$^1$H NMR (400 MHz, CDCl$_3$) δ 1.94-2.25 (2H, m), 2.29-3.05 (1H, m), 3.08 (3H, s), 3.13-4.40 (5H, m), 4.71-4.98 (1H, m), 6.86-7.18 (2H, m), 7.37-7.52 (2H, m), 7.57-7.65 (1H, m).

Example 282

N-{(6R)-2-[4-(2,6-Difluorophenyl)-6-fluoro-1,2-benzoxazol-3-yl]-7,7-difluoro-3-oxo-2,5,6,7-tetrahydro-3H-pyrrolo[1,2-c]imidazol-6-yl}ethanesulfonamide A) (2R,4R)—N-[4-(2,6-Difluorophenyl)-6-fluoro-1,2-benzoxazol-3-yl]-4-[(ethanesulfonyl)amino]-3,3-difluoro-2-(hydroxymethyl)pyrrolidine-1-carboxamide le;3qTo a solution of 2,2,2-trichloroethyl [4-(2,6-difluorophenyl)-6-fluoro-1,2-benzoxazol-3-yl]carbamate (195 mg) and N-[(3R,5R)-4,4-difluoro-5-(hydroxymethyl)pyrrolidin-3-yl]ethanesulfonamide hydrochloride (137 mg) in THF (7 mL) was added TEA (112 mg), then the mixture was stirred at 60° C. for 14 h. The reaction mixture was diluted with water and extracted with EtOAc. The combined organic layer was dried over anhydrous sodium sulfate and concentrated under reduced pressure. The residue was purified by silica gel column chromatography (EtOAc/petroleum ether) to give the title compound (234 mg).
le;3qMS: [M+H]$^+$ 535.0.

B) N-{(6R)-2-[4-(2,6-Difluorophenyl)-6-fluoro-1,2-benzoxazol-3-yl]-7,7-difluoro-1-hydroxy-3-oxohexahydro-1H-pyrrolo[1,2-c]imidazol-6-yl}ethanesulfonamide le;3qA mixture of (2R,4R)—N-[4-(2,6-difluorophenyl)-6-fluoro-1,2-benzoxazol-3-yl]-4-[(ethanesulfonyl)amino]-3,3-difluoro-2-(hydroxymethyl)pyrrolidine-1-carboxamide (234 mg) and sodium hydrogen carbonate (184 mg) in MeCN (4 mL) and water (2 mL) was stirred at 0° C. Then to the mixture were added iodosobenzene diacetate (170 mg), tetra-N-butylammonium bromide (28 mg) and 2,2,6,6-tetramethylpiperidine 1-oxyl (14 mg) at 0° C. The mixture was stirred at 0° C. for 15 min. The reaction mixture was diluted with water and extracted with EtOAc. The combined organic layer was dried over anhydrous sodium sulfate and concentrated under reduced pressure. The residue was purified by silica gel column chromatography (EtOAc/petroleum ether) to give the title compound (197 mg).
le;3qMS: [M+H]$^+$ 533.0.

C) N-{(6R)-2-[4-(2,6-Difluorophenyl)-6-fluoro-1,2-benzoxazol-3-yl]-7,7-difluoro-3-oxo-2,5,6,7-tetrahydro-3H-pyrrolo[1,2-c]imidazol-6-yl}ethanesulfonamide le;3qTo a solution of N-{(6R)-2-[4-(2,6-difluorophenyl)-6-fluoro-1,2-benzoxazol-3-yl]-7,7-difluoro-1-hydroxy-3-oxohexahydro-1H-pyrrolo[1,2-c]imidazol-6-yl}ethanesulfonamide (242 mg) and THF (8 mL) was added methyl N-(triethylammoniumsulfonyl)carbamate (542 mg). The mixture was stirred at 50° C. for 1 h. The reaction mixture was diluted with water and extracted with EtOAc. The combined organic layer was dried over anhydrous sodium sulfate and concentrated under reduced pressure. The residue was purified by preparative HPLC (column: Welch Xtimate C18, mobile phase: water containing ammonia hydroxide/MeCN) followed by lyophilization to give the title compound (132 mg).
le;3q$^1$H NMR (400 MHz, CDCl$_3$) δ 1.44 (3H, t, J=7.2 Hz), 3.03-3.22 (3H, m), 3.88-4.05 (1H, m), 4.41-4.65 (1H, m), 5.38-5.59 (1H, m), 6.72-6.78 (1H, m), 6.88-6.96 (2H, m), 7.16-7.23 (1H, m), 7.32-7.45 (2H, m).
le;3qThe compounds of Examples are shown in the following tables. MS in the tables means actual measured value. The compounds of Examples 2-15, 17-23, 25-32, 35-46, 48, 49, 51-70, 73, 74, 76, 78-91, 93-101, 103-123, 125, 127-143, 145-148, 150-170, 172, 173, 175-212, 214-241, 244-259, 261-264, 266-281 and 283-340 in the following tables were produced according to the methods described in the above-mentioned Examples, or methods analogous thereto.

TABLE 1-1

| Ex. No. | IUPAC Name | Structure | MS |
|---|---|---|---|
| 1 | N-{(6S,7aS)-2-[4-(2,6-difluorophenyl)-1,2-benzoxazol-3-yl]-3-oxohexahydro-1H-pyrrolo[1,2-c]imidazol-6-yl}ethanesulfonamide | 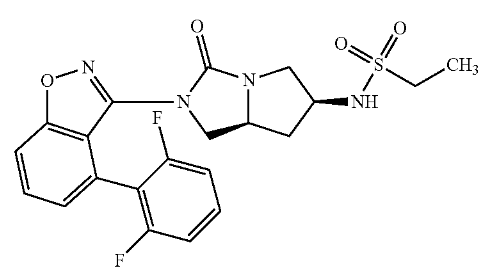 [SMILES: CCS(=O)(=O)N[C@H]1C[C@H]2CN(c3noc4cccc(-c5c(F)cccc5F)c34)C(=O)N2C1] | 463.1 |

TABLE 1-1-continued

| Ex. No. | IUPAC Name | Structure | MS |
|---|---|---|---|
| 2 | N-{(6S)-2-[4-(2,6-difluorophenyl)pyrazolo[1,5-a]pyridin-3-yl]-3-oxo-2,5,6,7-tetrahydro-3H-pyrrolo[1,2-c]imidazol-6-yl}ethanesulfonamide | 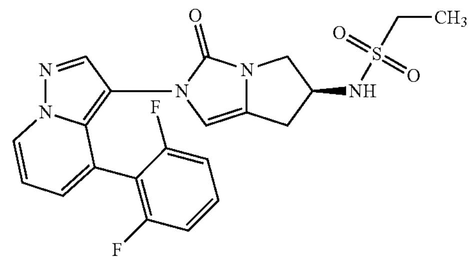 [SMILES: CCS(=O)(=O)N[C@H]1Cc2cn(-c3cnn4cccc(-c5c(F)cccc5F)c34)c(=O)n2C1] | 460.2 |
| 3 | N-{(6S,7aS)-2-[4-(1,4-dimethyl-1H-pyrazol-5-yl)-1,2-benzoxazol-3-yl]-3-oxohexahydro-1H-pyrrolo[1,2-c]imidazol-6-yl}ethanesulfonamide | 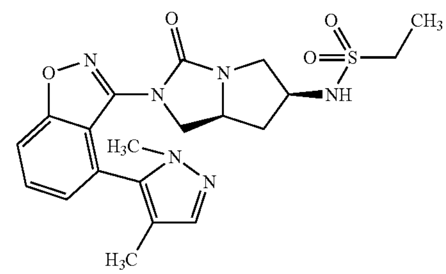 [SMILES: CCS(=O)(=O)N[C@H]1C[C@H]2CN(c3noc4cccc(-c5c(C)cnn5C)c34)C(=O)N2C1] | 445.1 |
| 4 | rel-N-{(6R,7S,7aR)-2-[4-(2,6-difluorophenyl)-1,2-benzoxazol-3-yl]-7-fluoro-3-oxohexahydro-1H-pyrrolo[1,2-c]imidazol-6-yl}ethanesulfonamide | 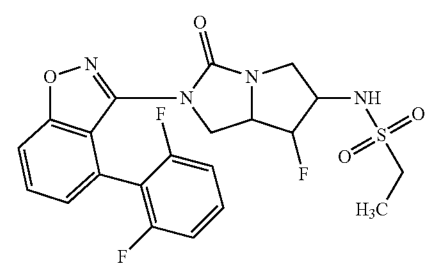 [SMILES: CCS(=O)(=O)NC1CN2C(=O)N(c3noc4cccc(-c5c(F)cccc5F)c34)CC2C1F] | 481.1 |
| 5 | N-{(6R*)-2-[4-(2,6-difluorophenyl)-1,2-benzoxazol-3-yl]-7,7-difluoro-3-oxo-2,5,6,7-tetrahydro-3H-pyrrolo[1,2-c]imidazol-6-yl}ethanesulfonamide | 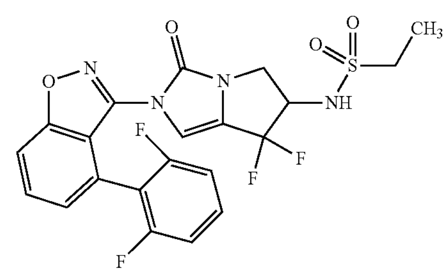 [SMILES: CCS(=O)(=O)NC1Cn2c(cn(-c3noc4cccc(-c5c(F)cccc5F)c34)c2=O)C1(F)F] | 497.0 |
| 6 | N-{(6S,7aS)-2-[4-(2,6-difluorophenyl)-1,2-benzoxazol-3-yl]-7,7-dimethyl-3-oxohexahydro-1H-pyrrolo[1,2-c]imidazol-6-yl}ethanesulfonamide | 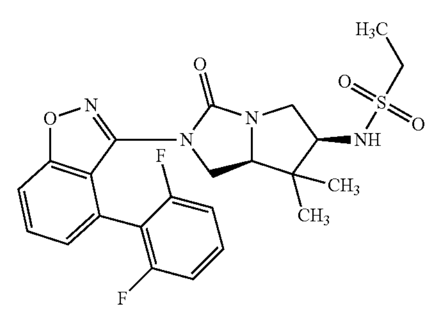 [SMILES: CCS(=O)(=O)N[C@@H]1CN2C(=O)N(c3noc4cccc(-c5c(F)cccc5F)c34)C[C@@H]2C1(C)C] | 491.1 |

TABLE 1-1-continued

| Ex. No. | IUPAC Name | Structure | MS |
|---|---|---|---|
| 7 | N-{(6R,7aR)-2-[4-(2,6-difluorophenyl)-5-fluoro-1,2-benzoxazol-3-yl]-7,7-difluoro-3-oxohexahydro-1H-pyrrolo[1,2-c]imidazol-6-yl}ethanesulfonamide | 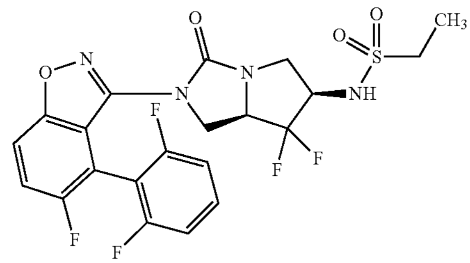 [SMILES: CCS(=O)(=O)N[C@@H]1CN2C(=O)N(c3noc4ccc(F)c(-c5c(F)cccc5F)c34)C[C@@H]2C1(F)F] | 517.1 |
| 8 | N-{(6R)-2-[4-(2,6-difluorophenyl)-6-(trifluoromethyl)-1,2-benzoxazol-3-yl]-7,7-difluoro-3-oxo-2,5,6,7-tetrahydro-3H-pyrrolo[1,2-c]imidazol-6-yl}ethanesulfonamide | 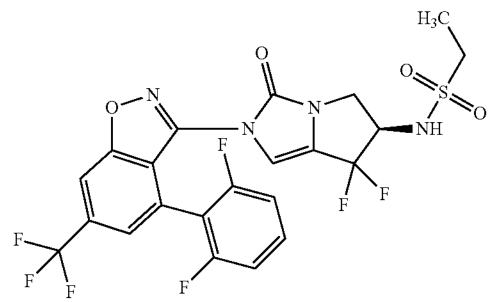 [SMILES: CCS(=O)(=O)N[C@@H]1Cn2c(cn(-c3noc4cc(C(F)(F)F)cc(-c5c(F)cccc5F)c34)c2=O)C1(F)F] | 565.0 |
| 9 | N-{(6R,7aR)-2-[6-chloro-4-(2,4,6-trifluorophenyl)-1,2-benzoxazol-3-yl]-7,7-difluoro-3-oxohexahydro-1H-pyrrolo[1,2-c]imidazol-6-yl}ethanesulfonamide | 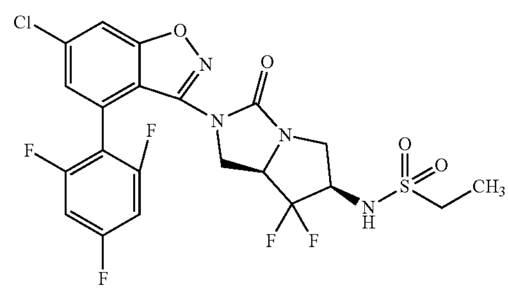 [SMILES: CCS(=O)(=O)N[C@@H]1CN2C(=O)N(c3noc4cc(Cl)cc(-c5c(F)cc(F)cc5F)c34)C[C@@H]2C1(F)F] | 551.0 |
| 10 | N-{(6S,7aS)-2-[4-(furan-3-yl)-1,2-benzoxazol-3-yl]-3-oxohexahydro-1H-pyrrolo[1,2-c]imidazol-6-yl}ethanesulfonamide | 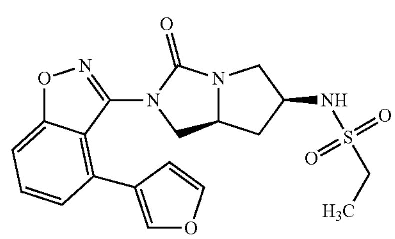 [SMILES: CCS(=O)(=O)N[C@H]1C[C@H]2CN(c3noc4cccc(-c5ccoc5)c34)C(=O)N2C1] | 417.1 |
| 11 | N-{(6S)-2-[4-(2,6-difluorophenyl)-1,2-benzoxazol-3-yl]-3-oxo-2,5,6,7-tetrahydro-3H-pyrrolo[1,2-c]imidazol-6-yl}ethanesulfonamide | 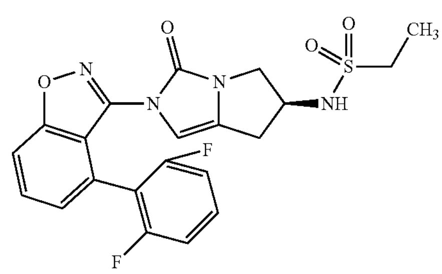 [SMILES: CCS(=O)(=O)N[C@H]1Cc2cn(-c3noc4cccc(-c5c(F)cccc5F)c34)c(=O)n2C1] | 461.1 |

TABLE 1-1-continued

| Ex. No. | IUPAC Name | Structure | MS |
|---|---|---|---|
| 12 | N-{(6S)-2-[4-(2,6-difluorophenyl)-1,2-benzoxazol-3-yl]-1-methyl-3-oxo-2,5,6,7-tetrahydro-3H-pyrrolo[1,2-c]imidazol-6-yl}ethanesulfonamide | 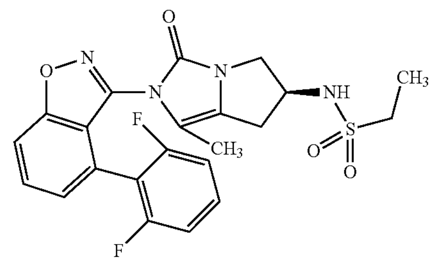 [SMILES: CCS(=O)(=O)N[C@H]1Cc2c(C)n(-c3noc4cccc(-c5c(F)cccc5F)c34)c(=O)n2C1] | 475.1 |
| 13 | N-{(6S,7aS)-2-[4-(2-chloro-4-fluorophenyl)-1,2-benzoxazol-3-yl]-3-oxohexahydro-1H-pyrrolo[1,2-c]imidazol-6-yl}ethanesulfonamide | 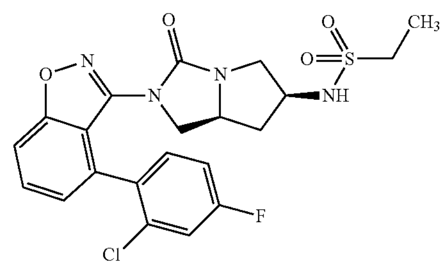 [SMILES: CCS(=O)(=O)N[C@H]1C[C@H]2CN(c3noc4cccc(-c5ccc(F)cc5Cl)c34)C(=O)N2C1] | 479.1 |
| 14 | N-{(6S)-2-[4-(2,6-difluorophenyl)-6-(trifluoromethyl)pyrazolo[1,5-a]pyridin-3-yl]-3-oxo-2,5,6,7-tetrahydro-3H-pyrrolo[1,2-c]imidazol-6-yl}ethanesulfonamide | 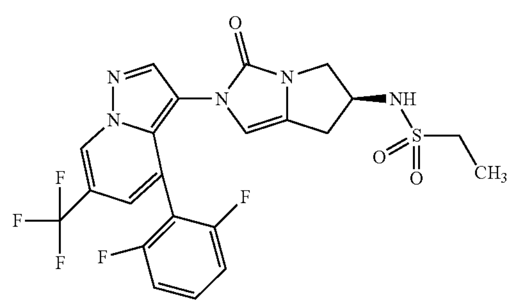 [SMILES: CCS(=O)(=O)N[C@H]1Cc2cn(-c3cnn4cc(C(F)(F)F)cc(-c5c(F)cccc5F)c34)c(=O)n2C1] | 528.1 |
| 15 | N-{(6S,7aS)-2-[4-(2,6-difluorophenyl)-2-methyl-2H-indazol-3-yl]-3-oxohexahydro-1H-pyrrolo[1,2-c]imidazol-6-yl}methanesulfonamide | 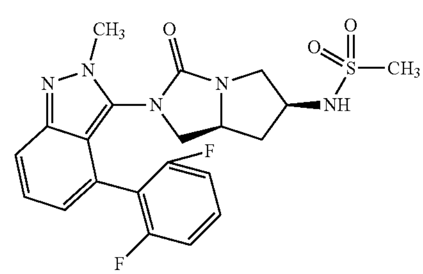 [SMILES: Cn1nc2cccc(-c3c(F)cccc3F)c2c1N1C[C@@H]2C[C@H](NS(C)(=O)=O)CN2C1=O] | 462.2 |
| 16 | N-{(6R)-7,7-difluoro-3-oxo-2-[4-(2,4,6-trifluorophenyl)-1,2-benzoxazol-3-yl]-2,5,6,7-tetrahydro-3H-pyrrolo[1,2-c]imidazol-6-yl}methanesulfonamide | 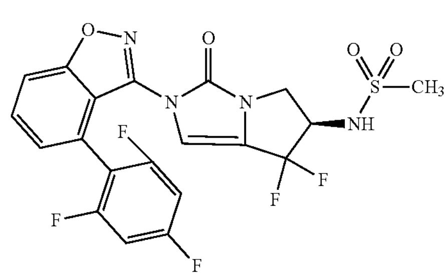 [SMILES: CS(=O)(=O)N[C@@H]1Cn2c(cn(-c3noc4cccc(-c5c(F)cc(F)cc5F)c34)c2=O)C1(F)F] | 501.1 |

TABLE 1-1-continued

| Ex. No. | IUPAC Name | Structure | MS |
|---|---|---|---|
| 17 | N-{(6R,7aR)-2-[4-(2,6-difluorophenyl)-1,2-benzoxazol-3-yl]-7,7-difluoro-3-oxohexahydro-1H-pyrrolo[1,2-c]imidazol-6-yl}-N'-methylsulfuric diamide | 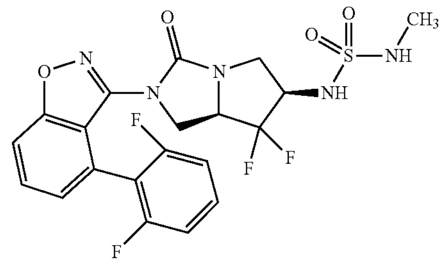 [SMILES: CNS(=O)(=O)N[C@@H]1CN2C(=O)N(c3noc4cccc(-c5c(F)cccc5F)c34)C[C@@H]2C1(F)F] | 500.1 |
| 18 | N-{(6S,7aS)-2-[4-(2,6-difluorophenyl)-6-(trifluoromethyl)-1,2-benzoxazol-3-yl]-3-oxohexahydro-1H-pyrrolo[1,2-c]imidazol-6-yl}ethanesulfonamide | 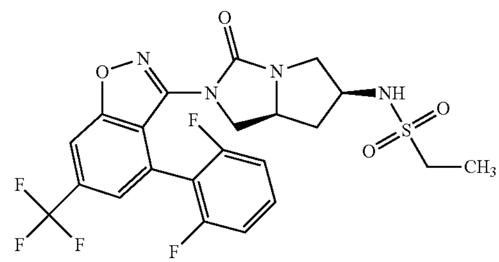 [SMILES: CCS(=O)(=O)N[C@H]1C[C@H]2CN(c3noc4cc(C(F)(F)F)cc(-c5c(F)cccc5F)c34)C(=O)N2C1] | 531.0 |
| 19 | N-{(6S,7aS)-2-[6-(azetidin-1-yl)-4-(2,6-difluorophenyl)-1,2-benzoxazol-3-yl]-3-oxohexahydro-1H-pyrrolo[1,2-c]imidazol-6-yl}ethanesulfonamide | 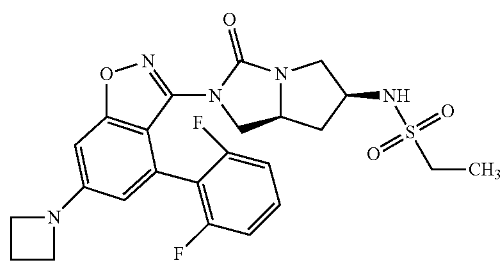 [SMILES: CCS(=O)(=O)N[C@H]1C[C@H]2CN(c3noc4cc(N5CCC5)cc(-c5c(F)cccc5F)c34)C(=O)N2C1] | 518.1 |
| 20 | N-{(6S,7aS)-2-[4-(2,6-difluorophenyl)-1,2-benzoxazol-3-yl]-3-oxohexahydro-1H-pyrrolo[1,2-c]imidazol-6-yl}-1-methoxymethanesulfonamide | 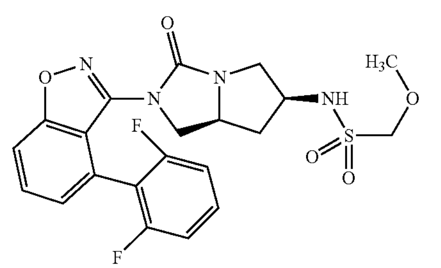 [SMILES: COCS(=O)(=O)N[C@H]1C[C@H]2CN(c3noc4cccc(-c5c(F)cccc5F)c34)C(=O)N2C1] | 479.0 |
| 21 | N-{(6S,7aS)-3-oxo-2-[4-(2,3,6-trifluorophenyl)-1,2-benzoxazol-3-yl]hexahydro-1H-pyrrolo[1,2-c]imidazol-6-yl}ethanesulfonamide | 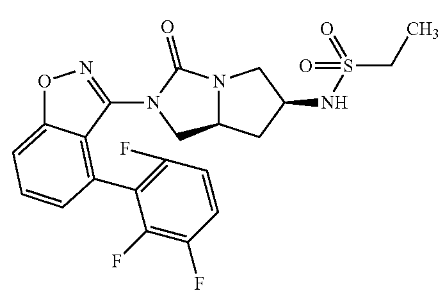 [SMILES: CCS(=O)(=O)N[C@H]1C[C@H]2CN(c3noc4cccc(-c5c(F)ccc(F)c5F)c34)C(=O)N2C1] | 481.2 |

TABLE 1-1-continued

| Ex. No. | IUPAC Name | MS |
|---|---|---|
| 22 | rel-N-{(6R, 8aS)-2-[4-(2,6-difluorophenyl)-1,2-benzoxazol-3-yl]-7,7-difluoro-3-oxooctahydroimidazo[1,5-a]pyridin-6-yl}methanesulfonamide | 499.0 |
| 23 | rel-N-{(7R,8aS)-2-[4-(2,6-difluorophenyl)-1,2-benzoxazol-3-yl]-3-oxooctahydroimidazo[1,5-a]pyridin-7-yl}methanesulfonamide | 463.1 |
| 24 | N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}ethanesulfonamide | 517.1 |
| 25 | N-{(6R,7aR)-2-[6-chloro-4-(2,4,6-trifluorophenyl)-1,2-benzoxazol-3-yl]-7,7-difluoro-3-oxohexahydro-1H-pyrrolo[1,2-c]imidazol-6-yl}methanesulfonamide | 537.0 |
| 26 | N-{(6S)-2-[4-(2,6-difluorophenyl)-1,2-benzoxazol-3-yl]-3-oxo-2,5,6,7-tetrahydro-3H-pyrrolo[1,2-c]imidazol-6-yl}methanesulfonamide | 447.1 |

TABLE 1-1-continued

| Ex. No. | IUPAC Name | Structure | MS |
|---|---|---|---|
| 27 | N-{(6S,7aS)-2-[4-(2,6-difluorophenyl)-6-fluoro-1,2-benzoxazol-3-yl]-3-oxohexahydro-1H-pyrrolo[1,2-c]imidazol-6-yl}ethanesulfonamide | 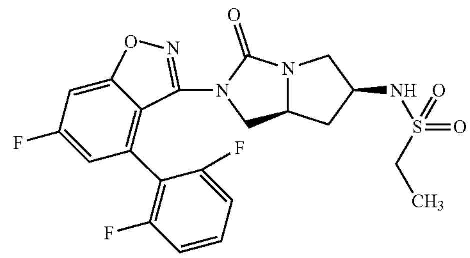 [SMILES: CCS(=O)(=O)N[C@H]1C[C@H]2CN(c3noc4cc(F)cc(-c5c(F)cccc5F)c34)C(=O)N2C1] | 481.1 |
| 28 | N'-{(6S,7aS)-2-[4-(2,6-difluorophenyl)-1,2-benzoxazol-3-yl]-3-oxohexahydro-1H-pyrrolo[1,2-c]imidazol-6-yl}-N,N-dimethylsulfuric diamide | 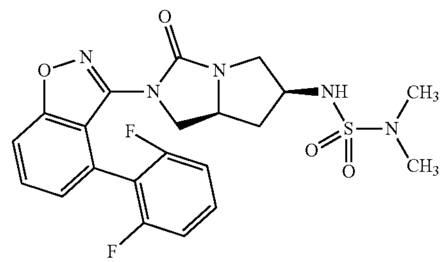 [SMILES: CN(C)S(=O)(=O)N[C@H]1C[C@H]2CN(c3noc4cccc(-c5c(F)cccc5F)c34)C(=O)N2C1] | 478.1 |
| 29 | N-{(6S,7aS)-2-[4-(2,6-difluorophenyl)-1,2-benzoxazol-3-yl]-3-oxohexahydro-1H-pyrrolo[1,2-c]imidazol-6-yl}-1-fluoromethanesulfonamide | 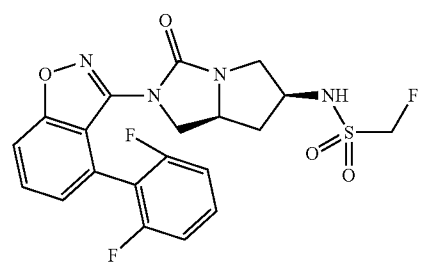 [SMILES: O=C1N(c2noc3cccc(-c4c(F)cccc4F)c23)C[C@@H]2C[C@H](NS(=O)(=O)CF)CN12] | 467.0 |
| 30 | N-{(6S,7aS)-2-[4-(2,6-difluorophenyl)-7-methyl-1,2-benzoxazol-3-yl]-3-oxohexahydro-1H-pyrrolo[1,2-c]imidazol-6-yl}ethanesulfonamide | 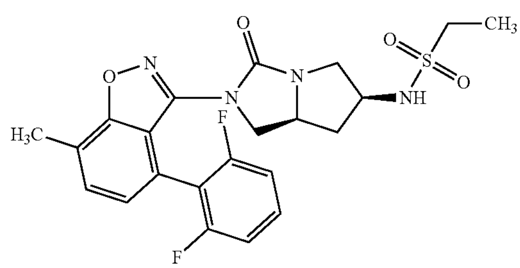 [SMILES: CCS(=O)(=O)N[C@H]1C[C@H]2CN(c3noc4c(C)ccc(-c5c(F)cccc5F)c34)C(=O)N2C1] | 477.1 |
| 31 | N-{(6S,7aS)-2-[4-(2,6-difluorophenyl)-7-fluoro-1,2-benzoxazol-3-yl]-3-oxohexahydro-1H-pyrrolo[1,2-c]imidazol-6-yl}ethanesulfonamide | 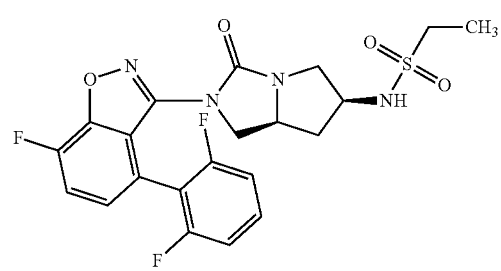 [SMILES: CCS(=O)(=O)N[C@H]1C[C@H]2CN(c3noc4c(F)ccc(-c5c(F)cccc5F)c34)C(=O)N2C1] | 481.0 |

TABLE 1-1-continued

| Ex. No. | IUPAC Name | Structure | MS |
|---|---|---|---|
| 32 | N-[ (6S,7aS)-2-{ 4-[2-fluoro-6-(trifluoromethyl)phenyl]-1,2-benzoxazol-3-yl}-3-oxohexahydro-1H-pyrrolo[1,2-c]imidazol-6-yl] ethanesulfonamide | 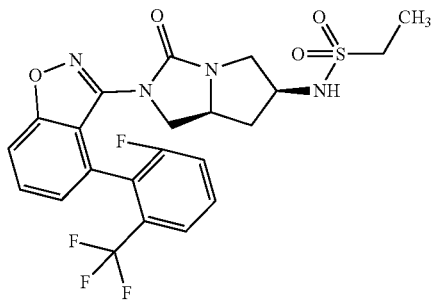 [SMILES: CCS(=O)(=O)N[C@H]1C[C@H]2CN(c3noc4cccc(-c5c(F)cccc5C(F)(F)F)c34)C(=O)N2C1] | 513.1 |
| 33 | N-{(6R,7aR)-2-[4-(2,6-difluorophenyl)-1,2-benzoxazol-3-yl]-7,7-difluoro-3-oxohexahydro-1H-pyrrolo[1,2-c]imidazol-6-yl}ethanesulfonamide | 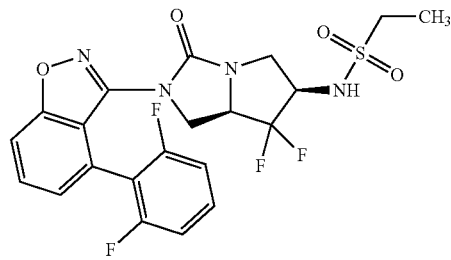 [SMILES: CCS(=O)(=O)N[C@@H]1CN2C(=O)N(c3noc4cccc(-c5c(F)cccc5F)c34)C[C@@H]2C1(F)F] | 499.2 |
| 34 | N-{(6R,7aR)-2-[4-(2,6-difluorophenyl)-1,2-benzoxazol-3-yl]-7,7-difluoro-3-oxohexahydro-1H-pyrrolo[1,2-c]imidazol-6-yl}methanesulfonamide | 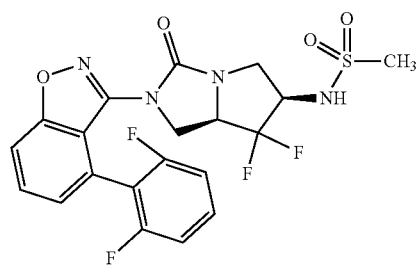 [SMILES: CS(=O)(=O)N[C@@H]1CN2C(=O)N(c3noc4cccc(-c5c(F)cccc5F)c34)C[C@@H]2C1(F)F] | 485.1 |
| 35 | N-{(6S,7aS)-2-[4-(2,6-difluorophenyl)-6-(methoxymethyl)-1,2-benzoxazol-3-yl]-3-oxohexahydro-1H-pyrrolo[1,2-c]imidazol-6-yl}ethanesulfonamide | 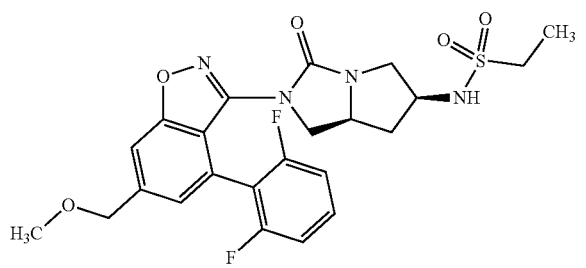 [SMILES: CCS(=O)(=O)N[C@H]1C[C@H]2CN(c3noc4cc(COC)cc(-c5c(F)cccc5F)c34)C(=O)N2C1] | 507.3 |
| 36 | N-{(6S,7aS)-2-[5-chloro-4-(2,6-difluorophenyl)-1,2-benzoxazol-3-yl]-3-oxohexahydro-1H-pyrrolo[1,2-c]imidazol-6-yl}ethanesulfonamide | 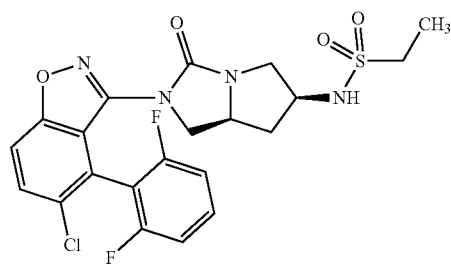 [SMILES: CCS(=O)(=O)N[C@H]1C[C@H]2CN(c3noc4ccc(Cl)c(-c5c(F)cccc5F)c34)C(=O)N2C1] | 497.1 |

TABLE 1-1-continued

| Ex. No. | IUPAC Name | Structure | MS |
|---|---|---|---|
| 37 | N-{(6S)-2-[5-(2,6-difluorophenyl)imidazo[1,2-a]pyridin-3-yl]-3-oxo-2,5,6,7-tetrahydro-3H-pyrrolo[1,2-c]imidazol-6-yl}ethanesulfonamide | 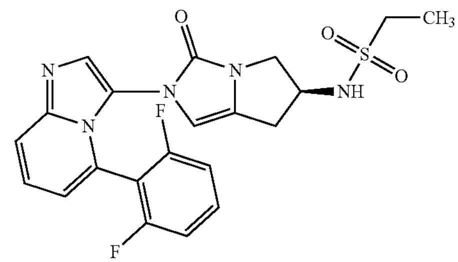 [SMILES: CCS(=O)(=O)N[C@H]1Cc2cn(-c3cnc4cccc(-c5c(F)cccc5F)n34)c(=O)n2C1] | 460.1 |
| 38 | N-{(6R,7aR)-2-[4-(2,6-difluorophenyl)-5-fluoro-1,2-benzoxazol-3-yl]-7,7-difluoro-3-oxohexahydro-1H-pyrrolo[1,2-c]imidazol-6-yl}methanesulfonamide | 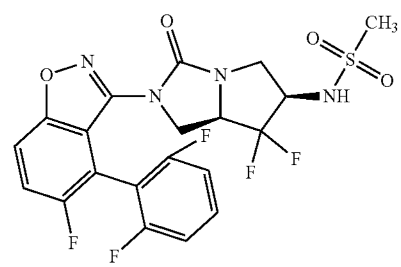 [SMILES: CS(=O)(=O)N[C@@H]1CN2C(=O)N(c3noc4ccc(F)c(-c5c(F)cccc5F)c34)C[C@@H]2C1(F)F] | 503.1 |
| 39 | N-{(6R)-2-[6-chloro-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}ethanesulfonamide | 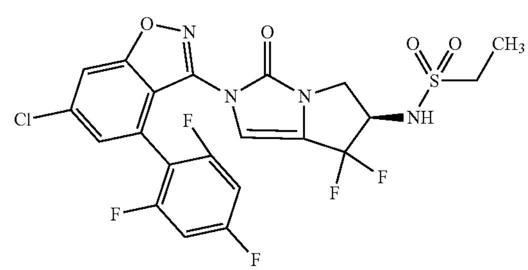 [SMILES: CCS(=O)(=O)N[C@@H]1Cn2c(cn(-c3noc4cc(Cl)cc(-c5c(F)cc(F)cc5F)c34)c2=O)C1(F)F] | 549.0 |
| 40 | N-{(6R,7aR)-2-[6-chloro-5-fluoro-4-(2,4,6-trifluorophenyl)-1,2-benzoxazol-3-yl]-7,7-difluoro-3-oxohexahydro-1H-pyrrolo[1,2-c]imidazol-6-yl}methanesulfonamide | 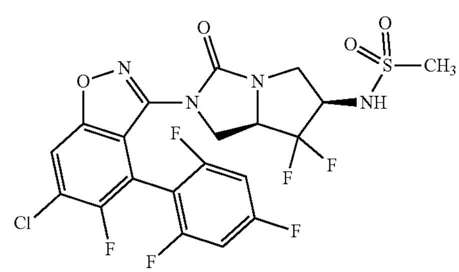 [SMILES: CS(=O)(=O)N[C@@H]1CN2C(=O)N(c3noc4cc(Cl)c(F)c(-c5c(F)cc(F)cc5F)c34)C[C@@H]2C1(F)F] | 554.9 |
| 41 | N-{(6S,7aS)-2-[4-(2,6-difluorophenyl)-6-methoxy-1,2-benzoxazol-3-yl]-3-oxohexahydro-1H-pyrrolo[1,2-c]imidazol-6-yl}ethanesulfonamide | 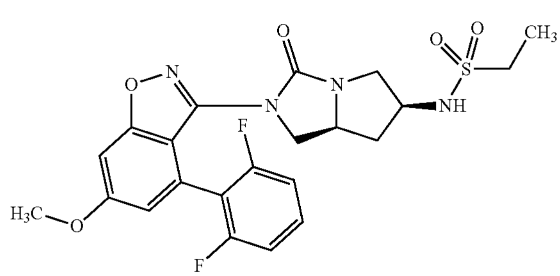 [SMILES: CCS(=O)(=O)N[C@H]1C[C@H]2CN(c3noc4cc(OC)cc(-c5c(F)cccc5F)c34)C(=O)N2C1] | 493.0 |

TABLE 1-1-continued

| Ex. No. | IUPAC Name | Structure | MS |
|---|---|---|---|
| 42 | 1-cyclopropyl-N-{(6S,7aS)-2-[4-(2,6-difluorophenyl)-1,2-benzoxazol-3-yl]-3-oxohexahydro-1H-pyrrolo[1,2-c]imidazol-6-yl}methanesulfonamide | 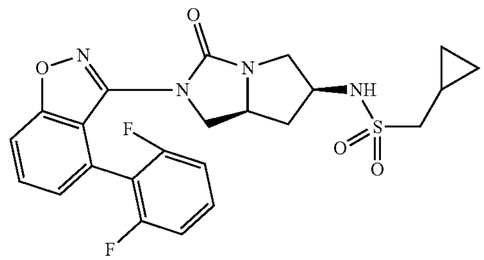 [SMILES: O=C1N(c2noc3cccc(-c4c(F)cccc4F)c23)C[C@@H]2C[C@H](NS(=O)(=O)CC3CC3)CN12] | 489.1 |
| 43 | N-{(6S,7aS)-2-[4-(2,6-difluorophenyl)-1,2-benzoxazol-3-yl]-3-oxohexahydro-1H-pyrrolo[1,2-c]imidazol-6-yl}-1,1-difluoromethanesulfonamide | 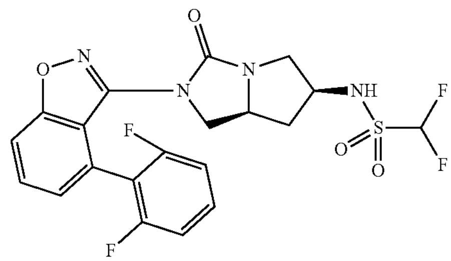 [SMILES: O=C1N(c2noc3cccc(-c4c(F)cccc4F)c23)C[C@@H]2C[C@H](NS(=O)(=O)C(F)F)CN12] | 485.1 |
| 44 | rel-N-{(6R,8aR)-2-[4-(2,6-difluorophenyl)-1,2-benzoxazol-3-yl]-3-oxooctahydroimidazo[1,5-a]pyridin-6-yl}methanesulfonamide | 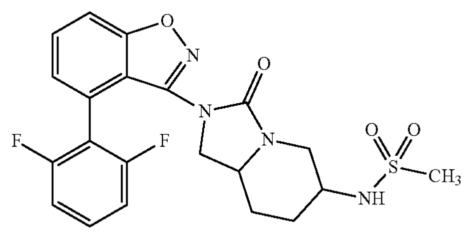 [SMILES: CS(=O)(=O)NC1CCC2CN(c3noc4cccc(-c5c(F)cccc5F)c34)C(=O)N2C1] | 463.1 |
| 45 | N-{(6S)-2-[6-chloro-4-(2,6-difluorophenyl)pyrazolo[1,5-a]pyridin-3-yl]-3-oxo-2,5,6,7-tetrahydro-3H-pyrrolo[1,2-c]imidazol-6-yl}ethanesulfonamide | 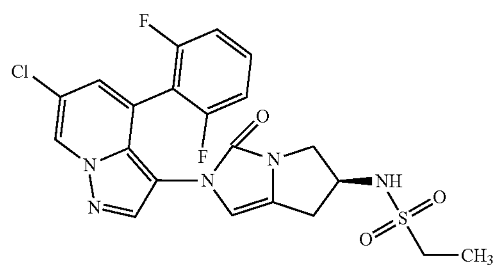 [SMILES: CCS(=O)(=O)N[C@H]1Cc2cn(-c3cnn4cc(Cl)cc(-c5c(F)cccc5F)c34)c(=O)n2C1] | 494.0 |
| 46 | N-{(6R)-2-[4-(2,6-difluorophenyl)-6-fluoro-1,2-benzoxazol-3-yl]-7,7-difluoro-3-oxo-2,5,6,7-tetrahydro-3H-pyrrolo[1,2-c]imidazol-6-yl}methanesulfonamide | 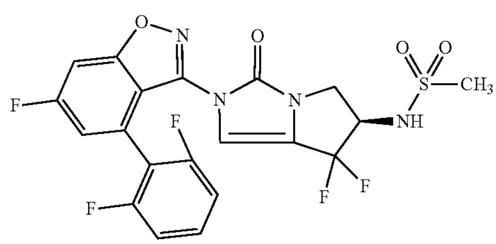 [SMILES: CS(=O)(=O)N[C@@H]1Cn2c(cn(-c3noc4cc(F)cc(-c5c(F)cccc5F)c34)c2=O)C1(F)F] | 501.0 |
| 47 | N-{(6R,7aR)-7,7-difluoro-2-[5-fluoro-4-(2,4,6-trifluorophenyl)-1,2-benzoxazol-3-yl]-3-oxohexahydro-1H-pyrrolo[1,2-c]imidazol-6-yl}methanesulfonamide | 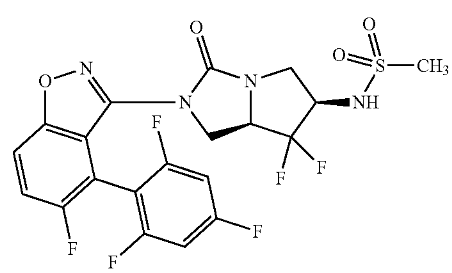 [SMILES: CS(=O)(=O)N[C@@H]1CN2C(=O)N(c3noc4ccc(F)c(-c5c(F)cc(F)cc5F)c34)C[C@@H]2C1(F)F] | 521.1 |

TABLE 1-1-continued

| Ex. No. | IUPAC Name | MS |
|---|---|---|
| 48 | N-{(6S,7aS)-2-[4-(2,6-difluorophenyl)-1,2-benzoxazol-3-yl]-3-oxohexahydro-1H-pyrrolo[1,2-c]imidazol-6-yl}methanesulfonamide | 449.1 |
| 49 | N-{(6S, 7aR)-2-[4-(2,6-difluorophenyl)-1,2-benzoxazol-3-yl]-3-oxohexahydro-1H-pyrrolo[1,2-c]imidazol-6-yl}ethanesulfonamide | 463.1 |
| 50 | N-{(6S,7aS)-2-[6-chloro-4-(2,6-difluorophenyl)-1,2-benzoxazol-3-yl]-3-oxohexahydro-1H-pyrrolo[1,2-c]imidazol-6-yl}ethanesulfonamide | 497.0 |
| 51 | N-[(6S,7aS)-3-oxo-2-(4-phenyl-1,2-benzoxazol-3-yl)hexahydro-1H-pyrrolo[1,2-c]imidazol-6-yl]ethanesulfonamide | 427.2 |
| 52 | N-{(6S,7aS)-2-[4-(2-fluorophenyl)-1,2-benzoxazol-3-yl]-3-oxohexahydro-1H-pyrrolo[1,2-c]imidazol-6-yl}ethanesulfonamide | 445.1 |
| 53 | N-{(6S,7aS)-3-oxo-2-[4-(thiophen-3-yl)-1,2-benzoxazol-3-yl]hexahydro-1H-pyrrolo[1,2-c]imidazol-6-yl}ethanesulfonamide | 433.1 |

TABLE 1-1-continued

| Ex. No. | IUPAC Name | Structure | MS |
|---|---|---|---|
| 54 | N-{(6S,7aS)-2-[6-bromo-4-(2,6-difluorophenyl)-1,2-benzoxazol-3-yl]-3-oxohexahydro-1H-pyrrolo[1,2-c]imidazol-6-yl}methanesulfonamide | 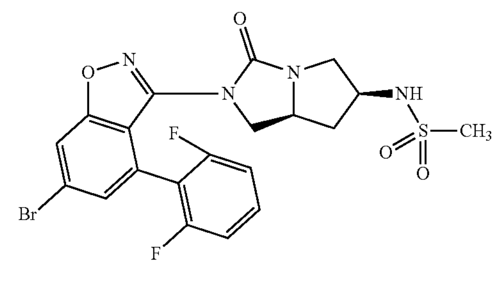 [SMILES: CS(=O)(=O)N[C@H]1C[C@H]2CN(c3noc4cc(Br)cc(-c5c(F)cccc5F)c34)C(=O)N2C1] | 526.9 |
| 55 | N-{(6S,7aS)-2-[4-(2,6-difluorophenyl)-1,2-benzothiazol-3-yl]-3-oxohexahydro-1H-pyrrolo[1,2-c]imidazol-6-yl}ethanesulfonamide | 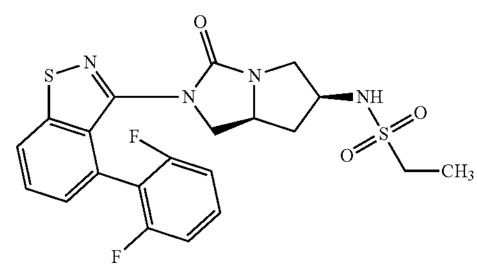 [SMILES: CCS(=O)(=O)N[C@H]1C[C@H]2CN(c3nsc4cccc(-c5c(F)cccc5F)c34)C(=O)N2C1] | 479.1 |
| 56 | N-{(6S,7aS)-2-[6-cyclopropyl-4-(2,6-difluorophenyl)-1,2-benzoxazol-3-yl]-3-oxohexahydro-1H-pyrrolo[1,2-c]imidazol-6-yl}ethanesulfonamide | 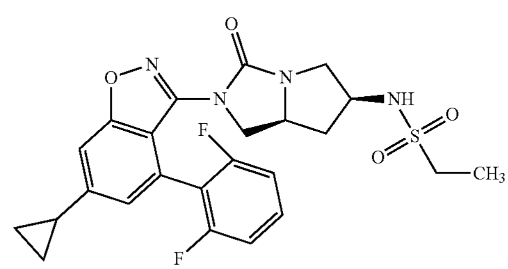 [SMILES: CCS(=O)(=O)N[C@H]1C[C@H]2CN(c3noc4cc(C5CC5)cc(-c5c(F)cccc5F)c34)C(=O)N2C1] | 503.1 |
| 57 | N-{(6S,7aS)-2-[4-(2,6-difluorophenyl)-1,2-benzoxazol-3-yl]-7a-methyl-3-oxohexahydro-1H-pyrrolo[1,2-c]imidazol-6-yl}ethanesulfonamide | 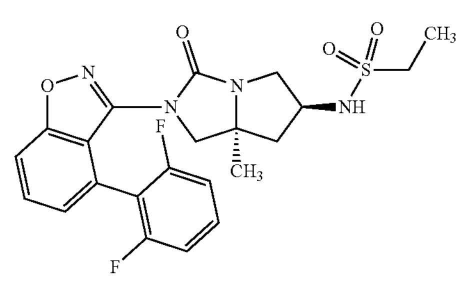 [SMILES: CCS(=O)(=O)N[C@@H]1CN2C(=O)N(c3noc4cccc(-c5c(F)cccc5F)c34)C[C@]2(C)C1] | 477.1 |
| 58 | N-{(6S,7aS)-2-[7-chloro-4-(2,6-difluorophenyl)-1,2-benzoxazol-3-yl]-3-oxohexahydro-1H-pyrrolo[1,2-c]imidazol-6-yl}ethanesulfonamide | 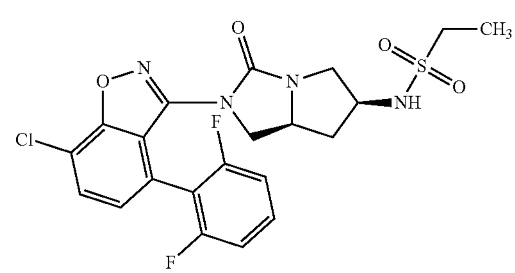 [SMILES: CCS(=O)(=O)N[C@H]1C[C@H]2CN(c3noc4c(Cl)ccc(-c5c(F)cccc5F)c34)C(=O)N2C1] | 497.0 |

TABLE 1-1-continued

| Ex. No. | IUPAC Name | Structure | MS |
|---|---|---|---|
| 59 | N-{(6S,7aS)-2-[4-(2,6-dimethylphenyl)-1,2-benzoxazol-3-yl]-3-oxohexahydro-1H-pyrrolo[1,2-c]imidazol-6-yl}ethanesulfonamide | 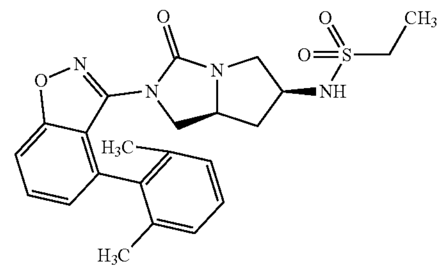 [SMILES: CCS(=O)(=O)N[C@H]1C[C@H]2CN(c3noc4cccc(-c5c(C)cccc5C)c34)C(=O)N2C1] | 455.2 |
| 60 | N-{(6S,7aS)-2-[4-(3-methoxythiophen-2-yl)-1,2-benzoxazol-3-yl]-3-oxohexahydro-1H-pyrrolo[1,2-c]imidazol-6-yl}ethanesulfonamide | 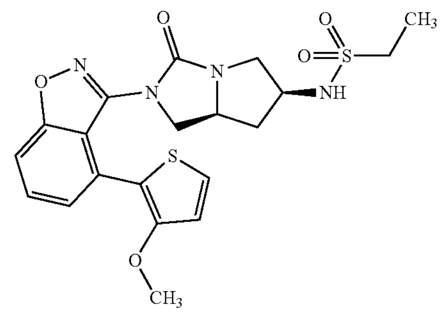 [SMILES: CCS(=O)(=O)N[C@H]1C[C@H]2CN(c3noc4cccc(-c5sccc5OC)c34)C(=O)N2C1] | 463.1 |
| 61 | N-{(6S,7aS)-3-oxo-2-[4-(thiophen-2-yl)-1,2-benzoxazol-3-yl]hexahydro-1H-pyrrolo[1,2-c]imidazol-6-yl}ethanesulfonamide | 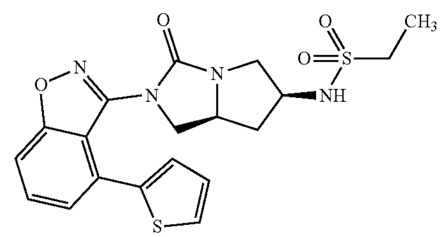 | 433.1 |
| 62 | N-{(6S,7aS)-3-oxo-2-[4-(1,3-thiazol-5-yl)-1,2-benzoxazol-3-yl]hexahydro-1H-pyrrolo[1,2-c]imidazol-6-yl}ethanesulfonamide | 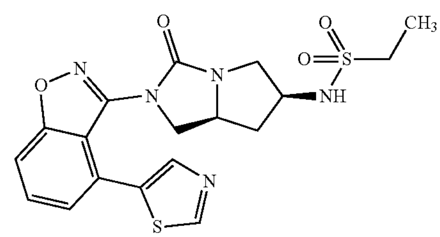 [SMILES: CCS(=O)(=O)N[C@H]1C[C@H]2CN(c3noc4cccc(-c5cncs5)c34)C(=O)N2C1] | 434.1 |
| 63 | rel-N-{(6R, 8aS)-2-[4-(2,6-difluorophenyl)-1,2-benzoxazol-3-yl]-3-oxooctahydroimidazo[1,5-a]pyridin-6-yl}methanesulfonamide | 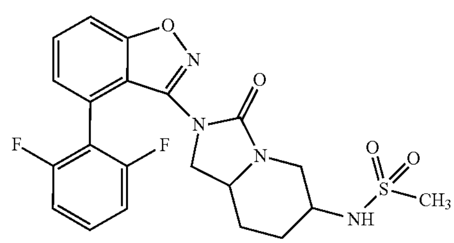 [SMILES: CS(=O)(=O)NC1CCC2CN(c3noc4cccc(-c5c(F)cccc5F)c34)C(=O)N2C1] | 463.1 |
| 64 | N-{(6S,7aS)-2-[6-(cyclopropylmethoxy)-4-(2,6-difluorophenyl)-1,2-benzoxazol-3-yl]-3-oxohexahydro-1H-pyrrolo[1,2-c]imidazol-6-yl}ethanesulfonamide | 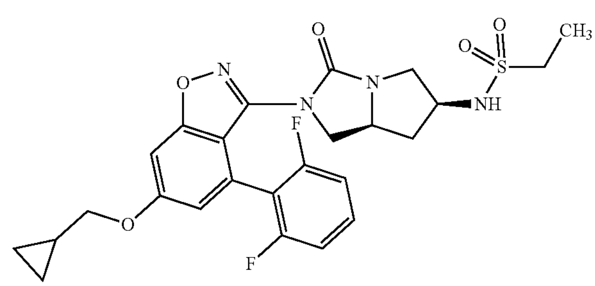 [SMILES: CCS(=O)(=O)N[C@H]1C[C@H]2CN(c3noc4cc(OCC5CC5)cc(-c5c(F)cccc5F)c34)C(=O)N2C1] | 533.1 |

TABLE 1-1-continued

| Ex. No. | IUPAC Name | Structure | MS |
|---|---|---|---|
| 65 | N-{(6S,7aS)-3-oxo-2-[4-(2,4,6-trifluorophenyl)-1,2-benzoxazol-3-yl] hexahydro-1H-pyrrolo[1,2-c]imidazol-6-yl}ethanesulfonamide | 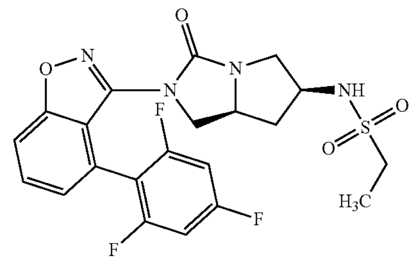 [SMILES: CCS(=O)(=O)N[C@H]1C[C@H]2CN(c3noc4cccc(-c5c(F)cc(F)cc5F)c34)C(=O)N2C1] | 481.1 |
| 66 | N-{(6S,7aS)-2-[4-(2,6-difluorophenyl)-5-fluoro-1,2-benzoxazol-3-yl]-3-oxohexahydro-1H-pyrrolo[1,2-c]imidazol-6-yl}ethanesulfonamide | 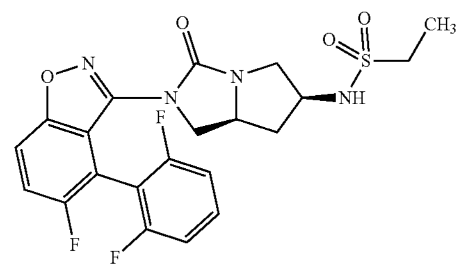 [SMILES: CCS(=O)(=O)N[C@H]1C[C@H]2CN(c3noc4ccc(F)c(-c5c(F)cccc5F)c34)C(=O)N2C1] | 481.2 |
| 67 | N-{(6R,7aR)-2-[6-chloro-4-(2,6-difluorophenyl)-1,2-benzoxazol-3-yl]-7,7-difluoro-3-oxohexahydro-1H-pyrrolo[1,2-c]imidazol-6-yl}ethanesulfonamide | 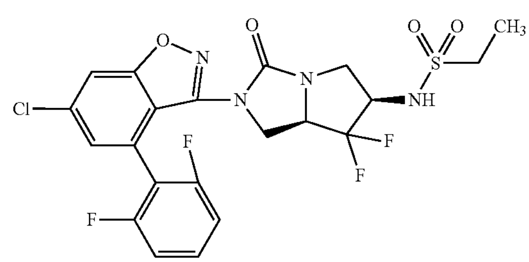 [SMILES: CCS(=O)(=O)N[C@@H]1CN2C(=O)N(c3noc4cc(Cl)cc(-c5c(F)cccc5F)c34)C[C@@H]2C1(F)F] | 533.1 |
| 68 | N-{(6R)-2-[6-chloro-4-(2,6-difluorophenyl)-1,2-benzoxazol-3-yl]-7,7-difluoro-3-oxo-2,5,6,7-tetrahydro-3H-pyrrolo[1,2-c]imidazol-6-yl}ethanesulfonamide | 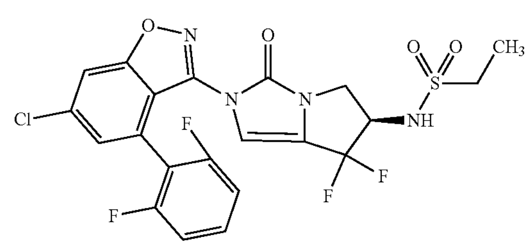 [SMILES: CCS(=O)(=O)N[C@@H]1Cn2c(cn(-c3noc4cc(Cl)cc(-c5c(F)cccc5F)c34)c2=O)C1(F)F] | 531.1 |
| 69 | N-{(6R,7aR)-2-[4-(2,6-difluorophenyl)-6-fluoro-1,2-benzoxazol-3-yl]-7,7-difluoro-3-oxohexahydro-1H-pyrrolo[1,2-c]imidazol-6-yl}ethanesulfonamide | 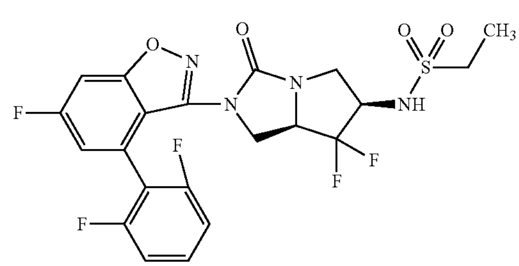 [SMILES: CCS(=O)(=O)N[C@@H]1CN2C(=O)N(c3noc4cc(F)cc(-c5c(F)cccc5F)c34)C[C@@H]2C1(F)F] | 517.1 |

TABLE 1-1-continued

| Ex. No. | IUPAC Name | Structure | MS |
|---|---|---|---|
| 70 | N-{(6S)-2-[4-(2,6-difluorophenyl)-1,2-benzoxazol-3-yl]-7,7-dimethyl-3-oxo-2,5,6,7-tetrahydro-3H-pyrrolo[1,2-c]imidazol-6-yl}ethanesulfonamide | 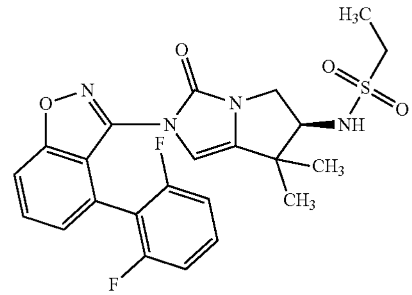 [SMILES: CCS(=O)(=O)N[C@@H]1Cn2c(cn(-c3noc4cccc(-c5c(F)cccc5F)c34)c2=O)C1(C)C] | 489.2 |
| 71 | N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}methanesulfonamide | 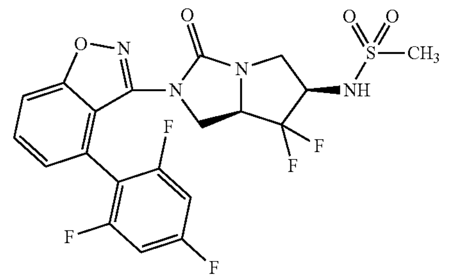 [SMILES: CS(=O)(=O)N[C@@H]1CN2C(=O)N(c3noc4cccc(-c5c(F)cc(F)cc5F)c34)C[C@@H]2C1(F)F] | 503.1 |
| 72 | N-{(6R,7aR)-2-[4-(2,6-difluorophenyl)-6-fluoro-1,2-benzoxazol-3-yl]-7,7-difluoro-3-oxohexahydro-1H-pyrrolo[1,2-c]imidazol-6-yl}methanesulfonamide | 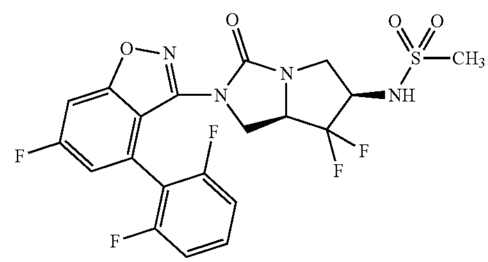 [SMILES: CS(=O)(=O)N[C@@H]1CN2C(=O)N(c3noc4cc(F)cc(-c5c(F)cccc5F)c34)C[C@@H]2C1(F)F] | 503.1 |
| 73 | N-{(6R)-2-[6-chloro-4-(2,6-difluorophenyl)-1,2-benzoxazol-3-yl]-7,7-difluoro-3-oxo-2,5,6,7-tetrahydro-3H-pyrrolo[1,2-c]imidazol-6-yl}methanesulfonamide | 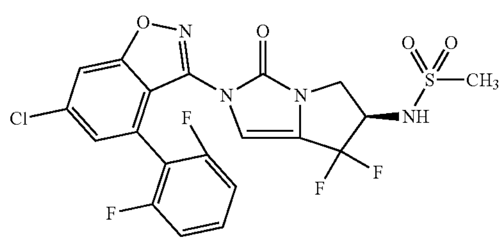 [SMILES: CS(=O)(=O)N[C@@H]1Cn2c(cn(-c3noc4cc(Cl)cc(-c5c(F)cccc5F)c34)c2=O)C1(F)F] | 517.1 |
| 74 | N-{(6R)-2-[4-(2,6-difluorophenyl)-6-(trifluoromethyl)-1,2-benzoxazol-3-yl]-7,7-difluoro-3-oxo-2,5,6,7-tetrahydro-3H-pyrrolo[1,2-c]imidazol-6-yl}methanesulfonamide | 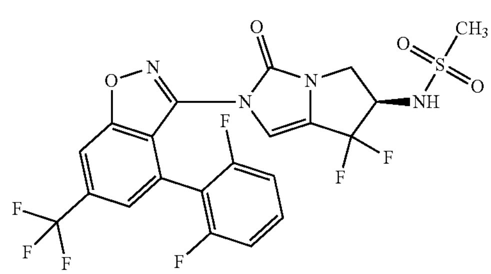 [SMILES: CS(=O)(=O)N[C@@H]1Cn2c(cn(-c3noc4cc(C(F)(F)F)cc(-c5c(F)cccc5F)c34)c2=O)C1(F)F] | 551.0 |

TABLE 1-1-continued

| Ex. No. | IUPAC Name | Structure | MS |
|---|---|---|---|
| 75 | N-{(6R)-2-[4-(2,6-difluorophenyl)-5-fluoro-1,2-benzoxazol-3-yl]-7,7-difluoro-3-oxo-2,5,6,7-tetrahydro-3H-pyrrolo[1,2-c]imidazol-6-yl}methanesulfonamide | 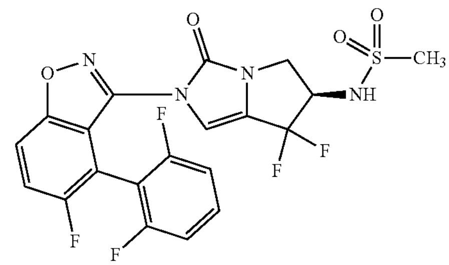 [SMILES: CS(=O)(=O)N[C@@H]1Cn2c(cn(-c3noc4ccc(F)c(-c5c(F)cccc5F)c34)c2=O)C1(F)F] | 501.1 |
| 76 | N-{(6R)-2-[4-(2,6-difluorophenyl)-5-fluoro-1,2-benzoxazol-3-yl]-7,7-difluoro-3-oxo-2,5,6,7-tetrahydro-3H-pyrrolo[1,2-c]imidazol-6-yl}ethanesulfonamide | 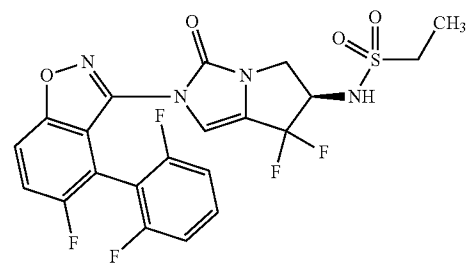 [SMILES: CCS(=O)(=O)N[C@@H]1Cn2c(cn(-c3noc4ccc(F)c(-c5c(F)cccc5F)c34)c2=O)C1(F)F] | 515.1 |
| 77 | N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide | 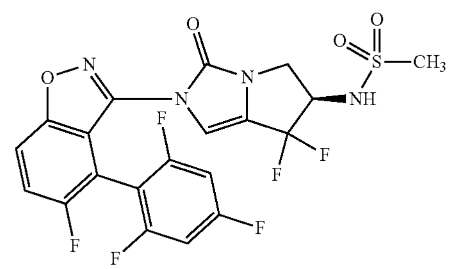 [SMILES: CS(=O)(=O)N[C@@H]1Cn2c(cn(-c3noc4ccc(F)c(-c5c(F)cc(F)cc5F)c34)c2=O)C1(F)F] | 519.1 |
| 78 | N-{(6R)-2-[6-chloro-4-(2,6-difluorophenyl)-5-fluoro-1,2-benzoxazol-3-yl]-7,7-difluoro-3-oxo-2,5,6,7-tetrahydro-3H-pyrrolo[1,2-c]imidazol-6-yl}ethanesulfonamide | 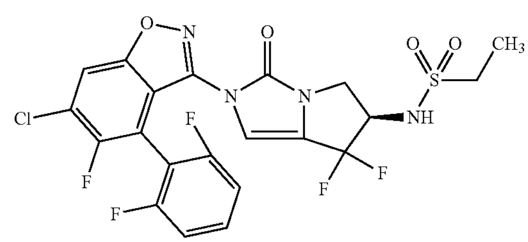 [SMILES: CCS(=O)(=O)N[C@@H]1Cn2c(cn(-c3noc4cc(Cl)c(F)c(-c5c(F)cccc5F)c34)c2=O)C1(F)F] | 549.0 |
| 79 | N-{(6R,7aR)-2-[6-chloro-4-(2,6-difluorophenyl)-5-fluoro-1,2-benzoxazol-3-yl]-7,7-difluoro-3-oxohexahydro-1H-pyrrolo[1,2-c]imidazol-6-yl}ethanesulfonamide | 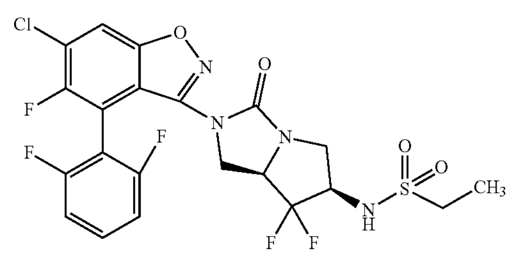 [SMILES: CCS(=O)(=O)N[C@@H]1CN2C(=O)N(c3noc4cc(Cl)c(F)c(-c5c(F)cccc5F)c34)C[C@@H]2C1(F)F] | 551.0 |
| 80 | N-{(6S,7aS)-2-[6-bromo-4-(2,6-difluorophenyl)-1,2-benzoxazol-3-yl]-3-oxohexahydro-1H-pyrrolo[1,2-c]imidazol-6-yl}ethanesulfonamide | 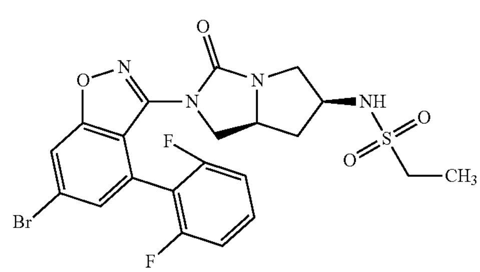 [SMILES: CCS(=O)(=O)N[C@H]1C[C@H]2CN(c3noc4cc(Br)cc(-c5c(F)cccc5F)c34)C(=O)N2C1] | 540.9 |

TABLE 1-1-continued

| Ex. No. | IUPAC Name | Structure | MS |
|---|---|---|---|
| 81 | N-{(6S,7aS)-2-[4-(2,6-difluorophenyl)-6-methyl-1,2-benzoxazol-3-yl]-3-oxohexahydro-1H-pyrrolo[1,2-c]imidazol-6-yl}methanesulfonamide | 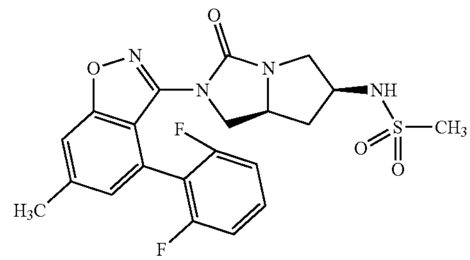 | 463.1 |
| 82 | N-{(6S,7aS)-2-[4-(furan-2-yl)-1,2-benzoxazol-3-yl]-3-oxohexahydro-1H-pyrrolo[1,2-c]imidazol-6-yl}ethanesulfonamide | 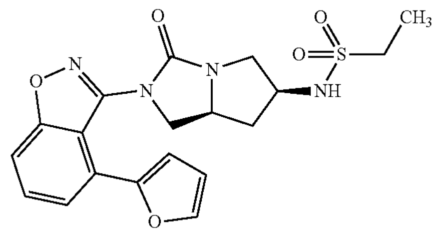 [SMILES: CCS(=O)(=O)N[C@H]1C[C@H]2CN(c3noc4cccc(-c5ccco5)c34)C(=O)N2C1] | 417.2 |
| 83 | N-{(6S,7aS)-2-[4-(3-methylthiophen-2-yl)-1,2-benzoxazol-3-yl]-3-oxohexahydro-1H-pyrrolo[1,2-c]imidazol-6-yl}ethanesulfonamide | 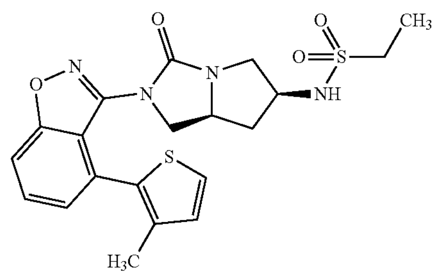 [SMILES: CCS(=O)(=O)N[C@H]1C[C@H]2CN(c3noc4cccc(-c5sccc5C)c34)C(=O)N2C1] | 447.1 |
| 84 | N-{(6S)-2-[4-(2,6-difluorophenyl)-6-(trifluoromethyl)-1,2-benzoxazol-3-yl]-3-oxo-2,5,6,7-tetrahydro-3H-pyrrolo[1,2-c]imidazol-6-yl}ethanesulfonamide | 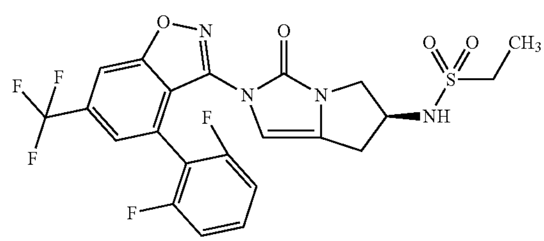 [SMILES: CCS(=O)(=O)N[C@H]1Cc2cn(-c3noc4cc(C(F)(F)F)cc(-c5c(F)cccc5F)c34)c(=O)n2C1] | 529.0 |
| 85 | N-{(6S)-2-[4-(2,6-difluorophenyl)-2-methylpyrazolo[1,5-a]pyridin-3-yl]-3-oxo-2,5,6,7-tetrahydro-3H-pyrrolo[1,2-c]imidazol-6-yl}ethanesulfonamide | 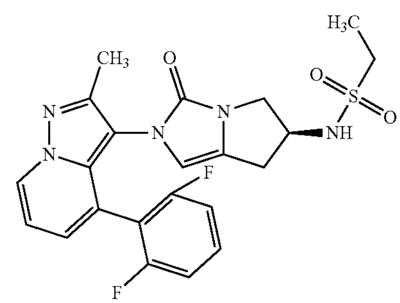 [SMILES: CCS(=O)(=O)N[C@H]1Cc2cn(-c3c(C)nn4cccc(-c5c(F)cccc5F)c34)c(=O)n2C1] | 474.2 |
| 86 | N-{(6S)-2-[4-(2,6-difluorophenyl)-6-(trifluoromethyl)-1,2-benzoxazol-3-yl]-1-methyl-3-oxo-2,5,6,7-tetrahydro-3H-pyrrolo[1,2-c]imidazol-6-yl}ethanesulfonamide | 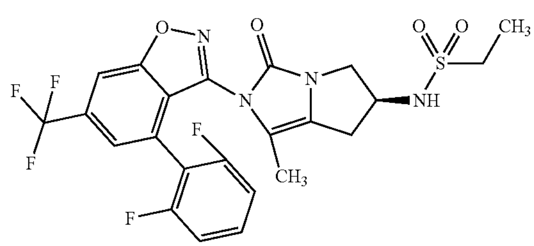 [SMILES: CCS(=O)(=O)N[C@H]1Cc2c(C)n(-c3noc4cc(C(F)(F)F)cc(-c5c(F)cccc5F)c34)c(=O)n2C1] | 543.1 |

TABLE 1-1-continued

| Ex. No. | IUPAC Name | Structure | MS |
|---|---|---|---|
| 87 | N-{(6R,7aR)-2-[6-chloro-4-(2,6-difluorophenyl)-1,2-benzoxazol-3-yl]-7,7-difluoro-3-oxohexahydro-1H-pyrrolo[1,2-c]imidazol-6-yl}methanesulfonamide | 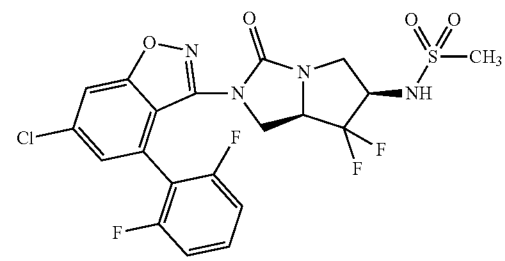 [SMILES: CS(=O)(=O)N[C@@H]1CN2C(=O)N(c3noc4cc(Cl)cc(-c5c(F)cccc5F)c34)C[C@@H]2C1(F)F] | 519.1 |
| 88 | N-{(6S)-2-[4-(2,6-difluorophenyl)-2-methyl-2H-indazol-3-yl]-3-oxo-2,5,6,7-tetrahydro-3H-pyrrolo[1,2-c]imidazol-6-yl}methanesulfonamide | 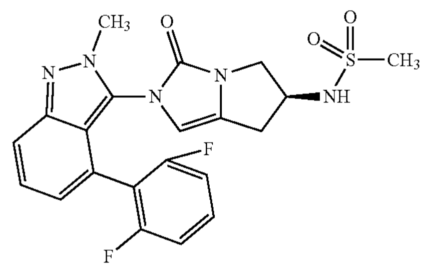 [SMILES: Cn1nc2cccc(-c3c(F)cccc3F)c2c1-n1cc2n(c1=O)C[C@@H](NS(C)(=O)=O)C2] | 460.1 |
| 89 | N-{(6R,7aR)-2-[4-(2,6-difluorophenyl)-1,2-benzoxazol-3-yl]-7,7-difluoro-3-oxohexahydro-1H-pyrrolo[1,2-c]imidazol-6-yl}cyclopropanesulfonamide | 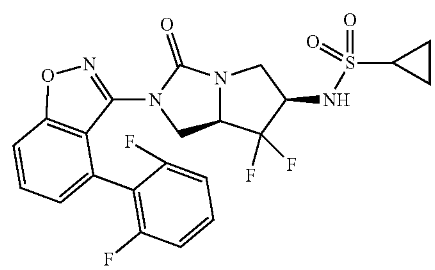 [SMILES: O=C1N(c2noc3cccc(-c4c(F)cccc4F)c23)C[C@H]2N1C[C@@H](NS(=O)(=O)C1CC1)C2(F)F] | 511.1 |
| 90 | N-{(6R)-2-[6-chloro-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}methanesulfonamide | 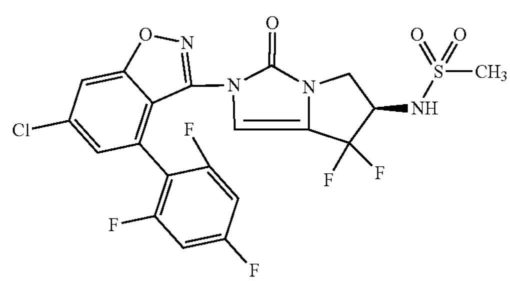 [SMILES: CS(=O)(=O)N[C@@H]1Cn2c(cn(-c3noc4cc(Cl)cc(-c5c(F)cc(F)cc5F)c34)c2=O)C1(F)F] | 535.0 |
| 91 | N-{(6R)-7,7-difluoro-3-oxo-2-[4-(2,4,6-trifluorophenyl)-1,2-benzoxazol-3-yl]-2,5,6,7-tetrahydro-3H-pyrrolo[1,2-c]imidazol-6-yl}ethanesulfonamide | 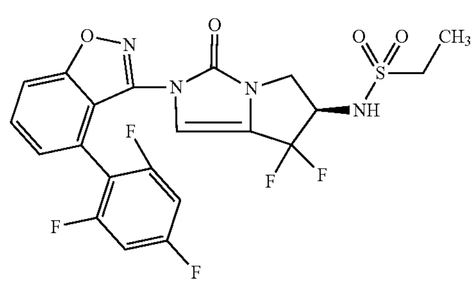 [SMILES: CCS(=O)(=O)N[C@@H]1Cn2c(cn(-c3noc4cccc(-c5c(F)cc(F)cc5F)c34)c2=O)C1(F)F] | 515.2 |

TABLE 1-1-continued

| Ex. No. | IUPAC Name | Structure | MS |
|---|---|---|---|
| 92 | N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}ethanesulfonamide | 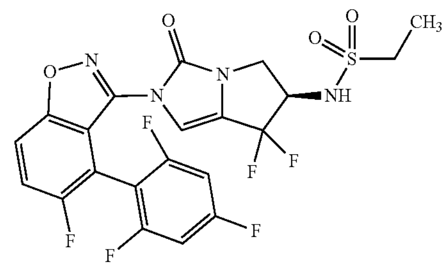 [SMILES: CCS(=O)(=O)N[C@@H]1Cn2c(cn(-c3noc4ccc(F)c(-c5c(F)cc(F)cc5F)c34)c2=O)C1(F)F] | 533.0 |
| 93 | N-{(6R,7aR)-2-[6-chloro-5-fluoro-4-(2,4,6-trifluorophenyl)-1,2-benzoxazol-3-yl]-7,7-difluoro-3-oxohexahydro-1H-pyrrolo[1,2-c]imidazol-6-yl}ethanesulfonamide | 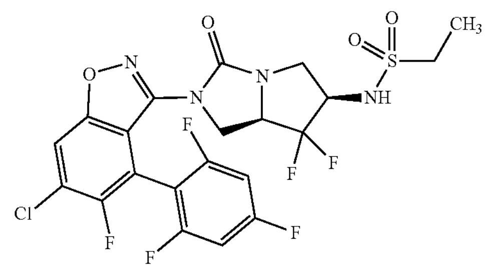 [SMILES: CCS(=O)(=O)N[C@@H]1CN2C(=O)N(c3noc4cc(Cl)c(F)c(-c5c(F)cc(F)cc5F)c34)C[C@@H]2C1(F)F] | 569.0 |
| 94 | N-{(6R)-2-[6-chloro-5-fluoro-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}ethanesulfonamide | 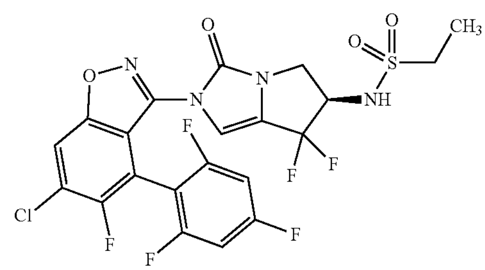 [SMILES: CCS(=O)(=O)N[C@@H]1Cn2c(cn(-c3noc4cc(Cl)c(F)c(-c5c(F)cc(F)cc5F)c34)c2=O)C1(F)F] | 566.9 |
| 95 | N-{(6R)-2-[6-chloro-4-(2,6-difluorophenyl)-5-fluoro-1,2-benzoxazol-3-yl]-7,7-difluoro-3-oxo-2,5,6,7-tetrahydro-3H-pyrrolo[1,2-c]imidazol-6-yl}methanesulfonamide | 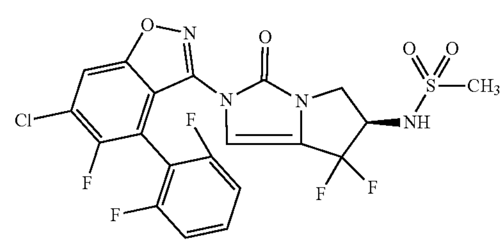 [SMILES: CS(=O)(=O)N[C@@H]1Cn2c(cn(-c3noc4cc(Cl)c(F)c(-c5c(F)cccc5F)c34)c2=O)C1(F)F] | 535.0 |
| 96 | N-{(6S,7aS)-2-[4-(2,6-difluorophenyl)-1,2-benzoxazol-3-yl]-3-oxohexahydro-1H-pyrrolo[1,2-c]imidazol-6-yl}cyclopropanesulfonamide | 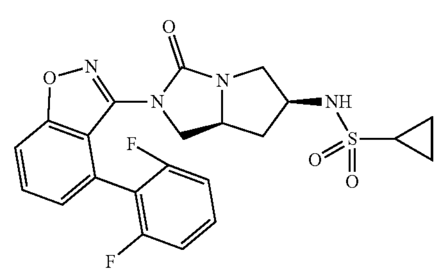 [SMILES: O=C1N(c2noc3cccc(-c4c(F)cccc4F)c23)C[C@@H]2C[C@H](NS(=O)(=O)C3CC3)CN12] | 475.1 |
| 97 | N-{(6S,7aS)-2-[4-(2,6-difluorophenyl)-6-hydroxy-1,2-benzoxazol-3-yl]-3-oxohexahydro-1H-pyrrolo[1,2-c]imidazol-6-yl}ethanesulfonamide | 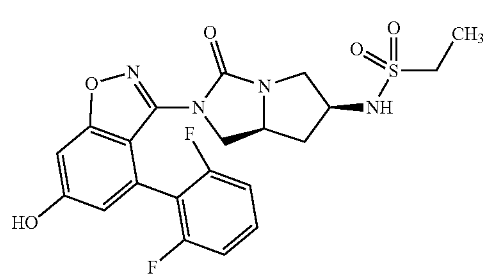 [SMILES: CCS(=O)(=O)N[C@H]1C[C@H]2CN(c3noc4cc(O)cc(-c5c(F)cccc5F)c34)C(=O)N2C1] | 479.1 |

TABLE 1-1-continued

| Ex. No. | IUPAC Name | Structure | MS |
|---|---|---|---|
| 98 | N-{(1R*,6S,7aS)-2-[4-(2,6-difluorophenyl)-1,2-benzoxazol-3-yl]-1-methyl-3-oxohexahydro-1H-pyrrolo[1,2-c]imidazol-6-yl}ethanesulfonamide | 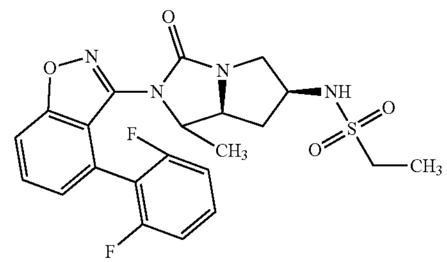 | 477.1 |
| 99 | N-{(6S,7aS)-2-[4-(2-fluoro-6-methylphenyl)-1,2-benzoxazol-3-yl]-3-oxohexahydro-1H-pyrrolo[1,2-c]imidazol-6-yl}ethanesulfonamide | 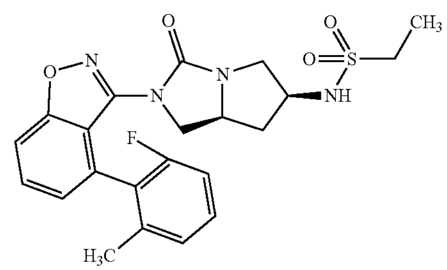 [SMILES: CCS(=O)(=O)N[C@H]1C[C@H]2CN(c3noc4cccc(-c5c(C)cccc5F)c34)C(=O)N2C1] | 459.2 |
| 100 | rel-N-{(6R, 8aR)-2-[4-(2,6-difluorophenyl)-1,2-benzoxazol-3-yl]-3-oxooctahydroimidazo[1,5-a]pyridin-6-yl}methanesulfonamide | 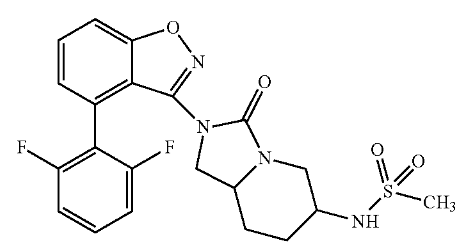 [SMILES: CS(=O)(=O)NC1CCC2CN(c3noc4cccc(-c5c(F)cccc5F)c34)C(=O)N2C1] | 463.1 |
| 101 | N-{(6S)-2-[4-(2,6-difluorophenyl)-6-(trifluoromethyl)-1,2-benzoxazol-3-yl]-3-oxo-2,5,6,7-tetrahydro-3H-pyrrolo[1,2-c]imidazol-6-yl}methanesulfonamide | 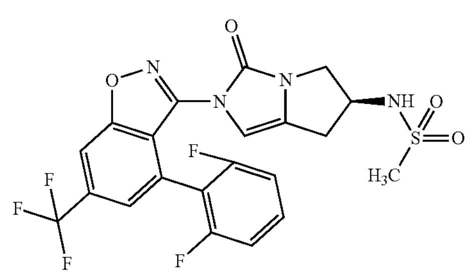 [SMILES: CS(=O)(=O)N[C@H]1Cc2cn(-c3noc4cc(C(F)(F)F)cc(-c5c(F)cccc5F)c34)c(=O)n2C1] | 515.0 |
| 102 | N-{(6R)-2-[4-(2,6-difluorophenyl)-1,2-benzoxazol-3-yl]-7,7-difluoro-3-oxo-2,5,6,7-tetrahydro-3H-pyrrolo[1,2-c]imidazol-6-yl}methanesulfonamide | 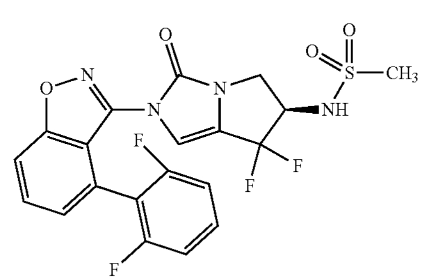 [SMILES: CS(=O)(=O)N[C@@H]1Cn2c(cn(-c3noc4cccc(-c5c(F)cccc5F)c34)c2=O)C1(F)F] | 483.1 |

TABLE 1-1-continued

| Ex. No. | IUPAC Name | Structure | MS |
|---|---|---|---|
| 103 | N-{(6S)-2-[4-(2,6-difluorophenyl)-1-methyl-1H-indazol-3-yl]-3-oxo-2,5,6,7-tetrahydro-3H-pyrrolo[1,2-c]imidazol-6-yl}methanesulfonamide | 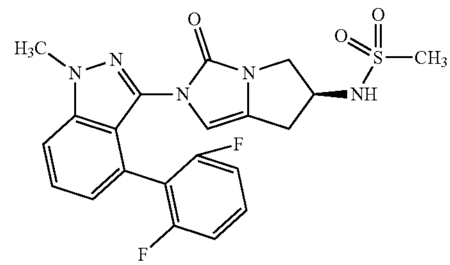 | 460.1 |
| 104 | N-{(6R,7aR)-2-[6-bromo-4-(2,6-difluorophenyl)-1,2-benzoxazol-3-yl]-7,7-difluoro-3-oxohexahydro-1H-pyrrolo[1,2-c]imidazol-6-yl}ethanesulfonamide | 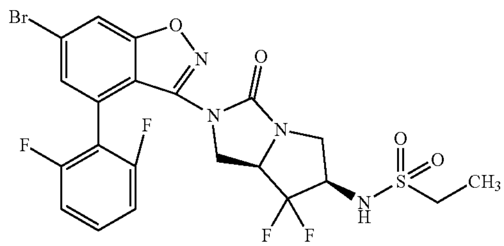 [SMILES: CCS(=O)(=O)N[C@@H]1CN2C(=O)N(c3noc4cc(Br)cc(-c5c(F)cccc5F)c34)C[C@@H]2C1(F)F] | 577.0 |
| 105 | N-{(6R,7aR)-7,7-difluoro-2-[5-fluoro-4-(2,4,6-trifluorophenyl)-1,2-benzoxazol-3-yl]-3-oxohexahydro-1H-pyrrolo[1,2-c]imidazol-6-yl}ethanesulfonamide | 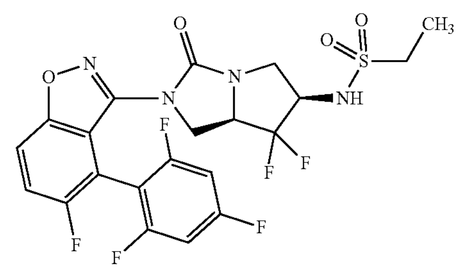 [SMILES: CCS(=O)(=O)N[C@@H]1CN2C(=O)N(c3noc4ccc(F)c(-c5c(F)cc(F)cc5F)c34)C[C@@H]2C1(F)F] | 535.1 |
| 106 | N-{(6R)-2-[6-chloro-5-fluoro-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}methanesulfonamide | 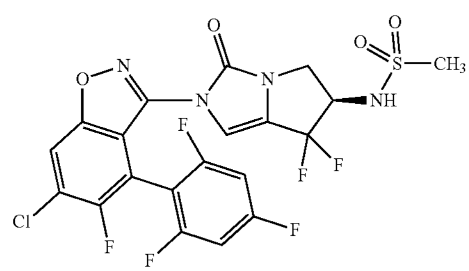 [SMILES: CS(=O)(=O)N[C@@H]1Cn2c(cn(-c3noc4cc(Cl)c(F)c(-c5c(F)cc(F)cc5F)c34)c2=O)C1(F)F] | 553.0 |
| 107 | N-{(6R,7aR)-2-[6-chloro-4-(2,6-difluorophenyl)-5-fluoro-1,2-benzoxazol-3-yl]-7,7-difluoro-3-oxohexahydro-1H-pyrrolo[1,2-c]imidazol-6-yl}methanesulfonamide | 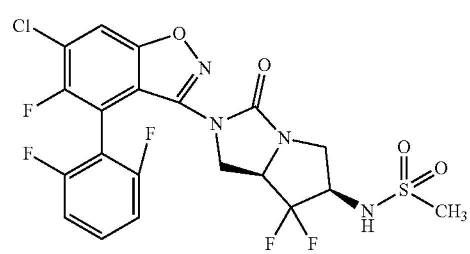 [SMILES: CS(=O)(=O)N[C@@H]1CN2C(=O)N(c3noc4cc(Cl)c(F)c(-c5c(F)cccc5F)c34)C[C@@H]2C1(F)F] | 537.0 |

TABLE 1-1-continued

| Ex. No. | IUPAC Name | Structure | MS |
|---|---|---|---|
| 108 | N-{(6R)-7,7-difluoro-2-[6-fluoro-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide | 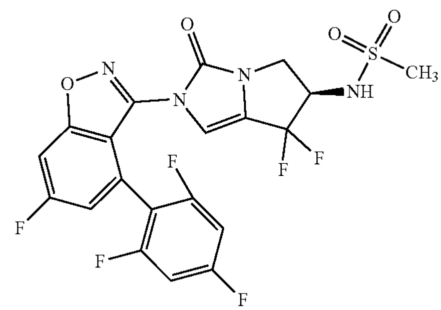 [SMILES: CS(=O)(=O)N[C@@H]1Cn2c(cn(-c3noc4cc(F)cc(-c5c(F)cc(F)cc5F)c34)c2=O)C1(F)F] | 519.1 |
| 109 | rel-N-{(6R,7S)-2-[4-(2,6-difluorophenyl)-1,2-benzoxazol-3-yl]-7-methyl-3-oxo-2,5,6,7-tetrahydro-3H-pyrrolo[1,2-c]imidazol-6-yl}ethanesulfonamide | 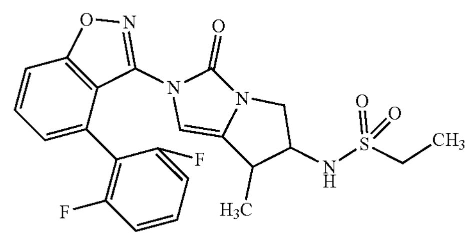 [SMILES: CCS(=O)(=O)NC1Cn2c(cn(-c3noc4cccc(-c5c(F)cccc5F)c34)c2=O)C1C] | 475.3 |
| 110 | N-{(6R)-2-[4-(2,6-difluorophenyl)-5-fluoro-6-methyl-1,2-benzoxazol-3-yl]-7,7-difluoro-3-oxo-2,5,6,7-tetrahydro-3H-pyrrolo[1,2-c]imidazol-6-yl}methanesulfonamide | 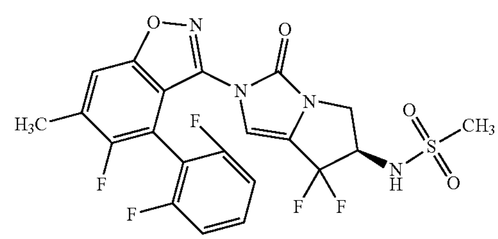 | 515.2 |
| 111 | N-{(6R)-7,7-difluoro-2-[6-(methoxymethyl)-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide | 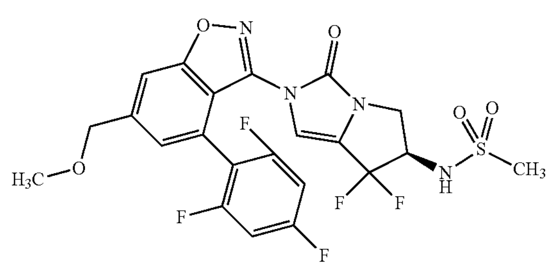 | 545.1 |
| 112 | N-{(6R)-2-[4-(2,6-difluorophenyl)-6-methyl[1,2]oxazolo[5,4-b]pyridin-3-yl]-7,7-difluoro-3-oxo-2,5,6,7-tetrahydro-3H-pyrrolo[1,2-c]imidazol-6-yl}ethanesulfonamide | 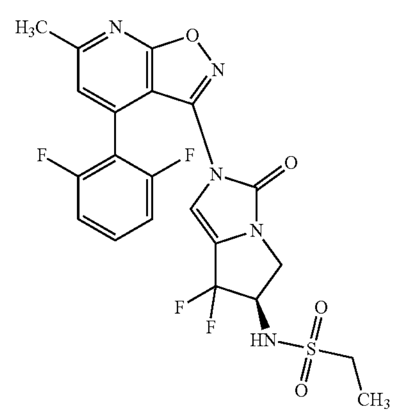 [SMILES: CCS(=O)(=O)N[C@@H]1Cn2c(cn(-c3noc4nc(C)cc(-c5c(F)cccc5F)c34)c2=O)C1(F)F] | 512.1 |

TABLE 1-1-continued

| Ex. No. | IUPAC Name | Structure | MS |
|---|---|---|---|
| 113 | N-{(6R)-2-[6-(difluoromethoxy)-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}methanesulfonamide | 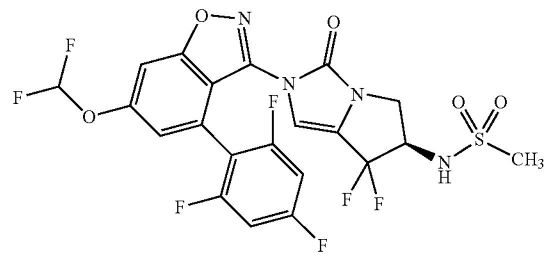 [SMILES: CS(=O)(=O)N[C@@H]1Cn2c(cn(-c3noc4cc(OC(F)F)cc(-c5c(F)cc(F)cc5F)c34)c2=O)C1(F)F] | 567.2 |
| 114 | N-{(6R)-2-[4-(2,6-difluorophenyl)-6-(trifluoromethoxy)-1,2-benzoxazol-3-yl]-7,7-difluoro-3-oxo-2,5,6,7-tetrahydro-3H-pyrrolo[1,2-c]imidazol-6-yl}ethanesulfonamide | 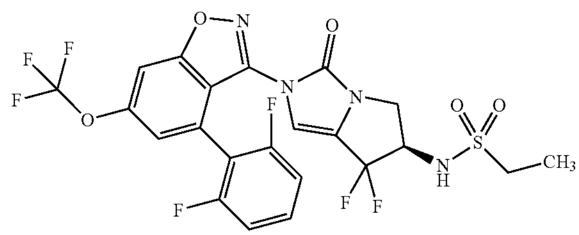 [SMILES: CCS(=O)(=O)N[C@@H]1Cn2c(cn(-c3noc4cc(OC(F)(F)F)cc(-c5c(F)cccc5F)c34)c2=O)C1(F)F] | 581.1 |
| 115 | N-{(6R,7aR)-2-[4-(2,6-difluorophenyl)-6-(trifluoromethoxy)-1,2-benzoxazol-3-yl]-7,7-difluoro-3-oxohexahydro-1H-pyrrolo[1,2-c]imidazol-6-yl}ethanesulfonamide | 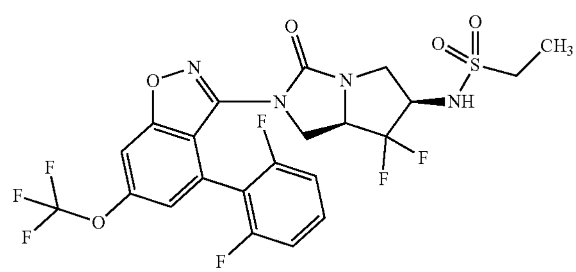 [SMILES: CCS(=O)(=O)N[C@@H]1CN2C(=O)N(c3noc4cc(OC(F)(F)F)cc(-c5c(F)cccc5F)c34)C[C@@H]2C1(F)F] | 583.1 |
| 116 | N-{(6R)-7,7-difluoro-2-[6-fluoro-4-(2,4,6-trifluorophenyl)-1,2-benzoxazol-3-yl]-3-oxo-2,5,6,7-tetrahydro-3H-pyrrolo[1,2-c]imidazol-6-yl}ethanesulfonamide | 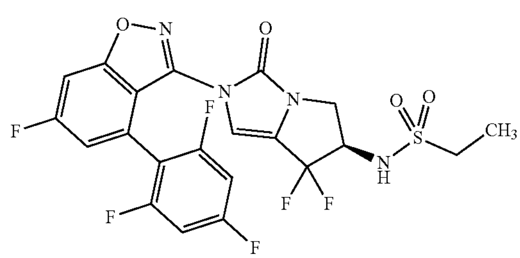 [SMILES: CCS(=O)(=O)N[C@@H]1Cn2c(cn(-c3noc4cc(F)cc(-c5c(F)cc(F)cc5F)c34)c2=O)C1(F)F] | 533.2 |
| 117 | N-{(6R*)-2-[4-(2,6-difluorophenyl)-1,2-benzoxazol-3-yl]-7,7-difluoro-3-oxo-2,3,5,6,7,8-hexahydroimidazo[1,5-a]pyridin-6-yl}methanesulfonamide | 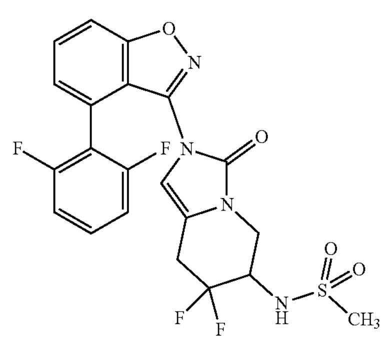 [SMILES: CS(=O)(=O)NC1Cn2c(cn(-c3noc4cccc(-c5c(F)cccc5F)c34)c2=O)CC1(F)F] | 497.3 |

TABLE 1-1-continued

| Ex. No. | IUPAC Name | MS |
|---|---|---|
| 118 | N-{(6R)-2-[4-(2,6-difluorophenyl)-6-methyl[1,2]oxazolo[5,4-b]pyridin-3-yl]-7,7-difluoro-3-oxo-2,5,6,7-tetrahydro-3H-pyrrolo[1,2-c]imidazol-6-yl}methanesulfonamide | 498.2 498.2 |
| 119 | N-{(6R,7aR)-7,7-difluoro-2-[5-fluoro-6-methyl-4-(2,4,6-trifluorophenyl)-1,2-benzoxazol-3-yl]-3-oxohexahydro-1H-pyrrolo[1,2-c]imidazol-6-yl}methanesulfonamide | 535.2 |
| 120 | N-{(6R,7aR)-2-[4-(2,6-difluorophenyl)-5-fluoro-6-methyl-1,2-benzoxazol-3-yl]-7,7-difluoro-3-oxohexahydro-1H-pyrrolo[1,2-c]imidazol-6-yl}ethanesulfonamide | 531.2 |
| 121 | N-{(6R)-2-[5,6-difluoro-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}ethanesulfonamide | 551.1 |
| 122 | N-{(6R)-2-[4-(2,6-difluorophenyl)-6-(trifluoromethoxy)-1,2-benzoxazol-3-yl]-7,7-difluoro-3-oxo-2,5,6,7-tetrahydro-3H-pyrrolo[1,2-c]imidazol-6-yl}methanesulfonamide | 567.2 |
| 123 | N-{(6R)-2-[4-(2,6-difluorophenyl)-6-ethoxy-1,2-benzoxazol-3-yl]-7,7-difluoro-3-oxo-2,5,6,7-tetrahydro-3H-pyrrolo[1,2-c]imidazol-6-yl}ethanesulfonamide | 541.2 |

TABLE 1-1-continued

| Ex. No. | IUPAC Name | Structure | MS |
|---|---|---|---|
| 124 | N-{(6R,7aR)-7,7-difluoro-2-[6-fluoro-4-(2,4,6-trifluorophenyl)-1,2-benzoxazol-3-yl]-3-oxohexahydro-1H-pyrrolo[1,2-c]imidazol-6-yl}ethanesulfonamide | 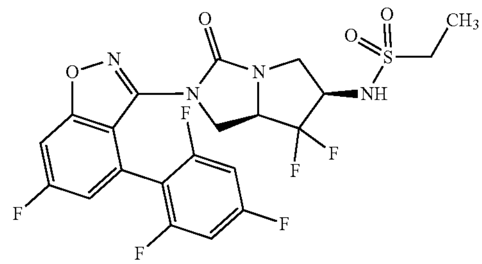 [SMILES: CCS(=O)(=O)N[C@@H]1CN2C(=O)N(c3noc4cc(F)cc(-c5c(F)cc(F)cc5F)c34)C[C@@H]2C1(F)F] | 535.2 |
| 125 | N-{(1R*,6R,7aR)-7,7-difluoro-1-hydroxy-3-oxo-2-[4-(2,4,6-trifluorophenyl)-1,2-benzoxazol-3-yl]hexahydro-1H-pyrrolo[1,2-c]imidazol-6-yl}methanesulfonamide | 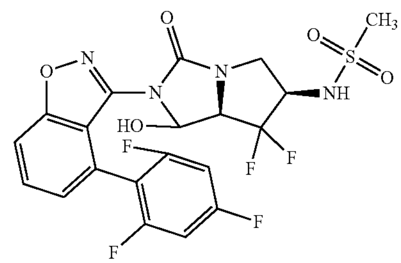 | 519.1 |
| 126 | N-{(6R,7aR)-2-[4-(2,6-difluorophenyl)-6-methyl-1,2-benzoxazol-3-yl]-7,7-difluoro-3-oxohexahydro-1H-pyrrolo[1,2-c]imidazol-6-yl}methanesulfonamide | 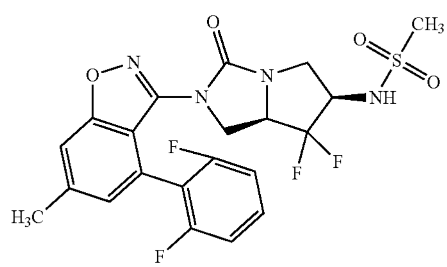 [SMILES: Cc1cc(-c2c(F)cccc2F)c2c(N3C[C@H]4N(C[C@@H](NS(C)(=O)=O)C4(F)F)C3=O)noc2c1] | 499.1 |
| 127 | N-{(6R)-7,7-difluoro-2-[6-methyl-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide | 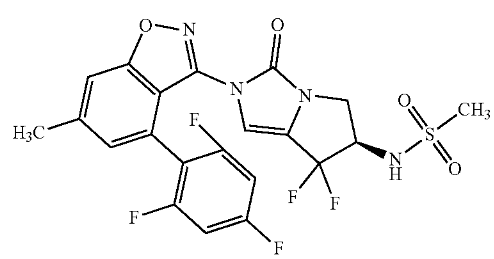 | 515.2 |
| 128 | N-{(6R)-7,7-difluoro-2-[6-(hydroxymethyl)-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide | 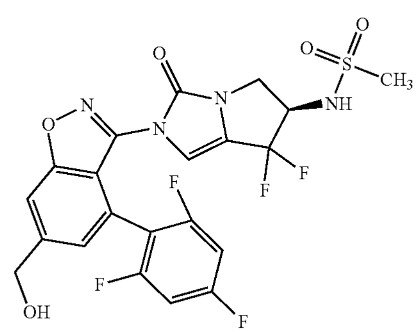 [SMILES: CS(=O)(=O)N[C@@H]1Cn2c(cn(-c3noc4cc(CO)cc(-c5c(F)cc(F)cc5F)c34)c2=O)C1(F)F] | 530.9 |

TABLE 1-1-continued

| Ex. No. | IUPAC Name | MS |
|---|---|---|
| 129 | rel-N-{(6R, 7R)-2-[4-(2,6-difluorophenyl)-1,2-benzoxazol-3-yl]-7-fluoro-3-oxo-2,5,6,7-tetrahydro-3H-pyrrolo[1,2-c]imidazol-6-yl}ethanesulfonamide | 479.2 |
| 130 | N-{(6R)-7,7-difluoro-3-oxo-2-[6-(trifluoromethyl)-4-(2,4,6-trifluorophenyl)-1,2-benzoxazol-3-yl]-2,5,6,7-tetrahydro-3H-pyrrolo[1,2-c]imidazol-6-yl}methanesulfonamide | 569.1 569.1 |
| 131 | rel-N-{(6R, 7R)-2-[4-(2,6-difluorophenyl)-1,2-benzoxazol-3-yl]-7-methyl-3-oxo-2,5,6,7-tetrahydro-3H-pyrrolo[1,2-c]imidazol-6-yl}ethanesulfonamide | 475.3 |
| 132 | N-{(6R)-2-[4-(2,6-difluorophenyl)-6-(methoxymethyl)-1,2-benzoxazol-3-yl]-7,7-difluoro-3-oxo-2,5,6,7-tetrahydro-3H-pyrrolo[1,2-c]imidazol-6-yl}methanesulfonamide | 527.2 |
| 133 | N-{(6R,7aR)-2-[6-(difluoromethoxy)-4-(2,6-difluorophenyl)-1,2-benzoxazol-3-yl]-7,7-difluoro-3-oxohexahydro-1H-pyrrolo[1,2-c]imidazol-6-yl}methanesulfonamide | 551.1 |

TABLE 1-1-continued

| Ex. No. | IUPAC Name | Structure | MS |
|---|---|---|---|
| 134 | N-{(6R,7aR)-7,7-difluoro-2-[6-(methoxymethyl)-4-(2,4,6-trifluorophenyl)-1,2-benzoxazol-3-yl]-3-oxohexahydro-1H-pyrrolo[1,2-c]imidazol-6-yl}ethanesulfonamide | 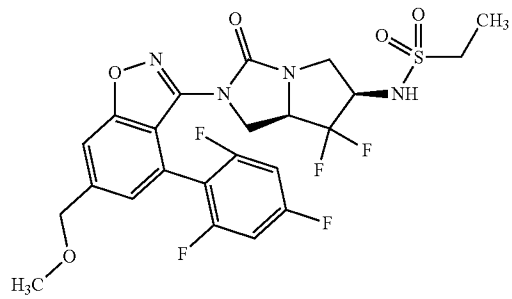 [SMILES: CCS(=O)(=O)N[C@@H]1CN2C(=O)N(c3noc4cc(COC)cc(-c5c(F)cc(F)cc5F)c34)C[C@@H]2C1(F)F] | 561.1 |
| 135 | N-{(6R)-2-[5,6-difluoro-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}methanesulfonamide | 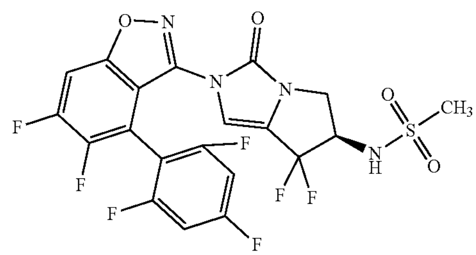 [SMILES: CS(=O)(=O)N[C@@H]1Cn2c(cn(-c3noc4cc(F)c(F)c(-c5c(F)cc(F)cc5F)c34)c2=O)C1(F)F] | 537.1<br>537.1 |
| 136 | N-{(6R)-2-[6-(difluoromethyl)-4-(2,6-difluorophenyl)-1,2-benzoxazol-3-yl]-7,7-difluoro-3-oxo-2,5,6,7-tetrahydro-3H-pyrrolo[1,2-c]imidazol-6-yl}methanesulfonamide | 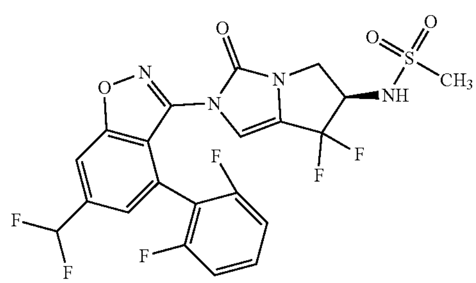 [SMILES: CS(=O)(=O)N[C@@H]1Cn2c(cn(-c3noc4cc(C(F)F)cc(-c5c(F)cccc5F)c34)c2=O)C1(F)F] | 533.1 |
| 137 | N-{(6R,7aR)-2-[4-(2,6-difluorophenyl)-5,6-difluoro-1,2-benzoxazol-3-yl]-7,7-difluoro-3-oxohexahydro-1H-pyrrolo[1,2-c]imidazol-6-yl}methanesulfonamide | 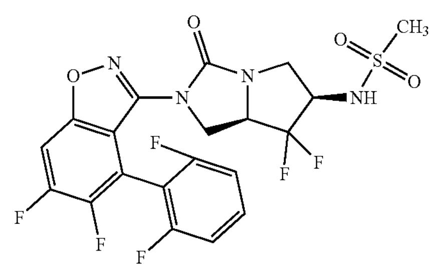 [SMILES: CS(=O)(=O)N[C@@H]1CN2C(=O)N(c3noc4cc(F)c(F)c(-c5c(F)cccc5F)c34)C[C@@H]2C1(F)F] | 521.1 |
| 138 | N-{(6R,7aR)-7,7-difluoro-2-[6-methyl-4-(2,4,6-trifluorophenyl)[1,2]oxazolo[5,4-b]pyridin-3-yl]-3-oxohexahydro-1H-pyrrolo[1,2-c]imidazol-6-yl}methanesulfonamide | 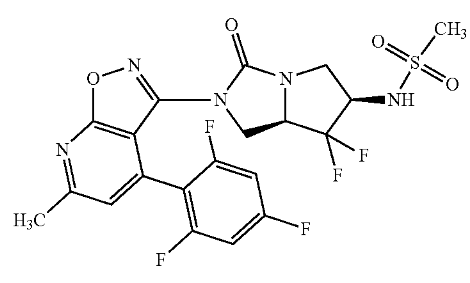 [SMILES: Cc1cc(-c2c(F)cc(F)cc2F)c2c(N3C[C@H]4N(C[C@@H](NS(C)(=O)=O)C4(F)F)C3=O)noc2n1] | 518.1 |

TABLE 1-1-continued

| Ex. No. | IUPAC Name | Structure | MS |
|---|---|---|---|
| 139 | N-{(6R)-7,7-difluoro-2-[6-fluoro-4-(2,4,6-trifluorophenyl)-1,2-benzoxazol-3-yl]-3-oxo-2,5,6,7-tetrahydro-3H-pyrrolo[1,2-c]imidazol-6-yl}-N'-methylsulfuric diamide | 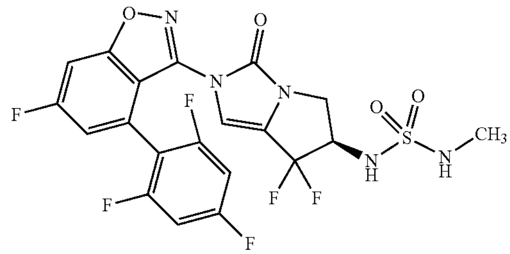 [SMILES: CNS(=O)(=O)N[C@@H]1Cn2c(cn(-c3noc4cc(F)cc(-c5c(F)cc(F)cc5F)c34)c2=O)C1(F)F] | 534.2 |
| 140 | N-{(6R,7aR)-7,7-difluoro-2-[6-methyl-4-(2,4,6-trifluorophenyl)-1,2-benzoxazol-3-yl]-3-oxohexahydro-1H-pyrrolo[1,2-c]imidazol-6-yl}methanesulfonamide | 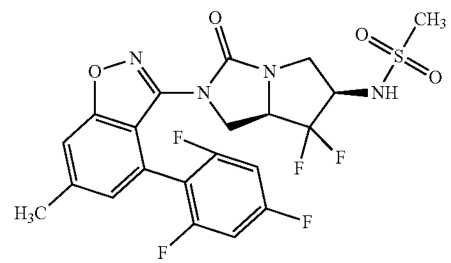 [SMILES: Cc1cc(-c2c(F)cc(F)cc2F)c2c(N3C[C@H]4N(C[C@@H](NS(C)(=O)=O)C4(F)F)C3=O)noc2c1] | 517.1 |
| 141 | N-{(6R)-2-[6-(difluoromethyl)-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}methanesulfonamide | 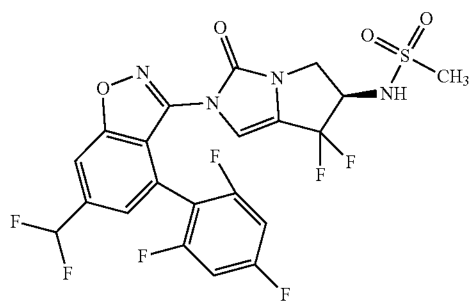 [SMILES: CS(=O)(=O)N[C@@H]1Cn2c(cn(-c3noc4cc(C(F)F)cc(-c5c(F)cc(F)cc5F)c34)c2=O)C1(F)F] | 551.1 |
| 142 | N-{(6R)-2-[4-(2,6-difluorophenyl)-5,6-difluoro-1,2-benzoxazol-3-yl]-7,7-difluoro-3-oxo-2,5,6,7-tetrahydro-3H-pyrrolo[1,2-c]imidazol-6-yl}methanesulfonamide | 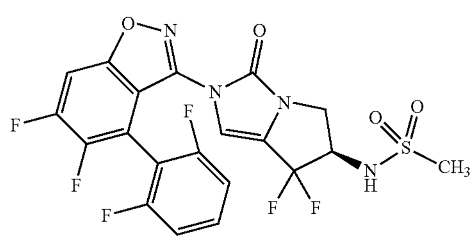 [SMILES: CS(=O)(=O)N[C@@H]1Cn2c(cn(-c3noc4cc(F)c(F)c(-c5c(F)cccc5F)c34)c2=O)C1(F)F] | 519.2<br>519.2 |
| 143 | N-{(6R,7aR)-2-[4-(2,6-difluorophenyl)-6-methyl[1,2]oxazolo[5,4-b]pyridin-3-yl]-7,7-difluoro-3-oxohexahydro-1H-pyrrolo[1,2-c]imidazol-6-yl}ethanesulfonamide | 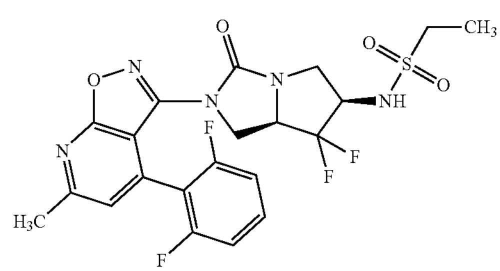 [SMILES: CCS(=O)(=O)N[C@@H]1CN2C(=O)N(c3noc4nc(C)cc(-c5c(F)cccc5F)c34)C[C@@H]2C1(F)F] | 514.2 |

TABLE 1-1-continued

| Ex. No. | IUPAC Name | Structure | MS |
|---|---|---|---|
| 144 | N-{(6R,7aR)-7,7-difluoro-2-[6-fluoro-4-(2,4,6-trifluorophenyl)-1,2-benzoxazol-3-yl]-3-oxohexahydro-1H-pyrrolo[1,2-c]imidazol-6-yl}-N'-methylsulfuric diamide | 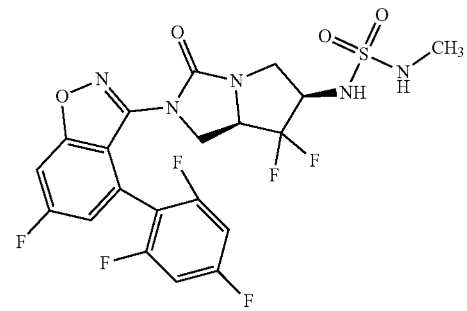 [SMILES: CNS(=O)(=O)N[C@@H]1CN2C(=O)N(c3noc4cc(F)cc(-c5c(F)cc(F)cc5F)c34)C[C@@H]2C1(F)F] | 536.2 |
| 145 | N-{(6R,7aR)-2-[4-(2,6-difluorophenyl)-6-ethoxy-1,2-benzoxazol-3-yl]-7,7-difluoro-3-oxohexahydro-1H-pyrrolo[1,2-c]imidazol-6-yl}methanesulfonamide | 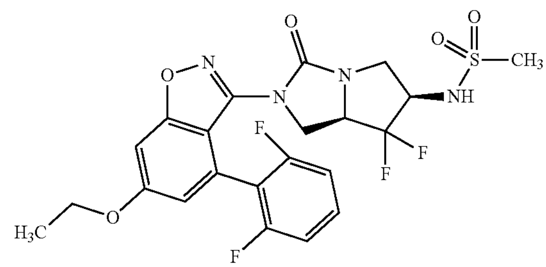 [SMILES: CCOc1cc(-c2c(F)cccc2F)c2c(N3C[C@H]4N(C[C@@H](NS(C)(=O)=O)C4(F)F)C3=O)noc2c1] | 529.2 |
| 146 | N-{(6R,7aR)-2-[4-(2,6-difluorophenyl)-6-ethoxy-1,2-benzoxazol-3-yl]-7,7-difluoro-3-oxohexahydro-1H-pyrrolo[1,2-c]imidazol-6-yl}ethanesulfonamide | 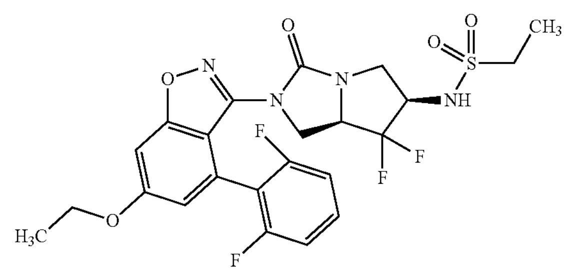 [SMILES: CCOc1cc(-c2c(F)cccc2F)c2c(N3C[C@H]4N(C[C@@H](NS(=O)(=O)CC)C4(F)F)C3=O)noc2c1] | 543.2 |
| 147 | N-{(6R,7aR)-2-[6-(difluoromethoxy)-4-(2,4,6-trifluorophenyl)-1,2-benzoxazol-3-yl]-7,7-difluoro-3-oxohexahydro-1H-pyrrolo[1,2-c]imidazol-6-yl}ethanesulfonamide | 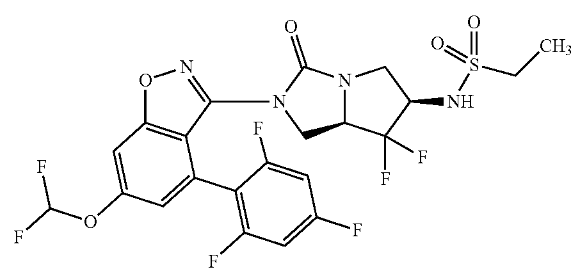 [SMILES: CCS(=O)(=O)N[C@@H]1CN2C(=O)N(c3noc4cc(OC(F)F)cc(-c5c(F)cc(F)cc5F)c34)C[C@@H]2C1(F)F] | 583.0 |
| 148 | N-{(1R,6S,7aS)-1-ethoxy-3-oxo-2-[4-(2,4,6-trifluorophenyl)-1,2-benzoxazol-3-yl]hexahydro-1H-pyrrolo[1,2-c]imidazol-6-yl}methanesulfonamide | 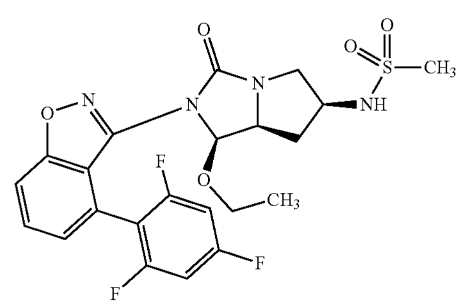 [SMILES: CCO[C@@H]1[C@@H]2C[C@H](NS(C)(=O)=O)CN2C(=O)N1c1noc2cccc(-c3c(F)cc(F)cc3F)c12] | 509.2 |

TABLE 1-1-continued

| Ex. No. | IUPAC Name | Structure | MS |
|---|---|---|---|
| 149 | N-{(6R,7aR)-7,7-difluoro-2-[6-fluoro-4-(2,4,6-trifluorophenyl)-1,2-benzoxazol-3-yl]-3-oxohexahydro-1H-pyrrolo[1,2-c]imidazol-6-yl}methanesulfonamide | 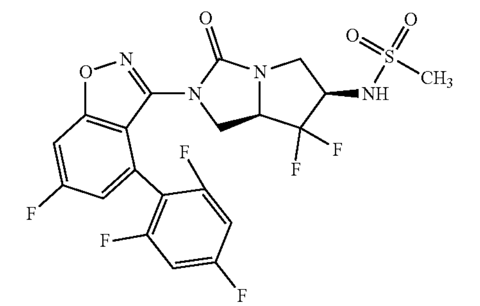 [SMILES: CS(=O)(=O)N[C@@H]1CN2C(=O)N(c3noc4cc(F)cc(-c5c(F)cc(F)cc5F)c34)C[C@@H]2C1(F)F] | 521.1<br>521.2<br>521.2<br>521.1 |
| 150 | N-{(6S,7aS)-2-[4-(2,6-difluorophenyl)-6-methyl[1,2]thiazolo[5,4-b]pyridin-3-yl]-3-oxohexahydro-1H-pyrrolo[1,2-c]imidazol-6-yl}ethanesulfonamide | 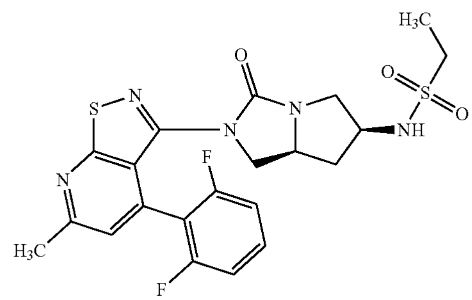 [SMILES: CCS(=O)(=O)N[C@H]1C[C@H]2CN(c3nsc4nc(C)cc(-c5c(F)cccc5F)c34)C(=O)N2C1] | 494.2 |
| 151 | N-{(6S,7aS)-2-[4-(2,6-difluorophenyl)pyrazolo[1,5-a]pyridin-3-yl]-3-oxohexahydro-1H-pyrrolo[1,2-c]imidazol-6-yl}methanesulfonamide | 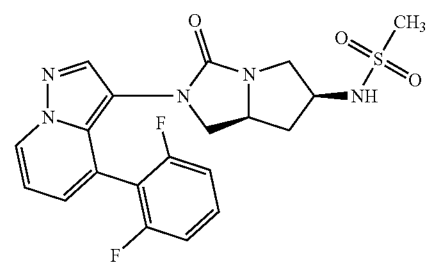 [SMILES: CS(=O)(=O)N[C@H]1C[C@H]2CN(c3cnn4cccc(-c5c(F)cccc5F)c34)C(=O)N2C1] | 448.3 |
| 152 | N-{(6S)-2-[4-(2,6-difluorophenyl)-6-methyl[1,2]thiazolo[5,4-b]pyridin-3-yl]-3-oxo-2,5,6,7-tetrahydro-3H-pyrrolo[1,2-c]imidazol-6-yl}ethanesulfonamide | 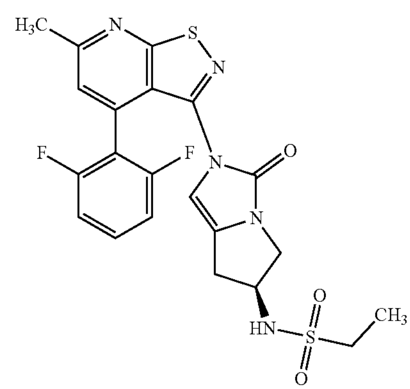 [SMILES: CCS(=O)(=O)N[C@H]1Cc2cn(-c3nsc4nc(C)cc(-c5c(F)cccc5F)c34)c(=O)n2C1] | 492.2 |
| 153 | N-{(6R,7aR)-7,7-difluoro-2-[6-methyl-4-(2,4,6-trifluorophenyl)-1,2-benzoxazol-3-yl]-3-oxohexahydro-1H-pyrrolo[1,2-c]imidazol-6-yl}ethanesulfonamide | 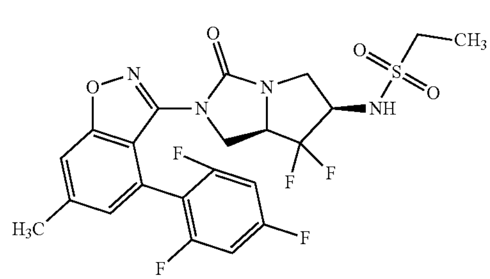 [SMILES: CCS(=O)(=O)N[C@@H]1CN2C(=O)N(c3noc4cc(C)cc(-c5c(F)cc(F)cc5F)c34)C[C@@H]2C1(F)F] | 531.2 |

TABLE 1-1-continued

| Ex. No. | IUPAC Name | Structure | MS |
|---|---|---|---|
| 154 | N-{(6R,7aR)-2-[4-(2,6-difluorophenyl)-6-methyl-1,2-benzoxazol-3-yl]-7,7-difluoro-3-oxohexahydro-1H-pyrrolo[1,2-c]imidazol-6-yl}ethanesulfonamide | 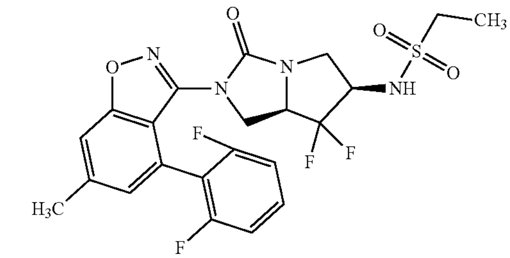 [SMILES: CCS(=O)(=O)N[C@@H]1CN2C(=O)N(c3noc4cc(C)cc(-c5c(F)cccc5F)c34)C[C@@H]2C1(F)F] | 513.2 |
| 155 | N-{(6R)-7,7-difluoro-2-[6-methyl-4-(2,4,6-trifluorophenyl)-1,2-benzoxazol-3-yl]-3-oxo-2,5,6,7-tetrahydro-3H-pyrrolo[1,2-c]imidazol-6-yl}ethanesulfonamide | 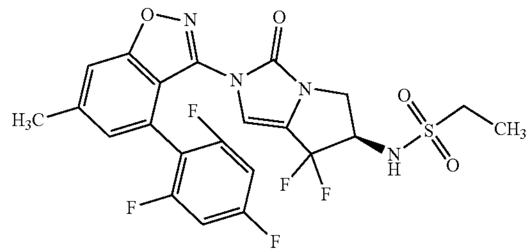 [SMILES: CCS(=O)(=O)N[C@@H]1Cn2c(cn(-c3noc4cc(C)cc(-c5c(F)cc(F)cc5F)c34)c2=O)C1(F)F] | 529.1 |
| 156 | N-{(6R)-2-[4-(2,6-difluorophenyl)-6-methyl-1,2-benzoxazol-3-yl]-7,7-difluoro-3-oxo-2,5,6,7-tetrahydro-3H-pyrrolo[1,2-c]imidazol-6-yl}ethanesulfonamide | 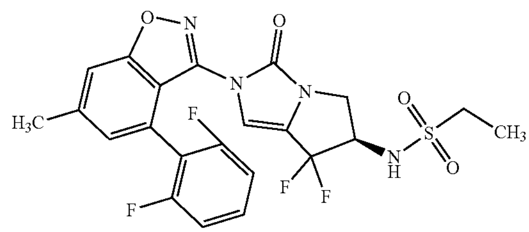 [SMILES: CCS(=O)(=O)N[C@@H]1Cn2c(cn(-c3noc4cc(C)cc(-c5c(F)cccc5F)c34)c2=O)C1(F)F] | 511.2 |
| 157 | N-{(6R)-7,7-difluoro-3-oxo-2-[6-(trifluoromethyl)-4-(2,4,6-trifluorophenyl)-1,2-benzoxazol-3-yl]-2,5,6,7-tetrahydro-3H-pyrrolo[1,2-c]imidazol-6-yl}ethanesulfonamide | 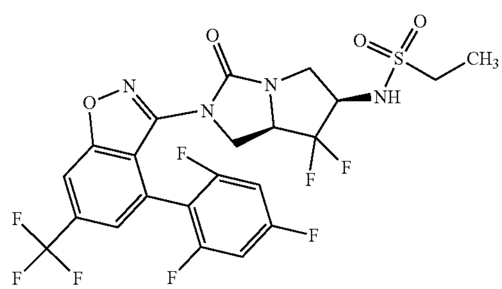 [SMILES: CCS(=O)(=O)N[C@@H]1CN2C(=O)N(c3noc4cc(C(F)(F)F)cc(-c5c(F)cc(F)cc5F)c34)C[C@@H]2C1(F)F] | 583.0 |
| 158 | N-{(6R*,7R*,7aS)-2-[4-(2,6-difluorophenyl)-1,2-benzoxazol-3-yl]-7-methyl-3-oxohexahydro-1H-pyrrolo[1,2-c]imidazol-6-yl}ethanesulfonamide | 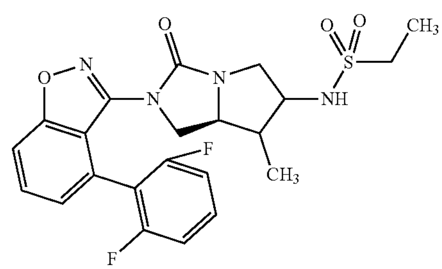 [SMILES: CCS(=O)(=O)NC1CN2C(=O)N(c3noc4cccc(-c5c(F)cccc5F)c34)C[C@@H]2C1C] | 477.3 |
| 159 | N-{(6R,7aR)-2-[4-(2,6-difluorophenyl)-6-(methoxymethyl)-1,2-benzoxazol-3-yl]-7,7-difluoro-3-oxohexahydro-1H-pyrrolo[1,2-c]imidazol-6-yl}methanesulfonamide | 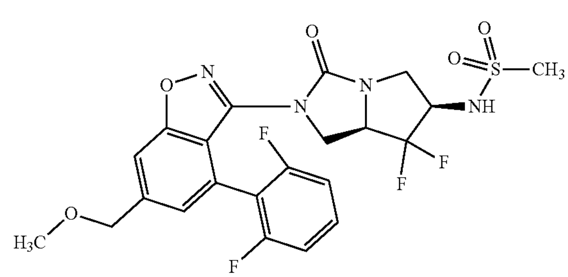 | 529.2 |

TABLE 1-1-continued

| Ex. No. | IUPAC Name | Structure | MS |
|---|---|---|---|
| 160 | N-{(6R,7aR)-2-[6-ethoxy-4-(2,4,6-trifluorophenyl)-1,2-benzoxazol-3-yl]-7,7-difluoro-3-oxohexahydro-1H-pyrrolo[1,2-c]imidazol-6-yl}methanesulfonamide | 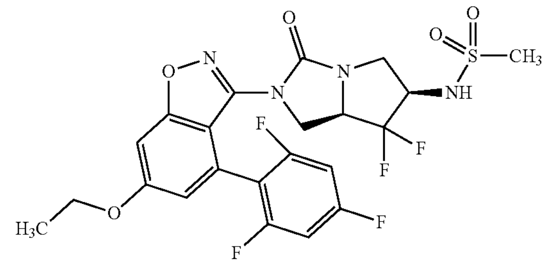 [SMILES: CCOc1cc(-c2c(F)cc(F)cc2F)c2c(N3C[C@H]4N(C[C@@H](NS(C)(=O)=O)C4(F)F)C3=O)noc2c1] | 547.1 547.1 |
| 161 | N-{(6R,7aR)-7,7-difluoro-2-[6-(methoxymethyl)-4-(2,4,6-trifluorophenyl)-1,2-benzoxazol-3-yl]-3-oxohexahydro-1H-pyrrolo[1,2-c]imidazol-6-yl}methanesulfonamide | 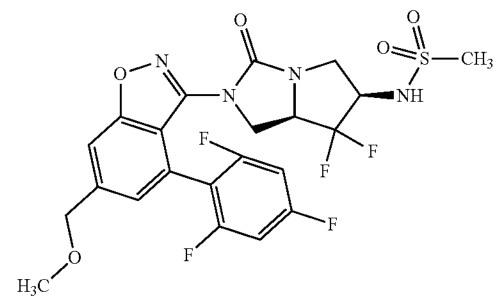 | 547.1 |
| 162 | N-{(6R,7aR)-7,7-difluoro-2-[5-fluoro-6-methyl-4-(2,4,6-trifluorophenyl)-1,2-benzoxazol-3-yl]-3-oxohexahydro-1H-pyrrolo[1,2-c]imidazol-6-yl}ethanesulfonamide | 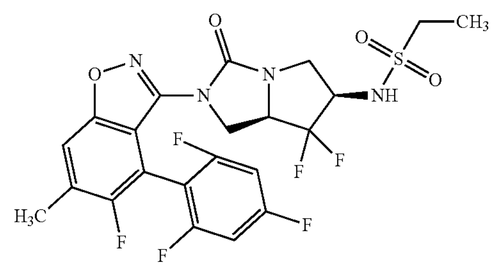 [SMILES: CCS(=O)(=O)N[C@@H]1CN2C(=O)N(c3noc4cc(C)c(F)c(-c5c(F)cc(F)cc5F)c34)C[C@@H]2C1(F)F] | 549.1 |
| 163 | N-{(6R)-7,7-difluoro-2-[5-fluoro-6-methyl-4-(2,4,6-trifluorophenyl)-1,2-benzoxazol-3-yl]-3-oxo-2,5,6,7-tetrahydro-3H-pyrrolo[1,2-c]imidazol-6-yl}ethanesulfonamide | 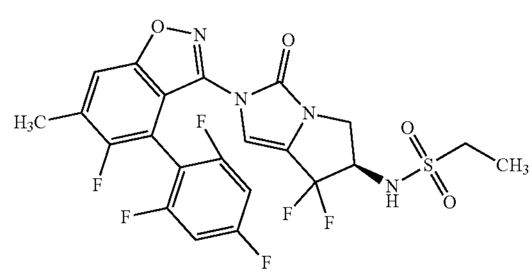 [SMILES: CCS(=O)(=O)N[C@@H]1Cn2c(cn(-c3noc4cc(C)c(F)c(-c5c(F)cc(F)cc5F)c34)c2=O)C1(F)F] | 547.1 |
| 164 | N-{(6R,7aR)-2-[4-(2,6-difluorophenyl)-6-methyl[1,2]oxazolo[5,4-b]pyridin-3-yl]-7,7-difluoro-3-oxohexahydro-1H-pyrrolo[1,2-c]imidazol-6-yl}methanesulfonamide | 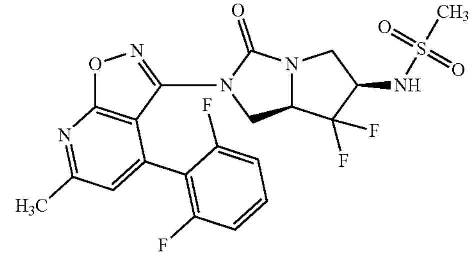 [SMILES: Cc1cc(-c2c(F)cccc2F)c2c(N3C[C@H]4N(C[C@@H](NS(C)(=O)=O)C4(F)F)C3=O)noc2n1] | 500.2 |

TABLE 1-1-continued

| Ex. No. | IUPAC Name | Structure | MS |
|---|---|---|---|
| 165 | N-{(6R)-2-[6-(difluoromethyl)-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}ethanesulfonamide | 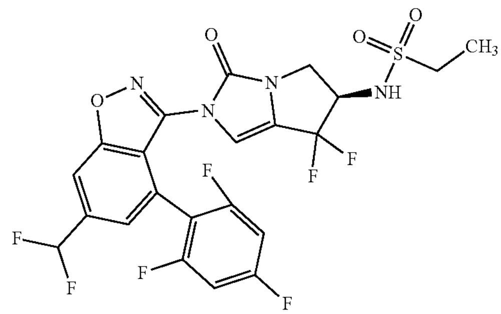 [SMILES: CCS(=O)(=O)N[C@@H]1Cn2c(cn(-c3noc4cc(C(F)F)cc(-c5c(F)cc(F)cc5F)c34)c2=O)C1(F)F] | 565.1 |
| 166 | N-{(6R)-7,7-difluoro-2-[6-(methoxymethyl)-4-(2,4,6-trifluorophenyl)-1,2-benzoxazol-3-yl]-3-oxo-2,5,6,7-tetrahydro-3H-pyrrolo[1,2-c]imidazol-6-yl}ethanesulfonamide | 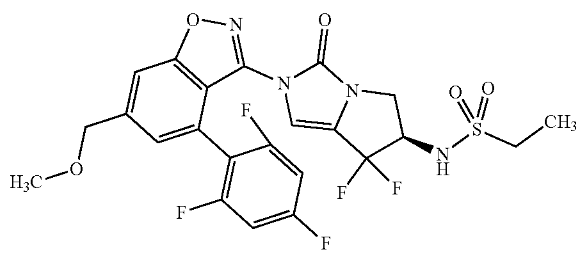 [SMILES: CCS(=O)(=O)N[C@@H]1Cn2c(cn(-c3noc4cc(COC)cc(-c5c(F)cc(F)cc5F)c34)c2=O)C1(F)F] | 559.1 559.1 |
| 167 | N-{(6R)-2-[4-(2,6-difluorophenyl)-6-(methoxymethyl)-1,2-benzoxazol-3-yl]-7,7-difluoro-3-oxo-2,5,6,7-tetrahydro-3H-pyrrolo[1,2-c]imidazol-6-yl}ethanesulfonamide | 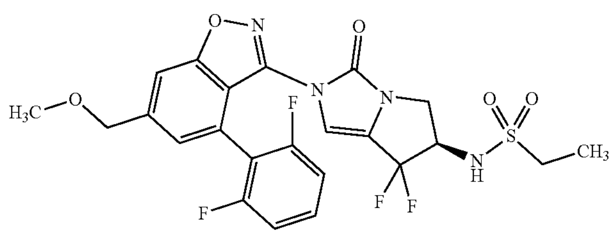 [SMILES: CCS(=O)(=O)N[C@@H]1Cn2c(cn(-c3noc4cc(COC)cc(-c5c(F)cccc5F)c34)c2=O)C1(F)F] | 541.2 |
| 168 | N-{(6R,7aR)-2-[4-(2,6-difluorophenyl)-5,6-difluoro-1,2-benzoxazol-3-yl]-7,7-difluoro-3-oxohexahydro-1H-pyrrolo[1,2-c]imidazol-6-yl}ethanesulfonamide | 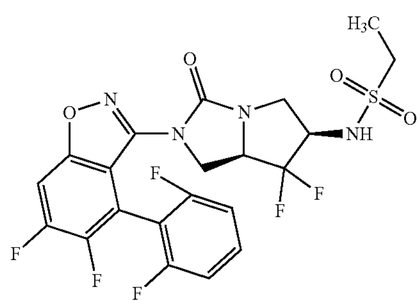 [SMILES: CCS(=O)(=O)N[C@@H]1CN2C(=O)N(c3noc4cc(F)c(F)c(-c5c(F)cccc5F)c34)C[C@@H]2C1(F)F] | 535.1 |
| 169 | N-{(6R)-2-[4-(2,6-difluorophenyl)-5-fluoro-6-methyl-1,2-benzoxazol-3-yl]-7,7-difluoro-3-oxo-2,5,6,7-tetrahydro-3H-pyrrolo[1,2-c]imidazol-6-yl}ethanesulfonamide | 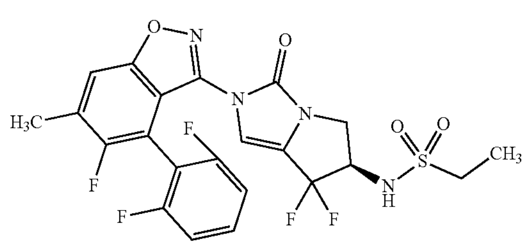 [SMILES: CCS(=O)(=O)N[C@@H]1Cn2c(cn(-c3noc4cc(C)c(F)c(-c5c(F)cccc5F)c34)c2=O)C1(F)F] | 529.1 |
| 170 | N-{(6R)-2-[4-(2,6-difluorophenyl)-5,6-difluoro-1,2-benzoxazol-3-yl]-7,7-difluoro-3-oxo-2,5,6,7-tetrahydro-3H-pyrrolo[1,2-c]imidazol-6-yl}ethanesulfonamide | 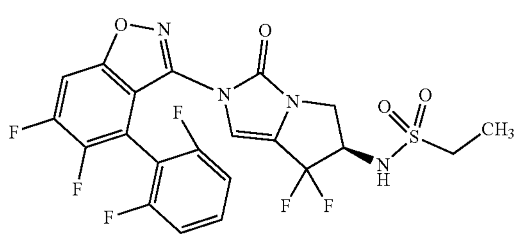 [SMILES: CCS(=O)(=O)N[C@@H]1Cn2c(cn(-c3noc4cc(F)c(F)c(-c5c(F)cccc5F)c34)c2=O)C1(F)F] | 533.1 |

TABLE 1-1-continued

| Ex. No. | IUPAC Name | Structure | MS |
|---|---|---|---|
| 171 | N-{(6R,7aR)-2-[5, 6-difluoro-4-(2,4,6-trifluorophenyl)-1,2-benzoxazol-3-yl]-7,7-difluoro-3-oxohexahydro-1H-pyrrolo[1,2-c]imidazol-6-yl}methanesulfonamide | 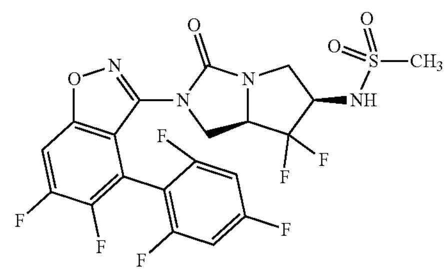 [SMILES: CS(=O)(=O)N[C@@H]1CN2C(=O)N(c3noc4cc(F)c(F)c(-c5c(F)cc(F)cc5F)c34)C[C@@H]2C1(F)F] | 539.1 |
| 172 | N-{(6R,7aR)-2-[5,6-difluoro-4-(2,4,6-trifluorophenyl)-1,2-benzoxazol-3-yl]-7,7-difluoro-3-oxohexahydro-1H-pyrrolo[1,2-c]imidazol-6-yl}ethanesulfonamide | 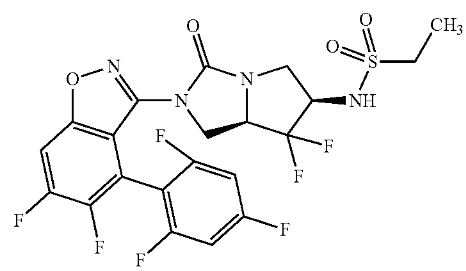 [SMILES: CCS(=O)(=O)N[C@@H]1CN2C(=O)N(c3noc4cc(F)c(F)c(-c5c(F)cc(F)cc5F)c34)C[C@@H]2C1(F)F] | 553.1 |
| 173 | N-{(6R)-2-[6-ethoxy-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}ethanesulfonamide | 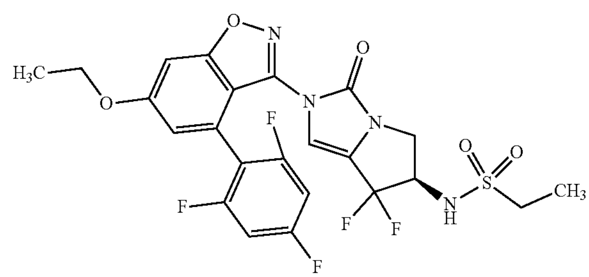 [SMILES: CCOc1cc(-c2c(F)cc(F)cc2F)c2c(-n3cc4n(c3=O)C[C@@H](NS(=O)(=O)CC)C4(F)F)noc2c1] | 559.1 |
| 174 | N-{(6R)-7,7-difluoro-2-[6-methyl-4-(2,4,6-trifluorophenyl)[1,2]oxazolo[5,4-b]pyridin-3-yl]-3-oxo-2,5,6,7-tetrahydro-3H-pyrrolo[1,2-c]imidazol-6-yl}methanesulfonamide | 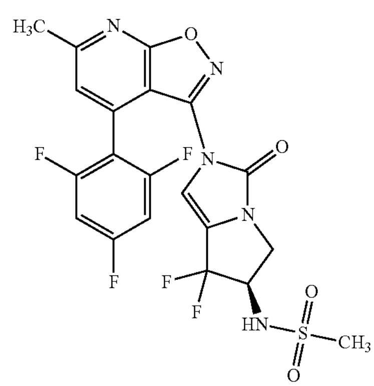 | 516.1 |
| 175 | N-{(6R,7aR)-7,7-difluoro-2-[6-methyl-4-(2,4,6-trifluorophenyl)[1,2]oxazolo[5,4-b]pyridin-3-yl]-3-oxohexahydro-1H-pyrrolo[1,2-c]imidazol-6-yl}ethanesulfonamide | 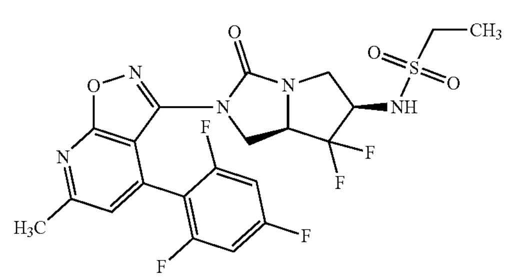 [SMILES: CCS(=O)(=O)N[C@@H]1CN2C(=O)N(c3noc4nc(C)cc(-c5c(F)cc(F)cc5F)c34)C[C@@H]2C1(F)F] | 532.1 |

TABLE 1-1-continued

| Ex. No. | IUPAC Name | Structure | MS |
|---|---|---|---|
| 176 | N-{(6R)-7,7-difluoro-3-oxo-2-[6-(trifluoromethoxy)-4-(2,4,6-trifluorophenyl)-1,2-benzoxazol-3-yl]-2,5,6,7-tetrahydro-3H-pyrrolo[1,2-c]imidazol-6-yl}methanesulfonamide | 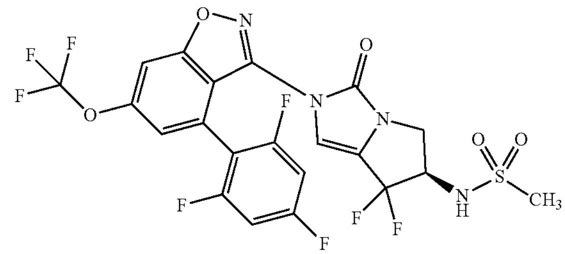 [SMILES: CS(=O)(=O)N[C@@H]1Cn2c(cn(-c3noc4cc(OC(F)(F)F)cc(-c5c(F)cc(F)cc5F)c34)c2=O)C1(F)F] | 585.2 |
| 177 | N-{(6R,7aR)-7,7-difluoro-3-oxo-2-[6-(trifluoromethoxy)-4-(2,4,6-trifluorophenyl)-1,2-benzoxazol-3-yl]hexahydro-1H-pyrrolo[1,2-c]imidazol-6-yl}ethanesulfonamide | 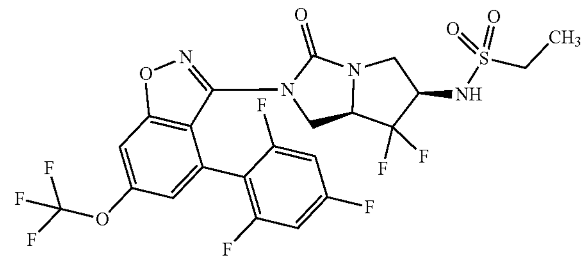 [SMILES: CCS(=O)(=O)N[C@@H]1CN2C(=O)N(c3noc4cc(OC(F)(F)F)cc(-c5c(F)cc(F)cc5F)c34)C[C@@H]2C1(F)F] | 601.1 |
| 178 | N-{(6R)-7,7-difluoro-3-oxo-2-[6-(trifluoromethoxy)-4-(2,4,6-trifluorophenyl)-1,2-benzoxazol-3-yl]-2,5,6,7-tetrahydro-3H-pyrrolo[1,2-c]imidazol-6-yl}ethanesulfonamide | 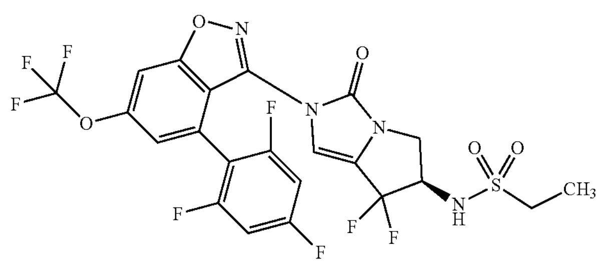 [SMILES: CCS(=O)(=O)N[C@@H]1Cn2c(cn(-c3noc4cc(OC(F)(F)F)cc(-c5c(F)cc(F)cc5F)c34)c2=O)C1(F)F] | 599.0 |
| 179 | N-{(6R)-2-[6-(difluoromethoxy)-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}ethanesulfonamide | 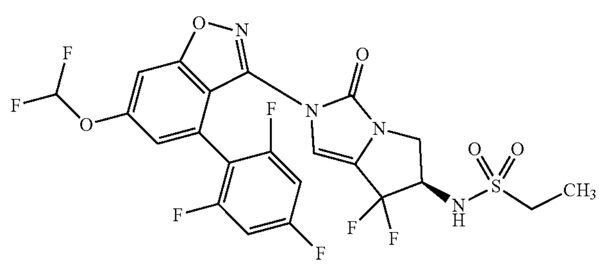 [SMILES: CCS(=O)(=O)N[C@@H]1Cn2c(cn(-c3noc4cc(OC(F)F)cc(-c5c(F)cc(F)cc5F)c34)c2=O)C1(F)F] | 581.1 |
| 180 | N-{(6R)-2-[4-(2,6-difluorophenyl)-6-methyl-1,2-benzoxazol-3-yl]-7,7-difluoro-3-oxo-2,5,6,7-tetrahydro-3H-pyrrolo[1,2-c]imidazol-6-yl}methanesulfonamide | 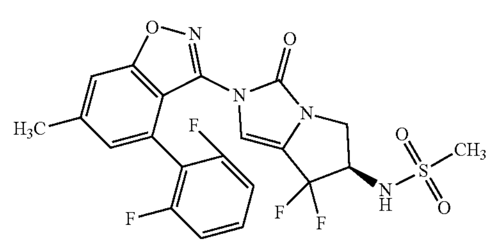 | 497.2 |

TABLE 1-1-continued

| Ex. No. | IUPAC Name | Structure | MS |
|---|---|---|---|
| 181 | N-{(6R*)-2-[4-(2,6-difluorophenyl)-1,2-benzoxazol-3-yl]-7,7-difluoro-3-oxo-2,3,5,6,7,8-hexahydroimidazo[1,5-a]pyridin-6-yl}ethanesulfonamide | 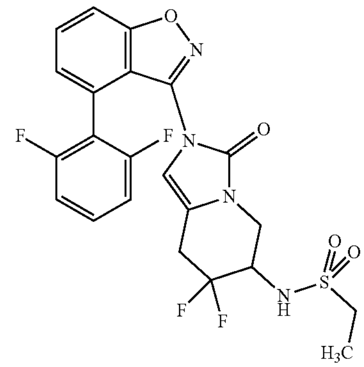 [SMILES: CCS(=O)(=O)NC1Cn2c(cn(-c3noc4cccc(-c5c(F)cccc5F)c34)c2=O)CC1(F)F] | 511.2 |
| 182 | N-{(6S,7aS)-2-[5-(2,6-difluorophenyl)imidazo[1,2-a]pyridin-3-yl]-3-oxohexahydro-1H-pyrrolo[1,2-c]imidazol-6-yl}ethanesulfonamide | 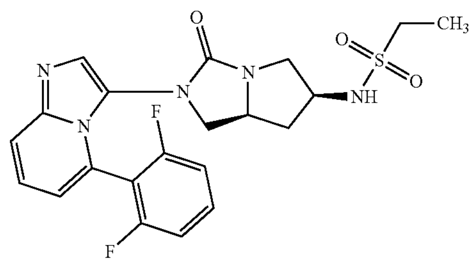 [SMILES: CCS(=O)(=O)N[C@H]1C[C@H]2CN(c3cnc4cccc(-c5c(F)cccc5F)n34)C(=O)N2C1] | 462.2 |
| 183 | N-{(6R*,7S*,7aS)-2-[4-(2,6-difluorophenyl)-1,2-benzoxazol-3-yl]-7-methyl-3-oxohexahydro-1H-pyrrolo[1,2-c]imidazol-6-yl}ethanesulfonamide | 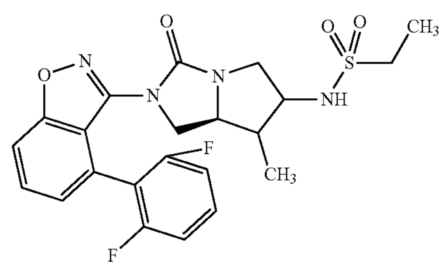 [SMILES: CCS(=O)(=O)NC1CN2C(=O)N(c3noc4cccc(-c5c(F)cccc5F)c34)C[C@@H]2C1C] | 477.2 |
| 184 | N-{(6R)-7,7-difluoro-2-[5-fluoro-6-methyl-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide | 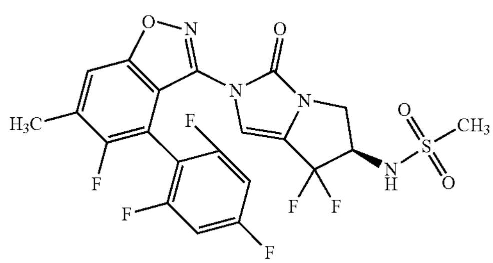 | 533.1 |
| 185 | N-{(6R)-7,7-difluoro-2-[5-fluoro-6-(hydroxymethyl)-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide | 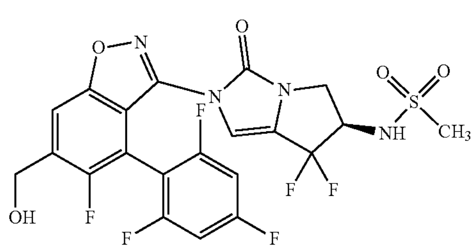 [SMILES: CS(=O)(=O)N[C@@H]1Cn2c(cn(-c3noc4cc(CO)c(F)c(-c5c(F)cc(F)cc5F)c34)c2=O)C1(F)F] | 549.1 |

TABLE 1-1-continued

| Ex. No. | IUPAC Name | MS |
|---|---|---|
| 186 | N-{(6R,7aR)-2-[4-(2,6-difluorophenyl)-5-fluoro-6-methyl-1,2-benzoxazol-3-yl]-7,7-difluoro-3-oxohexahydro-1H-pyrrolo[1,2-c]imidazol-6-yl}methanesulfonamide | 517.2 |
| 187 | N-{(6R,7aR)-2-[4-(2,6-difluorophenyl)-6-(methoxymethyl)-1,2-benzoxazol-3-yl]-7,7-difluoro-3-oxohexahydro-1H-pyrrolo[1,2-c]imidazol-6-yl}ethanesulfonamide | 543.1 |
| 188 | N-[(6R)-7,7-difluoro-2-{6-[(1RS)-1-hydroxyethyl]-4-(2,4,6-trifluorophenyl)-1,2-benzoxazol-3-yl}-3-oxo-2,5,6,7-tetrahydro-3H-pyrrolo[1,2-c]imidazol-6-yl]ethanesulfonamide | 559.2 |
| 189 | N-{(6R)-2-[6-ethoxy-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}methanesulfonamide | 545.1 |
| 190 | N-{(6R)-7,7-difluoro-2-[6-methyl-4-(2,4,6-trifluorophenyl)[1,2]oxazolo[5,4-b]pyridin-3-yl]-3-oxo-2,5,6,7-tetrahydro-3H-pyrrolo[1,2-c]imidazol-6-yl}ethanesulfonamide | 530.2 |

TABLE 1-1-continued

| Ex. No. | IUPAC Name | Structure | MS |
|---|---|---|---|
| 191 | N-{(6R,7aR)-7,7-difluoro-2-[6-methyl-4-(2,4,6-trifluorophenyl)[1,2]oxazolo[4,5-c]pyridin-3-yl]-3-oxohexahydro-1H-pyrrolo[1,2-c]imidazol-6-yl}methanesulfonamide | 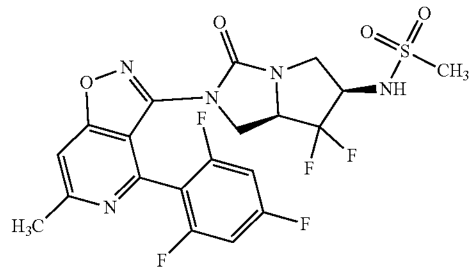 | 518.2 |
| 192 | N-{(6R,7aR)-2-[6-ethoxy-4-(2,4,6-trifluorophenyl)-1,2-benzoxazol-3-yl]-7,7-difluoro-3-oxohexahydro-1H-pyrrolo[1,2-c]imidazol-6-yl}ethanesulfonamide | 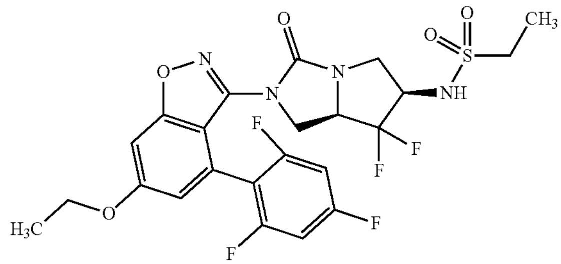 [SMILES: CCOc1cc(-c2c(F)cc(F)cc2F)c2c(N3C[C@H]4N(C[C@@H](NS(=O)(=O)CC)C4(F)F)C3=O)noc2c1] | 561.1 |
| 193 | N-{(6R,7aR)-2-[6-(difluoromethoxy)-4-(2,4,6-trifluorophenyl)-1,2-benzoxazol-3-yl]-7,7-difluoro-3-oxohexahydro-1H-pyrrolo[1,2-c]imidazol-6-yl}methanesulfonamide | 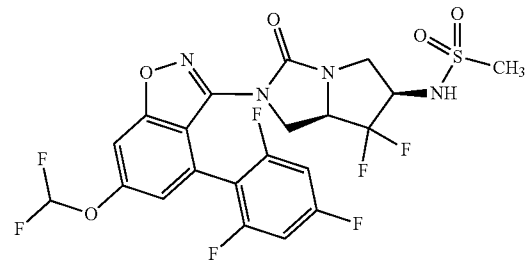 [SMILES: CS(=O)(=O)N[C@@H]1CN2C(=O)N(c3noc4cc(OC(F)F)cc(-c5c(F)cc(F)cc5F)c34)C[C@@H]2C1(F)F] | 569.2 |
| 194 | N-{(6R)-2-[4-(2,6-difluorophenyl)-6-ethoxy-1,2-benzoxazol-3-yl]-7,7-difluoro-3-oxo-2,5,6,7-tetrahydro-3H-pyrrolo[1,2-c]imidazol-6-yl}methanesulfonamide | 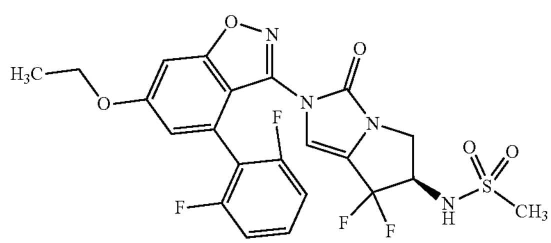 [SMILES: CCOc1cc(-c2c(F)cccc2F)c2c(-n3cc4n(c3=O)C[C@@H](NS(C)(=O)=O)C4(F)F)noc2c1] | 527.2 |
| 195 | N-{(4aR,6S)-1-oxo-2-[4-(2,4,6-trifluorophenyl)-1,2-benzoxazol-3-yl]octahydropyrrolo[1,2-c]pyrimidin-6-yl}ethanesulfonamide | 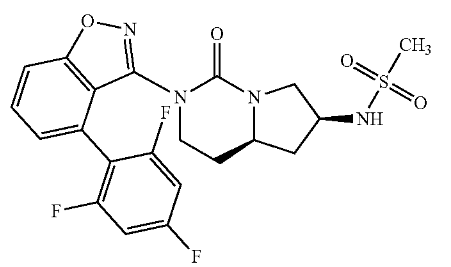 [SMILES: CS(=O)(=O)N[C@H]1C[C@H]2CCN(c3noc4cccc(-c5c(F)cc(F)cc5F)c34)C(=O)N2C1] | 480.8 |
| 196 | N-{(6R)-2-[4-(2,6-difluorophenyl)-6-methyl[1,2]oxazolo[4,5-c]pyridin-3-yl]-7,7-difluoro-3-oxo-2,5,6,7-tetrahydro-3H-pyrrolo[1,2-c]imidazol-6-yl}methanesulfonamide | 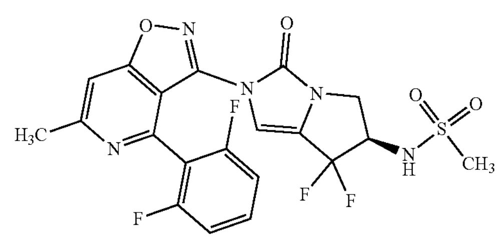 [SMILES: Cc1cc2onc(-n3cc4n(c3=O)C[C@@H](NS(C)(=O)=O)C4(F)F)c2c(-c2c(F)cccc2F)n1] | 498.0 |

TABLE 1-1-continued

| Ex. No. | IUPAC Name | Structure | MS |
|---|---|---|---|
| 197 | N-{(6R)-2-[6-cyclopropyl-4-(2,6-difluorophenyl)[1,2]oxazolo[5,4-b]pyridin-3-yl]-7,7-difluoro-3-oxo-2,5,6,7-tetrahydro-3H-pyrrolo[1,2-c]imidazol-6-yl}methanesulfonamide | 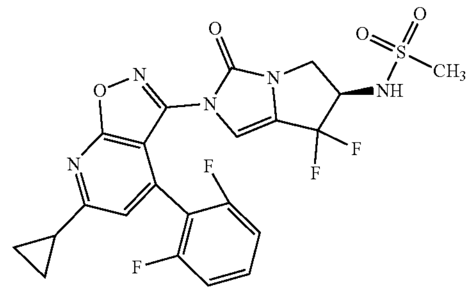 [SMILES: CS(=O)(=O)N[C@@H]1Cn2c(cn(-c3noc4nc(C5CC5)cc(-c5c(F)cccc5F)c34)c2=O)C1(F)F] | 524.2 |
| 198 | N-{(6R)-7,7-difluoro-2-[6-methyl-4-(2,4,6-trifluorophenyl)[1,2]oxazolo[4,5-c]pyridin-3-yl]-3-oxo-2,5,6,7-tetrahydro-3H-pyrrolo[1,2-c]imidazol-6-yl}ethanesulfonamide | 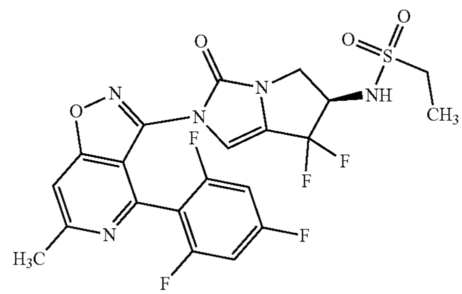 [SMILES: CCS(=O)(=O)N[C@@H]1Cn2c(cn(-c3noc4cc(C)nc(-c5c(F)cc(F)cc5F)c34)c2=O)C1(F)F] | 530.1 |
| 199 | N-{(4aR,6R)-2-[4-(2,6-difluorophenyl)-6-ethoxy-1,2-benzoxazol-3-yl]-5,5-difluoro-1-oxooctahydropyrrolo[1,2-c]pyrimidin-6-yl}methanesulfonamide | 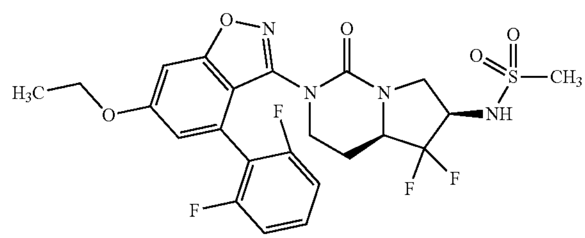 [SMILES: CCOc1cc(-c2c(F)cccc2F)c2c(N3CC[C@H]4N(C[C@@H](NS(C)(=O)=O)C4(F)F)C3=O)noc2c1] | 542.9 |
| 200 | N-{(4aR,6R)-2-[6-(difluoromethyl)-4-(2,4,6-trifluorophenyl)-1,2-benzoxazol-3-yl]-5,5-difluoro-1-oxooctahydropyrrolo[1,2-c]pyrimidin-6-yl}methanesulfonamide | 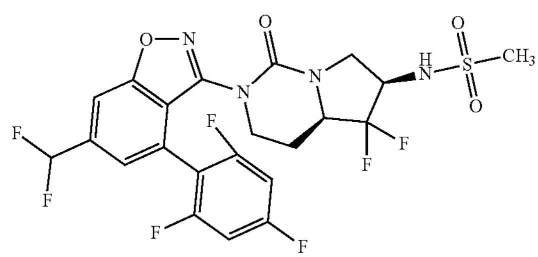 [SMILES: CS(=O)(=O)N[C@@H]1CN2C(=O)N(c3noc4cc(C(F)F)cc(-c5c(F)cc(F)cc5F)c34)CC[C@@H]2C1(F)F] | 566.9 |
| 201 | N-{(6R)-7,7-difluoro-2-[6-methyl-4-(2,4,6-trifluorophenyl)[1,2]oxazolo[4,5-c]pyridin-3-yl]-3-oxo-2,5,6,7-tetrahydro-3H-pyrrolo[1,2-c]imidazol-6-yl}-1-fluoromethanesulfonamide | 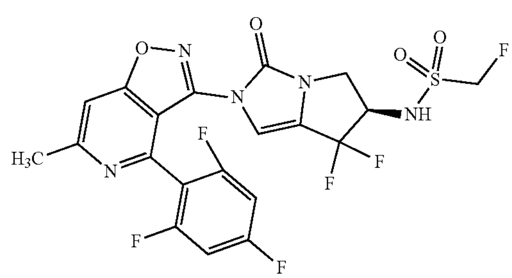 [SMILES: Cc1cc2onc(-n3cc4n(c3=O)C[C@@H](NS(=O)(=O)CF)C4(F)F)c2c(-c2c(F)cc(F)cc2F)n1] | 533.8 |

TABLE 1-1-continued

| Ex. No. | IUPAC Name | Structure | MS |
|---|---|---|---|
| 202 | N-{(4aR,6R)-2-[6-ethoxy-5-fluoro-4-(2,4,6-trifluorophenyl)-1,2-benzoxazol-3-yl]-5,5-difluoro-1-oxooctahydropyrrolo[1,2-c]pyrimidin-6-yl}methanesulfonamide | 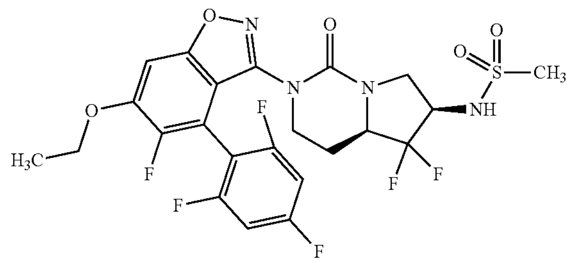 [SMILES: CCOc1cc2onc(N3CC[C@H]4N(C[C@@H](NS(C)(=O)=O)C4(F)F)C3=O)c2c(-c2c(F)cc(F)cc2F)c1F] | 578.9 |
| 203 | N-{(4aR,6R)-5,5-difluoro-1-oxo-2-[4-(2,4,6-trifluorophenyl)-1,2-benzoxazol-3-yl]octahydropyrrolo[1,2-c]pyrimidin-6-yl}-1-fluoromethanesulfonamide | 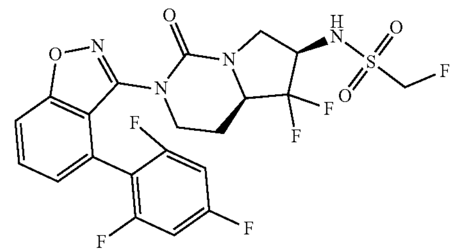 [SMILES: O=C1N(c2noc3cccc(-c4c(F)cc(F)cc4F)c23)CC[C@H]2N1C[C@@H](NS(=O)(=O)CF)C2(F)F] | 534.9 |
| 204 | N-{(4aR,6R)-5,5-difluoro-2-[5-fluoro-4-(2,4,6-trifluorophenyl)-1,2-benzoxazol-3-yl]-1-oxooctahydropyrrolo[1,2-c]pyrimidin-6-yl}ethanesulfonamide | 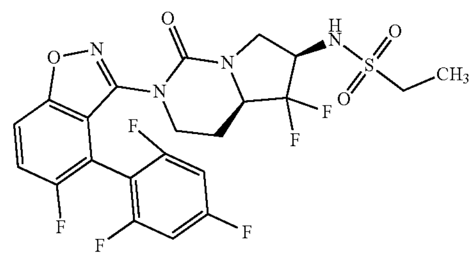 [SMILES: CCS(=O)(=O)N[C@@H]1CN2C(=O)N(c3noc4ccc(F)c(-c5c(F)cc(F)cc5F)c34)CC[C@@H]2C1(F)F] | 548.9 |
| 205 | N-{(4aR,6S)-1-oxo-2-[4-(2,4,6-trifluorophenyl)-1,2-benzoxazol-3-yl]octahydropyrrolo[1,2-c]pyrimidin-6-yl}ethanesulfonamide | 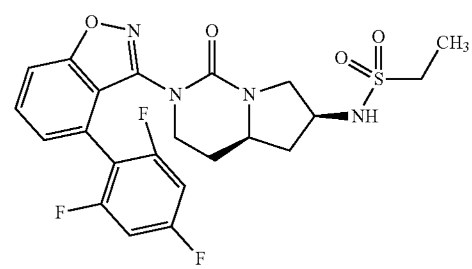 [SMILES: CCS(=O)(=O)N[C@H]1C[C@H]2CCN(c3noc4cccc(-c5c(F)cc(F)cc5F)c34)C(=O)N2C1] | 495.0 |
| 206 | N-{(4aR,6R)-2-[4-(2,6-difluorophenyl)-1,2-benzoxazol-3-yl]-5,5-difluoro-1-oxooctahydropyrrolo[1,2-c]pyrimidin-6-yl}methanesulfonamide | 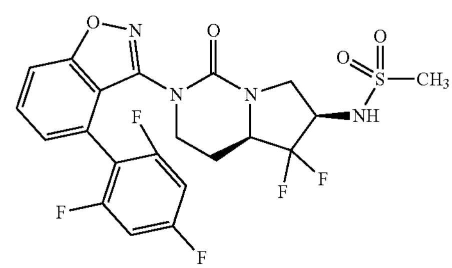 [SMILES: CS(=O)(=O)N[C@@H]1CN2C(=O)N(c3noc4cccc(-c5c(F)cc(F)cc5F)c34)CC[C@@H]2C1(F)F] | 498.9 |
| 207 | N-{(4aR,6R)-5,5-difluoro-2-[5-fluoro-4-(2,4,6-trifluorophenyl)-1,2-benzoxazol-3-yl]-1-oxooctahydropyrrolo[1,2-c]pyrimidin-6-yl}-1-fluoromethanesulfonamide | 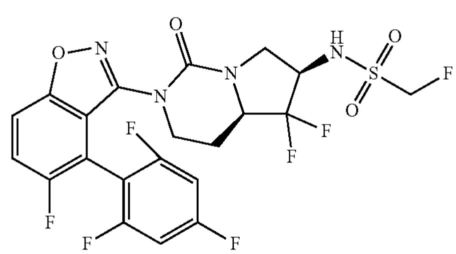 [SMILES: O=C1N(c2noc3ccc(F)c(-c4c(F)cc(F)cc4F)c23)CC[C@H]2N1C[C@@H](NS(=O)(=O)CF)C2(F)F] | 552.9 |

TABLE 1-1-continued

| Ex. No. | IUPAC Name | Structure | MS |
|---|---|---|---|
| 208 | N-{(4aR,6R)-5,5-difluoro-2-[6-fluoro-4-(2,4,6-trifluorophenyl)-1,2-benzoxazol-3-yl]-1-oxooctahydropyrrolo[1,2-c]pyrimidin-6-yl}methanesulfonamide | 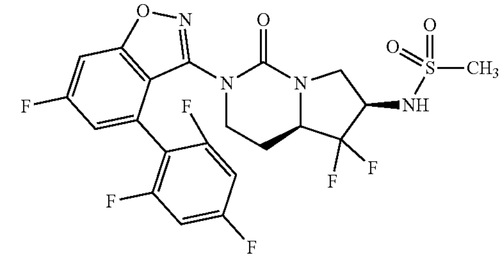 [SMILES: CS(=O)(=O)N[C@@H]1CN2C(=O)N(c3noc4cc(F)cc(-c5c(F)cc(F)cc5F)c34)CC[C@@H]2C1(F)F] | 535.1 |
| 209 | N-{(4aR,6R)-2-[4-(2,6-difluorophenyl)-6-methyl-1,2-benzoxazol-3-yl]-5,5-difluoro-1-oxooctahydropyrrolo[1,2-c]pyrimidin-6-yl}methanesulfonamide | 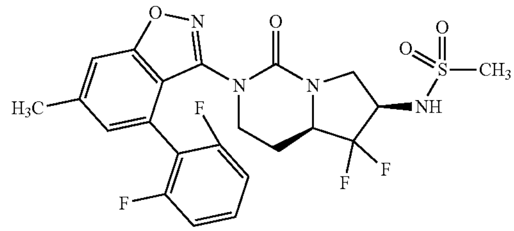 | 513.2 |
| 210 | N-{(4aR,6R)-5,5-difluoro-2-[6-(methoxymethyl)-4-(2,4,6-trifluorophenyl)-1,2-benzoxazol-3-yl]-1-oxooctahydropyrrolo[1,2-c]pyrimidin-6-yl}methanesulfonamide | 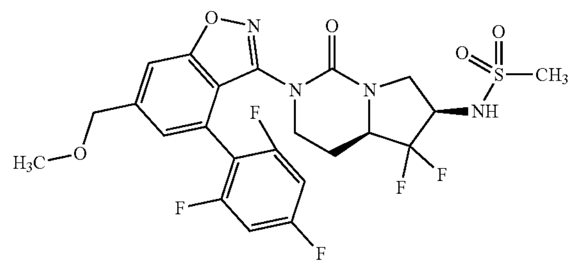 | 561.2 |
| 211 | N-{(6R)-2-[6-cyclopropyl-4-(2,6-difluorophenyl)[1,2]oxazolo[5,4-b]pyridin-3-yl]-7,7-difluoro-3-oxo-2,5,6,7-tetrahydro-3H-pyrrolo[1,2-c]imidazol-6-yl}ethanesulfonamide | 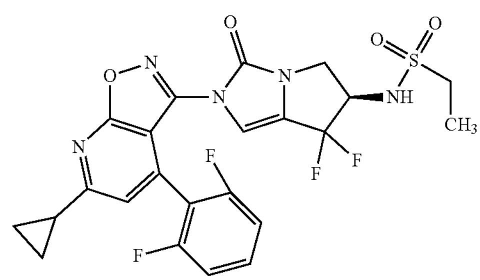 [SMILES: CCS(=O)(=O)N[C@@H]1Cn2c(cn(-c3noc4nc(C5CC5)cc(-c5c(F)cccc5F)c34)c2=O)C1(F)F] | 538.2 |
| 212 | N-{(6R)-2-[4-(2,6-difluorophenyl)-5-fluoro-6-(methoxymethyl)-1,2-benzoxazol-3-yl]-7,7-difluoro-3-oxo-2,5,6,7-tetrahydro-3H-pyrrolo[1,2-c]imidazol-6-yl}ethanesulfonamide | 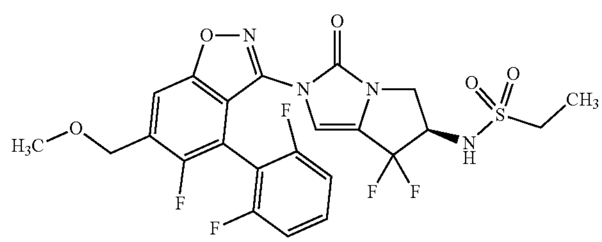 [SMILES: CCS(=O)(=O)N[C@@H]1Cn2c(cn(-c3noc4cc(COC)c(F)c(-c5c(F)cccc5F)c34)c2=O)C1(F)F] | 559.1 |
| 213 | N-{(4aR,6R)-5,5-difluoro-1-oxo-2-[4-(2,4,6-trifluorophenyl)-1,2-benzoxazol-3-yl]octahydropyrrolo[1,2-c]pyrimidin-6-yl}methanesulfonamide | 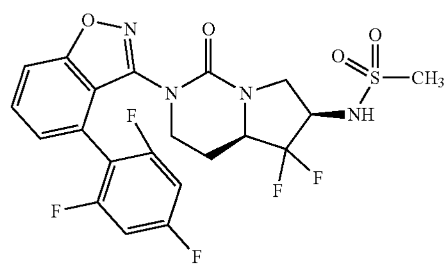 | 517.2 |

TABLE 1-1-continued

| Ex. No. | IUPAC Name | Structure | MS |
|---|---|---|---|
| 214 | N-{(6R*)-7,7-difluoro-2-[6-fluoro-4-(2,4,6-trifluorophenyl)-1,2-benzoxazol-3-yl]-3-oxo-2,3,5,6,7,8-hexahydroimidazo[1,5-a]pyridin-6-yl}methanesulfonamide | 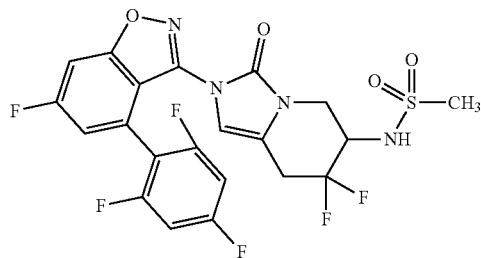 [SMILES: CS(=O)(=O)NC1Cn2c(cn(-c3noc4cc(F)cc(-c5c(F)cc(F)cc5F)c34)c2=O)CC1(F)F] | 533.1 |
| 215 | N-{(4aR,6R)-2-[4-(2,6-difluorophenyl)-6-(methoxymethyl)-1,2-benzoxazol-3-yl]-5,5-difluoro-1-oxooctahydropyrrolo[1,2-c]pyrimidin-6-yl}methanesulfonamide | 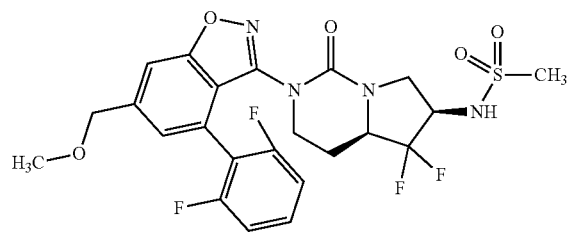 | 543.1 |
| 216 | rel-N-{(6R,8aR)-2-[4-(2,6-difluorophenyl)-1,2-benzoxazol-3-yl]-7,7-difluoro-3-oxooctahydroimidazo[1,5-a]pyridin-6-yl}methanesulfonamide | 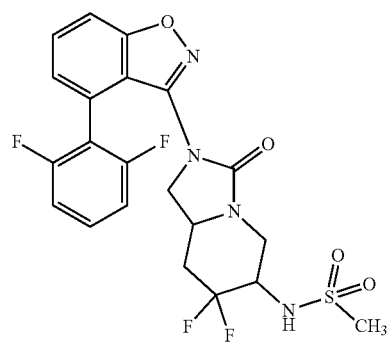 [SMILES: CS(=O)(=O)NC1CN2C(=O)N(c3noc4cccc(-c5c(F)cccc5F)c34)CC2CC1(F)F] | 499.0 |
| 217 | N-{(4aR,6R)-2-[6-ethoxy-4-(2,4,6-trifluorophenyl)-1,2-benzoxazol-3-yl]-5,5-difluoro-1-oxooctahydropyrrolo[1,2-c]pyrimidin-6-yl}methanesulfonamide | 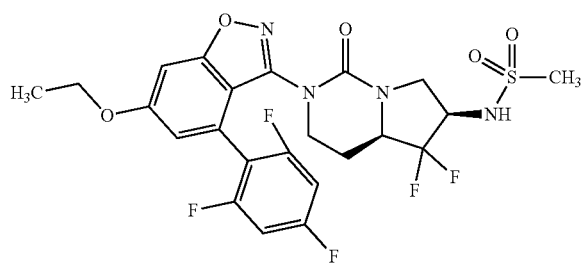 [SMILES: CCOc1cc(-c2c(F)cc(F)cc2F)c2c(N3CC[C@H]4N(C[C@@H](NS(C)(=O)=O)C4(F)F)C3=O)noc2c1] | 560.8 |
| 218 | N'-{(6R)-7,7-difluoro-2-[6-methyl-4-(2,4,6-trifluorophenyl)[1,2]oxazolo[4,5-c]pyridin-3-yl]-3-oxo-2,5,6,7-tetrahydro-3H-pyrrolo[1,2-c]imidazol-6-yl}-N,N-dimethylsulfuric diamide | 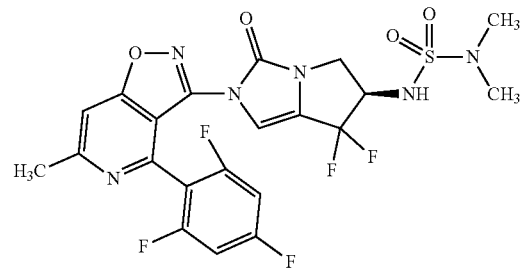 | 544.8 |

TABLE 1-1-continued

| Ex. No. | IUPAC Name | Structure | MS |
|---|---|---|---|
| 219 | N-{(6R)-7,7-difluoro-2-[6-methyl-4-(2,4,6-trifluorophenyl)[1,2]oxazolo[4,5-c]pyridin-3-yl]-3-oxo-2,5,6,7-tetrahydro-3H-pyrrolo[1,2-c]imidazol-6-yl}cyclopropanesulfonamide | 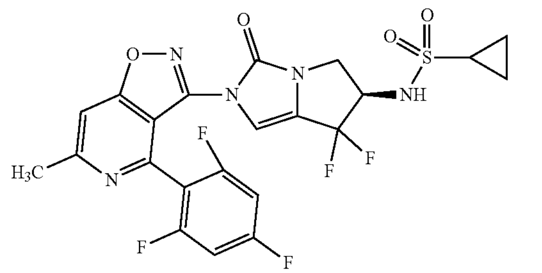 [SMILES: Cc1cc2onc(-n3cc4n(c3=O)C[C@@H](NS(=O)(=O)C3CC3)C4(F)F)c2c(-c2c(F)cc(F)cc2F)n1] | 541.9 |
| 220 | N-{(4aR,6R)-5,5-difluoro-2-[6-methyl-4-(2,4,6-trifluorophenyl)[1,2]oxazolo[4,5-c]pyridin-3-yl]-1-oxooctahydropyrrolo[1,2-c]pyrimidin-6-yl}ethanesulfonamide | 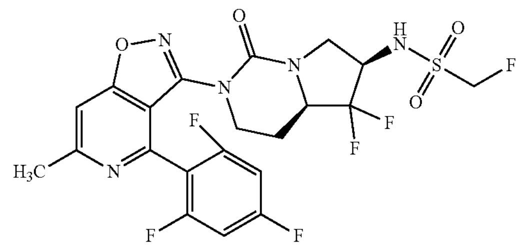 [SMILES: Cc1cc2onc(N3CC[C@H]4N(C[C@@H](NS(=O)(=O)CF)C4(F)F)C3=O)c2c(-c2c(F)cc(F)cc2F)n1] | 546.0 |
| 221 | N-{(4aR,6R)-2-[4-(2,6-difluorophenyl)-5-fluoro-6-(methoxymethyl)-1,2-benzoxazol-3-yl]-5,5-difluoro-1-oxooctahydropyrrolo[1,2-c]pyrimidin-6-yl}ethanesulfonamide | 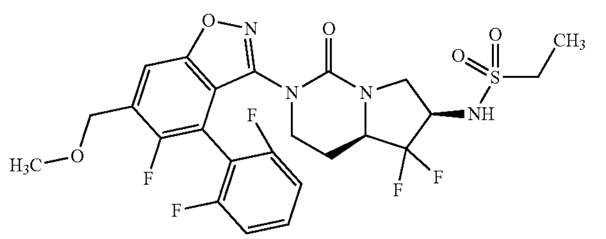 [SMILES: CCS(=O)(=O)N[C@@H]1CN2C(=O)N(c3noc4cc(COC)c(F)c(-c5c(F)cccc5F)c34)CC[C@@H]2C1(F)F] | 574.9 |
| 222 | N-{(4aR,6R)-5,5-difluoro-2-[6-(methoxymethyl)-4-(2,4,6-trifluorophenyl)-1,2-benzoxazol-3-yl]-1-oxooctahydropyrrolo[1,2-c]pyrimidin-6-yl}cyclopropanesulfonamide | 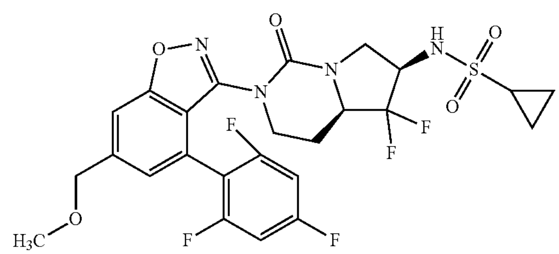 [SMILES: COCc1cc(-c2c(F)cc(F)cc2F)c2c(N3CC[C@H]4N(C[C@@H](NS(=O)(=O)C5CC5)C4(F)F)C3=O)noc2c1] | 587.0 |
| 223 | N-[(4aR,6R)-5,5-difluoro-1-oxo-2-(4-phenyl-1,2-benzoxazol-3-yl)octahydropyrrolo[1,2-c]pyrimidin-6-yl]methanesulfonamide | 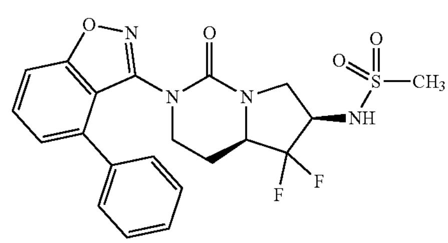 [SMILES: CS(=O)(=O)N[C@@H]1CN2C(=O)N(c3noc4cccc(-c5ccccc5)c34)CC[C@@H]2C1(F)F] | 462.9 |
| 224 | N-{(4aR,6R)-2-[6-bromo-4-(2,6-difluorophenyl)-1,2-benzoxazol-3-yl]-5,5-difluoro-1-oxooctahydropyrrolo[1,2-c]pyrimidin-6-yl}methanesulfonamide | 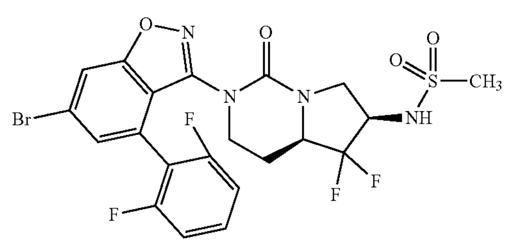 [SMILES: CS(=O)(=O)N[C@@H]1CN2C(=O)N(c3noc4cc(Br)cc(-c5c(F)cccc5F)c34)CC[C@@H]2C1(F)F] | 576.7 |

TABLE 1-1-continued

| Ex. No. | IUPAC Name | Structure | MS |
|---|---|---|---|
| 225 | N-{(4aR,6R)-5,5-difluoro-1-oxo-2-[6-(trifluoromethyl)-4-(2,4,6-trifluorophenyl)-1,2-benzoxazol-3-yl]octahydropyrrolo[1,2-c]pyrimidin-6-yl}methanesulfonamide | 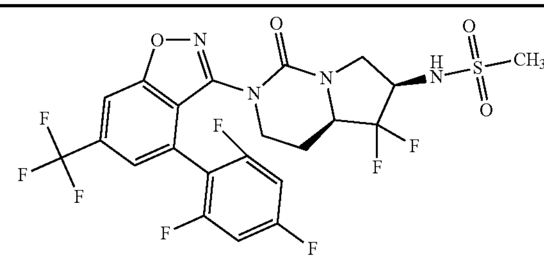 | 584.8 |
| 226 | N-{(6R)-2-[4-(2,6-difluorophenyl)-5-fluoro-6-(methoxymethyl)-1,2-benzoxazol-3-yl]-7,7-difluoro-3-oxo-2,5,6,7-tetrahydro-3H-pyrrolo[1,2-c]imidazol-6-yl}methanesulfonamide | 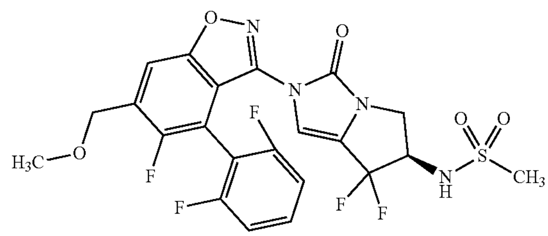 | 545.1 |
| 227 | N-{(4aR,6R)-5,5-difluoro-2-[5-fluoro-6-(methoxymethyl)-4-(2,4,6-trifluorophenyl)-1,2-benzoxazol-3-yl]-1-oxooctahydropyrrolo[1,2-c]pyrimidin-6-yl}methanesulfonamide | 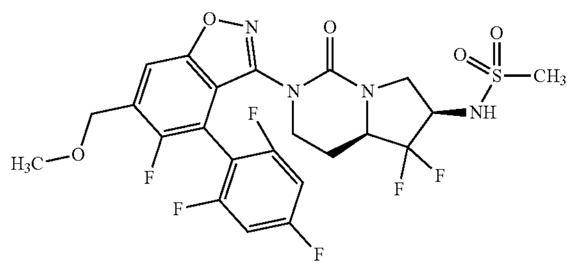 | 579.1 |
| 228 | N-{(4aR,6R)-2-[4-(2,6-difluorophenyl)-6-ethoxy-5-fluoro-1,2-benzoxazol-3-yl]-5,5-difluoro-1-oxooctahydropyrrolo[1,2-c]pyrimidin-6-yl}methanesulfonamide | 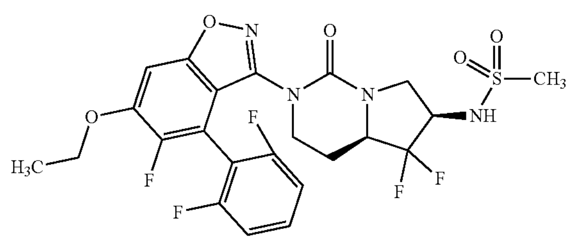 | 561.2 |
| 229 | N-{(6R)-7,7-difluoro-2-[6-methyl-4-(2,4,6-trifluorophenyl)[1,2]oxazolo[4,5-c]pyridin-3-yl]-3-oxo-2,5,6,7-tetrahydro-3H-pyrrolo[1,2-c]imidazol-6-yl}methanesulfonamide | 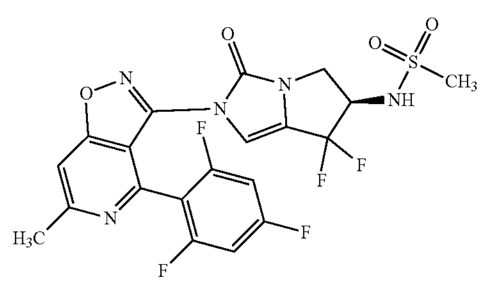 | 516.2 |
| 230 | N-{(6R)-2-[6-ethyl-4-(2,4,6-trifluorophenyl)[1,2]oxazolo[5,4-b]pyridin-3-yl]-7,7-difluoro-3-oxo-2,5,6,7-tetrahydro-3H-pyrrolo[1,2-c]imidazol-6-yl}methanesulfonamide | 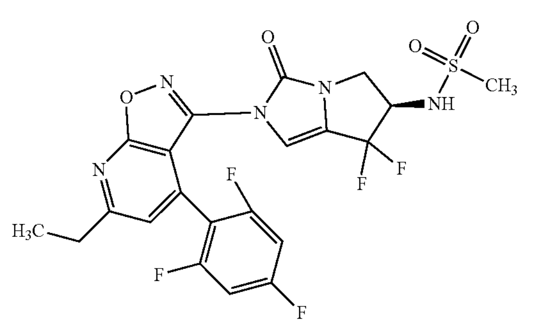 [SMILES: CCc1cc(-c2c(F)cc(F)cc2F)c2c(-n3cc4n(c3=O)C[C@@H](NS(C)(=O)=O)C4(F)F)noc2n1] | 530.2 |

TABLE 1-1-continued

| Ex. No. | IUPAC Name | Structure | MS |
|---|---|---|---|
| 231 | N-{(6R*)-7,7-difluoro-2-[5-fluoro-4-(2,4,6-trifluorophenyl)-1,2-benzoxazol-3-yl]-3-oxo-2,3,5,6,7,8-hexahydroimidazo[1,5-a]pyridin-6-yl}methanesulfonamide | 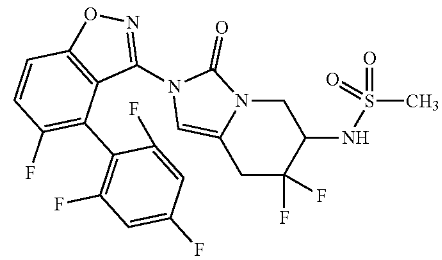 [SMILES: CS(=O)(=O)NC1Cn2c(cn(-c3noc4ccc(F)c(-c5c(F)cc(F)cc5F)c34)c2=O)CC1(F)F] | 533.0 |
| 232 | N-{(4aR,6R)-5,5-difluoro-2-[6-(methoxymethyl)-4-(2,4,6-trifluorophenyl)-1,2-benzoxazol-3-yl]-1-oxooctahydropyrrolo[1,2-c]pyrimidin-6-yl}ethanesulfonamide | 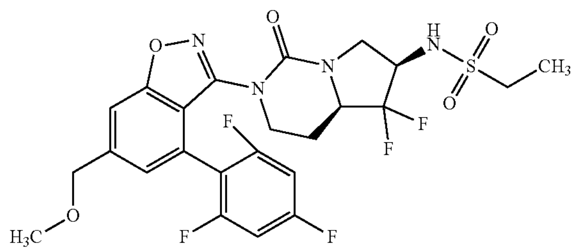 [SMILES: CCS(=O)(=O)N[C@@H]1CN2C(=O)N(c3noc4cc(COC)cc(-c5c(F)cc(F)cc5F)c34)CC[C@@H]2C1(F)F] | 574.8 |
| 233 | N-{(4aR,6R)-5,5-difluoro-2-[6-methyl-4-(2,4,6-trifluorophenyl)[1,2]oxazolo[4,5-c]pyridin-3-yl]-1-oxooctahydropyrrolo[1,2-c]pyrimidin-6-yl}cyclopropanesulfonamide | 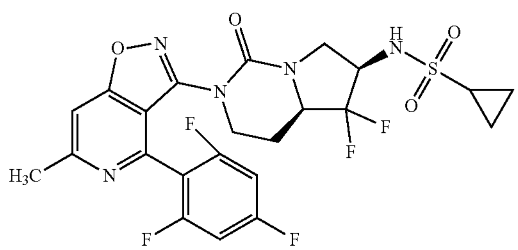 [SMILES: Cc1cc2onc(N3CC[C@H]4N(C[C@@H](NS(=O)(=O)C5CC5)C4(F)F)C3=O)c2c(-c2c(F)cc(F)cc2F)n1] | 557.8 |
| 234 | N-{(4aR,6R)-5,5-difluoro-2-[5-fluoro-4-(2,4,6-trifluorophenyl)-1,2-benzoxazol-3-yl]-1-oxooctahydropyrrolo[1,2-c]pyrimidin-6-yl}cyclopropanesulfonamide | 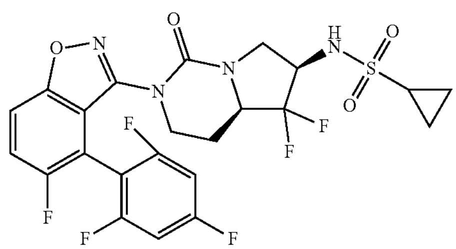 [SMILES: O=C1N(c2noc3ccc(F)c(-c4c(F)cc(F)cc4F)c23)CC[C@H]2N1C[C@@H](NS(=O)(=O)C1CC1)C2(F)F] | 560.9 |
| 235 | N-{(4aR,6R)-5,5-difluoro-1-oxo-2-[4-(2,4,6-trifluorophenyl)[1,2]oxazolo[5,4-b]pyridin-3-yl]octahydropyrrolo[1,2-c]pyrimidin-6-yl}ethanesulfonamide | 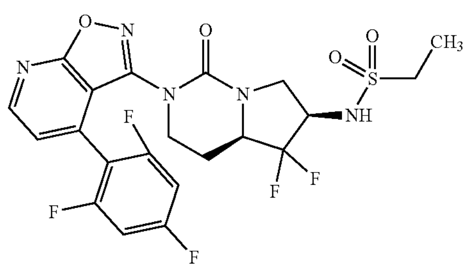 [SMILES: CCS(=O)(=O)N[C@@H]1CN2C(=O)N(c3noc4nccc(-c5c(F)cc(F)cc5F)c34)CC[C@@H]2C1(F)F] | 531.9 |
| 236 | N-{(4aR,6R)-5,5-difluoro-2-[6-fluoro-4-(2,4,6-trifluorophenyl)-1,2-benzoxazol-3-yl]-1-oxooctahydropyrrolo[1,2-c]pyrimidin-6-yl}-1-fluoromethanesulfonamide | 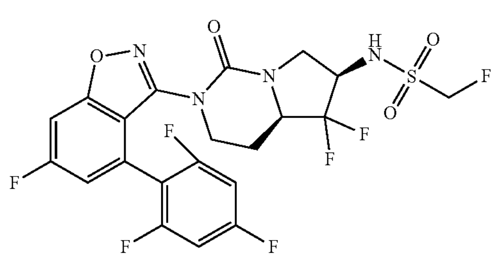 [SMILES: O=C1N(c2noc3cc(F)cc(-c4c(F)cc(F)cc4F)c23)CC[C@H]2N1C[C@@H](NS(=O)(=O)CF)C2(F)F] | 552.7 |

TABLE 1-1-continued

| Ex. No. | IUPAC Name | MS |
|---|---|---|
| 237 | N-{(4aR,6R)-5,5-difluoro-1-oxo-2-[4-(2,4,6-trifluorophenyl)[1,2]oxazolo[5,4-b]pyridin-3-yl]octahydropyrrolo[1,2-c]pyrimidin-6-yl}methanesulfonamide | 517.9 |
| 238 | N-{(4aR,6R)-2-[4-(2,6-difluorophenyl)-5-fluoro-6-(methoxymethyl)-1,2-benzoxazol-3-yl]-5,5-difluoro-1-oxooctahydropyrrolo[1,2-c]pyrimidin-6-yl}methanesulfonamide | 560.8 |
| 239 | N-{(6R)-7,7-difluoro-2-[5-fluoro-6-(methoxymethyl)-4-(2,4,6-trifluorophenyl)-1,2-benzoxazol-3-yl]-3-oxo-2,5,6,7-tetrahydro-3H-pyrrolo[1,2-c]imidazol-6-yl}ethanesulfonamide | 577.1 |
| 240 | N-{(6R*)-7,7-difluoro-2-[6-fluoro-4-(2,4,6-trifluorophenyl)-1,2-benzoxazol-3-yl]-3-oxo-2,3,5,6,7,8-hexahydroimidazo[1,5-a]pyridin-6-yl}ethanesulfonamide | 547.1 |
| 241 | N-{(4aR,6R)-5,5-difluoro-2-[5-fluoro-4-(2,4,6-trifluorophenyl)-1,2-benzoxazol-3-yl]-1-oxooctahydropyrrolo[1,2-c]pyrimidin-6-yl}methanesulfonamide | 535.1 |
| 242 | N-{(4aR,6R)-5,5-difluoro-1-oxo-2-[4-(2,4,6-trifluorophenyl)-1,2-benzoxazol-3-yl]octahydropyrrolo[1,2-c]pyrimidin-6-yl}cyclopropanesulfonamide | 542.9 |

TABLE 1-1-continued

| Ex. No. | IUPAC Name | Structure | MS |
|---|---|---|---|
| 243 | N-{(4aR,6R)-2-[5,6-difluoro-4-(2,4,6-trifluorophenyl)-1,2-benzoxazol-3-yl]-5,5-difluoro-1-oxooctahydropyrrolo[1,2-c]pyrimidin-6-yl}methanesulfonamide | 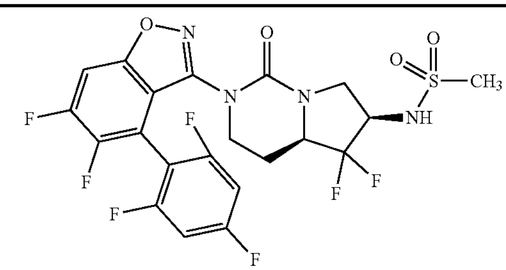 | 553.0 |
| 244 | N-{(6R)-7,7-difluoro-2-[5-fluoro-6-(methoxymethyl)-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide | 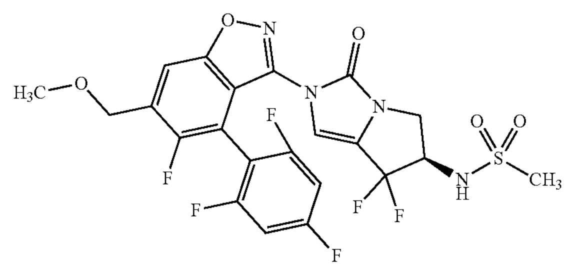 | 563.1 |
| 245 | N-{(6R*)-7,7-difluoro-2-[6-methyl-4-(2,4,6-trifluorophenyl)[1,2]oxazolo[5,4-b]pyridin-3-yl]-3-oxo-2,3,5,6,7,8-hexahydroimidazo[1,5-a]pyridin-6-yl}methanesulfonamide | 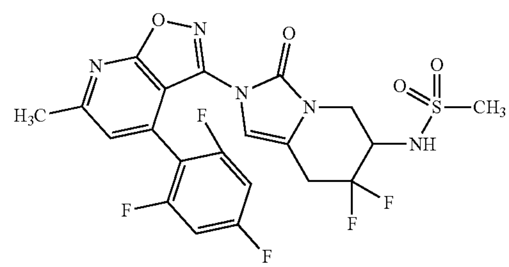 | 529.9 |
| 246 | N-{(6R*)-7,7-difluoro-2-[5-fluoro-4-(2,4,6-trifluorophenyl)-1,2-benzoxazol-3-yl]-3-oxo-2,3,5,6,7,8-hexahydroimidazo[1,5-a]pyridin-6-yl}ethanesulfonamide | 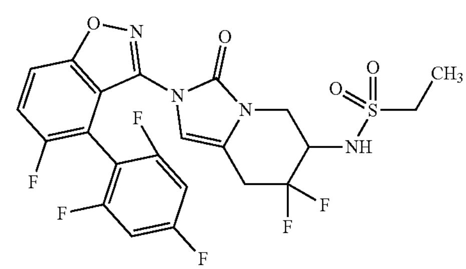 [SMILES: CCS(=O)(=O)NC1Cn2c(cn(-c3noc4ccc(F)c(-c5c(F)cc(F)cc5F)c34)c2=O)CC1(F)F] | 547.0 |
| 247 | N-{(4aR,6R)-2-[4-(2,6-difluorophenyl)-6-fluoro-1,2-benzoxazol-3-yl]-5,5-difluoro-1-oxooctahydropyrrolo[1,2-c]pyrimidin-6-yl}ethanesulfonamide | 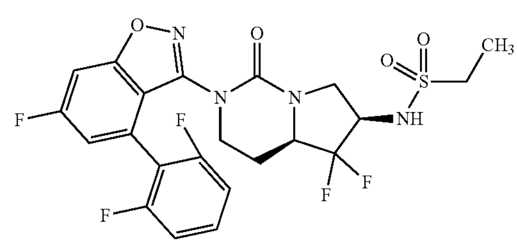 [SMILES: CCS(=O)(=O)N[C@@H]1CN2C(=O)N(c3noc4cc(F)cc(-c5c(F)cccc5F)c34)CC[C@@H]2C1(F)F] | 530.9 |
| 248 | N-{(4aR,6R)-5,5-difluoro-2-[6-methyl-4-(2,4,6-trifluorophenyl)[1,2]oxazolo[4,5-c]pyridin-3-yl]-1-oxooctahydropyrrolo[1,2-c]pyrimidin-6-yl}methanesulfonamide | 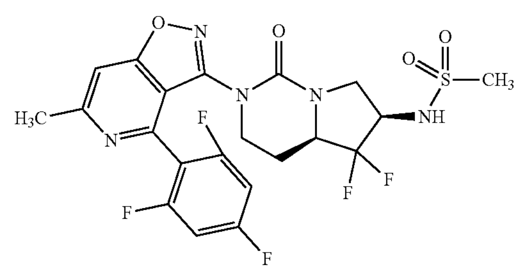 | 532.2 |

TABLE 1-1-continued

| Ex. No. | IUPAC Name | Structure | MS |
|---|---|---|---|
| 249 | N-{(4aR,6R)-2-[6-ethoxy-4-(2,4,6-trifluorophenyl)-1,2-benzoxazol-3-yl]-5,5-difluoro-1-oxooctahydropyrrolo[1,2-c]pyrimidin-6-yl}cyclopropanesulfonamide | 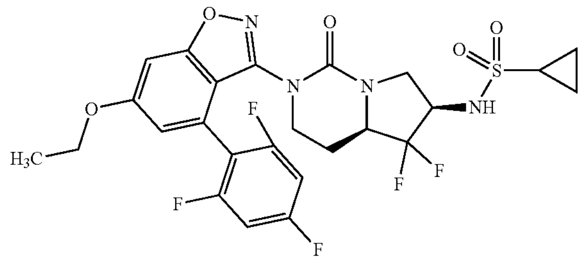 [SMILES: CCOc1cc(-c2c(F)cc(F)cc2F)c2c(N3CC[C@H]4N(C[C@@H](NS(=O)(=O)C5CC5)C4(F)F)C3=O)noc2c1] | 587.2 |
| 250 | N-{(6R)-7,7-difluoro-2-[6-methoxy-4-(2,4,6-trifluorophenyl)[1,2]oxazolo[5,4-b]pyridin-3-yl]-3-oxo-2,5,6,7-tetrahydro-3H-pyrrolo[1,2-c]imidazol-6-yl}methanesulfonamide | 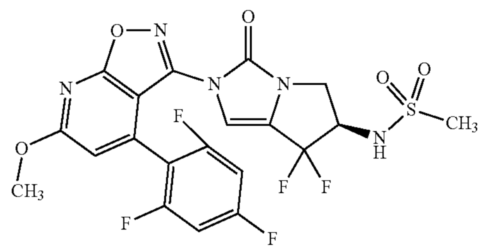 | 531.7 |
| 251 | N-{(4aR,6S)-2-[4-(2,6-difluorophenyl)-6-(trifluoromethyl)-1,2-benzoxazol-3-yl]-1-oxooctahydropyrrolo[1,2-c]pyrimidin-6-yl}methanesulfonamide | 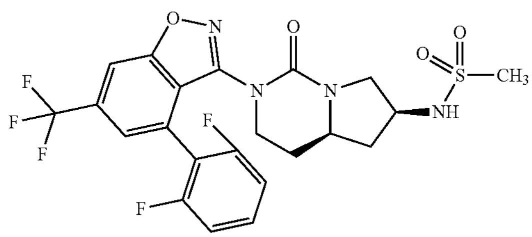 [SMILES: CS(=O)(=O)N[C@H]1C[C@H]2CCN(c3noc4cc(C(F)(F)F)cc(-c5c(F)cccc5F)c34)C(=O)N2C1] | 530.9 |
| 252 | N-{(4aR,6R)-2-[4-(2,6-difluorophenyl)-5,6-difluoro-1,2-benzoxazol-3-yl]-5,5-difluoro-1-oxooctahydropyrrolo[1,2-c]pyrimidin-6-yl}methanesulfonamide | 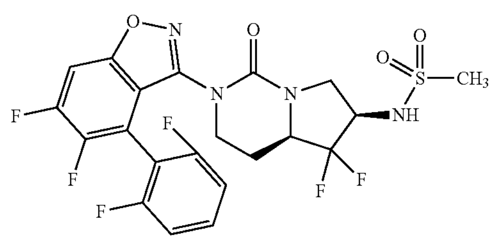 [SMILES: CS(=O)(=O)N[C@@H]1CN2C(=O)N(c3noc4cc(F)c(F)c(-c5c(F)cccc5F)c34)CC[C@@H]2C1(F)F] | 534.8 |
| 253 | N-{(4aR,6S)-2-[4-(2,6-difluorophenyl)-6-fluoro-1,2-benzoxazol-3-yl]-1-oxooctahydropyrrolo[1,2-c]pyrimidin-6-yl}methanesulfonamide | 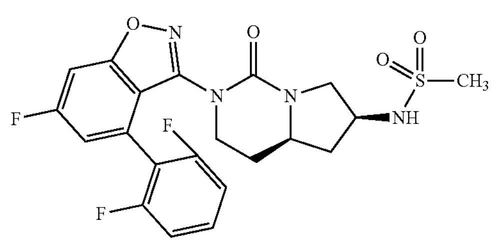 [SMILES: CS(=O)(=O)N[C@H]1C[C@H]2CCN(c3noc4cc(F)cc(-c5c(F)cccc5F)c34)C(=O)N2C1] | 481.0 |
| 254 | N-{(4aR,6R)-2-[4-(3,5-difluoropyridin-2-yl)-6-fluoro-1,2-benzoxazol-3-yl]-5,5-difluoro-1-oxooctahydropyrrolo[1,2-c]pyrimidin-6-yl}ethanesulfonamide | 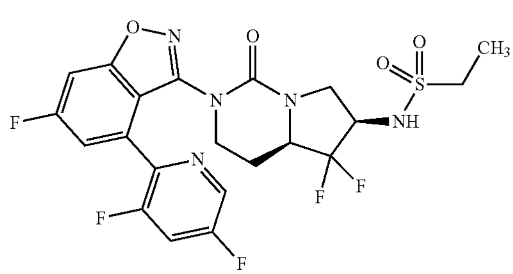 [SMILES: CCS(=O)(=O)N[C@@H]1CN2C(=O)N(c3noc4cc(F)cc(-c5ncc(F)cc5F)c34)CC[C@@H]2C1(F)F] | 531.8 |

TABLE 1-1-continued

| Ex. No. | IUPAC Name | Structure | MS |
|---|---|---|---|
| 255 | N-{(4aR,6R)-2-[6-(difluoromethoxy)-4-(2,6-difluorophenyl)-1,2-benzoxazol-3-yl]-5,5-difluoro-1-oxooctahydropyrrolo[1,2-c]pyrimidin-6-yl}ethanesulfonamide | 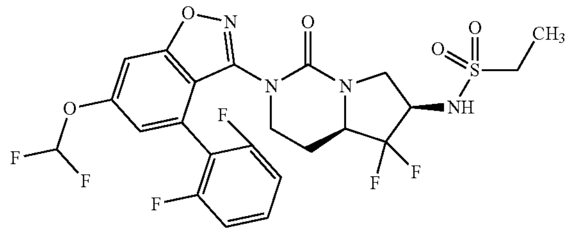 [SMILES: CCS(=O)(=O)N[C@@H]1CN2C(=O)N(c3noc4cc(OC(F)F)cc(-c5c(F)cccc5F)c34)CC[C@@H]2C1(F)F] | 578.8 |
| 256 | N-{(4aR,6R)-2-[6-(difluoromethoxy)-4-(2,6-difluorophenyl)-1,2-benzoxazol-3-yl]-5,5-difluoro-1-oxooctahydropyrrolo[1,2-c]pyrimidin-6-yl}cyclopropanesulfonamide | 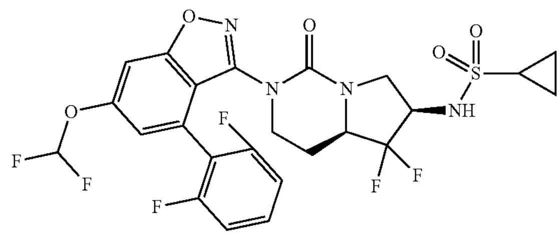 [SMILES: O=C1N(c2noc3cc(OC(F)F)cc(-c4c(F)cccc4F)c23)CC[C@H]2N1C[C@@H](NS(=O)(=O)C1CC1)C2(F)F] | 590.8 |
| 257 | N-{(6R)-7,7-difluoro-2-[6-methyl-4-(2,4,6-trifluorophenyl)[1,2]oxazolo[4,5-c]pyridin-3-yl]-3-oxo-2,5,6,7-tetrahydro-3H-pyrrolo[1,2-c]imidazol-6-yl}-N'-methylsulfuric diamide | 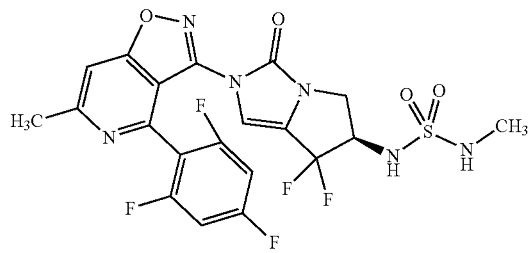 | 530.9 |
| 258 | N-{(4aR,6R)-5,5-difluoro-2-[6-methyl-4-(2,4,6-trifluorophenyl)[1,2]oxazolo[5,4-b]pyridin-3-yl]-1-oxooctahydropyrrolo[1,2-c]pyrimidin-6-yl}methanesulfonamide | 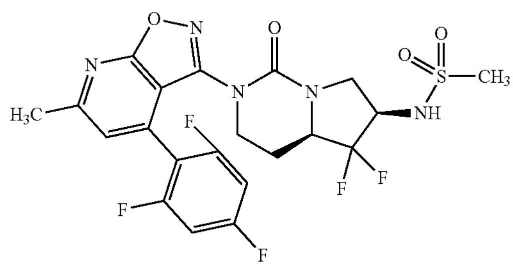 | 532.2 |
| 259 | N-{(4aR,6R)-2-[6-chloro-4-(2,6-difluorophenyl)-1,2-benzoxazol-3-yl]-5,5-difluoro-1-oxooctahydropyrrolo[1,2-c]pyrimidin-6-yl}methanesulfonamide | 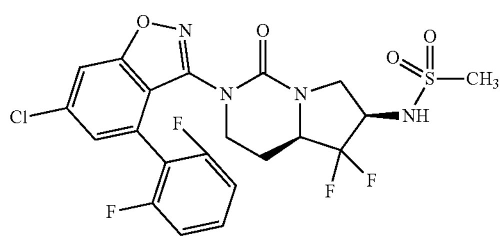 [SMILES: CS(=O)(=O)N[C@@H]1CN2C(=O)N(c3noc4cc(Cl)cc(-c5c(F)cccc5F)c34)CC[C@@H]2C1(F)F] | 533.2 |
| 260 | N-{(4aR,6R)-5,5-difluoro-1-oxo-2-[4-(2,4,6-trifluorophenyl)-1,2-benzoxazol-3-yl]octahydropyrrolo[1,2-c]pyrimidin-6-yl}ethanesulfonamide | 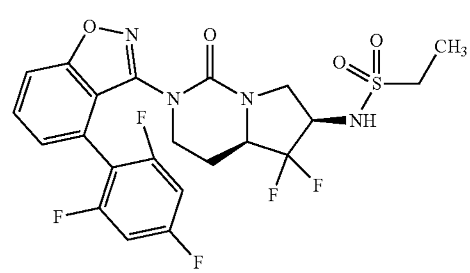 [SMILES: CCS(=O)(=O)N[C@@H]1CN2C(=O)N(c3noc4cccc(-c5c(F)cc(F)cc5F)c34)CC[C@@H]2C1(F)F] | 530.9 |

TABLE 1-1-continued

| Ex. No. | IUPAC Name | Structure | MS |
|---|---|---|---|
| 261 | N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}methanesulfonamide | 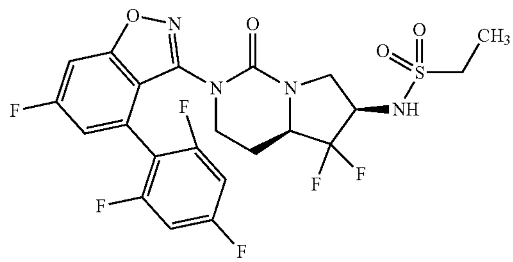 [SMILES: CCS(=O)(=O)N[C@@H]1CN2C(=O)N(c3noc4cc(F)cc(-c5c(F)cc(F)cc5F)c34)CC[C@@H]2C1(F)F] | 548.9 |
| 262 | N-{4aR,6R)-2-[4-(2,6-difluorophenyl)-1,2-benzoxazol-3-yl]-5,5-difluoro-1-oxooctahydropyrrolo[1,2-c]pyrimidin-6-yl}ethanesulfonamide | 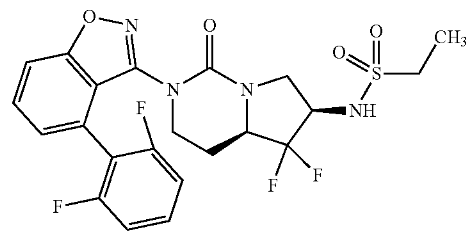 [SMILES: CCS(=O)(=O)N[C@@H]1CN2C(=O)N(c3noc4cccc(-c5c(F)cccc5F)c34)CC[C@@H]2C1(F)F] | 513.1 |
| 263 | N-{(4aR,6R)-2-[4-(2,6-difluorophenyl)-6-fluoro-1,2-benzoxazol-3-yl]-5,5-difluoro-1-oxooctahydropyrrolo[1,2-c]pyrimidin-6-yl}ethanesulfonamide | 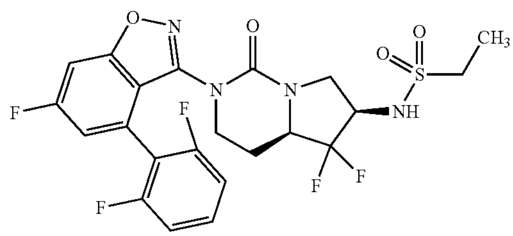 [SMILES: CCS(=O)(=O)N[C@@H]1CN2C(=O)N(c3noc4cc(F)cc(-c5c(F)cccc5F)c34)CC[C@@H]2C1(F)F] | 531.0 |
| 264 | N'-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}-N,N-dimethylsulfuric diamide | 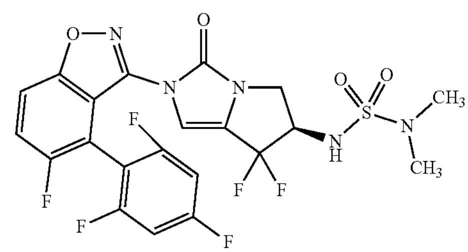 [SMILES: CN(C)S(=O)(=O)N[C@@H]1Cn2c(cn(-c3noc4ccc(F)c(-c5c(F)cc(F)cc5F)c34)c2=O)C1(F)F] | 547.7 |
| 265 | N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}methanesulfonamide | 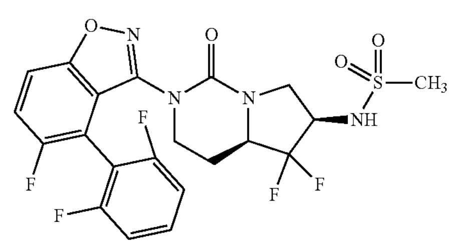 [SMILES: CS(=O)(=O)N[C@@H]1CN2C(=O)N(c3noc4ccc(F)c(-c5c(F)cccc5F)c34)CC[C@@H]2C1(F)F] | 517.0 |
| 266 | N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}methanesulfonamide | 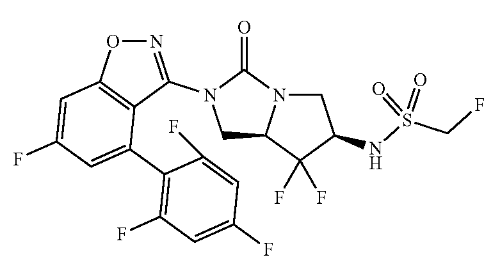 [SMILES: O=C1N(c2noc3cc(F)cc(-c4c(F)cc(F)cc4F)c23)C[C@H]2N1C[C@@H](NS(=O)(=O)CF)C2(F)F] | 538.9 |

TABLE 1-1-continued

| Ex. No. | IUPAC Name | Structure | MS |
|---|---|---|---|
| 267 | N-{(6R)-2-[6-(difluoromethyl)-4-(2,4,6-trifluorophenyl)-1,2-benzoxazol-3-yl]-7,7-difluoro-3-oxo-2,5,6,7-tetrahydro-3H-pyrrolo[1,2-c]imidazol-6-yl}-1-fluoromethanesulfonamide | 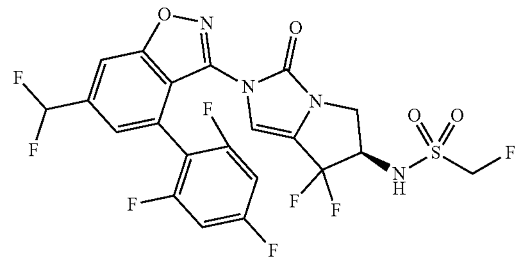 [SMILES: O=c1n(-c2noc3cc(C(F)F)cc(-c4c(F)cc(F)cc4F)c23)cc2n1C[C@@H](NS(=O)(=O)CF)C2(F)F] | 566.9 |
| 268 | N-{(4aR,6R)-2-[4-(2,6-difluorophenyl)-6-methyl[1,2]oxazolo[4,5-c]pyridin-3-yl]-5,5-difluoro-1-oxooctahydropyrrolo[1,2-c]pyrimidin-6-yl}cyclopropanesulfonamide | 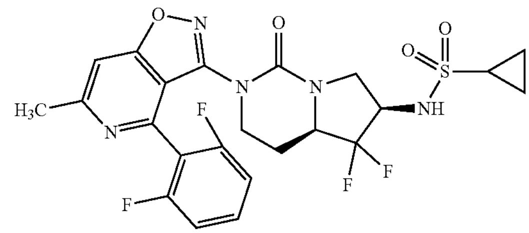 [SMILES: Cc1cc2onc(N3CC[C@H]4N(C[C@@H](NS(=O)(=O)C5CC5)C4(F)F)C3=O)c2c(-c2c(F)cccc2F)n1] | 539.9 |
| 269 | N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}ethanesulfonamide | 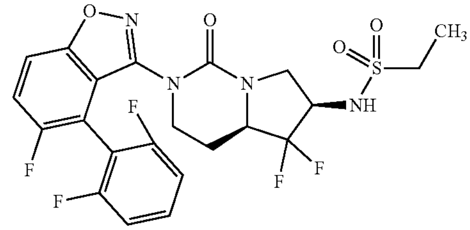 [SMILES: CCS(=O)(=O)N[C@@H]1CN2C(=O)N(c3noc4ccc(F)c(-c5c(F)cccc5F)c34)CC[C@@H]2C1(F)F] | 530.9 |
| 270 | N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}-1-fluoromethanesulfonamide | 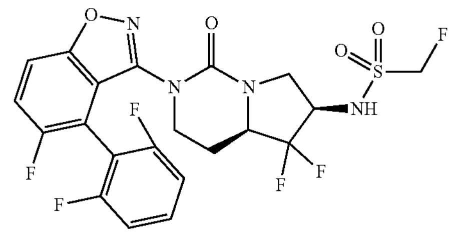 [SMILES: O=C1N(c2noc3ccc(F)c(-c4c(F)cccc4F)c23)CC[C@H]2N1C[C@@H](NS(=O)(=O)CF)C2(F)F] | 534.9 |
| 271 | N-{(4aR,6R)-2-[4-(2,6-difluorophenyl)-6-fluoro-1,2-benzoxazol-3-yl]-5,5-difluoro-1-oxooctahydropyrrolo[1,2-c]pyrimidin-6-yl}cyclopropanesulfonamide | 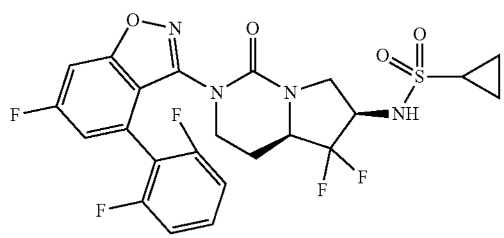 [SMILES: O=C1N(c2noc3cc(F)cc(-c4c(F)cccc4F)c23)CC[C@H]2N1C[C@@H](NS(=O)(=O)C1CC1)C2(F)F] | 542.7 |
| 272 | N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}cyclopropanesulfonamide | 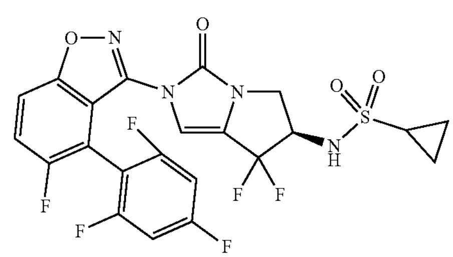 [SMILES: O=c1n(-c2noc3ccc(F)c(-c4c(F)cc(F)cc4F)c23)cc2n1C[C@@H](NS(=O)(=O)C1CC1)C2(F)F] | 544.8 |

TABLE 1-1-continued

| Ex. No. | IUPAC Name | Structure | MS |
|---|---|---|---|
| 273 | N-{(4aR,6R)-5,5-difluoro-2-[4-(2-fluorophenyl)-1,2-benzoxazol-3-yl]-1-oxooctahydropyrrolo[1,2-c]pyrimidin-6-yl}methanesulfonamide | 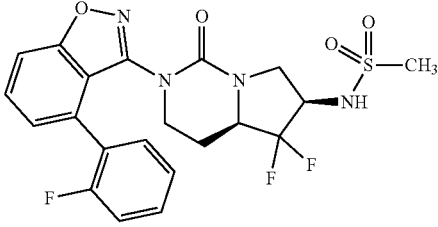 [SMILES: CS(=O)(=O)N[C@@H]1CN2C(=O)N(c3noc4cccc(-c5ccccc5F)c34)CC[C@@H]2C1(F)F] | 481.1 |
| 274 | N-{(6R,7aR)-2-[6-(difluoromethyl)-4-(2,4,6-trifluorophenyl)-1,2-benzoxazol-3-yl]-7,7-difluoro-3-oxohexahydro-1H-pyrrolo[1,2-c]imidazol-6-yl}methanesulfonamide | 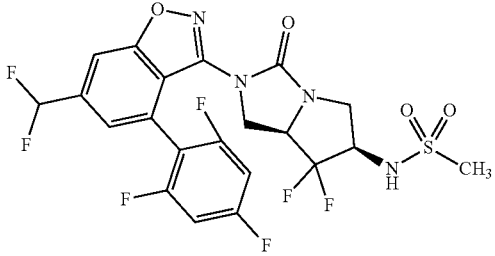 [SMILES: CS(=O)(=O)N[C@@H]1CN2C(=O)N(c3noc4cc(C(F)F)cc(-c5c(F)cc(F)cc5F)c34)C[C@@H]2C1(F)F] | 552.9 |
| 275 | N-{(4aR,6R)-2-[4-(2,6-difluorophenyl)-6-methyl[1,2]oxazolo[4,5-c]pyridin-3-yl]-5,5-difluoro-1-oxooctahydropyrrolo[1,2-c]pyrimidin-6-yl}ethanesulfonamide | 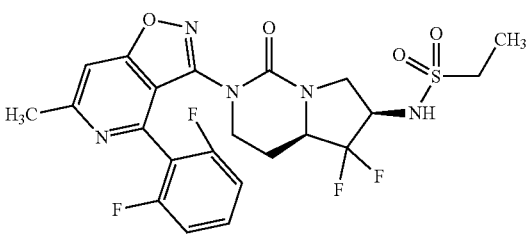 [SMILES: CCS(=O)(=O)N[C@@H]1CN2C(=O)N(c3noc4cc(C)nc(-c5c(F)cccc5F)c34)CC[C@@H]2C1(F)F] | 527.9 |
| 276 | N-{(4aR,6R)-2-[4-(2,3-difluorophenyl)-1,2-benzoxazol-3-yl]-5,5-difluoro-1-oxooctahydropyrrolo[1,2-c]pyrimidin-6-yl}methanesulfonamide | 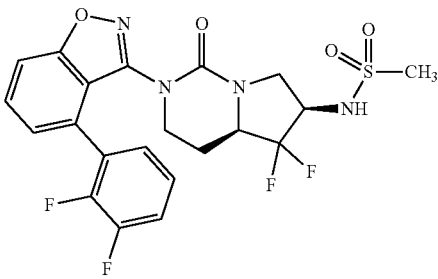 [SMILES: CS(=O)(=O)N[C@@H]1CN2C(=O)N(c3noc4cccc(-c5cccc(F)c5F)c34)CC[C@@H]2C1(F)F] | 498.9 |
| 277 | N-{(4aR,6R)-5,5-difluoro-2-[4-(4-fluorophenyl)-1,2-benzoxazol-3-yl]-1-oxooctahydropyrrolo[1,2-c]pyrimidin-6-yl}methanesulfonamide | 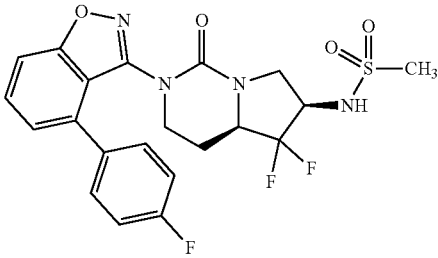 [SMILES: CS(=O)(=O)N[C@@H]1CN2C(=O)N(c3noc4cccc(-c5ccc(F)cc5)c34)CC[C@@H]2C1(F)F] | 480.9 |
| 278 | N-{(4aR,6R)-5,5-difluoro-1-oxo-2-[4-(thiophen-2-yl)-1,2-benzoxazol-3-yl]octahydropyrrolo[1,2-c]pyrimidin-6-yl}methanesulfonamide | 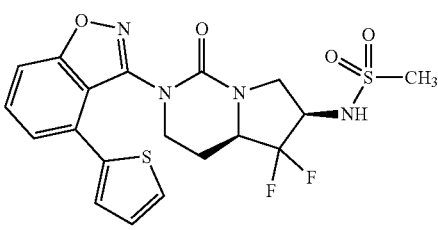 [SMILES: CS(=O)(=O)N[C@@H]1CN2C(=O)N(c3noc4cccc(-c5cccs5)c34)CC[C@@H]2C1(F)F] | 468.8 |

TABLE 1-1-continued

| Ex. No. | IUPAC Name | Structure | MS |
|---|---|---|---|
| 279 | N-{(4aR,6R)-2-[4-(2,6-difluorophenyl)-6-fluoro-1,2-benzoxazol-3-yl]-5,5-difluoro-1-oxooctahydropyrrolo[1,2-c]pyrimidin-6-yl}-1-fluoromethanesulfonamide | 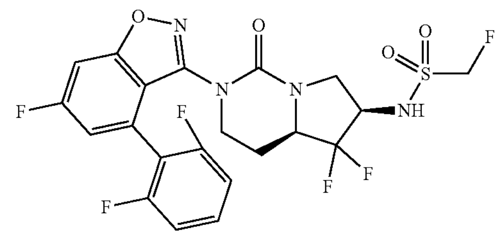 [SMILES: O=C1N(c2noc3cc(F)cc(-c4c(F)cccc4F)c23)CC[C@H]2N1C[C@@H](NS(=O)(=O)CF)C2(F)F] | 534.9 |
| 280 | N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}cyclopropanesulfonamide | 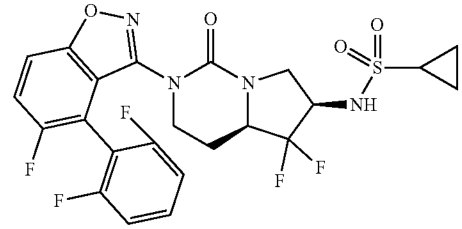 [SMILES: O=C1N(c2noc3ccc(F)c(-c4c(F)cccc4F)c23)CC[C@H]2N1C[C@@H](NS(=O)(=O)C1CC1)C2(F)F] | 542.8 |
| 281 | N-{(4aR,6R)-5,5-difluoro-2-[6-fluoro-4-(2,4,6-trifluorophenyl)-1,2-benzoxazol-3-yl]-1-oxooctahydropyrrolo[1,2-c]pyrimidin-6-yl}cyclopropanesulfonamide | 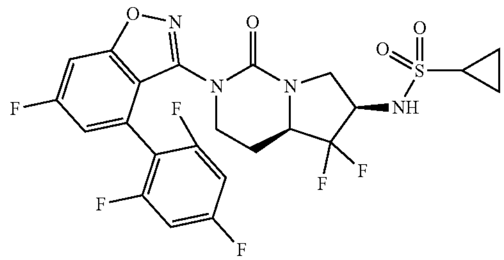 [SMILES: O=C1N(c2noc3cc(F)cc(-c4c(F)cc(F)cc4F)c23)CC[C@H]2N1C[C@@H](NS(=O)(=O)C1CC1)C2(F)F] | 560.9 |
| 282 | N-{(6R)-2-[4-(2,6-difluorophenyl)-6-fluoro-1,2-benzoxazol-3-yl]-7,7-difluoro-3-oxo-2,5,6,7-tetrahydro-3H-pyrrolo[1,2-c]imidazol-6-yl}ethanesulfonamide | 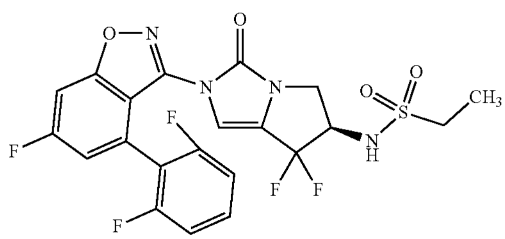 [SMILES: CCS(=O)(=O)N[C@@H]1Cn2c(cn(-c3noc4cc(F)cc(-c5c(F)cccc5F)c34)c2=O)C1(F)F] | 514.9 |
| 283 | N-{(6R)-2-[4-(2,6-difluorophenyl)-6-fluoro-1,2-benzoxazol-3-yl]-7,7-difluoro-3-oxo-2,5,6,7-tetrahydro-3H-pyrrolo[1,2-c]imidazol-6-yl}-1-fluoromethanesulfonamide | 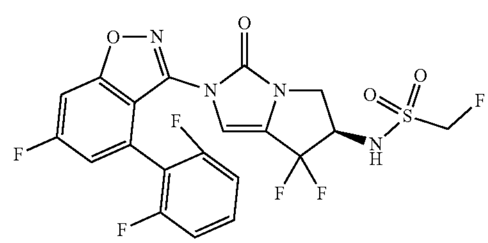 [SMILES: O=c1n(-c2noc3cc(F)cc(-c4c(F)cccc4F)c23)cc2n1C[C@@H](NS(=O)(=O)CF)C2(F)F] | 518.8 |
| 284 | N-{(4aR,6R)-2-[4-(2,6-difluorophenyl)-1,2-benzoxazol-3-yl]-5,5-difluoro-1-oxooctahydropyrrolo[1,2-c]pyrimidin-6-yl}-1-fluoromethanesulfonamide | 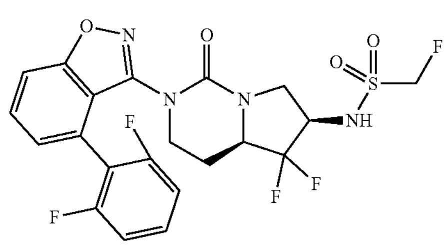 [SMILES: O=C1N(c2noc3cccc(-c4c(F)cccc4F)c23)CC[C@H]2N1C[C@@H](NS(=O)(=O)CF)C2(F)F] | 516.9 |

TABLE 1-1-continued

| Ex. No. | IUPAC Name | MS |
|---|---|---|
| 285 | N-{(4aR,6R)-2-[4-(2,6-difluorophenyl)-1,2-benzoxazol-3-yl]-5,5-difluoro-1-oxooctahydropyrrolo[1,2-c]pyrimidin-6-yl}cyclopropanesulfonamide | 524.9 |
| 286 | N'-{(6R)-2-[4-(2,6-difluorophenyl)-6-methyl[1,2]oxazolo[4,5-c]pyridin-3-yl]-7,7-difluoro-3-oxo-2,5,6,7-tetrahydro-3H-pyrrolo[1,2-c]imidazol-6-yl}-N,N-dimethylsulfuric diamide | 527.3 |
| 287 | N-{(6R,7aR)-2-[4-(2,6-difluorophenyl)-6-fluoro-1,2-benzoxazol-3-yl]-7,7-difluoro-3-oxohexahydro-1H-pyrrolo[1,2-c]imidazol-6-yl}-1-fluoromethanesulfonamide | 520.9 |
| 288 | N-{(6R)-7,7-difluoro-2-[6-fluoro-4-(2,4,6-trifluorophenyl)-1,2-benzoxazol-3-yl]-3-oxo-2,5,6,7-tetrahydro-3H-pyrrolo[1,2-c]imidazol-6-yl}-1-fluoromethanesulfonamide | 535.0 |
| 289 | N-{(6R*)-7,7-difluoro-2-[6-methyl-4-(2,4,6-trifluorophenyl)[1,2]oxazolo[4,5-c]pyridin-3-yl]-3-oxo-2,3,5,6,7,8-hexahydroimidazo[1,5-a]pyridin-6-yl}methanesulfonamide | 529.8 |
| 290 | N-{(4aR,6R)-2-[4-(2,4-difluorophenyl)-1,2-benzoxazol-3-yl]-5,5-difluoro-1-oxooctahydropyrrolo[1,2-c]pyrimidin-6-yl}methanesulfonamide | 498.9 |

TABLE 1-1-continued

| Ex. No. | IUPAC Name | Structure | MS |
|---|---|---|---|
| 291 | N-{(4aR,6R)-2-[4-(2-chlorophenyl)-1,2-benzoxazol-3-yl]-5,5-difluoro-1-oxooctahydropyrrolo[1,2-c]pyrimidin-6-yl}methanesulfonamide | 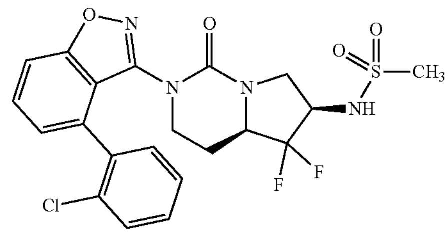 [SMILES: CS(=O)(=O)N[C@@H]1CN2C(=O)N(c3noc4cccc(-c5ccccc5Cl)c34)CC[C@@H]2C1(F)F] | 496.9 |
| 292 | N-{(4aR,6R)-2-[4-(2,5-difluorophenyl)-1,2-benzoxazol-3-yl]-5,5-difluoro-1-oxooctahydropyrrolo[1,2-c]pyrimidin-6-yl}methanesulfonamide | 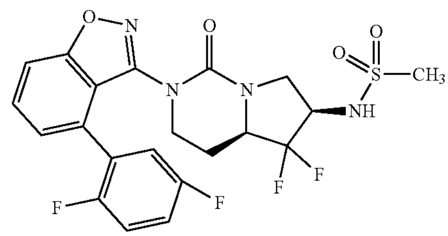 [SMILES: CS(=O)(=O)N[C@@H]1CN2C(=O)N(c3noc4cccc(-c5cc(F)ccc5F)c34)CC[C@@H]2C1(F)F] | 498.8 |
| 293 | N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}-1-fluoromethanesulfonamide | 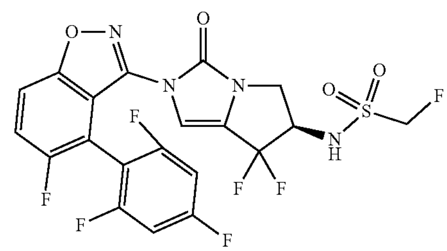 [SMILES: O=c1n(-c2noc3ccc(F)c(-c4c(F)cc(F)cc4F)c23)cc2n1C[C@@H](NS(=O)(=O)CF)C2(F)F] | 536.8 |
| 294 | N-{(4aR,6R)-5,5-difluoro-2-[6-methoxy-4-(2,4,6-trifluorophenyl)[1,2]oxazolo[5,4-b]pyridin-3-yl]-1-oxooctahydropyrrolo[1,2-c]pyrimidin-6-yl}methanesulfonamide | 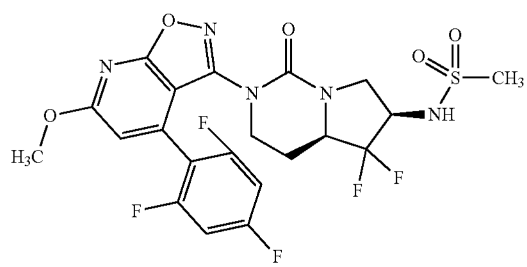 | 547.9 |
| 295 | N-{(4aR,6R)-2-[4-(3,5-difluoropyridin-2-yl)-6-fluoro-1,2-benzoxazol-3-yl]-5,5-difluoro-1-oxooctahydropyrrolo[1,2-c]pyrimidin-6-yl}methanesulfonamide | 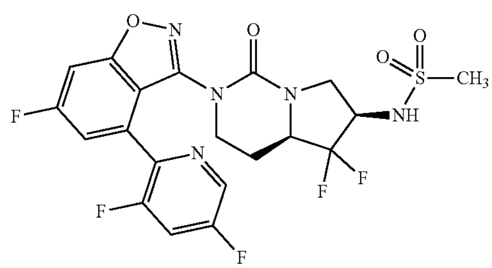 [SMILES: CS(=O)(=O)N[C@@H]1CN2C(=O)N(c3noc4cc(F)cc(-c5ncc(F)cc5F)c34)CC[C@@H]2C1(F)F] | 518.1 |
| 296 | N-{(4aR,6R)-2-[6-(difluoromethoxy)-4-(2,4,6-trifluorophenyl)-1,2-benzoxazol-3-yl]-5,5-difluoro-1-oxooctahydropyrrolo[1,2-c]pyrimidin-6-yl}methanesulfonamide | 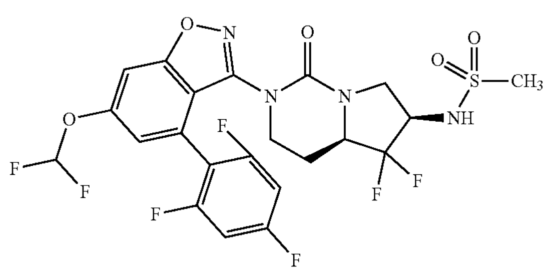 [SMILES: CS(=O)(=O)N[C@@H]1CN2C(=O)N(c3noc4cc(OC(F)F)cc(-c5c(F)cc(F)cc5F)c34)CC[C@@H]2C1(F)F] | 582.9 |

TABLE 1-1-continued

| Ex. No. | IUPAC Name | Structure | MS |
|---|---|---|---|
| 297 | N-{(4aR,6R)-2-[5,6-difluoro-4-(2,4,6-trifluorophenyl)-1,2-benzoxazol-3-yl]-5,5-difluoro-1-oxooctahydropyrrolo[1,2-c]pyrimidin-6-yl}-1-fluoromethanesulfonamide | 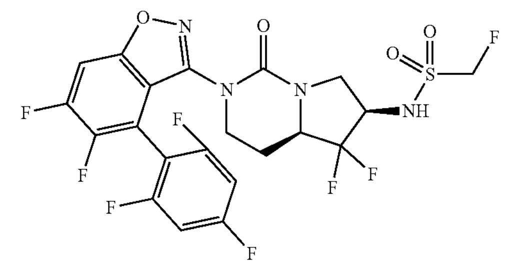 [SMILES: O=C1N(c2noc3cc(F)c(F)c(-c4c(F)cc(F)cc4F)c23)CC[C@H]2N1C[C@@H](NS(=O)(=O)CF)C2(F)F] | 570.8 |
| 298 | N-{(6R,7aR)-2-[6-(difluoromethyl)-4-(2,4,6-trifluorophenyl)-1,2-benzoxazol-3-yl]-7,7-difluoro-3-oxohexahydro-1H-pyrrolo[1,2-c]imidazol-6-yl}ethanesulfonamide | 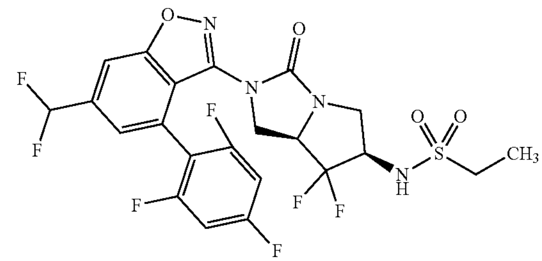 [SMILES: CCS(=O)(=O)N[C@@H]1CN2C(=O)N(c3noc4cc(C(F)F)cc(-c5c(F)cc(F)cc5F)c34)C[C@@H]2C1(F)F] | 566.8 |
| 299 | N-{(4aR,6R)-2-[4-(2,6-difluorophenyl)-6-ethoxy-1,2-benzoxazol-3-yl]-5,5-difluoro-1-oxooctahydropyrrolo[1,2-c]pyrimidin-6-yl}ethanesulfonamide | 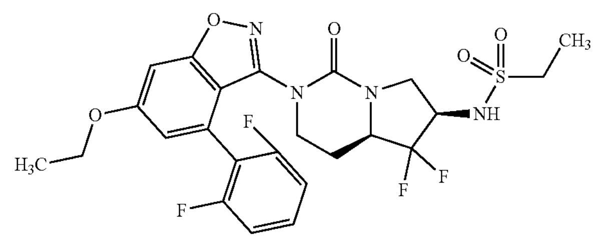 [SMILES: CCOc1cc(-c2c(F)cccc2F)c2c(N3CC[C@H]4N(C[C@@H](NS(=O)(=O)CC)C4(F)F)C3=O)noc2c1] | 556.9 |
| 300 | N-{(4aR,6R)-2-[4-(2,6-difluorophenyl)-6-ethoxy-1,2-benzoxazol-3-yl]-5,5-difluoro-1-oxooctahydropyrrolo[1,2-c]pyrimidin-6-yl}cyclopropanesulfonamide | 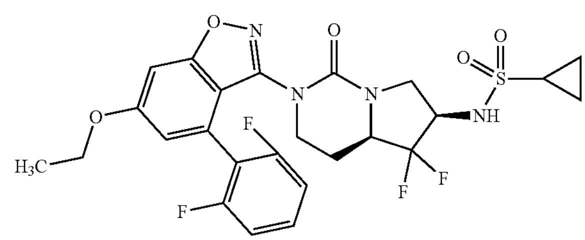 [SMILES: CCOc1cc(-c2c(F)cccc2F)c2c(N3CC[C@H]4N(C[C@@H](NS(=O)(=O)C5CC5)C4(F)F)C3=O)noc2c1] | 568.9 |
| 301 | N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}-N'-methylsulfuric diamide | 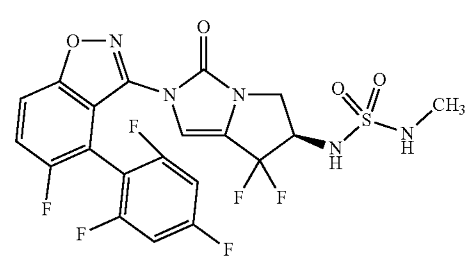 [SMILES: CNS(=O)(=O)N[C@@H]1Cn2c(cn(-c3noc4ccc(F)c(-c5c(F)cc(F)cc5F)c34)c2=O)C1(F)F] | 533.8 |
| 302 | N-{(6R)-2-[4-(2,6-difluorophenyl)-6-methyl[1,2]oxazolo[4,5-c]pyridin-3-yl]-7,7-difluoro-3-oxo-2,5,6,7-tetrahydro-3H-pyrrolo[1,2-c]imidazol-6-yl}-N'-methylsulfuric diamide | 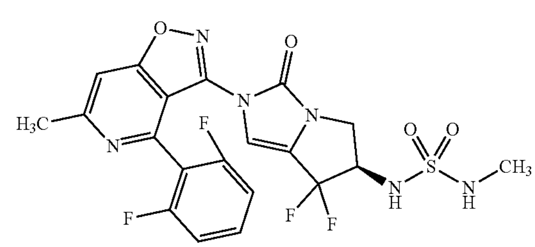 | 512.9 |

TABLE 1-1-continued

| Ex. No. | IUPAC Name | Structure | MS |
|---|---|---|---|
| 303 | N-{(4aR,6R)-2-[6-(difluoromethoxy)-4-(2,4,6-trifluorophenyl)-1,2-benzoxazol-3-yl]-5,5-difluoro-1-oxooctahydropyrrolo[1,2-c]pyrimidin-6-yl}ethanesulfonamide | 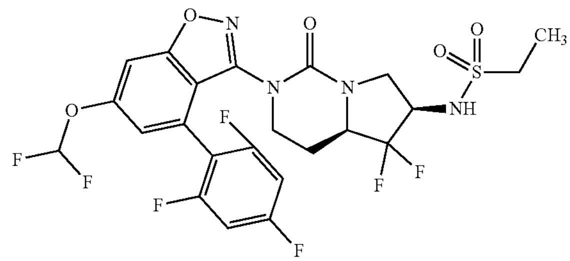 [SMILES: CCS(=O)(=O)N[C@@H]1CN2C(=O)N(c3noc4cc(OC(F)F)cc(-c5c(F)cc(F)cc5F)c34)CC[C@@H]2C1(F)F] | 596.9 |
| 304 | N-{(4aR,6R)-2-[5,6-difluoro-4-(2,4,6-trifluorophenyl)-1,2-benzoxazol-3-yl]-5,5-difluoro-1-oxooctahydropyrrolo[1,2-c]pyrimidin-6-yl}ethanesulfonamide | 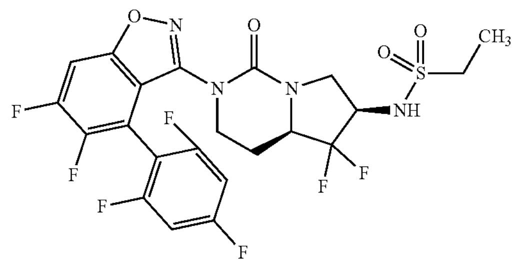 [SMILES: CCS(=O)(=O)N[C@@H]1CN2C(=O)N(c3noc4cc(F)c(F)c(-c5c(F)cc(F)cc5F)c34)CC[C@@H]2C1(F)F] | 566.9 |
| 305 | N-{(4aR,6R)-2-[5,6-difluoro-4-(2,4,6-trifluorophenyl)-1,2-benzoxazol-3-yl]-5,5-difluoro-1-oxooctahydropyrrolo[1,2-c]pyrimidin-6-yl}cyclopropanesulfonamide | 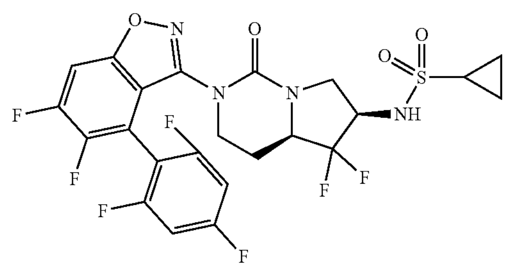 [SMILES: O=C1N(c2noc3cc(F)c(F)c(-c4c(F)cc(F)cc4F)c23)CC[C@H]2N1C[C@@H](NS(=O)(=O)C1CC1)C2(F)F] | 578.8 |
| 306 | N-{(6R)-2-[6-(difluoromethyl)-4-(2,6-difluorophenyl)-1,2-benzoxazol-3-yl]-7,7-difluoro-3-oxo-2,5,6,7-tetrahydro-3H-pyrrolo[1,2-c]imidazol-6-yl}-1-fluoromethanesulfonamide | 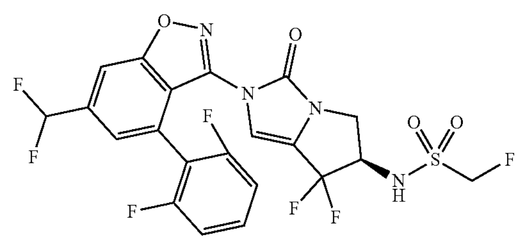 [SMILES: O=c1n(-c2noc3cc(C(F)F)cc(-c4c(F)cccc4F)c23)cc2n1C[C@@H](NS(=O)(=O)CF)C2(F)F] | 548.9 |
| 307 | N-{(4aR,6R)-2-[6-ethoxy-4-(2,4,6-trifluorophenyl)-1,2-benzoxazol-3-yl]-5,5-difluoro-1-oxooctahydropyrrolo[1,2-c]pyrimidin-6-yl}ethanesulfonamide | 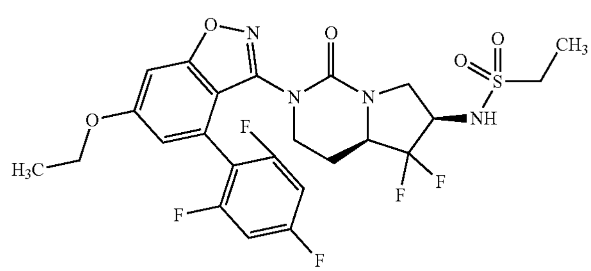 [SMILES: CCOc1cc(-c2c(F)cc(F)cc2F)c2c(N3CC[C@H]4N(C[C@@H](NS(=O)(=O)CC)C4(F)F)C3=O)noc2c1] | 575.1 |
| 308 | N-{(4aR,6R)-5,5-difluoro-2-[6-methoxy-4-(2,4,6-trifluorophenyl)[1,2]oxazolo[5,4-b]pyridin-3-yl]-1-oxooctahydropyrrolo[1,2-c]pyrimidin-6-yl}cyclopropanesulfonamide | 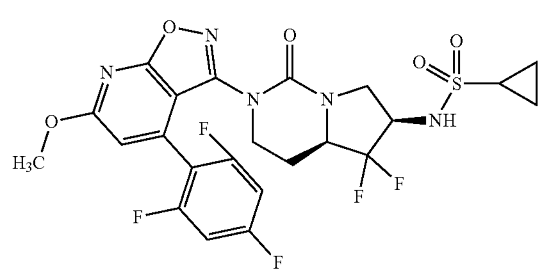 [SMILES: COc1cc(-c2c(F)cc(F)cc2F)c2c(N3CC[C@H]4N(C[C@@H](NS(=O)(=O)C5CC5)C4(F)F)C3=O)noc2n1] | 573.9 |

TABLE 1-1-continued

| Ex. No. | IUPAC Name | MS |
|---|---|---|
| 309 | N-{(6R)-7,7-difluoro-2-[6-methoxy-4-(2,4,6-trifluorophenyl)[1,2]oxazolo[5,4-b]pyridin-3-yl]-3-oxo-2,5,6,7-tetrahydro-3H-pyrrolo[1,2-c]imidazol-6-yl}ethanesulfonamide | 545.8 |
| 310 | N-{(6R,7aR)-2-[4-(2,6-difluorophenyl)-6-fluoro-1,2-benzoxazol-3-yl]-7,7-difluoro-3-oxohexahydro-1H-pyrrolo[1,2-c]imidazol-6-yl}-N'-methylsulfuric diamide | 517.9 |
| 311 | N-{(4aR,6R)-2-[4-(2,6-difluorophenyl)-5,6-difluoro-1,2-benzoxazol-3-yl]-5,5-difluoro-1-oxooctahydropyrrolo[1,2-c]pyrimidin-6-yl}ethanesulfonamide | 549.0 |
| 312 | N-{(4aR,6R)-2-[4-(2,6-difluorophenyl)-5,6-difluoro-1,2-benzoxazol-3-yl]-5,5-difluoro-1-oxooctahydropyrrolo[1,2-c]pyrimidin-6-yl}cyclopropanesulfonamide | 560.8 |
| 313 | N-{(4aR,6R)-2-[4-(2,6-difluorophenyl)-5,6-difluoro-1,2-benzoxazol-3-yl]-5,5-difluoro-1-oxooctahydropyrrolo[1,2-c]pyrimidin-6-yl}-1-fluoromethanesulfonamide | 552.9 |
| 314 | N-{(4aR,6R)-2-[4-(2,6-difluorophenyl)-6-fluoro-1,2-benzoxazol-3-yl]-5,5-difluoro-1-oxooctahydropyrrolo[1,2-c]pyrimidin-6-yl}methanesulfonamide | 516.9 |

TABLE 1-1-continued

| Ex. No. | IUPAC Name | Structure | MS |
|---|---|---|---|
| 315 | N-{(4aR,6R)-5,5-difluoro-2-[6-methoxy-4-(2,4,6-trifluorophenyl)[1,2]oxazolo[5,4-b]pyridin-3-yl]-1-oxooctahydropyrrolo[1,2-c]pyrimidin-6-yl}ethanesulfonamide | 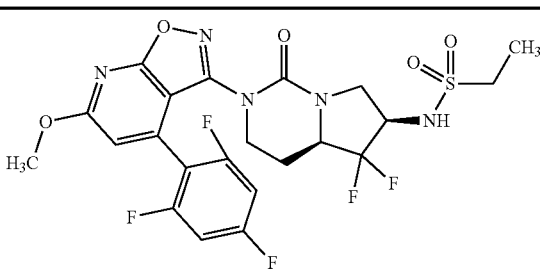 | 561.9 |
| 316 | N-{(4aR,6R)-2-[6-(difluoromethoxy)-4-(2,4,6-trifluorophenyl)-1,2-benzoxazol-3-yl]-5,5-difluoro-1-oxooctahydropyrrolo[1,2-c]pyrimidin-6-yl}cyclopropanesulfonamide | 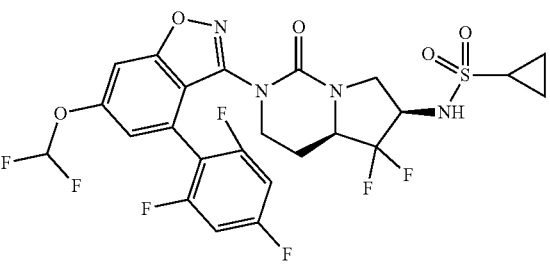 [SMILES: O=C1N(c2noc3cc(OC(F)F)cc(-c4c(F)cc(F)cc4F)c23)CC[C@H]2N1C[C@@H](NS(=O)(=O)C1CC1)C2(F)F] | 609.0 |
| 317 | N-{(4aR,6S)-2-[4-(2,6-difluorophenyl)-1,2-benzoxazol-3-yl]-1-oxooctahydropyrrolo[1,2-c]pyrimidin-6-yl}methanesulfonamide | 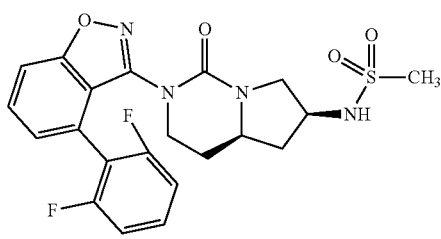 [SMILES: CS(=O)(=O)N[C@H]1C[C@H]2CCN(c3noc4cccc(-c5c(F)cccc5F)c34)C(=O)N2C1] | 462.8 |
| 318 | N-{(4aR,6R)-2-[4-(3,5-difluoropyridin-2-yl)-6-fluoro-1,2-benzoxazol-3-yl]-5,5-difluoro-1-oxooctahydropyrrolo[1,2-c]pyrimidin-6-yl}cyclopropanesulfonamide | 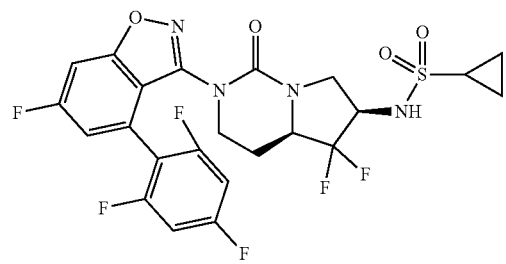 [SMILES: O=C1N(c2noc3cc(F)cc(-c4c(F)cc(F)cc4F)c23)CC[C@H]2N1C[C@@H](NS(=O)(=O)C1CC1)C2(F)F] | 544.1 |
| 319 | N-{(4aR,6R)-2-[4-(3,5-difluoropyridin-2-yl)-1,2-benzoxazol-3-yl]-5,5-difluoro-1-oxooctahydropyrrolo[1,2-c]pyrimidin-6-yl}cyclopropanesulfonamide | 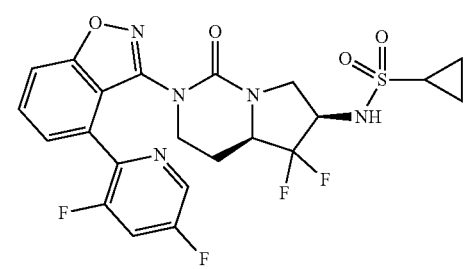 [SMILES: O=C1N(c2noc3cccc(-c4ncc(F)cc4F)c23)CC[C@H]2N1C[C@@H](NS(=O)(=O)C1CC1)C2(F)F] | 526.1 |
| 320 | N-{(4aR,6R)-2-[4-(3,5-difluoropyridin-2-yl)-1,2-benzoxazol-3-yl]-5,5-difluoro-1-oxooctahydropyrrolo[1,2-c]pyrimidin-6-yl}methanesulfonamide | 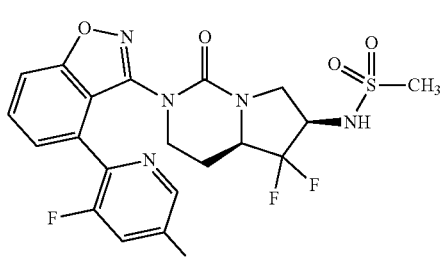 | 500.2 |

TABLE 1-1-continued

| Ex. No. | IUPAC Name | Structure | MS |
|---|---|---|---|
| 321 | N-{(4aR,6R)-2-[4-(3,5-difluoropyridin-2-yl)-1,2-benzoxazol-3-yl]-5,5-difluoro-1-oxooctahydropyrrolo[1,2-c]pyrimidin-6-yl}ethanesulfonamide | 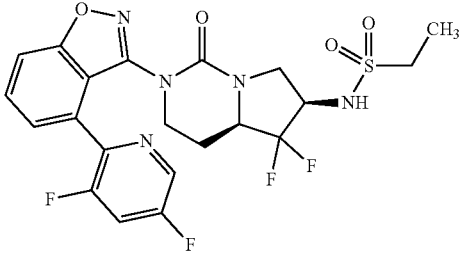 [SMILES: CCS(=O)(=O)N[C@@H]1CN2C(=O)N(c3noc4cccc(-c5ncc(F)cc5F)c34)CC[C@@H]2C1(F)F] | 514.1 |
| 322 | N-{(4aR,6R)-5,5-difluoro-2-[4-(2-methoxyphenyl)-1,2-benzoxazol-3-yl]-1-oxooctahydropyrrolo[1,2-c]pyrimidin-6-yl}ethanesulfonamide | 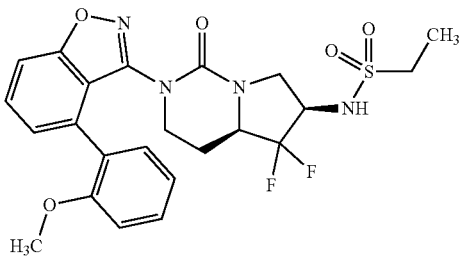 [SMILES: CCS(=O)(=O)N[C@@H]1CN2C(=O)N(c3noc4cccc(-c5ccccc5OC)c34)CC[C@@H]2C1(F)F] | 506.9 |
| 323 | N-{(4aR,6R)-5,5-difluoro-2-[4-(4-fluoro-2-methylphenyl)-1,2-benzoxazol-3-yl]-1-oxooctahydropyrrolo[1,2-c]pyrimidin-6-yl}ethanesulfonamide | 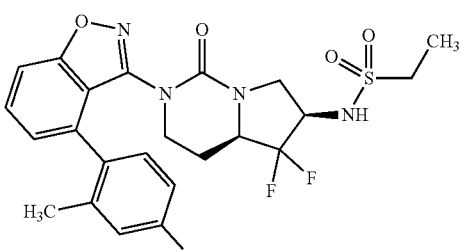 | 509.1 |
| 324 | N-{(4aR,6R)-5,5-difluoro-2-[4-(furan-2-yl)-1,2-benzoxazol-3-yl]-1-oxooctahydropyrrolo[1,2-c]pyrimidin-6-yl}ethanesulfonamide | 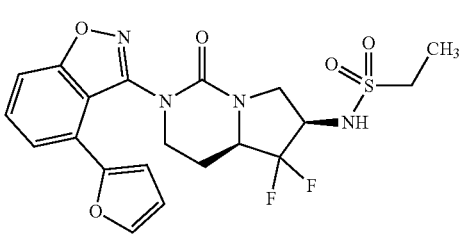 [SMILES: CCS(=O)(=O)N[C@@H]1CN2C(=O)N(c3noc4cccc(-c5ccco5)c34)CC[C@@H]2C1(F)F] | 467.0 |
| 325 | N-{(4aR,6R)-5,5-difluoro-2-[4-(2-methylphenyl)-1,2-benzoxazol-3-yl]-1-oxooctahydropyrrolo[1,2-c]pyrimidin-6-yl}ethanesulfonamide | 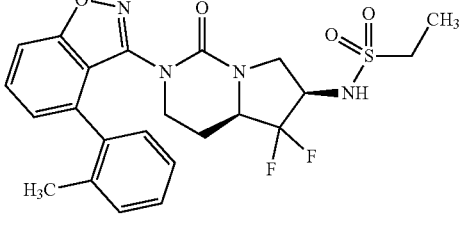 | 490.9 |
| 326 | N-{(4aR,6R)-5,5-difluoro-1-oxo-2-[4-(thiophen-3-yl)-1,2-benzoxazol-3-yl]octahydropyrrolo[1,2-c]pyrimidin-6-yl}ethanesulfonamide | 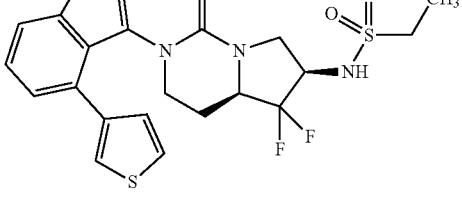 | 482.9 |

TABLE 1-1-continued

| Ex. No. | IUPAC Name | MS |
|---|---|---|
| 327 | N-{(4aR,6R)-2-[4-(2-chlorophenyl)-1,2-benzoxazol-3-yl]-5,5-difluoro-1-oxooctahydropyrrolo[1,2-c]pyrimidin-6-yl}ethanesulfonamide | 510.8 |
| 328 | N-{(4aR,6R)-5,5-difluoro-1-oxo-2-[4-(thiophen-2-yl)-1,2-benzoxazol-3-yl]octahydropyrrolo[1,2-c]pyrimidin-6-yl}ethanesulfonamide | 483.0 |
| 329 | N-{(4aR,6R)-2-[4-(2-chloro-4-fluorophenyl)-1,2-benzoxazol-3-yl]-5,5-difluoro-1-oxooctahydropyrrolo[1,2-c]pyrimidin-6-yl}ethanesulfonamide | 528.8 |
| 330 | N-{(4aR,6R)-5,5-difluoro-1-oxo-2-[4-(1,3-thiazol-2-yl)-1,2-benzoxazol-3-yl]octahydropyrrolo[1,2-c]pyrimidin-6-yl}ethanesulfonamide | 483.9 |
| 331 | N-[(4aR,6R)-2-(4-cyclobutyl-1,2-benzoxazol-3-yl)-5,5-difluoro-1-oxooctahydropyrrolo[1,2-c]pyrimidin-6-yl]ethanesulfonamide | 454.8 |
| 332 | N-{(4aR,6R)-5,5-difluoro-2-[4-(3-methylthiophen-2-yl)-1,2-benzoxazol-3-yl]-1-oxooctahydropyrrolo[1,2-c]pyrimidin-6-yl}ethanesulfonamide | 496.9 |

TABLE 1-1-continued

| Ex. No. | IUPAC Name | Structure | MS |
|---|---|---|---|
| 333 | N-{(4aR,6R)-5,5-difluoro-1-oxo-2-[4-(piperidin-1-yl)-1,2-benzoxazol-3-yl]octahydropyrrolo[1,2-c]pyrimidin-6-yl}ethanesulfonamide | 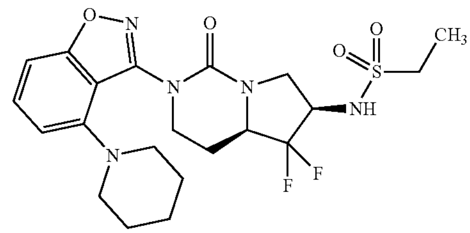 [SMILES: CCS(=O)(=O)N[C@@H]1CN2C(=O)N(c3noc4cccc(N5CCCCC5)c34)CC[C@@H]2C1(F)F] | 483.9 |
| 334 | N-{(4aR,6R)-5,5-difluoro-2-[4-(2-fluorophenyl)-1,2-benzoxazol-3-yl]-1-oxooctahydropyrrolo[1,2-c]pyrimidin-6-yl}ethanesulfonamide | 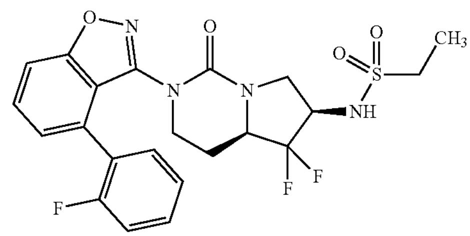 [SMILES: CCS(=O)(=O)N[C@@H]1CN2C(=O)N(c3noc4cccc(-c5ccccc5F)c34)CC[C@@H]2C1(F)F] | 495.1 |
| 335 | N-{(4aR,6R)-5,5-difluoro-2-[4-(5-fluoro-3-methylpyridin-2-yl)-1,2-benzoxazol-3-yl]-1-oxooctahydropyrrolo[1,2-c]pyrimidin-6-yl}ethanesulfonamide | 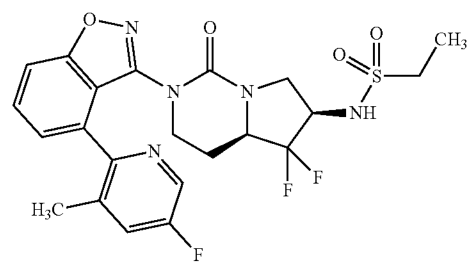 [SMILES: CCS(=O)(=O)N[C@@H]1CN2C(=O)N(c3noc4cccc(-c5ncc(F)cc5C)c34)CC[C@@H]2C1(F)F] | 510.2 |
| 336 | N-{(2R*)-6-[4-(2,6-difluorophenyl)-1,2-benzoxazol-3-yl]-7-methyl-5-oxo-2,3-dihydro-1H,5H-pyrazolo[1,2-a]pyrazol-2-yl}ethanesulfonamide | 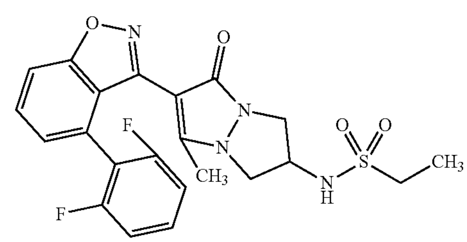 [SMILES: CCS(=O)(=O)NC1Cn2c(C)c(-c3noc4cccc(-c5c(F)cccc5F)c34)c(=O)n2C1] | 475.3 |
| 337 | rel-N-{(3aR,5R,6aS)-2-[4-(2,6-difluorophenyl)-1,2-benzoxazol-3-yl]-1-oxooctahydrocyclopenta[c]pyrrol-5-yl}methanesulfonamide | 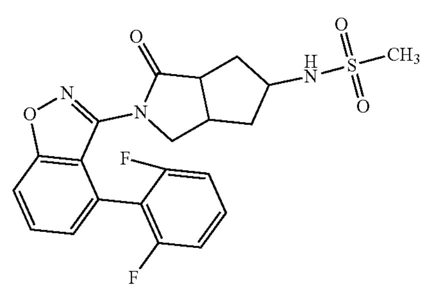 [SMILES: CS(=O)(=O)NC1CC2CN(c3noc4cccc(-c5c(F)cccc5F)c34)C(=O)C2C1] | 448.2 |
| 338 | rel-N-{(3aR,5S,6aS)-2-[4-(2,6-difluorophenyl)-1,2-benzoxazol-3-yl]-1-oxooctahydrocyclopenta[c]pyrrol-5-yl}methanesulfonamide | 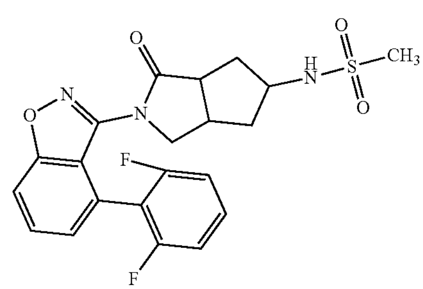 [SMILES: CS(=O)(=O)NC1CC2CN(c3noc4cccc(-c5c(F)cccc5F)c34)C(=O)C2C1] | 448.4 |

TABLE 1-1-continued

| Ex. No. | IUPAC Name | Structure | MS |
|---|---|---|---|
| 339 | N-{(2R*)-6-[4-(2,6-difluorophenyl)-1,2-benzoxazol-3-yl]-5-oxo-2,3-dihydro-1H,5H-pyrazolo[1,2-a]pyrazol-2-yl}ethanesulfonamide | 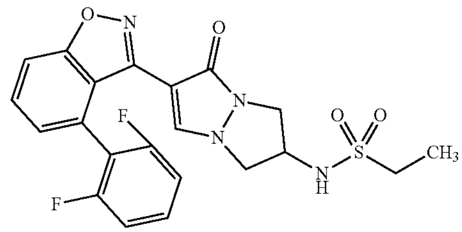 [SMILES: CCS(=O)(=O)NC1Cn2cc(-c3noc4cccc(-c5c(F)cccc5F)c34)c(=O)n2C1] | 461.2 |
| 340 | N-{(2R*)-6-[4-(2,6-difluorophenyl)-1,2-benzoxazol-3-yl]-7-methyl-5-oxo-2,3-dihydro-1H,5H-pyrazolo[1,2-a]pyrazol-2-yl}methanesulfonamide | 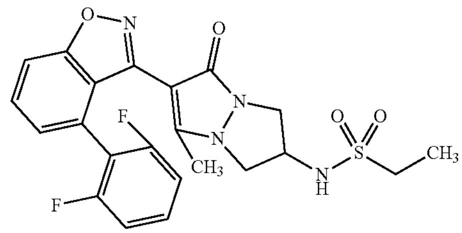 [SMILES: CCS(=O)(=O)NC1Cn2c(C)c(-c3noc4cccc(-c5c(F)cccc5F)c34)c(=O)n2C1] | 461.2 |

Experimental Example 1: Acquisition of Cells Stably Expressing Human Orexin Type 2 Receptor (hOX2R)

In order to obtain cell clones that stably express human orexin type 2 receptor, human orexin type 2 (residues 1-444, NCBI Reference Sequence: AK314279) was constructed in a pcDNA3.1 (+) vector (Invitrogen) to express in mammalian cells. This plasmid DNA was transfected into CHO-K1 cells by electroporation, and stable clones were obtained by limiting dilution using resistance to G418 as a selection marker.

Experimental Example 2: Measurement of Orexin Type 2 Receptor Agonist Activity

CHO cells in which human OX2 receptor was forcibly expressed were seeded at 10,000 cells/well into a 384-well black transparent bottom plate (BD falcon), and were incubated at 37° C., 5% CO2 for 1 day after incubation at room temperature for 30 minutes. After removing the cell plate medium, assay buffer containing calcium indicator A (HBSS (Thermo Fisher Scientific), 20 mM HEPES (Thermo Fisher Scientific), 0.1% BSA (Sigma-Aldrich), 2.5 μg/mL Fluo-4 AM (Dojin Kagaku), 0.08% Pluronic F127 (Dojin Kagaku), 1.25 mM probenecid (Dojin Kagaku)) was added at 30 μL/well. After incubation in a 5% CO2 incubator at 37° C. for 30 minutes, it was incubated at room temperature for another 30 minutes. Add 10 μL/well of the test compound diluted with assay buffer B (HBSS, 20 mM HEPES, 0.1% BSA), and use FDSS μCELL (Hamamatsu Photonics) to measure the fluorescence value every 1 second for 1 minute, and then every 2 seconds for 1 minute. It was measured for 1 minute and 40 seconds. The amount of fluorescence value when DMSO is added instead of the test compound is defined as 0%, and the amount of fluorescence value when orexin A (human) (Peptide Institute) with a final concentration of 10 nM is added is defined as 100%. The activity (%) of the test compound was calculated. Table 2 shows the activity of each compound at a concentration of 3 μM. As is clear from this result, the compound of the present invention was shown to have orexin type 2 receptor activating activity.

TABLE 2

| Test compound | OX2R agonist activity (3 uM, %) |
|---|---|
| 1 | 104 |
| 2 | 108 |
| 4 | 105 |
| 5 | 106 |
| 6 | 96 |
| 7 | 105 |
| 9 | 92 |
| 12 | 105 |
| 16 | 107 |
| 17 | 104 |
| 20 | 97 |
| 21 | 81 |
| 24 | 104 |
| 25 | 96 |
| 26 | 97 |
| 28 | 106 |
| 29 | 101 |
| 30 | 94 |
| 32 | 94 |
| 33 | 108 |
| 34 | 106 |
| 37 | 101 |
| 38 | 111 |
| 39 | 106 |
| 40 | 103 |
| 41 | 100 |
| 43 | 100 |
| 46 | 102 |
| 47 | 91 |
| 49 | 94 |
| 50 | 103 |
| 55 | 108 |
| 56 | 99 |
| 57 | 88 |
| 58 | 88 |
| 63 | 107 |
| 65 | 99 |
| 66 | 97 |
| 67 | 97 |
| 68 | 109 |
| 69 | 96 |
| 70 | 105 |
| 71 | 97 |
| 72 | 98 |
| 73 | 105 |
| 74 | 104 |

TABLE 2-continued

| Test compound | OX2R agonist activity (3 uM, %) |
|---|---|
| 75 | 99 |
| 76 | 105 |
| 77 | 100 |
| 78 | 104 |
| 79 | 99 |
| 83 | 84 |
| 84 | 92 |
| 85 | 95 |
| 86 | 103 |
| 87 | 91 |
| 88 | 79 |
| 89 | 95 |
| 90 | 107 |
| 91 | 103 |
| 92 | 98 |
| 93 | 99 |
| 94 | 106 |
| 95 | 104 |
| 102 | 100 |
| 103 | 106 |
| 105 | 96 |
| 106 | 103 |
| 107 | 101 |
| 108 | 109 |
| 109 | 103 |
| 111 | 90 |
| 112 | 99 |
| 113 | 102 |
| 116 | 93 |
| 117 | 97 |
| 118 | 91 |
| 119 | 105 |
| 121 | 93 |
| 124 | 101 |
| 125 | 103 |
| 126 | 97 |
| 127 | 102 |
| 128 | 98 |
| 129 | 103 |
| 130 | 99 |
| 131 | 96 |
| 132 | 94 |
| 135 | 100 |
| 136 | 99 |
| 139 | 101 |
| 140 | 100 |
| 141 | 94 |
| 142 | 99 |
| 144 | 102 |
| 145 | 105 |
| 149 | 95 |
| 152 | 92 |
| 153 | 96 |
| 154 | 98 |
| 155 | 96 |
| 156 | 102 |
| 157 | 96 |
| 158 | 103 |
| 160 | 99 |
| 162 | 102 |
| 163 | 103 |
| 164 | 108 |
| 165 | 97 |
| 166 | 92 |
| 167 | 97 |
| 168 | 102 |
| 169 | 103 |
| 170 | 94 |
| 171 | 100 |
| 172 | 98 |
| 174 | 95 |
| 175 | 98 |
| 176 | 89 |
| 179 | 109 |
| 180 | 100 |
| 181 | 105 |
| 182 | 84 |
| 183 | 101 |
| 184 | 101 |
| 185 | 104 |
| 186 | 101 |
| 189 | 103 |
| 190 | 96 |
| 191 | 98 |
| 193 | 103 |
| 194 | 92 |
| 195 | 106 |
| 196 | 106 |
| 197 | 115 |
| 198 | 112 |
| 199 | 105 |
| 200 | 122 |
| 201 | 114 |
| 202 | 99 |
| 203 | 114 |
| 204 | 109 |
| 205 | 107 |
| 206 | 110 |
| 207 | 113 |
| 208 | 102 |
| 209 | 96 |
| 210 | 94 |
| 211 | 108 |
| 212 | 100 |
| 213 | 104 |
| 214 | 106 |
| 215 | 99 |
| 216 | 101 |
| 217 | 104 |
| 218 | 108 |
| 219 | 103 |
| 220 | 112 |
| 221 | 104 |
| 222 | 107 |
| 223 | 104 |
| 224 | 109 |
| 225 | 106 |
| 226 | 93 |
| 227 | 98 |
| 228 | 102 |
| 229 | 113 |
| 230 | 111 |
| 231 | 103 |
| 232 | 107 |
| 233 | 109 |
| 234 | 111 |
| 235 | 113 |
| 236 | 108 |
| 237 | 110 |
| 238 | 106 |
| 239 | 95 |
| 240 | 106 |
| 241 | 100 |
| 242 | 105 |
| 243 | 109 |
| 244 | 89 |
| 245 | 108 |
| 246 | 107 |
| 247 | 101 |
| 248 | 107 |
| 249 | 102 |
| 250 | 99 |
| 251 | 109 |
| 252 | 96 |
| 253 | 101 |
| 254 | 95 |
| 255 | 107 |
| 256 | 103 |
| 257 | 110 |
| 258 | 100 |
| 259 | 96 |
| 260 | 108 |
| 261 | 105 |
| 262 | 114 |

TABLE 2-continued

| Test compound | OX2R agonist activity (3 uM, %) |
|---|---|
| 263 | 114 |
| 264 | 107 |
| 265 | 107 |
| 266 | 103 |
| 267 | 101 |
| 268 | 104 |
| 269 | 104 |
| 270 | 109 |
| 271 | 107 |
| 272 | 109 |
| 273 | 103 |
| 274 | 102 |
| 275 | 103 |
| 276 | 100 |
| 277 | 106 |
| 278 | 109 |
| 279 | 104 |
| 280 | 101 |
| 281 | 107 |
| 282 | 105 |
| 283 | 107 |
| 284 | 109 |
| 285 | 105 |
| 286 | 105 |
| 287 | 101 |
| 288 | 101 |
| 289 | 97 |
| 290 | 106 |
| 291 | 106 |
| 292 | 106 |
| 293 | 113 |
| 294 | 104 |
| 295 | 113 |
| 296 | 102 |
| 297 | 107 |
| 298 | 105 |
| 299 | 104 |
| 300 | 105 |
| 301 | 98 |
| 302 | 103 |
| 303 | 103 |
| 304 | 117 |
| 305 | 113 |
| 306 | 101 |
| 307 | 101 |
| 308 | 100 |
| 309 | 107 |
| 310 | 100 |
| 311 | 99 |
| 312 | 100 |
| 313 | 99 |
| 314 | 113 |
| 315 | 105 |
| 316 | 105 |
| 317 | 110 |
| 318 | 105 |
| 319 | 107 |
| 320 | 104 |
| 321 | 108 |
| 322 | 99 |
| 323 | 97 |
| 324 | 97 |
| 325 | 101 |
| 326 | 99 |
| 327 | 118 |
| 328 | 103 |
| 329 | 101 |
| 330 | 109 |
| 331 | 45 |
| 332 | 106 |
| 333 | 68 |
| 334 | 111 |
| 335 | 101 |
| 336 | 98 |
| 337 | 79 |
| 338 | 100 |
| 339 | 96 |
| 340 | 92 |

Experimental Example 3: Evaluation of Wake-Promoting Effects in Cynomolgus Monkeys The wake-promoting effects were evaluated by measuring the electroencephalogram (EEG), electromyogram (EMG) and locomotor activity in cynomolgus monkeys. Under isoflurane anesthesia (0.5-5%, Pfizer Japan Inc., Tokyo, Japan), male cynomolgus monkeys (2-3 years old, Hamri Co., Ltd., Ibaraki, Japan) were surgically implanted with radio-telemetry transmitters (L03-F3, Data Sciences International Inc., MN, USA). The two EEG electrodes were stereotaxically positioned at the parietal area and secured to the cranium with stainless-steel screws in contact with the dura. Bilateral EMG electrodes were implanted into the back cervical muscles. After at least a 1-month recovery period in home cages, the monkeys were habituated to the recording chamber (an acrylic cage 60W×55D×75H (cm)) located in a soundproof and electrically shielded room by the time animals sleep sufficiently in the experimental room. Cortical EEG, EMG and locomotor activity were recorded using the telemetry system (PhysioTel Digital telemetry platform, Data Sciences International Inc.). The signals were semi-automatically scored in 20-second epochs by a sleep scoring system (SleepSign, Kissei Comtec Co., Ltd., Nagano, Japan).

Test compound (1 or 3 mg/kg) suspended in 0.5% methylcellulose aqueous solution or vehicle (i.e., 0.5% methylcellulose aqueous solution) was administered orally (p.o.) to monkeys at zeitgeber time 12 in a volume of 5 mL/kg body weight with a pretest-posttest design (n=2-4), and then EEG, EMG and locomotor activity were recorded for 4 hours after administration. The time spent in wakefulness for 4 hours after administration (% of vehicle treatment) was calculated by using SleepSign. The results are shown in Table 3.

TABLE 3

| Example No. | Dose (mg/kg, p.o.) | Wakefulness time (% of vehicle treatment) (Mean, n = 2-4) |
|---|---|---|
| 1 | 3 | 382.91 |
| 16 | 1 | 545.98 |
| 24 | 1 | 392.55 |
| 50 | 1 | 175.82 |
| 71 | 1 | 702.60 |
| 77 | 1 | 645.09 |
| 142 | 1 | 690.49 |
| 149 | 1 | 731.22 |
| 213 | 1 | 447.05 |
| 243 | 1 | 618.15 |
| 265 | 1 | 472.45 |
| 282 | 1 | 417.62 |

As is clear from Table 3, the test compounds of the present invention increased the wakefulness time compared to the vehicle treatment group in cynomolgus monkeys. That is, these compounds were suggested to be potential therapeutics for narcolepsy.

| Formulation Example 1 (production of capsule) | |
| --- | --- |
| 1) compound of Example 1 | 30 mg |
| 2) crystalline cellulose | 10 mg |
| 3) lactose | 19 mg |
| 4) magnesium stearate | 1 mg |
| total | 60 mg |

1), 2), 3) and 4) are mixed and filled in a gelatin capsule.

| Formulation Example 2 (production of tablet) | |
| --- | --- |
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets | 140 g in total |

The total amount of 1), 2), 3) and 30 g of 4) are kneaded with water, vacuum dried and sieved. The sieved powder is mixed with 14 g of 4) and 1 g of 5), and the mixture is punched by a tableting machine. In this way, 1000 tablets containing 30 mg of the compound of Example 1 per tablet are obtained.

INDUSTRIAL APPLICABILITY

The compound of the present invention has an orexin type 2 receptor agonist activity, and is useful as an agent for the prophylaxis or treatment of narcolepsy.

This application is based on patent application No. 63/381,736 filed on Oct. 31, 2022 in United States, the contents of which are encompassed in full herein.

The invention claimed is:

1. A compound represented by the formula (Ia):

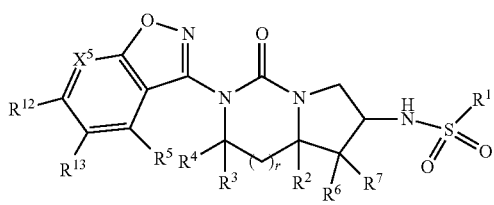

(Ia)

wherein
$R^1$ is a $C_{1-6}$ alkyl group, a $C_{3-10}$ cycloalkyl group, or a mono-$C_{1-6}$ alkylamino group;
r is 0 or 1;
$R^2$ and $R^3$ are each independently a hydrogen atom, or when r is 0, then $R^2$ and $R^3$ may be taken together to form a bond;
$R^4$ is a hydrogen atom;
$R^5$ is a phenyl group optionally substituted by 1 to 3 halogen atoms;
$R^6$ and $R^7$ are each independently a hydrogen atom, or a halogen atom;
$X^5$ is CH or N; and
$R^{12}$ and $R^{13}$ are each independently a hydrogen atom, a $C_{1-6}$ alkyl group, or a halogen atom;
or a salt thereof.

2. The compound according to claim 1, wherein
$R^1$ is a $C_{1-6}$ alkyl group;
r is 0 or 1;
$R^2$ and $R^3$ are each a hydrogen atom, or when r is 0, then $R^2$ and $R^3$ may be taken together to form a bond;
$R^4$ is a hydrogen atom;
$R^5$ is a phenyl group substituted by 1 to 3 halogen atoms;
$R^6$ and $R^7$ are each a halogen atom;
$X^5$ is CH; and
$R^{12}$ and $R^{13}$ are each independently a hydrogen atom, or a halogen atom;
or a salt thereof.

3. The compound according to claim 1, wherein the compound is selected from the group consisting of:
N-{(6S,7aS)-2-[4-(2,6-difluorophenyl)-1,2-benzoxazol-3-yl]-3-oxohexahydro-1H-pyrrolo[1,2-c]imidazol-6-yl}ethanesulfonamide;
N-{(6R)-7,7-difluoro-3-oxo-2-[4-(2,4,6-trifluorophenyl)-1,2-benzoxazol-3-yl]-2,5,6,7-tetrahydro-3H-pyrrolo[1,2-c]imidazol-6-yl}methanesulfonamide;
N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}ethanesulfonamide;
N-{(6S,7aS)-2-[6-chloro-4-(2,6-difluorophenyl)-1,2-benzoxazol-3-yl]-3-oxohexahydro-1H-pyrrolo[1,2-c]imidazol-6-yl}ethanesulfonamide;
N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}methanesulfonamide;
N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide;
N-{(6R,7aR)-7,7-difluoro-2-[6-fluoro-4-(2,4,6-trifluorophenyl)-1,2-benzoxazol-3-yl]-3-oxohexahydro-1H-pyrrolo[1,2-c]imidazol-6-yl}methanesulfonamide;
N-{(4aR,6R)-5,5-difluoro-1-oxo-2-[4-(2,4,6-trifluorophenyl)-1,2-benzoxazol-3-yl]octahydropyrrolo[1,2-c]pyrimidin-6-yl}methanesulfonamide;
N-{(4aR,6R)-2-[5,6-difluoro-4-(2,4,6-trifluorophenyl)-1,2-benzoxazol-3-yl]-5,5-difluoro-1-oxooctahydropyrrolo[1,2-c]pyrimidin-6-yl}methanesulfonamide;
N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}methanesulfonamide; and
N-{(6R)-2-[4-(2,6-difluorophenyl)-6-fluoro-1,2-benzoxazol-3-yl]-7,7-difluoro-3-oxo-2,5,6,7-tetrahydro-3H-pyrrolo[1,2-c]imidazol-6-yl}ethanesulfonamide;
or a salt thereof.

4. A pharmaceutical composition comprising the compound of claim 1 or a salt thereof and a pharmaceutically acceptable excipient.

5. A pharmaceutical composition comprising the compound or salt according to claim 3 and a pharmaceutically acceptable excipient.

6. The compound of claim 3, wherein the compound is N-{(6S,7aS)-2-[4-(2,6-difluorophenyl)-1,2-benzoxazol-3-yl]-3-oxohexahydro-1H-pyrrolo[1,2-c]imidazol-6-yl}ethanesulfonamide, or a salt thereof.

7. The compound of claim 3, wherein the compound is N-{(6R)-7,7-difluoro-3-oxo-2-[4-(2,4,6-trifluorophenyl)-1,2-benzoxazol-3-yl]-2,5,6,7-tetrahydro-3H-pyrrolo[1,2-c]imidazol-6-yl}methanesulfonamide, or a salt thereof.

8. The compound of claim 3, wherein the compound is N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}ethanesulfonamide, or a salt thereof.

9. The compound of claim 3, wherein the compound is N-{(6S,7aS)-2-[6-chloro-4-(2,6-difluorophenyl)-1,2-benzoxazol-3-yl]-3-oxohexahydro-1H-pyrrolo[1,2-c]imidazol-6-yl}ethanesulfonamide, or a salt thereof.

10. The compound of claim 3, wherein the compound is N-{(6R,7aR)-7,7-difluoro-3-oxo-2-[4-(2,4,6-trifluorophenyl)-1,2-benzoxazol-3-yl]hexahydro-1H-pyrrolo[1,2-c]imidazol-6-yl}methanesulfonamide, or a salt thereof.

11. The compound of claim 3, wherein the compound is N-{(6R)-7,7-difluoro-2-[5-fluoro-4-(2,4,6-trifluorophenyl)-1,2-benzoxazol-3-yl]-3-oxo-2,5,6,7-tetrahydro-3H-pyrrolo[1,2-c]imidazol-6-yl}methanesulfonamide, or a salt thereof.

12. The compound of claim 3, wherein the compound is N-{(6R,7aR)-7,7-difluoro-2-[6-fluoro-4-(2,4,6-trifluorophenyl)-1,2-benzoxazol-3-yl]-3-oxohexahydro-1H-pyrrolo[1,2-c]imidazol-6-yl}methanesulfonamide, or a salt thereof.

13. The compound of claim 3, wherein the compound is N-{(4aR,6R)-5,5-difluoro-1-oxo-2-[4-(2,4,6-trifluorophenyl)-1,2-benzoxazol-3-yl]octahydropyrrolo[1,2-c]pyrimidin-6-yl}methanesulfonamide, or a salt thereof.

14. The compound of claim 3, wherein the compound is N-{(4aR,6R)-2-[5,6-difluoro-4-(2,4,6-trifluorophenyl)-1,2-benzoxazol-3-yl]-5,5-difluoro-1-oxooctahydropyrrolo[1,2-c]pyrimidin-6-yl}methanesulfonamide, or a salt thereof.

15. The compound of claim 3, wherein the compound is N-{(4aR,6R)-2-[4-(2,6-difluorophenyl)-5-fluoro-1,2-benzoxazol-3-yl]-5,5-difluoro-1-oxooctahydropyrrolo[1,2-c]pyrimidin-6-yl}methanesulfonamide, or a salt thereof.

16. The compound of claim 3, wherein the compound is N-{(6R)-2-[4-(2,6-difluorophenyl)-6-fluoro-1,2-benzoxazol-3-yl]-7,7-difluoro-3-oxo-2,5,6,7-tetrahydro-3H-pyrrolo[1,2-c]imidazol-6-yl}ethanesulfonamide, or a salt thereof.

* * * * *